United States Patent
Xu et al.

(10) Patent No.: US 9,408,924 B2
(45) Date of Patent: *Aug. 9, 2016

(54) BIOCONJUGATES OF CYANINE DYES

(71) Applicant: LI-COR, INC., Lincoln, NE (US)

(72) Inventors: Xinshe Xu, Lincoln, NE (US); Daniel R. Draney, Lincoln, NE (US); Lael Cheung, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/552,396

(22) Filed: Nov. 24, 2014

(65) Prior Publication Data

US 2015/0119553 A1  Apr. 30, 2015

Related U.S. Application Data

(63) Continuation of application No. 13/831,345, filed on Mar. 14, 2013, now Pat. No. 8,927,719, which is a continuation of application No. PCT/US2011/057134, filed on Oct. 20, 2011.

(60) Provisional application No. 61/405,161, filed on Oct. 20, 2010, provisional application No. 61/405,158, filed on Oct. 20, 2010.

(51) Int. Cl.

| | |
|---|---|
| *C07D 401/06* | (2006.01) |
| *C07D 471/04* | (2006.01) |
| *A61K 49/00* | (2006.01) |
| *C09B 23/01* | (2006.01) |
| *C09B 23/08* | (2006.01) |
| *C09B 69/00* | (2006.01) |
| *G01N 33/574* | (2006.01) |
| *G01N 33/58* | (2006.01) |
| *C07F 9/6561* | (2006.01) |
| *C07K 19/00* | (2006.01) |
| *C08B 37/08* | (2006.01) |

(52) U.S. Cl.
CPC ......... *A61K 49/0058* (2013.01); *A61K 49/0032* (2013.01); *A61K 49/0052* (2013.01); *C07D 471/04* (2013.01); *C07F 9/6561* (2013.01); *C07K 19/00* (2013.01); *C08B 37/0072* (2013.01); *C09B 23/0008* (2013.01); *C09B 23/0016* (2013.01); *C09B 23/0025* (2013.01); *C09B 23/0066* (2013.01); *C09B 23/083* (2013.01); *C09B 23/086* (2013.01); *C09B 69/00* (2013.01); *G01N 33/574* (2013.01); *G01N 33/58* (2013.01); *G01N 33/582* (2013.01)

(58) Field of Classification Search
CPC .............................. C07D 401/06; C07D 471/04
USPC ....................................................... 546/113
See application file for complete search history.

(56) References Cited

U.S. PATENT DOCUMENTS

| | | |
|---|---|---|
| 3,723,419 A | 3/1973 | Mee et al. |
| 3,864,644 A | 2/1975 | Lincoln et al. |
| 4,011,086 A | 3/1977 | Simson |
| 4,264,694 A | 4/1981 | Pu et al. |
| 4,871,656 A | 10/1989 | Parton et al. |

(Continued)

FOREIGN PATENT DOCUMENTS

| | | |
|---|---|---|
| DE | 4445065 A1 | 6/1996 |
| EP | 0 341 958 A2 | 11/1989 |

(Continued)

OTHER PUBLICATIONS

Berezin et al., "Ratiometric Analysis of Fluorescence Lifetime for Probing Binding Sites in /albumin with Near-Infrared Fluorescent Molecular Probes," Photochemistry and Photobiology, 2007, vol. 83, pp. 1371-1378.

(Continued)

*Primary Examiner* — Nyeemah A Grazier
(74) *Attorney, Agent, or Firm* — Kilpatrick Townsend & Stockton LLP

(57) ABSTRACT

Compounds are disclosed that are useful for noninvasive imaging in the near-infrared spectral range. Bioconjugate cyanine compounds of Formula II are presented:

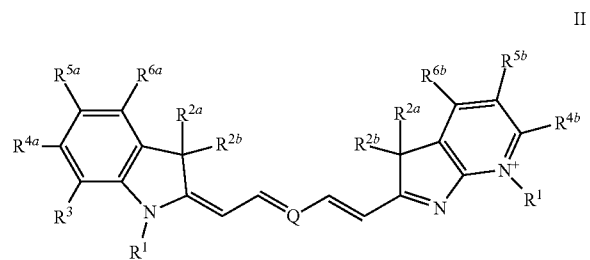

wherein Q is a portion of a polymethine bridge selected from the group consisting of:

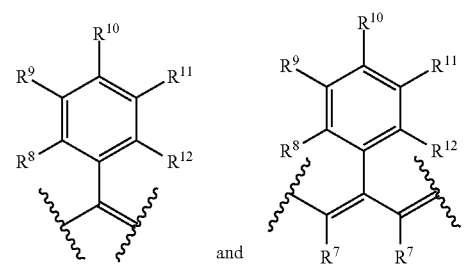

21 Claims, 31 Drawing Sheets

(56) References Cited

U.S. PATENT DOCUMENTS

| | | |
|---|---|---|
| 5,453,505 A | 9/1995 | Lee et al. |
| 5,571,388 A | 11/1996 | Patonay et al. |
| 5,639,874 A | 6/1997 | Middendorf et al. |
| 5,831,098 A | 11/1998 | Ollmann, Jr. |
| 6,048,982 A | 4/2000 | Waggoner |
| 6,083,485 A | 7/2000 | Licha et al. |
| 6,086,737 A | 7/2000 | Patonay et al. |
| 6,136,612 A | 10/2000 | Della Ciana et al. |
| 6,180,085 B1 | 1/2001 | Achilefu et al. |
| 6,217,848 B1 | 4/2001 | Achilefu et al. |
| 6,258,340 B1 | 7/2001 | Licha et al. |
| 6,287,662 B1 | 9/2001 | Takagishi et al. |
| 6,395,257 B1 | 5/2002 | Achilefu et al. |
| 6,534,041 B1 | 3/2003 | Licha et al. |
| 6,673,334 B1 | 1/2004 | Achilefu et al. |
| 6,706,254 B2 | 3/2004 | Achilefu et al. |
| 6,716,994 B1 | 4/2004 | Menchen et al. |
| 6,747,159 B2 | 6/2004 | Caputo et al. |
| 6,761,878 B2 | 7/2004 | Achilefu et al. |
| 6,794,509 B1 | 9/2004 | Nishigaki et al. |
| 6,913,743 B2 | 7/2005 | Licha et al. |
| 6,926,885 B2 | 8/2005 | Licha et al. |
| 6,949,635 B1 | 9/2005 | Kumar et al. |
| 6,974,873 B2 | 12/2005 | Leung et al. |
| 6,977,305 B2 | 12/2005 | Leung et al. |
| 7,025,949 B2 | 4/2006 | Licha et al. |
| 7,128,896 B2 | 10/2006 | Achilefu et al. |
| 7,172,907 B2 | 2/2007 | Chen et al. |
| 7,175,831 B2 | 2/2007 | Achilefu et al. |
| 7,201,892 B2 | 4/2007 | Achilefu et al. |
| 7,252,815 B2 | 8/2007 | Achilefu et al. |
| 7,445,767 B2 | 11/2008 | Licha et al. |
| 7,807,619 B2 | 10/2010 | Bertozzi et al. |
| 7,910,335 B2 | 3/2011 | Salic et al. |
| 8,481,752 B2 | 7/2013 | Xu et al. |
| 8,569,506 B2 | 10/2013 | Leung et al. |
| 8,927,719 B2 | 1/2015 | Xu et al. |
| 2001/0055567 A1 | 12/2001 | Licha et al. |
| 2002/0022004 A1 | 2/2002 | Licha et al. |
| 2003/0026763 A1 | 2/2003 | Licha et al. |
| 2003/0113755 A1 | 6/2003 | Nishigaki et al. |
| 2003/0170179 A1 | 9/2003 | Licha et al. |
| 2003/0180221 A1 | 9/2003 | Miwa et al. |
| 2003/0185756 A1 | 10/2003 | Achilefu et al. |
| 2004/0234454 A1 | 11/2004 | Achilefu et al. |
| 2004/0241095 A1 | 12/2004 | Achilefu et al. |
| 2004/0253182 A1 | 12/2004 | Achilefu et al. |
| 2005/0031542 A1 | 2/2005 | Achilefu et al. |
| 2005/0106106 A1 | 5/2005 | Licha et al. |
| 2005/0169844 A1 | 8/2005 | Licha et al. |
| 2005/0226815 A1 | 10/2005 | Kawakami et al. |
| 2005/0271592 A1 | 12/2005 | Achilefu et al. |
| 2005/0281741 A1 | 12/2005 | Achilefu et al. |
| 2006/0099638 A1 | 5/2006 | Leung et al. |
| 2006/0165598 A1 | 7/2006 | Licha et al. |
| 2006/0165599 A1 | 7/2006 | Licha et al. |
| 2006/0216760 A1 | 9/2006 | Dieterich et al. |
| 2006/0223076 A1 | 10/2006 | Diwu et al. |
| 2007/0021621 A1 | 1/2007 | Reddington |
| 2007/0090331 A1 | 4/2007 | Seo et al. |
| 2007/0128115 A1 | 6/2007 | Achilefu et al. |
| 2007/0140962 A1 | 6/2007 | Achilefu et al. |
| 2007/0178511 A1 | 8/2007 | Leung et al. |
| 2007/0232805 A1 | 10/2007 | Leung et al. |
| 2008/0267878 A1 | 10/2008 | Robillard et al. |
| 2009/0035809 A1 | 2/2009 | Leung et al. |
| 2009/0305410 A1 | 12/2009 | Mao et al. |
| 2010/0210854 A1 | 8/2010 | Popik et al. |
| 2010/0215748 A1 | 8/2010 | Ladet et al. |
| 2010/0234450 A1 | 9/2010 | Schultz et al. |
| 2010/0297250 A1 | 11/2010 | Boons et al. |
| 2011/0118142 A1 | 5/2011 | Clarke et al. |
| 2011/0118484 A1 | 5/2011 | Bernardin et al. |
| 2012/0028290 A1 | 2/2012 | Salic |
| 2012/0288871 A1 | 11/2012 | Leung et al. |

FOREIGN PATENT DOCUMENTS

| | | |
|---|---|---|
| EP | 1221465 A1 | 7/2002 |
| EP | 0796111 B1 | 4/2003 |
| EP | 1181940 B1 | 12/2004 |
| EP | 1815870 A1 | 8/2007 |
| FR | 2921838 A1 | 4/2009 |
| JP | 10 071766 A | 3/1998 |
| JP | 11-73679 A | 3/1999 |
| JP | 2002 109794 A | 4/2002 |
| JP | 2005 120026 A | 5/2005 |
| WO | 97/13490 A2 | 4/1997 |
| WO | 97/13810 A1 | 4/1997 |
| WO | 98/47538 A2 | 10/1998 |
| WO | 98/53940 A1 | 12/1998 |
| WO | 01/49790 A2 | 7/2001 |
| WO | 02/24815 A1 | 3/2002 |
| WO | 02/26891 A1 | 4/2002 |
| WO | 03/074091 A2 | 9/2003 |
| WO | 2004/065491 A1 | 8/2004 |
| WO | 2007/028118 A2 | 3/2007 |
| WO | 2007/028163 A2 | 3/2007 |
| WO | 2007/088129 A2 | 8/2007 |
| WO | 2010/039548 | 4/2010 |
| WO | 2010/121163 A2 | 10/2010 |
| WO | 2011/028507 | 3/2011 |

OTHER PUBLICATIONS

Berezin et al., Biophysical Journal, 2007, 93, 2892-2899.
Chang et al., "Copper-free click chemistry in living animals," PNAS, 2010, vol. 107, pp. 1821-1826.
Flanagan et al., "Near-Infrared Heavy-Atom-Modified fluorescent Dyes for Base-Calling in DNA-Sequencing Applications using Temporal Discrimination," Analytical Chemistry, 1998, vol. 70, No. 13, pp. 2676-2684.
Kolb et al., "Click Chemistry: Diverse Chemical Function from a Few Good Reactions," Angew. Chemie., 2001, vol. 40, pp. 2004-2021.
Lee et al., JOC, 2008, 73(2), 723-725.
Lee et al., JOC, 2006, 71(20), 7862-7865.
Moses et al., "The growing application of click chemistry," Chem. Soc. Rev., 2007, vol. 36, pp. 1249-1262.
International Search Report, Mail Date Jan. 27, 2012, PCT application No. PCT/US2011/057134, 3 pages.
Matsuoka, Infrared Absorbing Dyes, Infrared Photography, 1990, pp. 185-187, Plenum Press, New York, USA. ISBN 0-306-43478-4.
Daehne et al., Near Infrared Dyes for High Technology Applications, 1998, pp. 21-53, Kluwer Academic Publishers, Dordrecht, the Netherlands.
Bricks et al., Near-Infrared Cyanine Dyes: A New Approach to an Old Problem, 1998, pp. 417-425, Kluwer Academic Publishers, Dordrecht, the Netherlands.
Peng et al., Near-IR Fluorescent Dyes for Biological Applications, Fluorescence Labelling, 2004, Published in LPI.

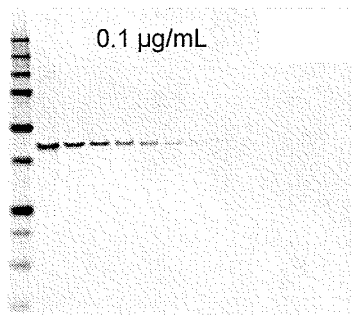
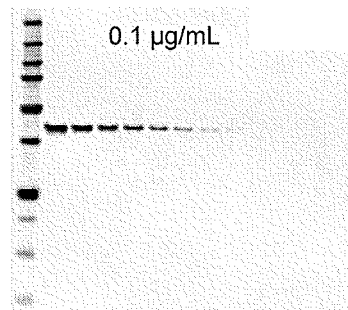
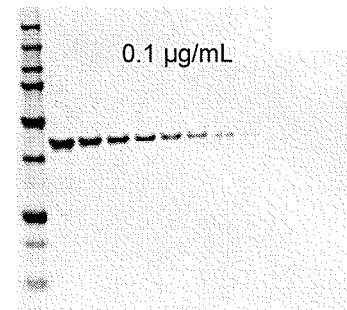
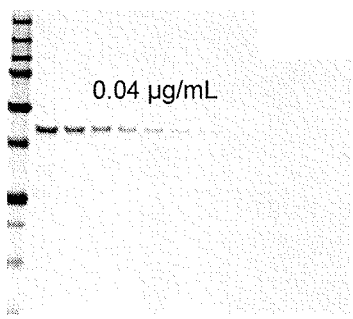
FIG. 22A     FIG. 22B     FIG. 22C

BIOCONJUGATES OF CYANINE DYES

CROSS-REFERENCES TO RELATED APPLICATIONS

This application is a continuation of U.S. Non-Provisional application Ser. No. 13/831,345 (filed Mar. 14, 2013), which is a continuation of the International PCT Application No. PCT/US2011/057134 (filed Oct. 20, 2011), which claims the benefit of U.S. Provisional Patent Application Nos. 61/405,158 and 61/405,161 (both filed Oct. 20, 2010), which are hereby incorporated by reference for all purposes.

BACKGROUND OF THE INVENTION

Cyanine dyes have been widely used for labeling ligands or biomolecules for a variety of applications such as DNA sequencing. (See, for example, U.S. Pat. No. 5,571,388 for exemplary methods of identifying strands of DNA by means of cyanine dyes.) More recently, they have been used for optical imaging of dye-labeled biomolecules, either in vivo or in vitro. (See, for example, U.S. Pat. No. 7,597,878.) Scientists favor using cyanine dyes in biological applications because, among other reasons, many of these dyes fluoresce in the near-infrared (NIR) region of the spectrum (600-1000 nm). This makes cyanine dyes less susceptible to interference from autofluorescence of biomolecules.

Other advantages of cyanine dyes include, for example: 1) cyanine dyes strongly absorb and fluoresce light; 2) many cyanine dyes do not rapidly bleach under a fluorescence microscope; 3) cyanine dye derivatives can be made that are effective coupling reagents; 4) many structures and synthetic procedures are available, and the class of dyes is versatile; and 5) cyanine dyes are relatively small (a typical molecular weight is about 1,000 daltons), so they do not cause appreciable steric interference in a way that might reduce the ability of a labeled biomolecule to reach its binding site or carry out its function.

Despite their advantages, many of the known cyanine dyes have a number of disadvantages. Some known cyanine dyes are not stable in the presence of certain reagents that are commonly found in bioassays. Such reagents include ammonium hydroxide, dithiothreitol (DTT), primary and secondary amines, and ammonium persulfate (APS). Further, some known cyanine dyes lack the thermal stability and photostability that is necessary for biological applications such as DNA sequencing and genotyping.

For these reasons, stable cyanine dyes are needed for use in labeling biomolecules as well as in vivo imaging for the diagnosis and prognosis of diseases such as cancer. Such compositions and methods would aid in the analysis of responses to various therapies. The present invention satisfies these and other needs.

BRIEF SUMMARY OF THE INVENTION

Various embodiments of the present invention provide compounds, bioconjugates, methods of labeling, and methods of measuring or detecting target molecules non-invasively, thus solving the problems of the above-described art.

As such, in one embodiment, the present invention provides a compound of Formula I:

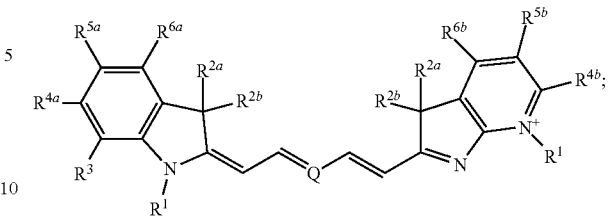

wherein Q is a portion of a polymethine bridge selected from the group of:

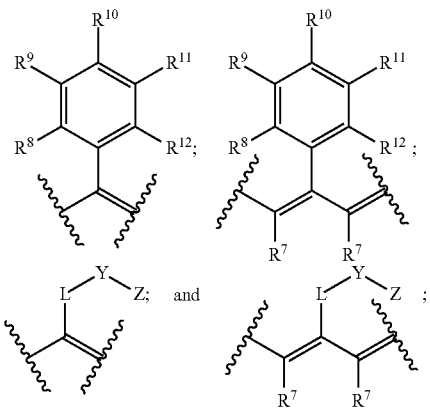

wherein Q is the central portion of either a five- or a seven-polymethine-carbon polymethine bridge;

each $R^1$ is a member independently selected from the group of -L-Y—Z and alkyl that is additionally substituted with from 0 to 1 $R^{13}$ and from 0 to 1 $R^{16}$; wherein the alkyl is optionally interrupted by at least one heteroatom;

each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 $R^{16}$; or, alternatively, a $R^{2a}$ and $R^{2b}$ pair, together with the ring carbon to which the $R^{2a}$ and $R^{2b}$ are bonded, join to form a spirocycloalkyl ring, wherein the spirocycloalkyl ring is additionally substituted with from 0 to 6 $R^{14}$ and from 0 to 1 $R^{16}$, or an exocyclic alkene, wherein the exocyclic alkene is additionally substituted with from 0 to 2 $R^{14}$ and from 0 to 1 $R^{16}$;

each $R^3$, $R^{4a}$, $R^{4b}$, $R^{5a}$, $R^{5b}$, $R^{6a}$, and $R^{6b}$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 $R^{16}$; or, alternatively, a pair of said members that is selected from the group consisting of $R^3$ and $R^{4a}$, an $R^{4a}$ and $R^{5a}$, and an $R^{5a}$ and $R^{6a}$, together with the pair of atoms to which the pair of said members is bonded, joins to form an aryl ring, wherein the aryl ring is additionally substituted with from 0 to 2 $R^{14}$ and from 0 to 1 $R^{16}$;

each $R^7$ is a member independently selected from the group consisting of hydrogen and alkyl; wherein the alkyl is additionally substituted with from 0 to 3 $R^{14}$ and from 0 to 1 $R^{16}$; or, alternatively, both $R^7$, together with the intervening segment of the polyene to which both $R^7$ are bonded, join to form a ring, wherein said ring is selected from the group consisting of a cycloalkyl and a heterocyclyl ring; wherein the ring is additionally substituted with from 0 to 3 $R^{14}$ and from 0 to 1 $R^{16}$;

$R^8$, $R^9$, $R^{10}$, $R^{11}$ and $R^{12}$ are each a member independently selected from the group consisting of hydrogen, alkyl, alkenyl, halo, alkoxy, sulfonato, hydroxyl, amino, carboxyl, alkoxycarbonyl, cyano, amido, thioacetyl, and -L-Y—Z; wherein, if present, at least one member selected from the group consisting of $R^8$, $R^9$, and $R^{10}$ is -L-Y—Z;

each $R^{13}$ is a member independently selected from the group consisting of hydroxyl, amino, carboxyl, alkoxycarbonyl, cyano, amido, sulfonato, and thioacetyl;

each $R^{14}$ is a member independently selected from the group consisting of alkyl, alkenyl, halo, hydroxyl, alkoxy, amino, cyano, carboxyl, alkoxycarbonyl, amido, sulfonato, alkoxycarbonylalkyl, and alkoxyalkyl; wherein the alkyl or alkenyl is additionally substituted with from 0 to 1 $R^{13}$ and from 0 to 1 $R^{16}$;

each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom;

each Y is an optional member independently selected from the group consisting of a bond, —O—, —S—, —NH—, —NHC(O)—, —C(O)NH—, —NR$^{15}$—, —NR$^{15}$C(O)—, —C(O)NR$^{15}$—, —N(Z)—, —N(Z)C(O)—, and —C(O)N(Z)—;

each Z is independently selected from the group consisting of -L-$R^{13}$ and -L-$R^{16}$, or in an alternative embodiment, —Y—Z is a member selected from the group of —N(Z)$_2$, —N(Z)C(O)Z, and —C(O)N(Z)$_2$, wherein the two Z groups may optionally be linked to form a cycloalkynyl group;

each $R^{15}$ is a member independently selected from the group consisting of alkyl and alkoxycarbonylalkyl; wherein the alkyl is optionally interrupted by at least one heteroatom;

each $R^{16}$ is independently a member selected from the group consisting of activated acyl, acrylamido, optionally substituted alkylsulfonate ester, azido, optionally substituted arylsulfonate ester, optionally substituted amino, aziridino, boronato, cycloalkynyl, cycloalkynylcarbonyl, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, cycloalkynyl, spirocycloalkynyl, a pegylated azido, a pegylated alkynyl, a pegylated cycloalkynyl, a pegylated spirocycloalkynyl, an ortho substituted phosphinyl aryl ester (e.g., TPPME), and an ortho substituted phosphine oxide aryl ester; and wherein said compound has a balanced charge.

In another embodiment, the present invention provides a bioconjugate of the Formula II:

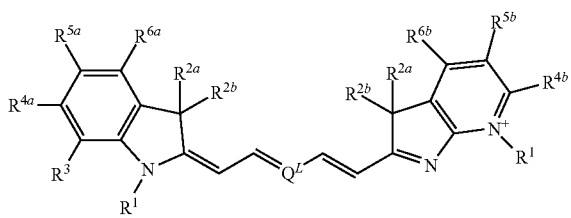

wherein $Q^L$ is a portion of a polymethine bridge selected from the group consisting of:

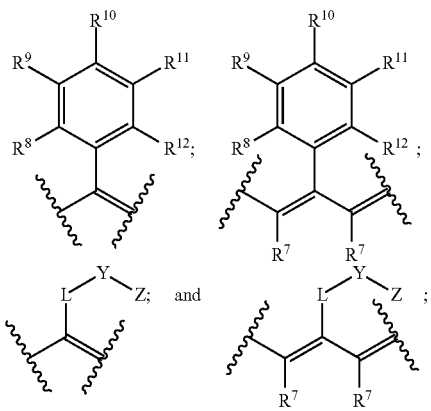

wherein $Q^L$ is the central portion of either a five- or a seven-polymethine-carbon polymethine bridge;

wherein $R^1$, $R^{2a}$, $R^{2b}$, $R^3$, $R^{4a}$, $R^{4b}$, $R^{5a}$, $R^{5b}$, $R^{6a}$, $R^{6b}$, $R^7$, $R^8$, $R^9$, $R^{10}$, $R^{11}$, $R^{12}$, $R^{13}$, $R^{14}$, $R^{15}$, $R^{16}$, L, and Y are as previously defined for the compound of Formula I;

each Z is independently selected from the group consisting of -L-$R^{13}$ and -L-$R^L$;

each $R^L$ comprises a linking group and a biomolecule connected thereto, wherein the compound comprises at least one $R^L$, and wherein the compound has a balanced charge.

In yet another embodiment, the present invention provides a method or process for labeling a ligand or biomolecule with a compound of Formula I, the method comprising contacting a ligand or biomolecule with a compound having Formula I to generate the corresponding bioconjugate compound of Formula II.

In still yet another embodiment, the compounds of Formula I or II can be used as in vitro or in vivo optical imaging agents of tissues and organs in various biomedical applications. In one aspect, the present invention provides a method for imaging, the method comprising administering a compound of Formula I or Formula II.

Further aspects, objects, and advantages of the invention will become apparent upon consideration of the detailed description and figures that follow.

BRIEF DESCRIPTION OF THE DRAWINGS

FIG. 7A shows a mouse in the top panels received 4 nmol intravenously (IV); FIG. 7B shows the mouse in the bottom panels received 4 nmol intraperitoneally (IP).

FIG. 10B and FIG. 10C compare fluorescence intensities, respectively.

FIG. 22A-C illustrate a Western blot total fluorescence comparison of β-actin GAM antibody conjugates with compound 20 (Panel A); IRDye® 680 (Panel B); and AlexaFluor® 680 (Panel C).

DETAILED DESCRIPTION OF THE INVENTION

Definitions

Figure 1:
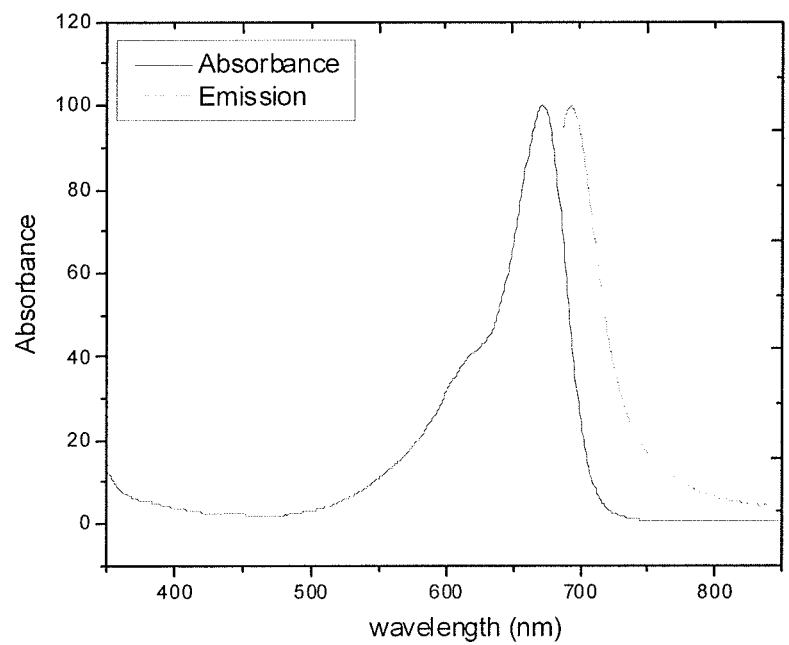
FIG. 1 illustrates the UV absorption and emission curves for compound 10.

The terms "a," "an," or "the" as used herein not only include aspects with one member, but also include aspects with more than one member. For example, an embodiment of a method of imaging that comprises using a compound set forth in claim 1 would include an aspect in which the method comprises using two or more compounds set forth in claim 1.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When the quantity "X" only allows whole-integer values (e.g., "X carbons") and X is at most 15, "about X" indicates from (X−1) to (X+1). In this case, "about X" as used herein specifically indicates at least the values X, X−1, and X+1. If X is at least 16, the values of 0.90X and 1.10X are rounded to the nearest whole-integer values to define the boundaries of the range.

When the modifier "about" is applied to describe the beginning of a numerical range, it applies to both ends of the range. Thus, "from about 700 to 850 nm" is equivalent to "from about 700 nm to about 850 nm." When "about" is applied to describe the first value of a set of values, it applies to all values in that set. Thus, "about 680, 700, or 750 nm" is equivalent to "about 680 nm, about 700 nm, or about 750 nm." However, when the modifier "about" is applied to describe only the end of the range or only a later value in the set of values, it applies only to that value or that end of the range. Thus, the range "about 2 to about 10" is the same as "about 2 to about 10," but the range "2 to about 10" is not.

"Activated acyl" as used herein includes a —C(O)-LG group. "Leaving group" or "LG" is a group that is susceptible to displacement by a nucleophilic acyl substitution (i.e., a nucleophilic addition to the carbonyl of —C(O)-LG, followed by elimination of the leaving group). Representative leaving groups include halo, cyano, azido, carboxylic acid derivatives such as t-butylcarboxy, and carbonate derivatives such as i-BuOC(O)O—. An activated acyl group may also be an activated ester as defined herein or a carboxylic acid activated by a carbodiimide to form an anhydride or mixed anhydride —OC(O)R$^a$ or —OC(NR$^a$)NHR$^b$, wherein R$^a$ and R$^b$ are members independently selected from the group consisting of $C_1$-$C_6$ alkyl, $C_1$-$C_6$ perfluoroalkyl, $C_1$-$C_6$ alkoxy, cyclohexyl, 3-dimethylaminopropyl, or N-morpholinoethyl. Preferred activated acyl groups include activated esters.

"Activated ester" as used herein includes a derivative of a carboxyl group that is more susceptible to displacement by nucleophilic addition and elimination than an ethyl ester group (e.g., an NHS ester, a sulfo-NHS ester, a PAM ester, or a halophenyl ester). Representative carbonyl substituents of activated esters include succinimidyloxy (—$OC_4H_4NO_2$), sulfosuccinimidyloxy (—$OC_4H_3NO_2SO_3H$), -1-oxybenzotriazolyl (—$OC_6H_4N_3$); 4-sulfo-2,3,5,6-tetrafluorophenyl; or an aryloxy group that is optionally substituted one or more times by electron-withdrawing substituents such as nitro, fluoro, chloro, cyano, trifluoromethyl, or combinations thereof (e.g., pentafluorophenyloxy). Preferred activated esters include succinimidyloxy and sulfosuccinimidyloxy esters.

"Acyl" as used herein includes an alkanoyl, aroyl, heterocycloyl, or heteroaroyl group as defined herein. Representative acyl groups include acetyl, benzoyl, nicotinoyl, and the like.

"Alkanoyl" as used herein includes an alkyl-C(O)— group wherein the alkyl group is as defined herein. Representative alkanoyl groups include acetyl, ethanoyl, and the like.

"Alkenyl" as used herein includes a straight or branched aliphatic hydrocarbon group of 2 to about 15 carbon atoms that contains at least one carbon-carbon double bond. Preferred alkenyl groups have 2 to about 12 carbon atoms. More preferred alkenyl groups contain 2 to about 6 carbon atoms. "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, heptenyl, octenyl, decenyl, and the like.

"Alkenylene" as used herein includes a straight or branched bivalent hydrocarbon chain containing at least one carbon-carbon double or triple bond. Preferred alkenylene groups include from 2 to about 12 carbons in the chain, and more preferred alkenylene groups include from 2 to 6 carbons in the chain. In one aspect, hydrocarbon groups that contain a carbon-carbon double bond are preferred. In a second aspect, hydrocarbon groups that contain a carbon-carbon triple bond are preferred. Representative alkenylene groups include —CH=CH—, —$CH_2$—CH=CH—, —C($CH_3$)=CH—, —$CH_2$CH=CH$CH_2$—, ethynylene, propynylene, n-butynylene, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" as used herein includes an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxycarbonyl" as used herein includes an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" as used herein includes an alkyl-O—CO-alkylene- group wherein alkyl and alkylene are as defined herein. Representative alkoxycarbonylalkyl include methoxycarbonylmethyl, ethoxycarbonylmethyl, methoxycarbonylethyl, and the like.

"Alkyl" as used herein includes an aliphatic hydrocarbon group, which may be straight or branched-chain, having about 1 to about 20 carbon atoms in the chain. Preferred alkyl groups have 1 to about 12 carbon atoms in the chain. More preferred alkyl groups have 1 to 10 or 1 to 6 carbon atoms in the chain. "Branched-chain" as used herein includes that one or more lower alkyl groups such as methyl, ethyl or propyl are attached to a linear alkyl chain. "Lower alkyl" as used herein includes 1 to about 6 carbon atoms, preferably 5 or 6 carbon atoms in the chain, which may be straight or branched. Representative alkyl groups include methyl, ethyl, n-propyl, isopropyl, n-butyl, t-butyl, n-pentyl, and 3-pentyl.

"Alkylene" as used herein includes a straight or branched bivalent hydrocarbon chain of 1 to about 6 carbon atoms. Preferred alkylene groups are the lower alkylene groups having 1 to about 4 carbon atoms. Representative alkylene groups include methylene, ethylene, and the like.

"Alkylsulfonate ester" as used herein includes an alkyl-$SO_3$— group wherein the alkyl group is as defined herein. Preferred alkylsulfonate ester groups are those wherein the alkyl group is lower alkyl. Representative alkylsulfonate ester groups include mesylate ester (i.e., methylsulfonate ester).

An "optionally substituted" alkylsulfonate ester includes an alkylsulfonate ester as defined herein, wherein the aryl group is additionally substituted with from 0 to 3 halo, alkyl, aryl, haloalkyl, or haloaryl groups as defined herein. Preferred optionally substituted alkylsulfonate groups include triflate ester (i.e., trifluoromethylsulfonate ester).

"Alkylthio" as used herein includes an alkyl-S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkylthioalkyl" as used herein includes an alkylthio-alkylene- group wherein alkylthio and alkylene are defined herein. Representative alkylthioalkyl groups include methylthiomethyl, ethylthiopropyl, isopropylthioethyl, and the like.

"Alkynyl" as used herein includes a straight or branched aliphatic hydrocarbon group of 2 to about 15 carbon atoms that contains at least one carbon-carbon triple bond. Preferred alkynyl groups have 2 to about 12 carbon atoms. More preferred alkynyl groups contain 2 to about 6 carbon atoms. "Lower alkynyl" as used herein includes alkynyl of 2 to about 6 carbon atoms. Representative alkynyl groups include propynyl, 2-butynyl, 3-methylbutynyl, n-pentynyl, heptynyl, and the like.

"Amido" as used herein includes a group of formula $Y_1Y_2$N—C(O)— wherein $Y_1$ and $Y_2$ are independently hydrogen, alkyl, or alkenyl; or $Y_1$ and $Y_2$, together with the nitrogen through which $Y_1$ and $Y_2$ are linked, join to form a 4- to 7-membered azaheterocyclyl group (e.g., piperidinyl). Representative amido groups include primary amido ($H_2$N—C(O)—), methylamido, dimethylamido, diethylamido, and the like. Preferably, "amido" is an —C(O)NRR' group where R and R' are members independently selected from the group consisting of H and alkyl. More preferably, at least one of R and R' is H.

"Amidoalkyl" as used herein includes an amido-alkylene-group wherein amido and alkylene are defined herein. Representative amidoalkyl groups include amidomethyl, amidoethyl, dimethylamidomethyl, and the like.

"Amino" as used herein includes a group of formula $Y_1Y_2N$— wherein $Y_1$ and $Y_2$ are independently hydrogen, acyl, aryl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N$—), methylamino, dimethylamino, diethylamino, tritylamino, and the like. Preferably, "amino" is an —NRR' group where R and R' are members independently selected from the group consisting of H and alkyl. Preferably, at least one of R and R' is H.

"Aminoalkyl" as used herein includes an amino-alkylene-group wherein amino and alkylene are defined herein. Representative aminoalkyl groups include aminomethyl, aminoethyl, dimethylaminomethyl, and the like.

"Aroyl" as used herein includes an aryl-CO— group wherein aryl is defined herein. Representative aroyl include benzoyl, naphth-1-oyl and naphth-2-oyl.

"Aryl" as used herein includes an aromatic monocyclic or multicyclic ring system of 6 to about 14 carbon atoms, preferably of 6 to about 10 carbon atoms. Representative aryl groups include phenyl and naphthyl.

"Arylsulfonate ester" as used herein includes an aryl-$SO_3$— group wherein the aryl group is as defined herein. Representative arylsulfonate ester groups include phenylsulfonate ester.

An "optionally substituted" arylsulfonate ester includes an arylsulfonate ester as defined herein, wherein the aryl group is additionally substituted with from 0 to 3 halo, alkyl, aryl, haloalkyl, or haloaryl groups as defined herein. Preferred optionally substituted arylsulfonate esters include tosylate ester (i.e., p-tolylsulfonate ester).

"Aromatic ring" as used herein includes 5-12 membered aromatic monocyclic or fused polycyclic moieties that may include from zero to four heteroatoms selected from the group consisting of oxygen, sulfur, selenium, and nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, and the like. The aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Balanced charge" as used herein includes the condition that the net charge for a compound and its associated counterions be zero under standard physiological conditions. In order to achieve a balanced charge, a skilled person will understand that after the first additional sulfonato group that balances the +1 charge of the indolinium ring of the compounds herein, a cationic counterion (e.g., the cation of a Group I metal such as sodium) must be added to balance the negative charge from additional sulfonato groups. Similarly, anionic counterions must be added to balance any additional cationic groups (e.g., most amino groups under physiological conditions).

"Biomolecule" as used herein includes a natural or synthetic molecule for use in biological systems. Preferred biomolecules include a protein, a peptide, an enzyme substrate, a hormone, an antibody, an antigen, a hapten, an avidin, a streptavidin, a carbohydrate, a carbohydrate derivative, an oligosaccharide, a polysaccharide, a nucleic acid, a deoxynucleic acid, a fragment of DNA, a fragment of RNA, nucleotide triphosphates, acyclo terminator triphosphates, PNA, and the like. More preferred biomolecules include a protein, a peptide, an antibody, an avidin, a streptavidin, and the like. Even more preferred biomolecules include a peptide, an antibody, an avidin, and a streptavidin.

"Carboxy" and "carboxyl" as used herein include a HOC(O)— group (i.e., a carboxylic acid) or a salt thereof.

"Carboxyalkyl" as used herein includes a HOC(O)-alkylene- group wherein alkylene is defined herein. Representative carboxyalkyls include carboxymethyl (i.e., HOC(O)$CH_2$—) and carboxyethyl (i.e., HOC(O)$CH_2CH_2$—).

"Cycloalkenyl" as used herein includes a cyclic hydrocarbon group of 4 to about 15 carbon atoms that contains at least one carbon-carbon double bond. The cycloalkenyl ring may include from 0 to 6 $R^{14}$ substituents and 0 to 2 $R^L$ substituents, and when present, the ring-fused aryl or heteroaryl rings may also include from 0 to 4 $R^{14}$ substituents and 0 to 2 $R^L$ substituents. Preferred alkenyl groups have 5 to about 12 carbon atoms. More preferred alkenyl groups contain 7 to about 14 carbon atoms. Representative cycloalkenyl groups include cyclopentenyl, cyclohexenyl, and the like.

"Cycloalkynyl" as used herein includes a cyclic hydrocarbon group of 5 to about 15 carbon atoms that contains at least one carbon-carbon triple bond. In a preferred aspect, the cyclic hydrocarbon may optionally be interrupted by a heteroatom (e.g., N, O, S; preferably N) and may include at least one ring-fused aryl or heteroaryl ring (e.g., DBCO or DBCO-1). The cycloalkynyl ring may include from 0 to 6 $R^{14}$ substituents and 0 to 2 $R^L$ substituents, and when present, the ring-fused aryl or heteroaryl rings may also include from 0 to 4 $R^{14}$ substituents and 0 to 2 $R^L$ substituents. In some aspect, the $R^L$ substituent includes a ring-fused heteroaryl group as part of the linking group with the biomolecule (e.g., the reaction of DBCO with an azide-substituted biomolecule). Preferred alkynyl groups have 5 to about 12 carbon atoms. More preferred alkynyl groups contain 7 to about 14 carbon atoms. Representative cycloalkynyl groups include cyclopentynyl, cyclohexynyl, cyclooctynyl, dibenzocyclooctynyl (or DBCO, which includes a nitrogen in the "octyne" ring or DBCO-1), BARAC, DIFO, DIBO, TMDIBO, DIFO3 and the like.

"Cycloalkynylcarbonyl" includes the definition of cycloalkynyl above with an exocylic carbonyl, for example, a dibenzocyclooctynylcarbonyl or C(O)DBCO, which includes a nitrogen in the "octyne" ring and an exocyclic carbonyl group, and the like.

"Cycloalkyl" as used herein includes a non-aromatic mono- or multicyclic ring system of about 3 to about 10 carbon atoms, preferably of about 5 to about 10 carbon atoms. More preferred cycloalkyl rings contain 5 or 6 ring atoms. A cycloalkyl group optionally comprises at least one $sp^2$-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

"Cycloalkylene" as used herein includes a bivalent cycloalkyl having about 4 to about 8 carbon atoms. Preferred cycloalkylenyl groups include 1,2-, 1,3-, or 1,4-cis- or trans-cyclohexylene.

"Cyanine dye" as used herein includes a compound having two substituted or unsubstituted nitrogen-containing heterocyclic rings joined by an unsaturated bridge. Examples include the structures of Formula I.

"Exocyclic alkene" or "exocyclic olefin" as used interchangeably herein include an alkene having one alkene carbon that is part of a ring and the other alkene carbon not part of the same ring. The second alkene carbon can be unsubstituted or substituted. If the second alkene carbon is disubstituted, the substituents can be the same (e.g., 1,1-dimethyl substitution) or different (e.g., 1-methyl-1-(2-ethoxyethyl) substitution). Examples of compounds with exocyclic alkenes include methylenecyclohexane; (E)-1-ethylidene-2,3-dihydro-1H-indene; pentan-3-ylidenecycloheptane; 2-cyclobutyl-idenepropan-1-ol; and (3-methoxycyclopent-2-enylidene) cyclohexane.

"Geminal" substituents as used herein includes two or more substituents that are directly attached to the same atom. An example is 3,3-dimethyl substitution on a cyclohexyl or spirocyclohexyl ring.

"Halo" or "halogen" as used herein include fluoro, chloro, bromo, or iodo.

"Haloalkyl" as used herein includes an alkyl group wherein the alkyl group includes one or more halo-substituents.

"Haloaryl" as used herein includes an alkyl group wherein the aryl group includes one or more halo-substituents.

"Heptamethine" as used herein includes a polymethine containing seven polymethine carbons. In a preferred embodiment, the heptamethine is substituted at the 4-position.

"Heteroatom" as used herein includes an atom other than carbon or hydrogen. Representative heteroatoms include O, S, and N. The nitrogen or sulfur atom of the heteroatom is optionally oxidized to the corresponding N-oxide, S-oxide (sulfoxide), or S,S-dioxide (sulfone). In a preferred aspect, a heteroatom has at least two bonds to alkylene carbon atoms (e.g., —$C_1$-$C_9$ alkylene-O—$C_1$-$C_9$ alkylene-). In some embodiments, a heteroatom is further substituted with an acyl, alkyl, aryl, cycloalkyl, heterocyclyl, or heteroaryl group (e.g., —N(Me)-; —N(Ac)—).

"Heteroaroyl" as used herein includes a heteroaryl-C(O)— group wherein heteroaryl is as defined herein. Representative heteroaroyl groups include thiophenoyl, nicotinoyl, pyrrol-2-ylcarbonyl, pyridinoyl, and the like.

"Heterocycloyl" as used herein includes a heterocyclyl-C(O)— group wherein heterocyclyl is as defined herein. Representative heterocycloyl groups include N-methyl prolinoyl, tetrahydrofuranoyl, and the like.

"Heterocyclyl" as used herein includes a non-aromatic saturated monocyclic or multicyclic ring system of about 3 to about 10 ring atoms, preferably about 5 to about 10 ring atoms, in which one or more of the atoms in the ring system is an element or elements other than carbon, e.g., nitrogen, oxygen or sulfur. Preferred heterocyclyl groups contain about 5 to about 6 ring atoms. A heterocyclyl group optionally comprises at least one $sp^2$-hybridized atom (e.g., a ring incorporating an carbonyl, endocyclic olefin, or exocyclic olefin). The prefix "aza," "oxa," or "thia" before heterocyclyl means that at least a nitrogen, oxygen or sulfur atom respectively is present as a ring atom. The nitrogen or sulfur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylene" as used herein includes a bivalent heterocyclyl group. Representative cycloalkylenyl groups include 1,2-, 1,3-, or 1,4-piperidinylene as well as 2,3- or 2,4-cis- or trans-piperidinylene.

"Heteroaryl" as used herein includes an aromatic monocyclic or multicyclic ring system of about 5 to about 14 ring atoms, preferably about 5 to about 10 ring atoms, in which at least one of the atoms in the ring system is an element other than carbon, i.e., nitrogen, oxygen or sulfur. Preferred heteroaryls contain about 5 to about 6 ring atoms. The prefix "aza," "oxa," or "thia" before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Hydroxyalkyl" as used herein includes an alkyl group as defined herein substituted with one or more hydroxy groups. Preferred hydroxyalkyls contain lower alkyl. Representative hydroxyalkyl groups include hydroxymethyl and 2-hydroxyethyl.

When any two substituent groups or any two instances of the same substituent group are "independently selected" from a list of alternatives, they may be the same or different. For example, if $R^a$ and $R^b$ are independently selected from the group consisting of methyl, hydroxymethyl, ethyl, hydroxyethyl, and propyl, then a molecule with two $R^a$ groups and two $R^b$ groups could have all groups be methyl. Alternatively, the first $R^a$ could be methyl, the second $R^a$ could be ethyl, the first $R^b$ could be propyl, and the second $R^b$ could be hydroxymethyl (or any other substituents taken from the group). Alternatively, both $R^a$ and the first $R^b$ could be ethyl, while the second $R^b$ could be hydroxymethyl (i.e., some pairs of substituent groups may be the same, while other pairs may be different).

"Linking group" as used herein includes the atoms joining a compound of Formula I with a biomolecule. Table 1 includes a list of preferred bonds for linking groups (i.e., Column C); the linking group comprises the resulting bond and optionally can include additional atoms. See also R. Haugland, Molecular Probes Handbook of Fluorescent Probes and Research Chemicals, Molecular Probes, Inc. (1992). In one embodiment, $R^{16}$ represents a linking group precursor before the attachment reaction with a biomolecule, and $R^L$ represents the resultant attachment between the compound of Formula I and the biomolecule (i.e., $R^L$ comprises the linking group and the biomolecule linked thereby). Preferred reactive functionalities include phosphoramidite groups, an activated ester (e.g., an NHS ester), thiocyanate, isothiocyanate, maleimide and iodoacetamide.

"Methine carbon" or "polymethine carbon" as used herein include a carbon that is directly connecting the two heterocyclic rings by means of the polymethine bridge. In a preferred embodiment, at least one polymethine carbon of a polymethine bridge is additionally substituted with another group such as alkyl, cycloalkyl, or aryl (e.g., —CH=CH—C(Ar) =CH—CH= or =CH—CH=C(Ar)—(CH=CH)$_2$—).

"Oxo" as used herein includes a group of formula >C=O (i.e., a carbonyl group —C(O)—).

"Pentamethine" as used herein includes a polymethine containing five polymethine carbons. In a preferred embodiment, the pentamethine is substituted at the 3-position.

A "photoactivatable moiety" is a chemical group or molecule that, upon exposure to light, absorbs a photon to enter an excited state. The excited-state group or molecule undergoes a chemical reaction or series of reactions. Alternatively, the excitation changes the light-emitting properties of the group or molecules (e.g., photoactivatable fluorescent dyes). Examples of photoactivatable moieties include aryl azides, benzophenones (e.g., 4-benzoyloxybenzoic acid as well as its esters and amides), nitroaryl groups (e.g., 5-carboxymethoxy-2-nitrobenzyl (CMNB); α-carboxy-2-nitrobenzyl (CNB); 4,5-dimethoxy-2-nitrobenzyl (DMNB); 1-(4,5-dimethoxy-2-nitrophenyl)ethyl (DMNPE); nitrophenyl (NP); and 1-(2-nitrophenyl)ethyl (NPE) groups), coumarins, diazo groups, photoactivatable fluorescent dyes (e.g., 5-carboxyfluorescein-bis-(5-carboxymethoxy-2-nitrobenzyl)ether, β-alanine-carboxamide, succinimidyl ester), and tetrazoles.

"Polyene" as used herein includes a straight or branched bivalent hydrocarbon chain containing at least two "alkenylene" groups as defined herein that are in conjugation. The polyene is optionally substituted with one or more "alkylene group substituents" as defined herein. A portion of the polyene may be incorporated into a ring (i.e., =C(R)—, wherein R and the terminal bond are linked in a larger ring; or —C(R$^1$)=C(R$^2$)—, wherein R$^1$ and R$^2$ are linked in a larger ring). Representative polyenes include —CH=CH—CH=CH—, —CH=CH—C(Ar)=CH—CH=C(R)—, —C(R)=CH—CH=C(Ar)—(CH=CH)$_2$—, and the like.

"Polymethine" or "polymethine bridge" as used herein includes the series of conjugated, sp$^2$-hybridized carbons that form the unsaturated bridge directly connecting the two nitrogen-containing heterocyclic rings of a compound of Formula I. In a preferred embodiment, the polymethine has five or seven carbons directly connecting the heterocyclic rings (i.e., pentamethine or heptamethine).

"Phosphoramidityl" as used herein includes a trivalent phosphorous atom bonded to two alkoxy groups and an amino group.

"Spirocycloalkyl" as used herein includes a cycloalkyl in which geminal substituents on a carbon atom are replaced to form a 1,1-substituted ring; a spirocycloalkynyl is a cycloalkynyl in which geminal substituents on a carbon atom are replaced to form a 1,1-substituted ring. A preferred example is BCN.

"Sulfonato" as used herein includes an —SO$_3$$^-$ group, preferably balanced by a cation such as H$^+$, Na$^+$, K$^+$, and the like.

"Sulfonatoalkyl" as used herein includes an sulfonatoalkylene- group wherein sulfonato and alkylene are as defined herein. A more preferred embodiment includes alkylene groups having from 2 to 6 carbon atoms, and a most preferred embodiment includes alkylene groups having 2, 3, or 4 carbons. Representative sulfonatoalkyls include sulfonatomethyl, 3-sulfonatopropyl, 4-sulfonatobutyl, 5-sulfonatopentyl, 6-sulfonatohexyl, and the like.

In general, the unit prefix "u" as used herein is equivalent to "µ" or "micro." For example, "ul" is equivalent to "µl" or "microliters."

Cyanine Dye Compounds

In one embodiment, the present invention provides a compound of Formula I:

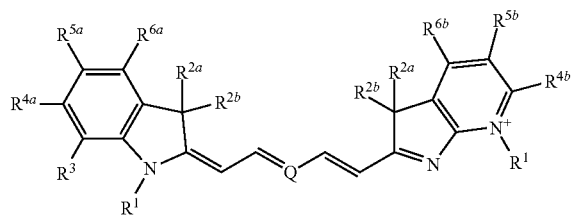

wherein Q is a member selected from the group of one-methine-carbon segment and three-methine-carbon segments:

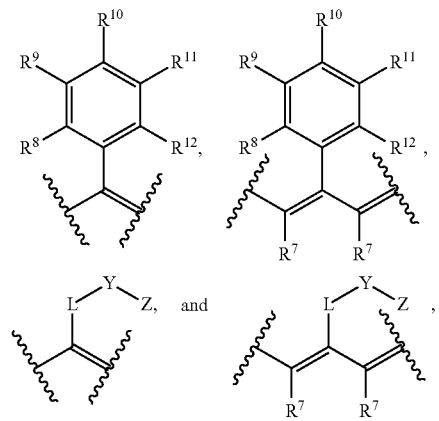

respectively; wherein the segment is the central portion of either a five- or a seven-methine-carbon polymethine bridge.

In a preferred aspect, Q is a portion of a polymethine bridge that is a pentamethine:

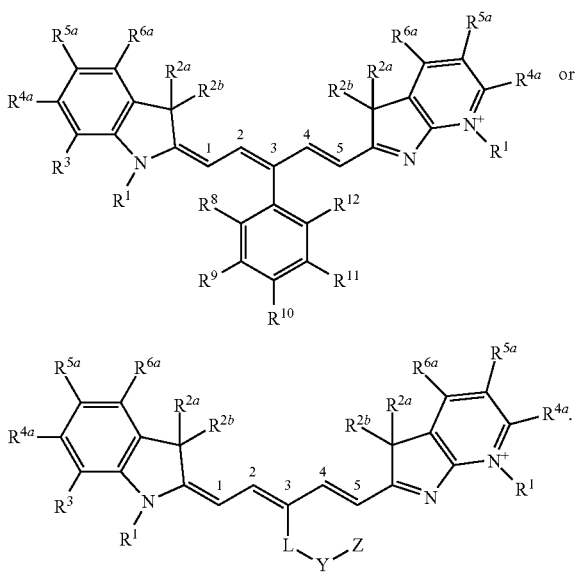

More preferably, Q is

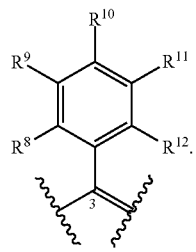

In a second preferred aspect, Q is a portion of a polymethine bridge that is a heptamethine:

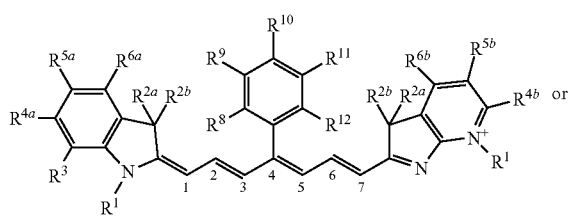

More preferably, Q is

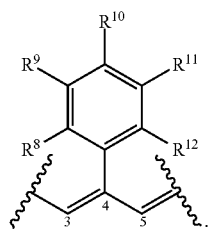

In an alternative preferred aspect, Q is a portion of a polymethine bridge that is a substituted heptamethine:

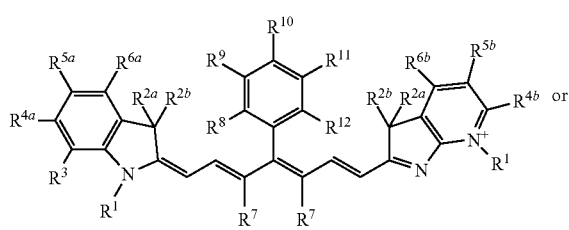

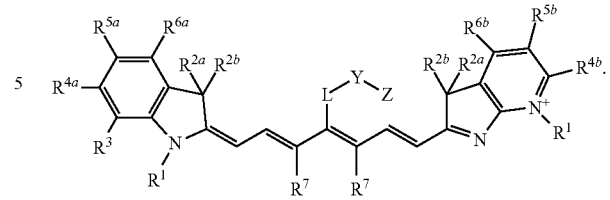

More preferably, Q is

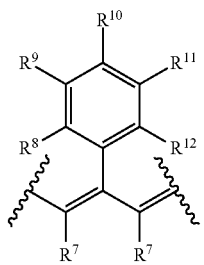

In an alternative, more preferred aspect, the substituted heptamethine includes a cycloalkyl ring:

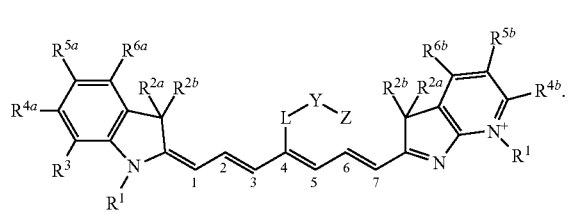

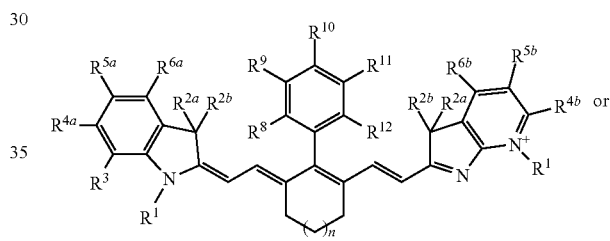

Still more preferably, Q is

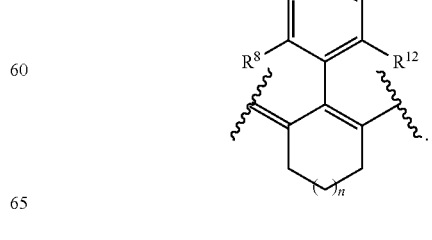

In a third preferred aspect, Q is selected from the group consisting of:

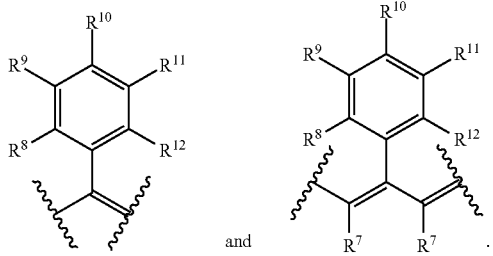

and

More preferably, Q is

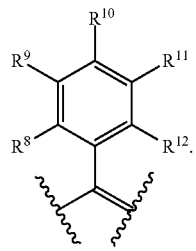

In a fourth preferred aspect, Q is selected from the group consisting of:

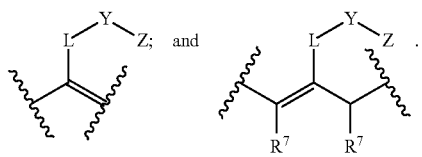

Each $R^1$ is a member selected from the group consisting of L-Y—Z and an alkyl group that is additionally substituted with from 0 to 1 $R^{13}$ and from 0 to 1 $R^{16}$; wherein the alkyl is optionally interrupted by at least one heteroatom.

In a preferred aspect, $R^1$ is $C_1$-$C_{20}$ alkyl. In a more preferred aspect, $R^1$ is $C_1$-$C_{12}$ or $C_2$-$C_8$ alkyl. In a still more preferred aspect, $R^1$ is $C_2$-$C_6$ alkyl. In a yet still more preferred aspect, $R^1$ is ethyl, propyl, butyl, or pentyl, and $R^1$ is additionally substituted with 1 $R^{13}$.

In a preferred aspect, $R^1$ is not interrupted by a heteroatom. Alternatively, $R^1$ is interrupted by at least one ether, thioether, substituted amino, or amido group.

In another preferred aspect, $R^1$ is $(CH_2)_rSO_3H$ or $(CH_2)_rSO_3^-$; and r is an integer from 1 to 20. In a more preferred aspect, r is 2, 3, or 4.

In still another preferred aspect, $R^1$ is an alkyl group that is additionally substituted with 1 $R^{13}$ that is selected from the group of hydroxyl, amino, carboxy, and sulfonato. In a more preferred aspect, the $R^{13}$ substituent of $R^1$ is carboxy or sulfonato. In a still more preferred aspect, the $R^{13}$ substituent of $R^1$ is sulfonato. In a yet still more preferred aspect, $R^1$ is sulfonatoethyl, sulfonatopropyl, sulfonatobutyl, or sulfonatopentyl.

In yet another preferred aspect, $R^1$ is an unbranched alkyl group that is additionally substituted with 1 $R^{13}$. In a more preferred aspect, $R^1$ is an unbranched alkyl group that is substituted with $R^{13}$ at the end of the alkyl group opposite to its attachment point to the cyanine dye heterocyclic nitrogen. In a still more preferred aspect, $R^1$ is 2-sulfonatoethyl, 3-sulfonatopropyl, 4-sulfonatobutyl, or 5-sulfonatopentyl. In a yet still more preferred aspect, $R^1$ is 3-sulfonatopropyl or 4-sulfonatobutyl; more preferably, $R^1$ is 3-sulfonatopropyl.

In still another preferred aspect, $R^1$ is L-Y—Z. For example, L is a $C_1$-$C_{20}$ alkylene group such as $C_2$-$C_8$ alkylene; Y is a C(O)NH group; and Z is L-$R^{16}$, wherein L is a $C_1$-$C_{20}$ alkylene group such as $C_2$-$C_8$ alkylene and $R^{16}$ is a cycloalkynylcarbonyl like C(O)DBCO (see for example, compound 66). In another aspect, $R^1$ is L-Y—Z, wherein L is a $C_1$-$C_{20}$ alkylene group such as $C_2$-$C_8$ alkylene; Y is a C(O)NH group; and Z is L-$R^{16}$, wherein L is a $C_1$-$C_{20}$ alkylene group such as $C_2$-$C_8$ alkylene optionally interrupted by a heteroatom (e.g., $((CH_2CH_2O)_3$—$CH_2CH_2$—) and $R^{16}$ is an azido group (see for example, compound 67).

Each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 $R^{16}$; or, alternatively, a $R^{2a}$ and $R^{2b}$ pair, together with the ring carbon to which the $R^{2a}$ and $R^{2b}$ are bonded, join to form a spirocycloalkyl ring, wherein the spirocycloalkyl ring is additionally substituted with from 0 to 6 $R^{14}$ and from 0 to 1 $R^{16}$, or an exocyclic alkene, wherein the exocyclic alkene is additionally substituted with from 0 to 2 $R^{14}$ and from 0 to 1 $R^{16}$.

In a preferred aspect, all $R^{2a}$ are the same substituent. Alternatively, all $R^{2b}$ are the same substituent. More preferably, all $R^{2a}$ are the same substituent, and all $R^{2b}$ are the same substituent.

In another preferred aspect, $R^{2a}$ and $R^{2b}$ are the same. In a more preferred aspect, $R^{2a}$ and $R^{2b}$ are alkyl, alkenyl, aminoalkyl, carboxyalkyl, or sulfonatoalkyl. In a still more preferred aspect, $R^{2a}$ and $R^{2b}$ are alkyl, carboxyalkyl, or sulfonatoalkyl. In a yet still more preferred aspect, $R^{2a}$ and $R^{2b}$ are methyl.

In an alternative aspect, $R^{2a}$ and $R^{2b}$ are different. In a more preferred aspect, $R^{2a}$ is alkyl, and $R^{2b}$ is selected from the group of alkyl, alkenyl, aminoalkyl, carboxyalkyl, or sulfonatoalkyl. In a still more preferred aspect, $R^{2a}$ is alkyl, and $R^{2b}$ is selected from the group of alkyl, carboxyalkyl, or sulfonatoalkyl. Yet still more preferably, $R^{2a}$ is methyl.

In another preferred aspect, $R^{2a}$ and $R^{2b}$, together with the ring carbon to which $R^{2a}$ and $R^{2b}$ are bonded, join to form a spirocycloalkyl ring, wherein the spirocycloalkyl ring is additionally substituted with from 0 to 6 $R^{14}$. In a more preferred aspect, $R^{2a}$ and $R^{2b}$ form a cyclopentyl or sulfonatoalkyl. In a still more preferred aspect, $R^{14}$ is alkyl. In a yet still more preferred aspect, $R^{14}$ is methyl.

In an alternative aspect, $R^{2a}$ and $R^{2b}$, together with the ring carbon to which $R^{2a}$ and $R^{2b}$ are bonded, join to form an exocyclic alkene, wherein the exocyclic alkene is additionally substituted with from 0 to 2 $R^{14}$. In a more preferred aspect, the exocyclic alkene is symmetrically substituted (e.g., unsubstituted; dialkyl; dicyano). Alternatively, the exocyclic alkene is substituted with two $R^{14}$ groups. Still more preferably, the exocylic alkene's $R^{14}$ substituent is cyano.

In an alternative preferred aspect, $R^{2a}$ and $R^{2b}$, together with the atom to which $R^{2a}$ and $R^{2b}$ are bonded, join to form a spirocycloalkyl ring. In a more preferred aspect, $R^{2a}$ and $R^{2b}$ form a cyclopentyl or cyclohexyl ring. In an alternative more preferred aspect, $R^{2a}$ and $R^{2b}$ form a cyclopentyl or cyclohexyl ring additionally substituted with from 0 to 6 $R^{14}$. In a still more preferred aspect, $R^{14}$ is alkyl.

Alternatively and preferably, the spirocycloalkyl ring has at least one pair of geminal $R^{14}$ alkyl substituents. More preferably, these geminal $R^{14}$ substituents are methyl (e.g., 3,3- or 4,4-dimethyl substitution).

Each $R^3$, $R^{4a}$, $R^{4b}$, $R^{5a}$, $R^{5b}$, $R^{6a}$, and $R^{6b}$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 $R^{16}$; or, alternatively, a pair of said members that is selected from the group consisting of $R^3$ and $R^{4a}$, an $R^{4a}$ and $R^{5a}$, and an $R^{5a}$ and $R^{6a}$, together with the pair of atoms to which the pair of said members is bonded, joins to form an aryl ring, wherein the aryl ring is additionally substituted with from 0 to 2 $R^{14}$ and from 0 to 1 $R^{16}$.

In a first aspect, each $R^3$, $R^{4a}$, $R^{4b}$, $R^{5a}$, $R^{5b}$, $R^{6a}$, and $R^{6b}$ is a member independently selected from the group consisting of hydrogen, alkyl, alkenyl, halo, alkoxy, cyano, carboxyl, alkoxycarbonyl, amido, sulfonato, alkoxyalkyl, carboxyalkyl, alkoxycarbonylalkyl, and sulfonatoalkyl. In a preferred aspect, each $R^3$, $R^{4a}$, $R^{4b}$, $R^{5a}$, $R^{5b}$, $R^{6a}$, and $R^{6b}$ is a member independently selected from the group of hydrogen, alkyl, carboxy, carboxyalkyl, halo, sulfanato, and sulfanatoalkyl. In a more preferred embodiment, each $R^3$, $R^{4a}$, $R^{4b}$, $R^{5a}$, $R^{5b}$, $R^{6a}$, and $R^{6b}$ is a member independently selected from the group of hydrogen, halo, and sulfanato.

In an alternative aspect, at least one member of the group $R^3$, $R^{4a}$, $R^{4b}$, $R^{5a}$, $R^{5b}$, $R^{6a}$, and $R^{6b}$ is hydrogen. Alternatively, exactly one member of the group $R^3$, $R^{4a}$, $R^{4b}$, $R^{5a}$, $R^{5b}$, $R^{6a}$, and $R^{6b}$ is hydrogen. In a preferred aspect, at least one pair of substituents selected from the pairs $R^3$ and $R^{4a}$; $R^3$ and $R^{5a}$; $R^3$ and $R^{6a}$; $R^{4a}$ and $R^{5a}$; $R^{4a}$ and $R^{6a}$; $R^{5a}$ and $R^{6a}$, $R^3$ and $R^{4b}$; $R^3$ and $R^{5b}$; $R^3$ and $R^{6b}$; $R^{4b}$ and $R^{5b}$; $R^{4b}$ and $R^{6b}$; and $R^{5b}$ and $R^{6b}$ is hydrogen. Alternatively, exactly two, exactly three, exactly four, exactly five, or exactly six members of the group $R^3$, $R^{4a}$, $R^{4b}$, $R^{5a}$, $R^{5b}$, $R^{6a}$, and $R^{6b}$ are hydrogen. In a more preferred aspect, exactly four members of the group $R^3$, $R^{4a}$, $R^{4b}$, $R^{5a}$, $R^{5b}$, $R^{6a}$, and $R^{6b}$ are hydrogen. Alternatively, exactly five members of the group $R^3$, $R^{4a}$, $R^{4b}$, $R^{5a}$, $R^{5b}$, $R^{6a}$, and $R^{6b}$ are hydrogen. In a still more preferred aspect, $R^3$, $R^{4a}$, $R^{6a}$, $R^{4b}$, $R^{6b}$ are hydrogen.

In another alternative aspect, at least one member of the group $R^3$, $R^{4a}$, $R^{4b}$, $R^{5a}$, $R^{5b}$, $R^{6a}$, and $R^{6b}$ is sulfonato or sulfonatoalkyl. Alternatively, exactly one substituent selected from the group $R^3$, $R^{4a}$, $R^{4b}$, $R^{5a}$, $R^{5b}$, $R^{6a}$, and $R^{6b}$ is sulfonato or sulfonatoalkyl. In a preferred aspect, $R^{5a}$ is sulfonato. In still another aspect, both members of a pair of substituents selected from the pairs $R^3$ and $R^{4a}$; $R^3$ and $R^{5a}$; $R^3$ and $R^{6a}$; $R^{4a}$ and $R^{5a}$; $R^{4a}$ and $R^{6a}$; $R^{5a}$ and $R^{6a}$, $R^3$ and $R^{4b}$; $R^3$ and $R^{5b}$; $R^3$ and $R^{6b}$; $R^{4b}$ and $R^{5b}$; $R^{4b}$ and $R^{6b}$; and $R^{5b}$ and $R^{6b}$ are each a member independently selected from the group of sulfonato or sulfonatoalkyl. Alternatively, exactly two, exactly three, exactly four, exactly five, or exactly six members of the group $R^3$, $R^{4a}$; $R^{4b}$, $R^{5a}$, $R^{5b}$, $R^{6a}$, and $R^{6b}$ are each a member independently selected from the group of sulfonato or sulfonatoalkyl.

In another alternative aspect, at least one member of the group $R^3$, $R^{4a}$, $R^{4b}$, $R^{5a}$, $R^{5b}$, $R^{6a}$, and $R^{6b}$ is anionic at physiological pH (e.g., sulfonato —$SO_3^-$, carboxyl —$CO_2^-$). Alternatively, exactly one member of the group $R^3$, $R^{4a}$, $R^{4b}$, $R^{5a}$, $R^{5b}$, $R^{6a}$, and, and $R^{6b}$ is anionic at physiological pH. In a preferred aspect, $R^{5a}$ is anionic at physiological pH. In still another aspect, each member of a pair of substituents selected from the pairs $R^3$ and $R^{4a}$; $R^3$ and $R^{5a}$; $R^3$ and $R^{6a}$; $R^{4a}$ and $R^{5a}$; $R^{4a}$ and $R^{6a}$; $R^{5a}$ and $R^{6a}$, $R^3$ and $R^{4b}$; $R^3$ and $R^{5b}$; $R^3$ and $R^{6b}$; $R^{4b}$ and $R^{5b}$; $R^{4b}$ and $R^{6b}$; and $R^{5b}$ and $R^{6b}$ is anionic at physiological pH. Alternatively, exactly two, exactly three, exactly four, exactly five, or exactly six members of the group $R^3$, $R^{4a}$, $R^{4b}$, $R^{5a}$, $R^{5b}$, $R^{6a}$, and, and $R^{6b}$ are anionic at physiological pH. exactly two, exactly three, or exactly four members of the group $R^3$, $R^{4a}$, $R^{4b}$, $R^{5a}$, $R^{5b}$, $R^{6a}$, and, and $R^{6b}$ are anionic at physiological pH.

In another alternative aspect, at least one member of the group $R^3$, $R^{4a}$, $R^{4b}$, $R^{5a}$, $R^{5b}$, $R^{6a}$, and, and $R^{6b}$ is halo. Alternatively, exactly one substituent selected from the group $R^3$, $R^{4a}$, $R^{4b}$, $R^{5a}$, $R^{5b}$, $R^{6a}$, and, and $R^{6b}$ is halo. In a preferred aspect, $R^{5b}$ is halo; more preferably, $R^{5b}$ is chloro. In still another aspect, both members of a pair of substituents selected from the pairs $R^3$ and $R^{4a}$; $R^3$ and $R^{5a}$; $R^3$ and $R^{6a}$; $R^{4a}$ and $R^{5a}$; $R^{4a}$ and $R^{6a}$; $R^{5a}$ and $R^{6a}$, $R^3$ and $R^{4b}$; $R^3$ and $R^{5b}$; $R^3$ and $R^{6b}$; $R^{4b}$ and $R^{5b}$; $R^{4b}$ and $R^{6b}$; and $R^{5b}$ and $R^{6b}$ are each an independently selected halo. Alternatively, exactly two, exactly three, exactly four, exactly five, or exactly six members of the group $R^3$, $R^{4a}$, $R^{4b}$, $R^{5a}$, $R^{5b}$, $R^{6a}$, and, and $R^{6b}$ are each an independently selected halo.

In a second aspect, a pair of members that is selected from the group of $R^3$ and $R^{4a}$, $R^{4a}$ and $R^{5a}$, $R^{5a}$ and $R^{6a}$, $R^{4b}$ and $R^{5b}$, and $R^{5b}$ and $R^{6b}$, together with the pair of atoms to which the pair of members is bonded, joins to form an aryl ring (i.e., the aryl ring formed from $R^n$ and $R^{n+1}$), wherein the aryl ring is additionally substituted with from 0 to 2 $R^{14}$. In a preferred aspect, the pair of members $R^{5a}$ and $R^{6a}$ or $R^{5b}$ and $R^{6b}$, together with the pair of atoms to which the pair of members is bonded, joins to form a phenyl ring that is additionally substituted with from 0 to 2 $R^{14}$. In a more preferred aspect, the phenyl ring is additionally substituted with from 1 to 2 $R^{14}$. In a still more preferred aspect, the phenyl ring is additionally substituted with 2 $R^{14}$.

In a preferred aspect, the $R^{14}$ substituents of the aryl ring formed from $R^n$ and $R^{n+1}$ (e.g., the aryl ring formed from $R^{5a}$ and $R^{6a}$) are carboxy, carboxyalkyl, halo, sulfonato, or sulfonatoalkyl. In a still more preferred aspect, the $R^{14}$ substituents are sulfonato or sulfonatoalkyl. In a yet still more preferred aspect, the benzindolinium $R^{14}$ substituents are sulfonato.

In a more preferred aspect, the aryl ring formed from $R^n$ and $R^{n+1}$ is additionally substituted with from 1 to 2 $R^{14}$, and a $R^{14}$ substituent of the aryl ring is attached to a carbon adjacent to the ring junction with the indolinium ring. Alternatively, the aryl ring is additionally substituted with from 1 to 2 $R^{14}$, and a $R^{14}$ substituent of the aryl ring is attached to a carbon non-adjacent to the ring junction with the indolinium ring. Alternatively, the aryl ring is additionally substituted with one adjacent substituent and one non-adjacent substituent (e.g., the compound of Formula Ia).

Alternatively, in a preferred aspect, the compound has Formula Ia:

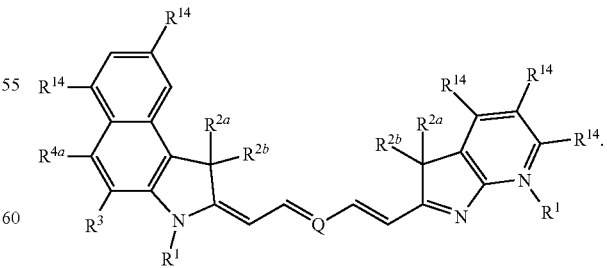

In a still more preferred aspect, the benzindolinium $R^{14}$ substituents of Formula Ia are carboxy, carboxyalkyl, halo, sulfonato, or sulfonatoalkyl. In a still more preferred aspect, the benzindolinium $R^{14}$ substituents are sulfonato or sulfonatoalkyl. In a yet still more preferred aspect, the benzindolinium $R^{14}$ substituents are sulfonato.

Each $R^7$ is a member independently selected from the group consisting of hydrogen and alkyl; wherein the alkyl is additionally substituted with from 0 to 3 $R^{14}$ and from 0 to 1 $R^{16}$; or, alternatively, both $R^7$, together with the intervening segment of the polyene to which both $R^7$ are bonded, join to form a ring, wherein said ring is selected from the group consisting of a cycloalkyl and a heterocyclyl ring; wherein the ring is additionally substituted with from 0 to 3 $R^{14}$ and from 0 to 1 $R^{16}$.

In one aspect, both $R^7$, together with the intervening segment of the polyene to which both $R^7$ are bonded, join to form a ring selected from the group of a five-membered ring and a six-membered ring, wherein the ring is additionally substituted with from 0 to 3 $R^{14}$. In a more preferred aspect, the ring is a six-membered ring. In a still more preferred aspect, the ring is cyclohexyl (i.e., both $R^7$ combine to form a —(CH$_2$)$_3$— linking group). In an alternative more preferred aspect, the ring is a five-membered ring. In a still more preferred aspect, the ring is cyclopentyl (i.e., both $R^7$ combine to form a —(CH$_2$)$_2$— linking group).

$R^8$, $R^9$, $R^{10}$, $R^{11}$ and $R^{12}$ are each a member independently selected from the group consisting of alkyl, alkenyl, halo, alkoxy, sulfonato, sulfonatoalkyl, hydroxyl, amino, carboxyl, alkoxycarbonyl, cyano, amido, thioacetyl, and -L-Y—Z; wherein, if present, at least one member selected from the group consisting of $R^8$, $R^9$, and $R^{10}$ is -L-Y—Z.

In one aspect, $R^8$ is -L-Y—Z. Preferably, $R^9$, $R^{10}$, $R^{11}$, and $R^{12}$ are each a member independently selected from the group consisting of hydrogen, alkyl, halo, sulfonato, and sulfonatoalkyl.

In a second aspect, $R^8$ is hydrogen, alkyl, alkoxy, or halo. In a more preferred aspect, $R^8$ is hydrogen.

Alternatively, $R^8$ is a carboxyalkyl. Preferably, $R^8$ is a lower alkyl group with a carboxyl substituent. More preferably, $R^8$ is 5-carboxypentyl, 4-carboxybutyl, 3-carboxypropyl, 2-carboxyethyl, or carboxymethyl. Still more preferably, $R^8$ is 5-carboxypentyl or 2-carboxyethyl.

Alternatively, $R^8$ is carboxyl, alkoxycarbonyl, or amido; more preferably, $R^8$ is carboxyl.

In one aspect, $R^{10}$ is -L-Y—Z. Preferably, $R^8$, $R^9$, $R^{11}$, and $R^{12}$ are each a member independently selected from the group consisting of hydrogen, alkyl, halo, sulfonato, and sulfonatoalkyl.

In a second aspect, $R^{10}$ is hydrogen, alkyl, alkoxy, or halo. In a more preferred aspect, $R^{10}$ is hydrogen.

Alternatively, $R^{10}$ is a carboxyalkyl. Preferably, $R^{10}$ is a lower alkyl group with a carboxyl substituent. More preferably, $R^{10}$ is 5-carboxypentyl, 4-carboxybutyl, 3-carboxypropyl, 2-carboxyethyl, or carboxymethyl. Still more preferably, $R^{10}$ is 5-carboxypentyl or 2-carboxyethyl.

Alternatively, $R^{10}$ is carboxyl, alkoxycarbonyl, or amido; more preferably, $R^{10}$ is carboxyl.

In one aspect, $R^9$ is -L-Y—Z. Preferably, $R^8$, $R^{10}$, $R^{11}$, and $R^{12}$ are each a member independently selected from the group consisting of hydrogen, alkyl, halo, sulfonato, and sulfonatoalkyl.

In a second aspect, $R^9$ is hydrogen, alkyl, alkoxy, or halo. In a more preferred aspect, $R^9$ is hydrogen.

Alternatively, $R^9$ is a carboxyalkyl. Preferably, $R^9$ is a lower alkyl group with a carboxyl substituent. More preferably, $R^9$ is 5-carboxypentyl, 4-carboxybutyl, 3-carboxypropyl, 2-carboxyethyl, or carboxymethyl. Still more preferably, $R^9$ is 5-carboxypentyl or 2-carboxyethyl.

Alternatively, $R^9$ is carboxyl, alkoxycarbonyl, or amido; more preferably, $R^9$ is carboxyl.

In one aspect, $R^{11}$ and $R^{12}$ are each a member independently selected from the group of hydrogen, alkyl, alkenyl, halo, alkoxy, sulfonato, hydroxyl, amino, carboxyl, alkoxycarbonyl, cyano, amido, thioacetyl, and -L-Y—Z. Preferably, $R^{11}$ and $R^{12}$ are each a member independently selected from the group of hydrogen, alkyl, halo, sulfonato, and sulfonatoalkyl. More preferably, $R^{11}$ and $R^{12}$ are each a member independently selected from the group of hydrogen, halo, and sulfonato.

In a second aspect, $R^{11}$ is hydrogen, alkyl, alkoxy, or halo. In a more preferred aspect, $R^{11}$ is hydrogen. In a still more preferred aspect, $R^{10}$ and $R^{11}$ are hydrogen.

In a third aspect, $R^{12}$ is hydrogen, alkyl, alkoxy, or halo. In a more preferred aspect, $R^{12}$ is hydrogen. In a still more preferred aspect, $R^{10}$ and $R^{12}$ are hydrogen. Alternatively, $R^{11}$ and $R^{12}$ are hydrogen. In a yet still more preferred aspect, $R^{10}$, $R^{11}$, and $R^{12}$ are hydrogen.

In a fourth aspect, the phenyl ring substituted with $R^8$, $R^9$, $R^{10}$, $R^{11}$, and $R^{12}$ is 1,2,3-substituted with independently selected substituents other than hydrogen, and the 1-substituent is the polymethine bridge (e.g., $R^8$ is -L-Y—Z and $R^9$ is alkyl; $R^8$ is halo- and $R^9$ is -L-Y—Z). Alternatively, the ring is 1,2,4-substituted. Alternatively, the ring is 1,2,5-substituted. Alternatively, the ring is 1,2,6-substituted. Alternatively, the ring is 1,3,4-substituted. Alternatively, the ring is 1,3,5-substituted. Alternatively, the ring is 1,3,6-substituted.

In a fifth aspect, the phenyl ring substituted with $R^8$, $R^9$, $R^{10}$, $R^{11}$, and $R^{12}$ is 1,2,3,4-substituted with independently selected substituents other than hydrogen, and the 1-substituent is the polymethine bridge. Alternatively, the ring is 1,2,3,5-substituted. Alternatively, the ring is 1,2,3,6-substituted. Alternatively, the ring is 1,2,4,5-substituted. Alternatively, the ring is 1,2,4,6-substituted. Alternatively, the ring is 1,2,5,6-substituted. Alternatively, the ring is 1,3,4,5-substituted. Alternatively, the ring is 1,3,4,6-substituted. Alternatively, the ring is 1,3,5,6-substituted.

In a sixth aspect, the phenyl ring substituted with $R^8$, $R^9$, $R^{10}$, $R^{11}$, and $R^{12}$ is 1,2,3,4,5-substituted with independently selected substituents other than hydrogen, and the 1-substituent is the polymethine bridge. Alternatively, the ring is 1,3,4,5,6-substituted. Alternatively, the ring is 1,2,4,5,6-substituted. Alternatively, the ring is 1,2,3,5,6-substituted. Alternatively, the ring is 1,2,3,4,6-substituted. Alternatively, the ring is independently substituted at each ring position.

In a seventh aspect, $R^8$, $R^{10}$, $R^{11}$, and $R^{12}$ are each a member independently selected from the group of hydrogen, alkyl, halo, sulfonato, and sulfonatoalkyl.

In an eighth aspect, the combination of the phenyl ring and its substituents $R^8$, $R^9$, $R^{10}$, $R^{11}$, and $R^{12}$ has at least ten carbons.

Each $R^{13}$ is a member independently selected from the group of hydroxyl, amino, carboxyl, alkoxycarbonyl, amido, sulfonato, and thioacetyl. In a preferred embodiment, $R^{13}$ is carboxyl, amido, or alkoxycarbonyl. In a more preferred embodiment, $R^{13}$ is carboxyl. Alternatively, $R^{13}$ is sulfonato.

Each $R^{14}$ is a member independently selected from the group consisting of alkyl, alkenyl, halo, hydroxyl, alkoxy, amino, cyano, carboxyl, alkoxycarbonyl, amido, sulfonato, alkoxycarbonylalkyl, and alkoxyalkyl; wherein the alkyl or alkenyl is additionally substituted with from 0 to 1 $R^{13}$ and from 0 to 1 $R^{16}$. In a preferred aspect, $R^{14}$ is alkyl, alkenyl, carboxyl, alkoxycarbonyl, amido, alkoxycarbonylalkyl, or halo. Alternatively, $R^{14}$ is carboxyalkyl, hydroxyalkyl, halo, or sulfonatoalkyl. In a more preferred aspect, $R^{14}$ is alkyl or alkyl substituted with 1 $R^{13}$. Alternatively, $R^{14}$ is halo or sulfonato.

Each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom. In a preferred aspect, L is a bond. Alternatively, L is a $C_1$-$C_{14}$ alkylene; more preferably, L is a $C_1$-$C_{10}$ alkylene or a $C_1$-$C_6$ alkylene. Alternatively, L is a $C_1$-$C_{12}$ alkylene interrupted by ether linkages (e.g., a polyethylene glycol oligomer).

In a preferred aspect, the alkylene or alkenylene is not interrupted by a heteroatom. Alternatively, L is interrupted by at least one ether, thioether, substituted amino, or amido group.

Each Y is an optional member independently selected from the group consisting of a bond, —O—, —S—, —NH—, —NHC(O)—, —C(O)NH—, —NR$^{15}$—, —NR$^{15}$C(O)—, —C(O)NR$^{15}$—, —N(Z)—, —N(Z)C(O)—, and —C(O)N(Z)—. In a preferred aspect, Y is a bond. Alternatively, Y is —O—. Alternatively, Y is an amido group optionally substituted with $R^{15}$ at the amido nitrogen.

Each Z is independently selected from the group consisting of -L-$R^{13}$ and -L-$R^{16}$. In a preferred aspect, the -L- is a $C_1$-$C_{20}$ alkylene; more preferably, a $C_1$-$C_{12}$ alkylene; and still more preferably, a $C_1$-$C_{10}$ alkylene. Alternatively, the -L- is a bond. Yet still more preferably, the -L- is $C_1$-$C_6$ alkyl. Alternatively, the -L- is interrupted by ether linkages (e.g., a polyethylene glycol oligomer). In a still more preferred aspect, Z is carboxyalkyl or sulfonatoalkyl. In a yet still more preferred aspect, Z is 5-carboxypentyl or 4-carboxybutyl.

In an alternative preferred aspect, Z is a carboxyalkyl. Preferably, Z is a lower alkyl group with a carboxy-substituent. More preferably, Z is 5-carboxypentyl, 4-carboxybutyl, 3-carboxypropyl, 2-carboxyethyl, or carboxymethyl. Still more preferably, Z is 5-carboxypentyl or 2-carboxyethyl.

In another alternative preferred aspect, -L-Y— is $(CH_2)_t$; Z is carboxyl or activated acyl; and t is an integer from 0 to 10.

In still another alternative preferred aspect, -L-Y— is a bond. More preferably, Z is directly bonded to the phenyl ring or the polymethylene bridge.

In still another alternative preferred aspect, the Z group's L group is a bond, and $R^{13}$ or $R^{16}$ is connected directly to -L-Y— or directly bonded to the phenyl ring itself if L and Y are absent.

In yet still another alternative preferred aspect, -L-Y—Z has at least three carbons. Alternatively, Z has at least three carbons.

In an alternative embodiment, —Y—Z is a member selected from the group consisting of —N(Z)$_2$, —N(Z)C(O)Z, and —C(O)N(Z)$_2$, and the two Z groups may optionally be linked to form a cycloalkynyl group. Examples of —N(Z)$_2$ cycloalkynyl groups are DBCO or DBCO-1 illustrated as follows:

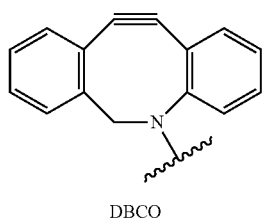

DBCO or

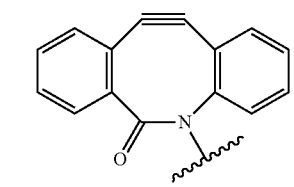

DBCO-1

Each $R^{15}$ is a member independently selected from the group consisting of alkyl and alkoxycarbonylalkyl; wherein the alkyl is optionally interrupted by at least one heteroatom. In a preferred aspect, $R^{15}$ is alkyl. In a more preferred aspect, $R^{15}$ is lower alkyl. Alternatively, $R^{15}$ is interrupted by ether linkages (e.g., a polyethylene glycol oligomer).

In a preferred aspect, the alkyl is not interrupted by a heteroatom. In a preferred aspect, $R^{15}$ is alkyl. In a more preferred aspect, $R^{15}$ is lower alkyl.

Alternatively, L is interrupted by at least one ether, thioether, substituted amino, or amido group. Preferably, $R^{15}$ is interrupted by at least one ether group (e.g., a polyethylene glycol oligomer).

Each $R^{16}$ is independently a member selected from the group consisting of activated acyl, acrylamido, optionally substituted alkylsulfonate ester, azido, optionally substituted arylsulfonate ester, optionally substituted amino, aziridino, boronato, cycloalkynyl, cycloalkynylcarbonyl, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, a pegylated azido, a pegylated alkynyl, a pegylated cycloalkynyl, an ortho substituted phosphinyl aryl ester (e.g., TPPME), a spirocycloalkynyl, and an ortho substituted phosphine oxide aryl ester.

In certain aspects, $R^{16}$ has the following structures:

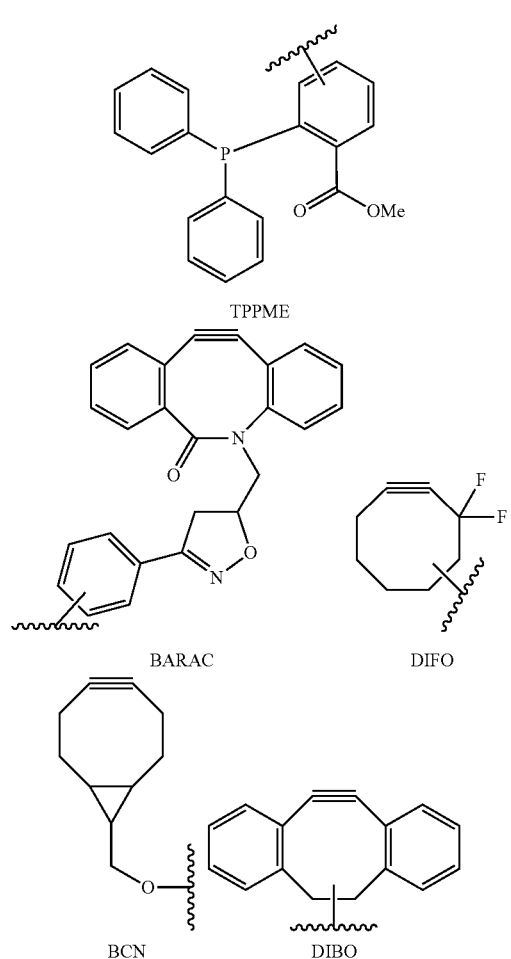

-continued

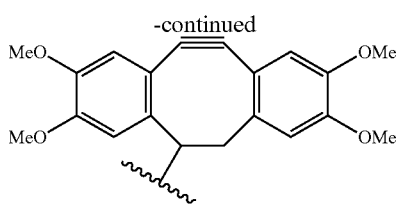

TMDIBO

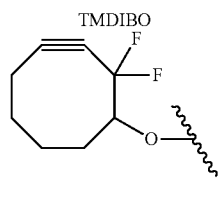

DIFO3

In a preferred aspect, $R^{16}$ is activated acyl, maleimidyl, phosphoramidityl, or glycidyl. In a more preferred embodiment, $R^{16}$ is activated acyl. Alternatively, $R^{16}$ is activated ester. In a still more preferred embodiment, $R^{16}$ is succinimidyloxy-ester or sulfosuccinimidyloxy-ester.

The compound has a balanced charge. In a preferred aspect, the compound's net anionic charge is balanced by alkali metal counterions (e.g., sodium or potassium). In a more preferred aspect, at least one of the counterions is sodium. Alternatively, all of the counterions are sodium.

In an alternative embodiment, the compound has a balanced charge in which positively and negatively charged substituents are balanced so that the dye molecule has a net charge of −1, 0, or +1 (preferably, 0), even without its counterions (i.e., the dye counterion has a net charge of −1, 0, or +1). In some aspects, this net charge is produced by including numbers of positively and negatively charged substituent groups that produce a dye net charge of −1, 0, or +1. This type of charge balancing is discussed in U.S. Provisional Application 61/150,522 (filed Feb. 9, 2009) and WO 2010/091243 (filed Feb. 5, 2010), which are incorporated by reference.

In a preferred aspect, Q is

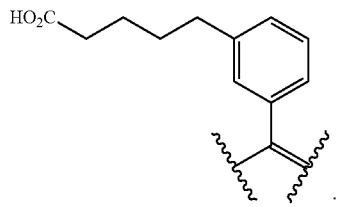 [SMILES: *C(=*)c1cccc(CCCCC(=O)O)c1]

For example, the compounds set forth in Formula I comprise said preferred aspect of Q. More preferably, each $R^3$, $R^{4a}$, $R^{4b}$, $R^{5a}$, $R^{5b}$, $R^{6a}$, and $R^{6b}$ are a member independently selected from the group of hydrogen, halo, and sulfonato.

In a preferred aspect, Q is

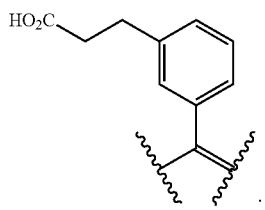 [SMILES: *C(=*)c1cccc(CCC(=O)O)c1]

For example, the compounds set forth in Formula I comprise said preferred aspect of Q. More preferably, each $R^3$, $R^{4a}$, $R^{4b}$, $R^{5a}$, $R^{5b}$, $R^{6a}$, and $R^{6b}$ are a member independently selected from the group of hydrogen, halo, and sulfonato.

In a more preferred aspect, the compound has the formula:

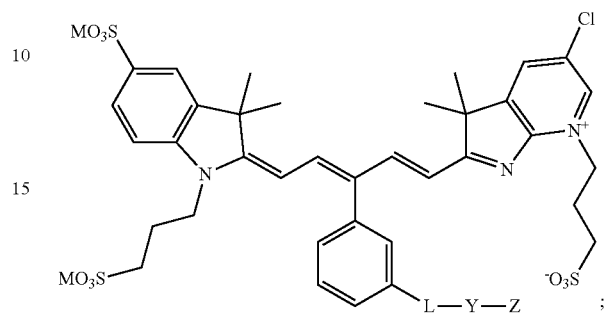

wherein M is a cationic counterion. More preferably, M is an alkali metal ion.

In an alternative aspect, the compound has the formula:

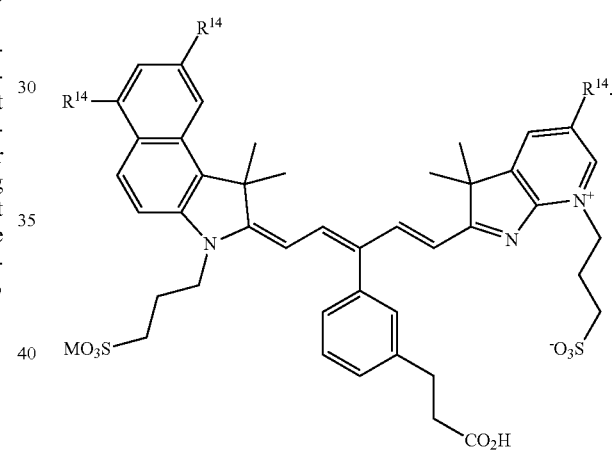

In another alternative aspect, the compound has the formula:

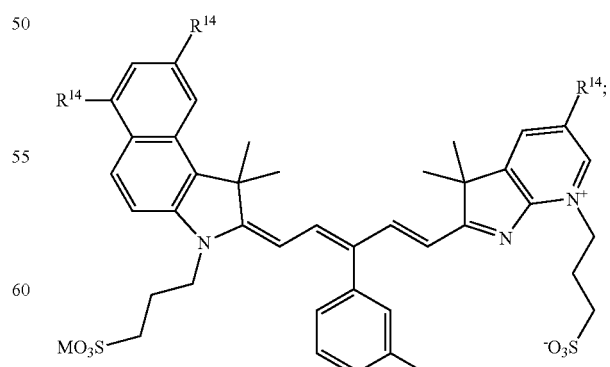

wherein M is a cationic counterion. More preferably, M is an alkali metal ion.

In another preferred aspect, the compound has the formula:

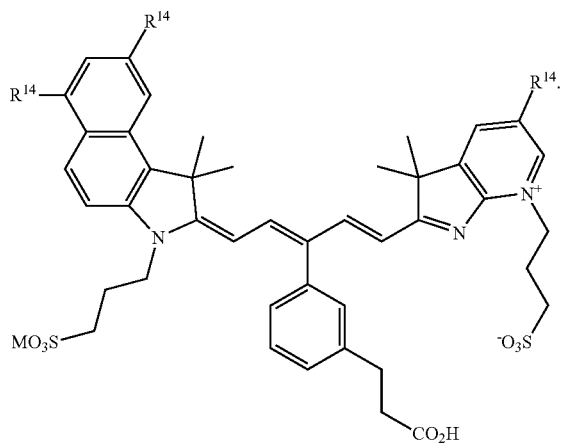

Alternatively, the compound has the formula:

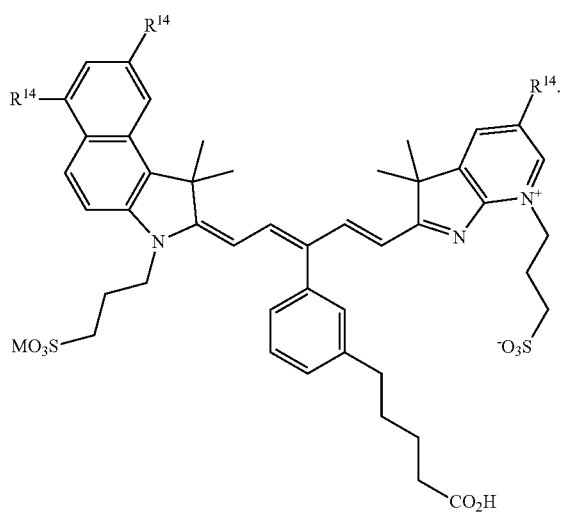

Alternatively, the compound has the formula:

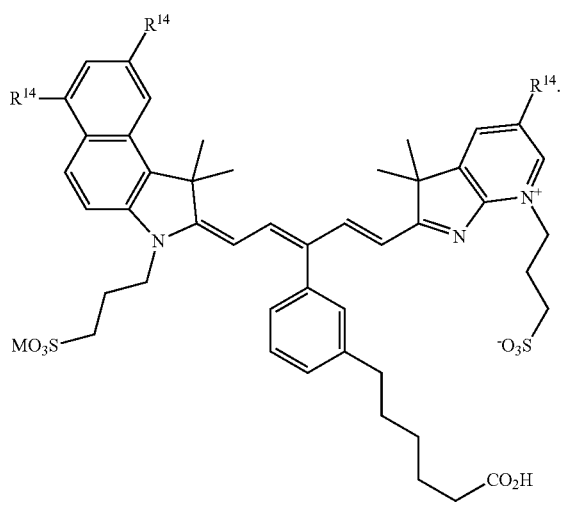

In certain aspects, an activated acyl group is present in place of the carboxy group. In a still more preferred aspect, the activated acyl group is an activated ester. In a still yet more preferred aspect, the activated ester is a succinimidyloxy-ester.

In a first aspect, the compound of Formula I, Ia, II, or IIa has a fluorescence absorption maximum at a wavelength within the range of about 550 nm to about 1000 nm. Preferably, the compound has a fluorescence absorption maximum at a wavelength within the range of about 600 nm to about 1000 nm. More preferably, the compound has a fluorescence absorption maximum at a wavelength within the range of about 600 nm to about 850 nm. Still more preferably, the compound has a fluorescence absorption maximum at a wavelength within the range of about 600 nm to about 725 nm. Alternatively, the compound has a fluorescence absorption maximum at a wavelength within the range of about 725 nm to about 850 nm.

The present application broadly encompasses all possible stereoisomers of the compounds as described herein, including the various diasteromers, enantiomers, and olefin stereoisomers apparent to one of skill in the art. This application is further directed to all methods of purifying cyanine dye compound stereoisomers that are well-known in the art as well as the purified compounds available by these methods.

Preparation of Compounds of Formula I

In one aspect, the preferred cyanine compounds set forth in Formula I are prepared by means of an organometallic coupling to incorporate a substituent to the polymethine bridge. More preferably, the substituent is installed by means of a palladium coupling. The substituent can optionally be modified after its inclusion (e.g., deprotected, activated for reaction with a biomolecule, or reacted to form a linking group).

The Miyaura-Suzuki reaction, also known as the Suzuki coupling, has been extensively used in organic synthesis since its discovery: Miyaura, N.; Yamada, K.; Suzuki, A. *Tetrahedron Lett.* 1979, 36, 3437-3440. Recently a Suzuki coupling was used to install a substituted aryl substituent at the central position of a heptamethine bridge in a water-soluble cyanine dye: Lee, H.; Mason, J. C.; Achilefu, S. *J. Org. Chem.* 2006, 71, 7862-7865.

However, because many cyanine dyes decompose under standard Suzuki coupling conditions of heating with a base, few examples of its use for the synthesis of cyanine dyes are known.

In a particularly preferred aspect of the instant invention, the substituent of a compound of Formula I is incorporated by means of a Suzuki coupling reaction, some of which are detailed in the examples of this specification. In one embodiment, the polymethine substrate for the Suzuki coupling is a 3-halopentamethine or a 4-haloheptamethine. In a preferred embodiment, the halo-substituent is a chloride or a bromide. In a more preferred embodiment, the halo-substituent is a bromide.

Other means of preparing cyanine dyes and their synthetic precursors are included in Hamer, F. M., *Cyanine Dyes and Related Compounds*, Weissberger, Mass., ed. Wiley Interscience, N.Y. 1964; and Mojzych, M., Henary, M. "Synthesis of Cyanine Dyes," *Top. Heterocycl. Chem.*, vol. 14, Springer Berlin, Heildelberg, 2008, pp. 1-9. Further, U.S. Pat. Nos. 4,337,063; 4,404,289; and 4,405,711 describe a synthesis for a variety of cyanine dyes having N-hydroxysuccinimide active ester groups. U.S. Pat. No. 4,981,977 describes a synthesis for cyanine dyes having carboxylic acid groups. U.S. Pat. No. 5,268,486 discloses a method for making arylsulfonate cyanine dyes. U.S. Pat. No. 6,027,709 discloses methods for making cyanine dyes having phosphoramidite groups.

U.S. Pat. No. 6,048,982 discloses methods for making cyanine dyes having a reactive group selected from the group of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

One common synthetic route involves preparing substituted or unsubstituted indolesulfonate quaternary salts according to procedures that are well-known in the art, some of which are detailed in the examples of this specification. Particularly preferred indole quaternary salts include, among others, indolesulfonate and benzindolesulfonate quaternary salts, which are exemplified in this specification.

The pair of synthesized salts are then reacted with a dialdehyde or a dialdehyde equivalent (e.g., a Schiff base) to form the polymethine bridge by means of techniques and reaction conditions that are well-known in the art, some of which are detailed in the examples of this specification. Preferably, one of the dialdehydes is protected or masked to allow incorporation of one polycyclic side of the bridge (e.g., the indoline ring), followed by deprotection or unmasking of the aldehyde and by incorporation or construction of the other polycyclic group (e.g., the pyrrolopyridine). Schiff bases can be purchased from commercial suppliers (e.g., Sigma-Aldrich) or prepared according to procedures that are well-known in the art (e.g., the method of Example 5).

Methods of Labeling Biomolecules

The cyanine compounds of Formula I can be attached to biomolecules, which are defined above. Methods of linking dyes to various types of biomolecules are well-known in the art. For a thorough review of, e.g., oligonucleotide labeling procedures, see R. Haugland in Excited States of Biopolymers, Steiner ed., Plenum Press (1983), Fluorogenic Probe Design and Synthesis: A Technical Guide, PE Applied Biosystems (1996), and G. T. Herman, Bioconjugate Techniques, Academic Press (1996).

"Click" chemistry provides one possible way for linking the inventive dyes to biomolecules. Click chemistry uses simple, robust reactions, such as the copper-catalyzed cycloaddition of azides and alkynes, to create intermolecular linkages. For a review of click chemistry, see Kolb, H. C.; Finn, M. G.; Sharpless, K. B. *Angew. Chem.* 2001, 40, 2004.

Connection (or ligation) of two fragments to make a larger molecule or structure is often achieved with the help of so-called "click chemistry" described by Sharpless et al. *Angew. Chem, Int. Ed.* 40: 2004 (2001). This term is used to describe a set of bimolecular reactions between two different reactants such as azides and acetylenes. The formation of 1,2,3-triazoles in 1,3-dipolar cycloaddition of azides to a triple bond is known, but because the activation energy of acetylene-azide cycloaddition is relatively high, the reaction is slow under ambient conditions.

The utility of the reaction of azides with alkynes was expanded by the discovery of Cu (I) catalysis. 1,3-cycloaddition of azides to terminal acetylenes in the presence of catalytic amounts of cuprous salts is facile at room temperature in organic or aqueous solutions.

U.S. Pat. No. 7,807,619 to Bertozzi et al. teaches modified cycloalkyne compounds and method of use of such compounds in modifying biomolecules. Bertozzi et al. teach a cycloaddition reaction that can be carried out under physiological conditions. As disclosed therein, a modified cycloalkyne is reacted with an azide moiety on a target biomolecule, generating a covalently modified biomolecule.

The present invention provides cyanine dyes with click chemistry functionalities useful for labeling biomolecules.

As such, in one aspect, the present invention provides compounds of Formula I or II, in which I one embodiment, each $R^{16}$ is independently a member selected from the group consisting of activated acyl, acrylamido, optionally substituted alkylsulfonate ester, azido, optionally substituted arylsulfonate ester, amino, azido, aziridino, boronato, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, a pegylated azido group, and a pegylated alkynyl group; and in which at least one $R^{16}$ is independently a member selected from the group azido, alkynyl, a pegylated azido and a pegylated alkynyl.

In yet other aspects, the present invention relates to two components that interact with each other to form a stable covalent bio-orthogonal bond. Bio-orthogonal reactions are reactions of materials with each other, wherein each material has limited or essentially no reactivity with functional groups found in vivo. These components are of use in chemical and biological assays, as chemical reagents, medical imaging and therapy, and more particularly, in nucleic acid modification techniques. According to a particular embodiment of the invention, the covalent bio-orthogonal bond is obtained by the [3+2] cycloaddition of azides and alkynes.

In still other aspects, one of the two components that interact with each other to form a stable covalent bio-orthogonal bond is a near infrared dye, such as a cyanine dye. In a preferred aspect, the cyanine dyes of the present invention comprise either an azide or an alkyne group for use as a reactant in a click chemistry reaction and the other reactant is a biomolecule such as a nucleotide comprising either an alkyne or azide group.

Azide reactive groups such as an alkyne compounds can react with at least one 1,3-dipole-functional compound such as an alkyne reactive group (e.g., a azido group) in a cyclization reaction to form a heterocyclic compound. In certain embodiments, the reaction can be carried out in the presence of an added catalyst (e.g., Cu(I)). In other embodiments, the reaction is carried out in the absence of such catalysts. Exemplary 1,3-dipole-functional compounds include, but are not limited to, azide-functional compounds, nitrile oxide-functional compounds, nitrone-functional compounds, azoxy-functional compounds, and/or acyl diazo-functional compounds. Preferably, azide-functional compounds are used.

Suitable biomolecule moieties for click reaction include, for example, monomeric and polymeric derivatives of nucleotides, carbohydrates, amino acids, lipids, glycols, alkanes, alkenes, arene, silicates, as well as biologically active and inactive compounds obtained from nature or from artificial synthesis.

Other suitable biological molecules include those having a azido or alkynyl functionality, which include, but are not limited to, an antibody, an antigen, an avidin, a carbohydrate, a deoxy nucleic acid, a dideoxy nucleotide triphosphate, an enzyme cofactor, an enzyme substrate, a fragment of DNA, a fragment of RNA, a hapten, a hormone, a nucleic acid, a nucleotide, a nucleotide triphosphate, a nucleotide phosphate, a nucleotide polyphosphate, an oligosaccharide, a peptide, PNA, a polysaccharide, a protein, a streptavidin, and the like. These biological molecules will in turn be reacted with the dye compounds of the present invention comprising either an azide or an alkyne group for use in click chemistry reactions.

In one aspect, the cyanine compounds of Formula I have sufficient solubility in aqueous solutions that once they are conjugated to a soluble ligand or biomolecule, the ligand or biomolecule retains its solubility. In certain instances, the bioconjugates also have good solubility in organic media (e.g., DMSO or DMF), which provides considerable versatility in synthetic approaches to the labeling of desired materials.

In another aspect, the present invention provides a method or process for labeling a ligand or biomolecule with a compound of Formula I, the method comprising: contacting a ligand or biomolecule with a compound having Formula I or Ia to generate the corresponding bioconjugate compound of Formula II or IIa.

In one preferred embodiment, the $R^{16}$ group or the $R^{13}$ group reacts with a thiol, a hydroxyl, a carboxyl, or an amino group on a biomolecule, forming a linking group between the dye and the biomolecule. In a more preferred embodiment, this reaction is carried out in mixtures of aqueous buffer and an organic solvent such as DMF at pH 8 to 9. Alternatively, this reaction is carried out in distilled water or in an aqueous buffer solution. For thiols or for acidic groups, a pH of 7 or lower is preferred for the reaction solvent, especially if a substrate also contains a reactive amino group.

Selected examples of reactive functionalities useful for attaching a compound of Formula I to a ligand or biomolecule are shown in Table 1, wherein the bond results from the reaction of a dye with a ligand or biomolecule. Column A of Table 1 is a list of the reactive functionalities, which can be on the compound of Formula I or the biomolecule. Column B is a list of the complementary reactive groups (preferably, a carboxyl, hydroxyl, thiol, or amino functionality), which can be on the biomolecule or the compound of Formula I, and which react with the indicated functionality of Column A to form the bond of Column C. Those of skill in the art will know of other bonds suitable for use in the present invention.

TABLE 1

Exemplary Bonds for Linking Groups

| A<br>Reactive Functionality<br>(Compound of Formula I<br>or Biomolecule) | B<br>Complementary Group<br>(Biomolecule or<br>Compound of Formula I) | C<br>Resulting Linking Group |
|---|---|---|
| activated esters* | amines/anilines | amides |
| acrylamides | thiols | thioethers |
| acyl azides** | amines/anilines | amides |
| acyl halides | amines/anilines | amides |
| acyl halides | alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | amides/imides |
| aryl halides | thiols | thiophenols |
| aryl halides | amines | aryl amines |
| azides | alkynes | 1,2,3-triazoles |
| azides | ester with phosphine reagent (e.g., o-diphenylphosphino group) | amide (and phosphine oxide) |
| aziridines | thiols | thioethers |
| boronates | glycols | boronate esters |
| boronates/boronic acids | aryl halides | C—C bond to aryl ring |
| boronates/boronic acids | alkenyl halides | C—C bond to alkenyl group |
| activated carboxylic acids | amines/anilines | amides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| electron-rich diene | dienophile (e.g., electron-poor alkene) | cyclohexene (Diels-Alder cycloaddition) |
| epoxides | thiols | thioethers |
| epoxides | amines | alkyl amines |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| photoactivatable group | varies; see definition | varies; see definition |
| quadricyclanes | π-electrophile (e.g., Ni bis(dithiolene)) | norbornene cycloaddition product |
| silyl halides | alcohols | silyl ethers |

TABLE 1-continued

Exemplary Bonds for Linking Groups

| A<br>Reactive Functionality<br>(Compound of Formula I<br>or Biomolecule) | B<br>Complementary Group<br>(Biomolecule or<br>Compound of Formula I) | C<br>Resulting Linking Group |
|---|---|---|
| sulfonyl azides | thiocarboxylic acids | N-acyl sulfonamides |
| sulfonate esters | amines/anilines | alkyl amines |
| sulfonate esters | carboxylic acids | esters |
| sulfonate esters | thiols | thioethers |
| sulfonate esters | alcohols/phenols | ethers |
| sulfonyl halides | amines/anilines | sulfonamides |
| 1,2,4,5-tetrazine | alkene | dihydropyradazine |
| vinyl sulfonyl | thiols | thioethers |
| vinyl sulfonyl | activated diene | cyclohexenyl (Diels-Alder) |

*Activated esters, as understood in the art, generally have the formula —C(O)OM, where —OM is a leaving group (e.g. succinimidyloxy (—OC$_4$H$_4$NO$_2$), sulfosuccinimidyloxy (—OC$_4$H$_3$NO$_2$SO$_3$H), -1-oxybenzotriazolyl (—OC$_6$H$_4$N$_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or —C(O)OM is a carboxylic acid activated by a carbodiimide to form an anhydride or mixed anhydride —C(O)OC(O)R$^a$ or —C(O)OC(NR$^a$)NHR$^b$, wherein R$^a$ and R$^b$ are members independently selected from the group consisting of C$_1$—C$_6$ alkyl, C$_1$—C$_6$ perfluoroalkyl, C$_1$—C$_6$ alkoxy, cyclohexyl, 3-dimethylaminopropyl, or N-morpholinoethyl).
**Acyl azides can also rearrange to isocyanates.

Some methods of forming linking groups include those taught in Sletten and Bertozzi, *J. Am. Chem. Soc.* electronic publication at dx.doi.org/10.1021/ja2072934; Devaraj and Weissleder, *Acc. Chem. Res.* electronic publication at dx.doi.org/10.1021/ar200037t; Krishnamoorthy and Begley, *J. Am. Chem. Soc.* electronic publication at dx.doi.org/10.1021/ja1034107; and the like.

When linking a compound of Formula I having a carboxylic acid with an amine-containing ligand or biomolecule, the carboxylic acid can first be converted to a more reactive form, e.g, a N-hydroxy succinimide (NHS) ester or a mixed anhydride, by means of an activating reagent. The amine-containing ligand or biomolecule is treated with the resulting activated acyl to form an amide linkage. In a more preferred embodiment, this reaction is carried out in aqueous buffer at pH 8 to 9 with DMSO or DMF as an optional co-solvent. Alternatively, this reaction is carried out in distilled water or in an aqueous buffer solution.

Similarly, the attachment of an isocyanate- or isothiocyanate-containing compound of Formula I is analogous to the procedure for the carboxy dye, but no activation step is required. The amine-containing ligand or biomolecule is treated directly with the activated acyl compound to form a urea or a thiourea linkage. In a more preferred embodiment, the reaction is carried out in aqueous buffer at pH 9 to 10 with DMSO or DMF as an optional co-solvent. Alternatively, this reaction is carried out in distilled water or in an aqueous buffer solution.

If the compound of Formula I or biomolecule has a reactive hydroxyl group, it can be linked to a ligand or biomolecule by means of phosphoramidite chemistry, which ultimately forms a phosphate linkage between the dye and the biomolecule. For examples of such labeling methods, see U.S. Pat. No. 6,027,709, which discloses many preferred linking groups, linking methods, and biomolecules that can be readily labeled. In one embodiment, solid-phase synthesis is preferred, as disclosed in U.S. Pat. No. 6,027,709.

In a preferred embodiment, the biomolecule is DNA or RNA. Use of phosphoramidite chemistry allows labeling of a DNA or an RNA during the synthesis process. The protected nucleotide is labeled while attached to a solid-phase support. The free 5'-OH group is reacted with the phosphoramidite and a tetrazole activator to form a phosphite linkage which subsequently is oxidized to phosphate. The labeled DNA or RNA is then cleaved from the solid phase by means of ammonia or by another standard procedure.

It is generally preferred to prepare a phosphoramidite of a cyanine dye to label DNA molecules in a DNA synthesizer. It is also preferred to attach the dye to the 5' end of a protected, support-bonded oligonucleotide through standard phosphoramidite chemistry. For a list of preferred label terminators for use in DNA sequencing, see U.S. Pat. No. 5,332,666.

In another preferred embodiment, the biomolecule is an antibody. It is preferred that antibody labeling is carried out in a buffer optionally including an organic co-solvent, under basic pH conditions, and at room temperature. It is also preferred that the labeled antibody be purified by dialysis or by gel permeation chromatography using equipment such as a SEPHADEX® G-50 column to remove any unconjugated compound of Formula I. Those of skill in the art will know of other ways and means for purification.

In still another preferred embodiment, the biomolecule contains a thiol group that forms the linking group by reaction with a maleimidyl substituent at $R^{16}$. In a more preferred embodiment, the biomolecule is a protein, a peptide, an antibody, a thiolated nucleotide, or a thiolated deoxynucleotide.

In yet other aspects, the linking group or biomolecule comprises a polymer. In a preferred embodiment, the polymer is a member selected from the group of a PEG, a copolymer of PEG-polyurethane, and a copolymer of PEG-polypropylene. In still yet other aspects, the linking group is a member selected from the group of a polysaccharide, a polypeptide, an oligosaccharide, a polymer, a co-polymer and an oligonucleotide.

In one aspect, biomolecules can be labeled according to the present invention by means of a kit. In certain instances, the kit comprises a buffer and a dye as disclosed in the instant application (i.e., a compound of Formula I or Formula Ia). Preferably, the kit contains a coupling buffer such as 1 M KH$_2$PO$_4$ (pH 5), optionally with added acid or base to modify the pH (e.g., pH 8.5 is preferred for reactions with succinimide esters and pH 7 is preferred for reactions with maleimides). Preferably, the buffer has a qualified low fluorescence background.

Optionally, the kit can contain a purification sub-kit. After labeling a biomolecule with a preferred dye, the labeled biomolecule may be separated from any side reaction products and any free hydrolyzed product resulting from normal hydrolysis. For biomolecules containing 13 or fewer amino acids, preparative thin layer chromatography (TLC) can remove impurities. In certain instances, preparative TLC, optionally performed with commercially available TLC kits, can be used to purify dye-labeled peptides or proteins.

For larger biomolecules such as larger peptides or proteins, a SEPHADEX® G-15, G-25, or G-50 resin may remove unwanted derivatives. In certain instances, a Gel Filtration of Proteins Kit, which is commercially available from Life Sciences, can be used to separate dye-labeled peptides and proteins from free dye. The labeled biomolecules that remain after desalting can often be used successfully without further purification. In some cases, it may be necessary to resolve and assess the activity of the different products by means of HPLC or other chromatographic techniques.

Bioconjugate Compounds

In another embodiment of the invention, a bioconjugate of the Formula II is provided:

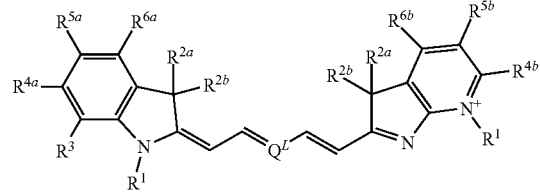

II wherein $Q^L$ is a member selected from the group of a one-polymethine-carbon segment and a three-polymethine-carbon segment:

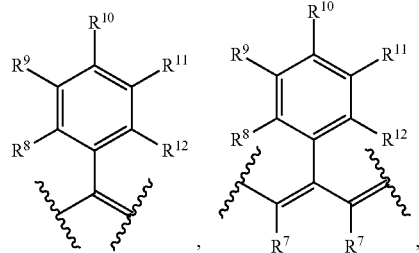

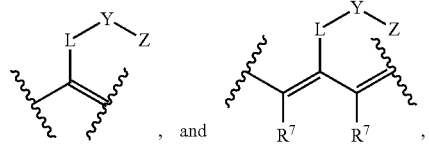

, and respectively; wherein the segment is the central portion of either a five- or a seven-polymethine-carbon polymethine bridge.

In a preferred aspect, $Q^L$ is a portion of a polymethine bridge that is a pentamethine:

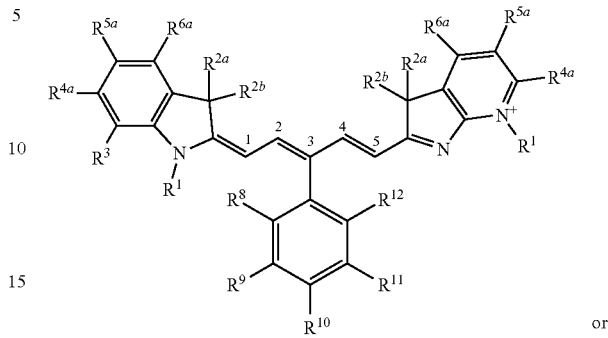

or

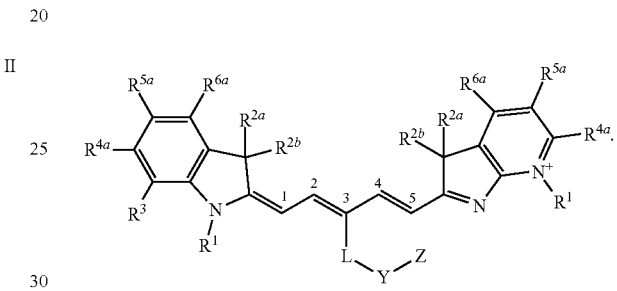

More preferably, $Q^L$ is

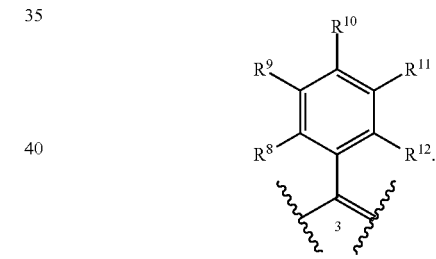

In a second preferred aspect, $Q^L$ is a portion of a polymethine bridge that is a heptamethine:

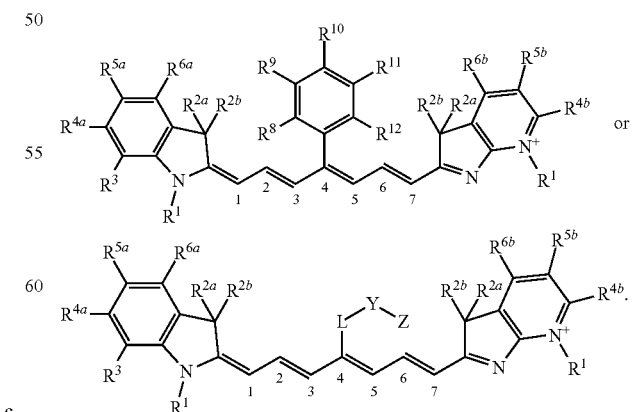

More preferably, $Q^L$ is

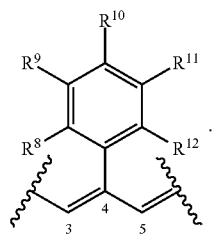

In an alternative preferred aspect, $Q^L$ is a portion of a polymethine bridge that is a substituted heptamethine:

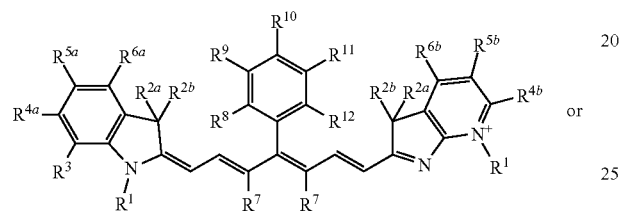

More preferably, $Q^L$ is

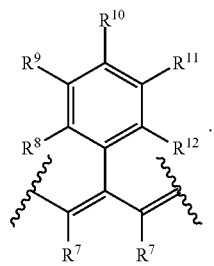

In an alternative, more preferred aspect, the substituted heptamethine includes a cycloalkyl ring:

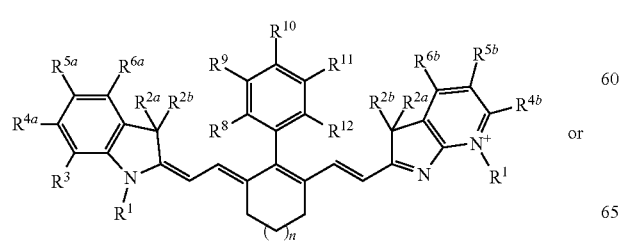

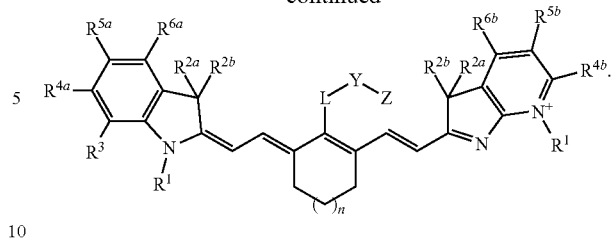

Still more preferably, $Q^L$ is

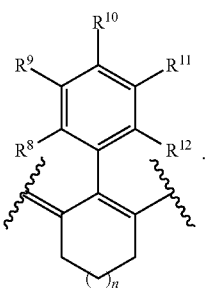

In a third preferred aspect, $Q^L$ is selected from the group consisting of:

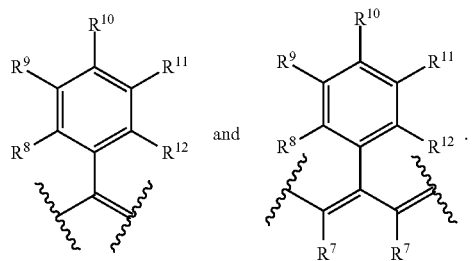

More preferably, $Q^L$ is

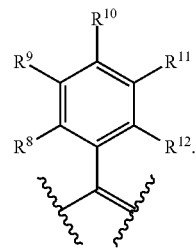

In a fourth preferred aspect, $Q^L$ is selected from the group consisting of:

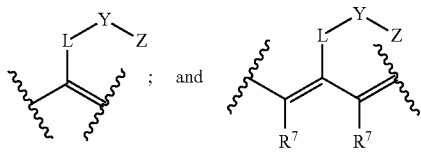

$R^1$, $R^{2a}$, $R^{2b}$, $R^3$, $R^{4a}$, $R^{4b}$, $R^{5a}$, $R^{5b}$, $R^{6a}$, $R^{6b}$, $R^7$, $R^8$, $R^9$, $R^{10}$, $R^{11}$, $R^{12}$, $R^{13}$, $R^{14}$, $R^{15}$, L, and Y are as previously defined for the compound of Formula I, including all preferred embodiments that are identified herein.

Each Z is independently selected from the group consisting of -L-$R^{13}$ and -L-$R^L$. In a more preferred aspect, Z is -L-$R^L$, wherein L is a bond.

Each $R^L$ comprises 1) a linking group that connects the cyanine dye compound to a biomolecule; and 2) the biomolecule to which it is connected (i.e., the linking group and the biomolecule connected thereby), wherein the compound comprises at least one $R^L$. Preferred linking groups are indicated in Table 1 (column C). In a particularly preferred aspect, the linking group is an amide or an ester. In a more particularly preferred aspect, the linking group is an amide.

The compound has a balanced charge. In a preferred aspect, the compound's net anionic charge is balanced by alkali metal counterions (e.g., sodium or potassium). In a more preferred aspect, at least one of the counterions is sodium. Alternatively, all of the counterions are sodium.

In another preferred embodiment of the bioconjugate, any preferred embodiments or aspects of the inventive compound of Formulas I and Ia can included in the embodiment of a bioconjugate. Representative examples of preferred compounds of Formulas I and Ia that correspond to preferred bioconjugate embodiments are described in the dependent claims of the instant application.

A more preferred aspect of the bioconjugate has the following structure:

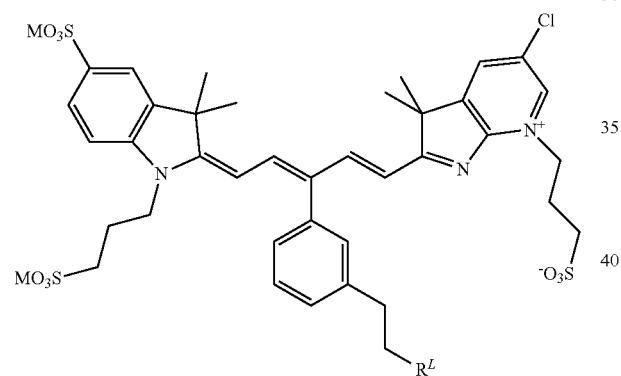

wherein M is a cationic counterion.

Another preferred aspect of the bioconjugate has the following structure:

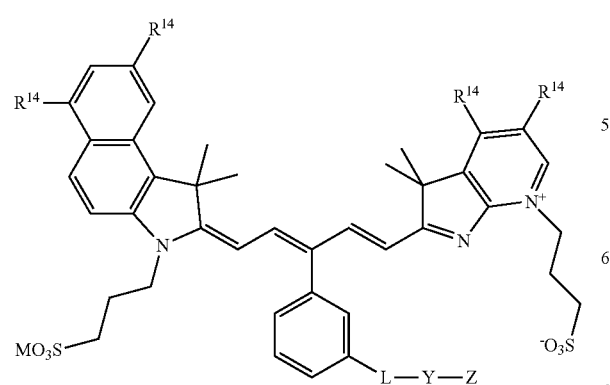

wherein M is a cationic counterion.

More preferably, the compound has the following structure:

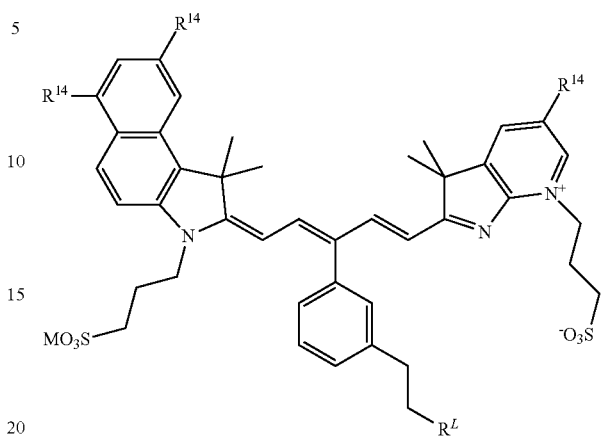

Alternatively, the bioconjugate has the following structure:

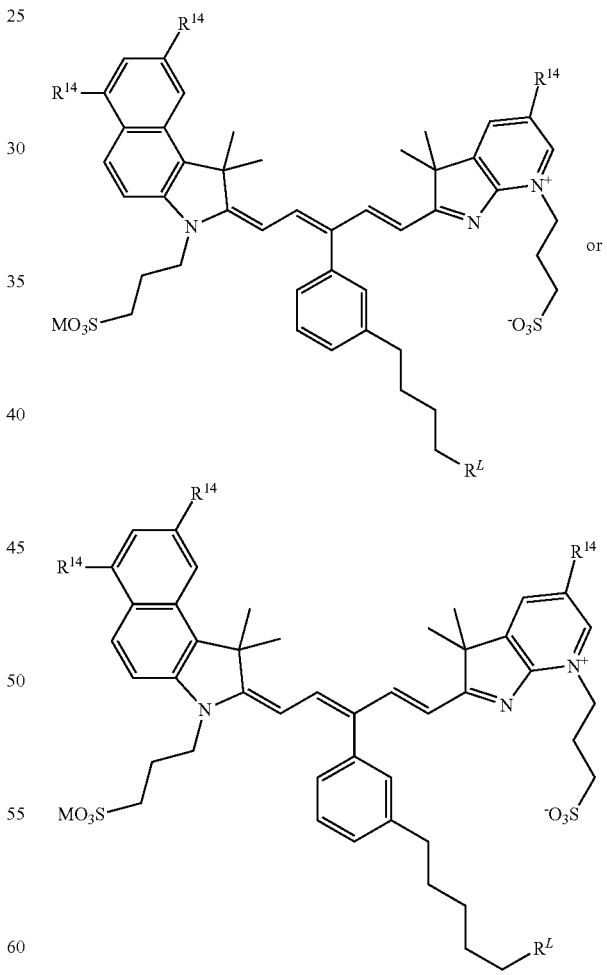

wherein M is a cationic counterion.

In certain aspects, a preferred biomolecule for the instant invention is selected from the group containing an acyclo terminator triphosphate, an antibody, an antigen, an avidin, a carbohydrate, a deoxy nucleic acid, a dideoxy nucleotide triphosphate, an enzyme cofactor, an enzyme substrate, a fragment of DNA, a fragment of RNA, a hapten, a hormone, a nucleic acid, a nucleotide, a nucleotide triphosphate, a nucleotide phosphate, a nucleotide polyphosphate, an oligosaccharide, a peptide, PNA, a polysaccharide, a protein, a streptavidin, and the like.

Suitable nucleotides include nucleoside polyphosphates, including, but not limited to, deoxyribonucleoside polyphosphates, ribonucleoside polyphosphates, dideoxynucleoside polyphosphates, carbocyclic nucleoside polyphosphates and acyclic nucleoside polyphosphates and analogs thereof. Suitable nucleotides also include nucleotides containing 3, 4, 5, 6, or more phosphate groups, in the polyphosphate chain, where the phosphate (e.g., $\alpha$, $\beta$, $\gamma$, $\epsilon$, or terminal phosphate), sugar, base, or combination thereof is labeled with a compound of Formula I. The polyphosphate nucleotides include, but are not limited to, tetraphosphates, pentaphosphates, hexaphosphates, heptaphosphates, and the like. The bases include for example, purines, (adenine and guanine) pyrimidines, (thymine, uracil and cytosine) and derivatives thereof.

In certain instances, the dye of Formula I is attached to the phosphate (e.g. $\alpha$, $\beta$, $\gamma$, $\epsilon$-phosphate or terminal phosphate) through a phosphorothioate linkage (see, for example, U.S. Pat. No. 6,323,186, incorporated herein by reference), heteroatom, or functional group A, or B, resulting in linkage C of Table I. See also U.S. Pat. No. 6,399,335 (incorporated herein by reference) entitled "$\gamma$-phosphoester nucleoside triphosphates," which provides methods and compositions for polymerizing particular nucleotides with a polymerase using $\gamma$-phosphoester linked nucleoside triphosphates. Other ways of linking the compounds of Formula I to a nucleotide are known to those of skill in the art. Using these nucleotides with a DNA polymerase can lead to identification of specific nucleotides in a DNA or RNA sequence by identification of the labeled pyrophosphate or polyphosphate released upon incorporation of the nucleotide base into RNA or DNA. (See for example, U.S. Pat. No. 6,232,075, US Pub. No. 2004/0241716 and U.S. Pat. No. 7,452,698 each of which is incorporated herein by reference).

More preferred aspects include an antibody, an avidin, and a streptavidin. Even more preferred aspects include a goat anti-mouse (GAM) antibody, a goat anti-rabbit (GAR) antibody, and streptavidin.

In certain other aspects, preferred biomolecules for the instant invention include somatostatin, endostatin, a carbohydrate, an oligosaccharide, an aptamer, a liposome, PEG, an angiopoietin, angiostatin, angiotensin II, $\alpha_2$-antiplasmin, annexin V, $\beta$-cyclodextrin tetradecasulfate, endoglin, endosialin, endostatin, epidermal growth factor, fibrin, fibrinopeptide $\beta$, fibroblast growth factor, FGF-3, basic fibronectin, fumagillin, heparin, hepatocycle growth factor, hyaluronan, an insulin-like growth factor, an interferon-$\alpha$, $\beta$ inhibitor, IL inhibitor, laminin, leukemia inhibitory factor, linomide, a metalloproteinase, a metalloproteinase inhibitor, an antibody, an antibody fragment, an acyclic RGD peptide, a cyclic RGD peptide, placental growth factor, placental proliferin-related protein, plasminogen, plasminogen activator, plasminogen activator inhibitor-1, a platelet activating factor antagonist, platelet-derived growth factor, a platelet-derived growth factor receptor, a platelet-derived growth factor receptor, platelet-derived endothelial cell growth factor, pleiotropin, proliferin, proliferin-related protein, a selectin, SPARC, a snake venom, substance P, suramin, a tissue inhibitor of a metalloproteinase, thalidomide, thrombin, thrombin-receptor-activating tetradecapeptide, transformin growth factor-$\alpha$, $\beta$, transforming growth factor receptor, tumor growth factor-$\alpha$, tumor necrosis factor, vitronectin, and the like.

In still other aspects, preferred biomolecules include a carbohydrate and a carbohydrate derivative. Representative examples include glucosamine, a glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, and a derivative thereof. Even more preferred biomolecules include 2-deoxy-D-glucose, 2-deoxy-L-glucose, and racemic 2-deoxyglucose.

In yet still other aspects, the biomolecule can be a ligand that has affinity for a receptor selected from the group of EGFR, Her2, PDGFR, IGFR, c-Ryk, c-Kit, CD24, integrins, FGFR, KFGR, VEGFR, TRAIL decoy receptors, retinoid receptor, growth receptor, PPAR, vitamin receptor, glucocordicosteroid receptor, Retinoid-X receptor, RHAMM, high affinity folate receptors, Met receptor, estrogen receptor and Ki67. Preferably, the biomolecule is a ligand that has affinity for an integrin receptor.

Alternatively, the biomolecule is selected from the group of somatostatin, endostatin, a carbohydrate, a monosaccharide, a disaccharide, a trisaccharide, an oligosaccharide, aptamer, liposome and polyethylene glycol.

In yet another aspect, the biomolecule is a small-molecule drug or drug-like molecule such as a tetracycline antibiotic, a tetracycline derivative, and calcein.

Alternatively, the biomolecule is a small-molecule drug or peptide.

In other aspects, a cyanine dye set forth in an embodiment of the present invention is conjugated to a biological cell. Preferably, the dye is conjugated by means of an $R^L$ linking group.

In other aspects, a preferred biomolecule for the instant invention is selected from the group containing an antigen and a hapten. Preferably, the biomolecule is an immunogen.

In other aspects, a preferred biomolecule for the instant invention is selected from the group containing an enzyme cofactor and an enzyme substrate.

In other aspects, a preferred biomolecule for the instant invention is selected from the group containing an amino acid, a carbohydrate, a hapten, a hormone, a glycoprotein, a liposome, a nucleic acid, a nucleotide, a nucleotide triphosphate, a nucleotide polyphosphate, an oligosaccharide, a peptide, a peptide nucleic acid, a polyalkylene glycol, a polysaccharide, a protein, a small-molecule drug, and a snake venom.

More preferably, the preferred biomolecule is selected from the group containing angiostatin, endostatin, fumagillin, a fumagillin derivative, placental proliferin-related protein, plasminogen, somatostatin, and thalidomide.

Alternatively, the biomolecule is an aptamer.

Alternatively, the biomolecule is an a small-molecule drug. Preferably, the drug is selected from the group of tetracyclin, a tetracyclin antibiotic, and a derivative thereof.

Alternatively, the biomolecule is an integrin.

Alternatively, the biomolecules is selected from the group containing an antibody and an antibody fragment.

Alternatively, the biomolecule is selected from the group containing polyethylene glycol.

Alternatively, the biomolecule is selected from the group containing an angiopoietin, epidermal growth factor, a fibroblast growth factor, hepatocyte growth factor, an insulin-like growth factor, placental growth factor, platelet-derived growth factor, a platelet-derived growth factor receptor, a platelet-derived endothelial cell growth factor, transforming growth factor-$\alpha$, transforming growth factor-$\beta$, and transforming growth factor receptor. More preferably, the fibroblast growth factor is fibroblast growth factor 3.

Alternatively, the biomolecule is selected from the group containing an acyclic RGD peptide, a cyclic RGD peptide, endosialin, and a derivative thereof. Preferably, the biomolecule is an acyclic RGD peptide, a cyclic RGD peptide, or a derivative thereof. More preferably, the cyclic RGD peptide is cyclo (Arg-Gly-Asp-D-Phe-Lys) (i.e., c(RGDfK)).

Alternatively, the biomolecule is selected from the group containing $\alpha_2$-antiplasmin, plasminogen, plasminogen activator, plasminogen activator inhibitor-1, and plasminogen activator inhibitor-2.

Alternatively, the biomolecule is selected from the group containing fibrin, fibrinopeptide $\beta$, thrombin, and thrombin-receptor-activating tetradecapeptide.

Alternatively, the biomolecule is selected from the group containing an acyclo terminator triphosphate, a deoxynucleic acid, a ribonucleic acid, a nucleotide, a nucleotide triphosphate, a nucleotide polyphosphate, and a peptide nucleic acid.

Alternatively, the biomolecule is selected from the group containing a fragment of RNA and a fragment of DNA.

Alternatively, the biomolecule is selected from the group containing angiotensin II and substance P.

Alternatively, the biomolecule is selected from the group containing a lectin and a selectin.

Alternatively, the biomolecule is selected from the group containing endoglin, a laminin, a fibronectin, SPARC, and vitronectin.

Alternatively, the biomolecule is selected from the group containing a metalloproteinase and a metalloproteinase inhibitor.

Alternatively, the biomolecule is a tissue inhibitor of a metalloproteinase.

Alternatively, the biomolecule is a platelet activating factor antagonist.

Alternatively, the biomolecule is selected from the group containing $\beta$-cyclodextrin tetradecasulfate, heparin, hyaluronan, and a derivative thereof. Preferably, the biomolecule is selected from the group consisting of hyaluronan and a derivative thereof.

Alternatively, the biomolecule is an annexin.

Alternatively, the biomolecule is selected from the group containing interleukin inhibitor, leukemia inhibitory factor, pleiotropin, and tumor necrosis factor. More preferably, the biomolecule is an interleukin-1 receptor antagonist.

Alternatively, the biomolecule is selected from the group containing proliferin and a proliferin-related protein.

Alternatively, the biomolecule is selected from the group containing calcein, laquinimod, linomide, and suramin.

Alternatively, the biomolecule is an interferon-$\alpha,\beta$ inhibitor.

Alternatively, the biomolecule is selected from the group containing tyramine and a tyramine derivative.

Alternatively, the biomolecule is selected from the group containing an avidin, biotin, and a streptavidin.

Alternatively, the biomolecule is selected from the group containing a glucosamine, a glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, and a derivative thereof. More preferably, the biomolecules include 2-deoxy-D-glucose, 2-deoxy-L-glucose, and racemic 2-deoxyglucose.

Methods of Imaging

In another embodiment, the compounds of Formula I or Ia can be used as in vitro or in vivo optical imaging agents of tissues and organs in various biomedical applications. In one embodiment, the present invention provides a method for imaging, the method comprising administering a compound of Formula I or Ia.

In certain preferred aspects of the invention, any of the embodiments or aspects of the inventive compound of Formula I or Ia that are described herein can be used in the method of imaging. Representative examples of preferred compounds for use in the method are described in the specification and the dependent claims of the instant application.

In another embodiment, the present invention provides a method for imaging, the method comprising administering a compound of Formula II or IIa.

In certain preferred aspects of the invention, any of the embodiments or aspects of the inventive compound of Formula II or IIa that are described herein can be used in the method of imaging. Representative examples of preferred compounds for use in the method are described in the specification and the dependent claims of the instant application.

In certain preferred aspects, the compounds of the present invention are used as in vivo imaging agents of tissues and organs in various biomedical applications including, but not limited to, tomographic imaging of organs, monitoring of organ functions, coronary angiography, fluorescence endoscopy, imaging of tumors, laser guided surgery, photoacoustic and sonofluorescence methods, and the like. In one aspect, the compounds of the invention are useful for the detection of the presence of tumors and other abnormalities by monitoring the blood clearance profile of the dyes. In another aspect of the invention, the compounds are useful for laser assisted guided surgery for the detection of micro-metastases of tumors upon laparoscopy. In yet another aspect, the compounds are useful in the diagnosis of atherosclerotic plaques and blood clots.

In further aspects, the compounds of the present invention are used in the imaging of: (1) ocular diseases in ophthalmology, for example, to enhance visualization of chorioretinal diseases, such as vascular disorders, retinopathies, neovascularization, and tumors via direct microscopic imaging; (2) skin diseases such as skin tumors via direct microscopic imaging; (3) gastrointestinal, oral, bronchial, cervical, and urinary diseases and tumors via endoscopy; (4) atherosclerotic plaques and other vascular abnormalities via flexible endoscopic catheters; (5) breast tumors via 2D- or 3D-image reconstruction; and (6) brain tumors, perfusion, and stroke via 2D- or 3D-image reconstruction.

In certain aspects, the compounds of the invention that are bioconjugates are particularly useful for imaging tumors, tissues, and organs in a subject. For example, the existence of cancer cells or cancer tissues can be verified by labeling an anti-tumor antibody with a compound of Formula I and then administering the bioconjugated antibody to the subject for detection and imaging of the tumor. Conjugates between the dye compound and other antibodies, peptides, polypeptides, proteins, ligands for cell surface receptors, small molecules, and the like are also useful agents for the in vivo imaging of tumors, tissues, and organs in a subject.

In certain aspects, the compounds of the invention may be administered either systemically or locally to the organ or tissue to be imaged, prior to the imaging procedure. In one aspect, the compounds are administered intravenously. In another aspect, the compounds are administered parenterally. In yet another aspect, the compounds are administered enterally. The compositions used for administration of the compound typically contain an effective amount of the compound or conjugate along with conventional pharmaceutical carriers and excipients appropriate for the type of administration contemplated. For example, parenteral formulations advantageously contain a sterile aqueous solution or suspension of a compound of Formula I (or Ia) or a bioconjugate of Formula II (or IIa). Compositions for enteral administration typically contain an effective amount of the compound or bioconjugate in aqueous solution or suspension that may optionally include buffers, surfactants, thixotropic agents, flavoring agents, and the like.

In certain aspects, the compositions are administered in doses effective to achieve the desired optical image of a tumor, tissue, or organ. Such doses may vary widely, depending upon the particular compound or bioconjugate employed, the tumor, tissue, or organ subjected to the imaging procedure, the imaging equipment being used, and the like.

In an alternative aspect, the method of the present invention provides for administering to the subject a therapeutically effective amount of a compound; a targeting agent, such as a bioconjugate; or mixtures thereof. In one aspect, the targeting agent selectively binds to the target tissue. Light at a wavelength or waveband corresponding to that which is absorbed by the photosensitizing agent is then administered. In another aspect, the compounds of the present invention act agents capable of binding to one or more types of target cells or tissues, when exposed to light of an appropriate waveband, absorb the light, causing substances to be produced that illuminate, impair or destroy the target cells or tissues. Preferably, the compound is nontoxic to the subject to which it is administered or is capable of being formulated in a nontoxic composition that can be administered to the subject. In addition, following exposure to light, the compound in any resulting photodegraded form is also preferably nontoxic.

In yet another aspect, the compounds of the present invention are administered by any means known in the art, including, but not limited to, ingestion, injection, transcutaneous administration, transdermal administration, intravenously, subcutaneously and the like. Preferably, the compounds are administered transcutaneously, intravenously, subcutaneously, or intramuscularly to a subject.

In certain aspects, during imaging, the light passes through unbroken tissue. Where the tissue layer is skin or dermis, such transcutaneous imaging includes transdermal imaging, and it will be understood that the light source is external to the outer skin layer. In some aspects (i.e., transillumination), the light passes through a tissue layer, such as the outer surface layer of an organ (e.g., the liver). In such cases, the light source is preferably external to the organ, but internal or implanted within the subject or patient.

In further aspects of the invention, the target tumor, tissue, or organ for treatment is selected from the group of vascular endothelial tissue, an abnormal vascular wall of a tumor, a solid tumor, a tumor of the head, a tumor of the neck, a tumor of a the gastrointestinal tract, a tumor of the liver, a tumor of the breast, a tumor of the prostate, a tumor of the ovary, a tumor of the uterus, a tumor of the testicle, a tumor of the lung, a nonsolid tumor, malignant cells of one of a hematopoietic tissue and a lymphoid tissue, lesions in the vascular system, a diseased bone marrow, neuronal tissue or diseased neuronal tissue, and diseased cells in which the disease is one of an autoimmune and an inflammatory disease. In yet a further aspect, the target tissue is a lesion in the vascular system of a type selected from the group of atherosclerotic lesions, arteriovenous malformations, aneurysms, and venous lesions.

In still further aspects, the forms of energy include, but are not limited to, light (i.e., radiation), thermal, sonic, ultrasonic, chemical, light, microwave, ionizing (such as x-ray and gamma ray), mechanical, and electrical. The term "radiation" as used herein includes all wavelengths and wavebands. Preferably, the radiation wavelength or waveband is selected to correspond with or at least overlap the wavelengths or wavebands that excite the photosensitizing agent. Compounds of the instant invention typically have one or more absorption wavebands that excite them to produce the substances which illuminate, damage or destroy target cells, tissues, organs, or tumors. Preferably, the radiation wavelength or waveband matches the excitation wavelength or waveband of the photosensitizing agent and has low absorption by the non-target cells and the rest of the subject, including blood proteins. More preferably, the radiation wavelength or waveband is within the NIR range of about 600 nm to about 1000 nm or a related range thereof (e.g., the ranges that are described in the instant claims).

In certain aspects, the compounds of the present invention are used to directly stain or label a sample so that the sample can be identified or quantitated. For instance, such compounds can be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like.

A detectable optical response as used herein includes a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some compounds of the invention may exhibit little fluorescence emission, but are still useful as quenchers or chromophoric dyes. Such chromophores are useful as energy acceptors in FRET applications, or to simply impart the desired color to a sample or portion of a sample.

FRET is a process by which a donor molecule (e.g., a dye) absorbs light, entering an excited state. Rather than emitting light, the first molecule transfers its excited state to a acceptor molecule with other properties (e.g., a dye fluorescing at a different wavelength or a quencher), and the acceptor fluoresces or quenches the excitation. Because the efficiency of the transfer is dependant on the two molecules' proximity, it can indicate information about molecular complex formation or biomolecular structure. It can also indicate where a particular complex is located within a cell or organism (e.g., FRET optical microscopy). For ways to use similar dyes as acceptors (quenchers) in FRET processes, see X. Peng, H. Chen, D. R. Draney, W. Volcheck, A. Schultz-Geschwender, and D. M. Olive, "A nonfluorescent, broad-range quencher dye for Förster resonance energy transfer assays," *Anal. Biochem* 2009, 388(2): 220-228.

In certain aspects, for biological applications, the compounds of the invention are typically used in an aqueous, mostly aqueous, or aqueous-miscible solution prepared according to methods generally known in the art. The exact concentration of compound is dependent upon the experimental conditions and the desired results, but ranges of 0.00001 mM up to 0.1 mM, such as about 0.001 mM to about 0.01 mM, are possible. The optimal concentration is determined by systematic variation until satisfactory results with minimal background fluorescence is accomplished.

In certain aspects, the method may involve treatment of an animal or sample with a dose comprising a compound of Formula I, a bioconjugate of Formula II, or any of the aspects or embodiments thereof. The exact concentration of compound is dependent upon the subject and the desired results. In certain embodiments, a dose of at least about 0.001, 0.005, 0.01, 0.025, 0.05, or 0.075 mg/kg is used. Alternatively, a dose of at most about 0.001, 0.005, 0.01, 0.025, 0.05, or 0.075 mg/kg is used. In certain other embodiments, a dose of at least about 0.1, 0.25, 0.5, or 0.75 mg/kg is used. Alternatively, a dose of at most about 0.1, 0.25, 0.5, or 0.75 mg/kg is used. In still other embodiments, a dose of at least about 0.1, 0.25, 0.5, or 0.75 mg/kg is used. Alternatively, a dose of at most about 0.1, 0.25, 0.5, or 0.75 mg/kg is used. In yet still other embodiments, a dose of at least about 1, 2.5, 5, or 7.5 mg/kg is used. Alternatively, a dose of at most about 1, 2.5, 5, or 7.5 mg/kg is used. In additional other embodiments, a dose of at least about 10, 25, 50, or 75 mg/kg is used. Alternatively, a dose of at most about 10, 25, 50, or 75 mg/kg is used. In additional still other embodiments, a dose of at least about 100, 250, 500, or 750 mg/kg is used. Alternatively, a dose of at most about 100, 250, 500, or 750 mg/kg is used. Other amounts for administration of an effective dose may be readily determined by one of skill in the art.

In certain aspects, in vitro, the compounds are advantageously used to stain samples with biological components. The sample can comprise heterogeneous mixtures of components (e.g., mixtures including intact cells, fixed cells, cell extracts, bacteria, viruses, organelles, and combinations thereof), or a single component or homogeneous group of components (e.g. natural or synthetic amino acid, nucleic acid or carbohydrate polymers, or lipid membrane complexes). Within the concentrations of use, these compounds are generally non-toxic to living cells and other biological components.

The compound is combined with the sample in any way that facilitates contact between the compound and the sample components of interest. Typically, the compound or a solution containing the compound is simply added to the sample. Certain compounds of the invention, particularly those that are substituted by one or more sulfonic acid moieties, tend to be impermeant to membranes of biological cells, and once inside viable cells, they are typically well-retained. Treatments that permeabilize the plasma membrane, such as electroporation, shock treatments or high extracellular ATP, can be used to introduce selected compounds into cells. Alternatively, selected dye compounds can be physically inserted into cells, e.g., by pressure microinjection, scrape loading, patch clamp methods, or phagocytosis.

Alternatively, dye compounds can be conjugated to a biomolecule that increases their uptake into cells (e.g., cell-penetrating peptides such as Tat, penetratin, transportin, derivatives thereof (e.g., Tat derivatives incorporating β- and γ-amino acids), and the like). This general approach is usable in vitro or in vivo.

In certain aspects, at any time after or during staining, the sample is illuminated with a wavelength of light selected to give a detectable optical response, and observed with a means for detecting the optical response. Equipment that is useful for illuminating the compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred aspects of the invention are compounds that are excitable at or near the wavelengths 633-636 nm, 647 nm, 649 nm, 651 nm, 647-651 nm, 660 nm, 674 nm, 675 nm, 678 nm, 680 nm, 674-680 nm, 685 nm, 674-685 nm, 680-685 nm, 685-690 nm, 690-695 nm, 690-700 nm, and beyond 700 nm, such as 780 nm, 810 nm and 850 nm, as these regions closely match the output of exemplary compounds or of relatively inexpensive excitation sources.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined by means of a flow cytometer, examination of the sample optionally includes sorting portions of the sample according to their fluorescence response.

EXAMPLES

Below, the present invention will be described by way of examples, which are provided for illustrative purposes only. Accordingly, they are not to be construed as limiting the scope of the present invention as defined by the appended claims.

Example 1

Preparation of
5-Chloro-2,3,3-trimethyl-3H-pyrrolo[2,3-b]pyridine
(1)

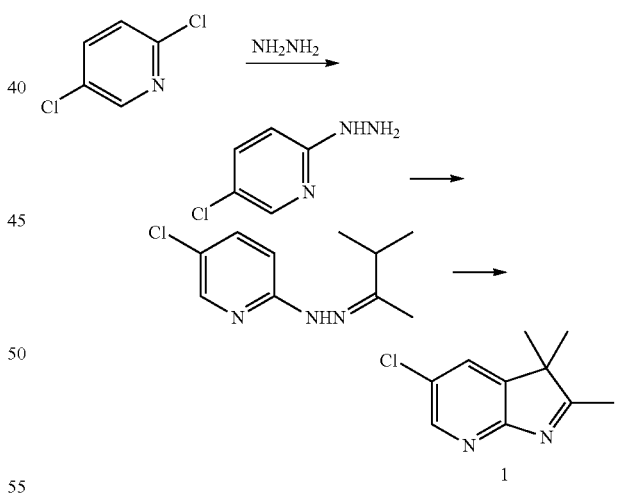

5-Chloro-2,3,3-trimethyl-3H-pyrrolo[2,3-b]pyridine
(1)

To 2,5-dichloropyridine (40. g, 0.27 mol) in 2-methoxyethanol (200 mL) was added anhydrous hydrazine (20.0 mL, 0.625 mol). The mixture was heated at 110° C. for 3 h to generate the 5-chloro-hydrazinopyridine. To form the hydrazone, a mixture of 10 g of the hydrazinopyridine and 11 mL of 3-methyl-2-butanone in 40 mL of benzene was heated at reflux overnight in a flask equipped with a Dean-Stark trap.

All of the volatile components were removed under reduced pressure, and the resulting hydrazone residue was heated in 50 g of polyphosphoric acid at 135° C. for 45 min. The reaction mixture was poured into water, neutralized with sodium hydroxide, and extracted with ethyl acetate. The resulting crude residue was purified by chromatography on silica gel (1:1 ethyl acetate/hexanes) to yield 2.50 g of 5-chloro-2,3,3-trimethyl-3H-pyrrolo[2,3-b]pyridine (1).

Example 2

Preparation of 2,3,3-Trimethyl-3H-pyrrolo[2,3-b]pyridine (2)

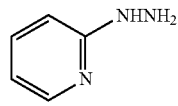
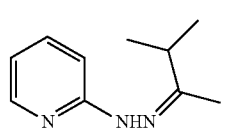

2,3,3-Trimethyl-3H-pyrrolo[2,3-b]pyridine (2)

Compound 2 is prepared analogously to compound 1 (Example 1), except that 2-hydrazinopyridine is used as a starting material.

Example 3

Preparation of 5-Bromo-2,3,3-trimethyl-3H-pyrrolo[2,3-b]pyridine (3)

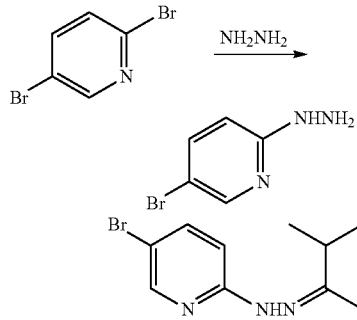
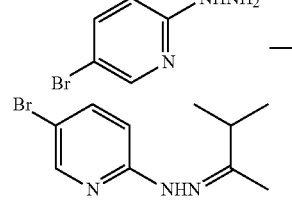
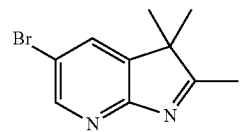

5-Bromo-2,3,3-trimethyl-3H-pyrrolo[2,3-b]pyridine (3)

Compound 3 was prepared analogously to compound 1 (Example 1), except that 2,5-dibromopyridine was used as a starting material.

Example 4

Preparation of Sodium 2,3,3-Trimethyl-1-(3-sulfonatopropyl)-3H-indolium-5-sulfonate (4)

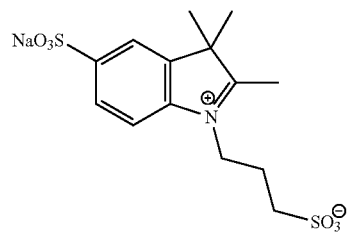

Sodium 2,3,3-Trimethyl-1-(3-sulfonatopropyl)-3H-indolium-5-sulfonate 4)

A mixture of 14 g of sodium 2,3,3-trimethyl-3H-indole-5-sulfonate and 14 g 1,3-propanesultone in 100 mL dicholorobenzene was heated at 110° C. for 2 h. After it cooled down, the solvent is decanted. The resulting solid was then dissolved in 100 mL of acetonitrile, and 300 mL of ethyl acetate was added. The resulting sticky solid was again stirred in 300 mL of ethyl acetate to yield 20 g of the product.

Example 5

Preparation of 3-(5-Chloro-2,3,3-trimethyl-3H-pyrrolo[2,3-b]pyridin-7-ium-7-yl)propane-1-sulfonate (5)

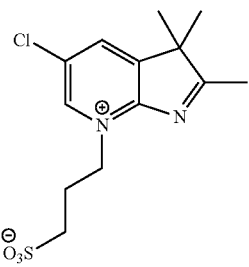

3-(5-Chloro-2,3,3-trimethyl-3H-pyrrolo[2,3-b]pyridin-7-ium-7-yl)propane-1-sulfonate (5)

A mixture of 1 g of 5-chloro-2,3,3-trimethyl-3H-pyrrolo[2,3-b]pyridine and 1.60 g of 1,3-propanesultone was heated at 65° C. for 2 h. Ethyl acetate (ca. 100 mL) was added and the resulting mixture was stirred at room temperature overnight to yield 2.50 g of the product.

Example 6

Preparation of 3-(5-Bromo-2,3,3-trimethyl-3H-pyrrolo[2,3-b]pyridin-7-ium-7-yl)propane-1-sulfonate (6)

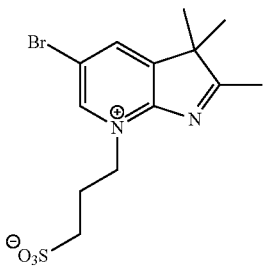

3-(5-Bromo-2,3,3-trimethyl-3H-pyrrolo[2,3-b]pyridin-7-ium-7-yl)propane-1-sulfonate (6)

Compound 6 was prepared analogously to compound 5 (Example 5), except that 5-bromo-2,3,3-trimethyl-3H-pyrrolo[2,3-b]pyridine (50) was used as a starting material.

Example 7

Preparation of 3-(2,3,3-Trimethyl-3H-pyrrolo[2,3-b]pyridin-7-ium-7-yl)propane-1-sulfonate (7)

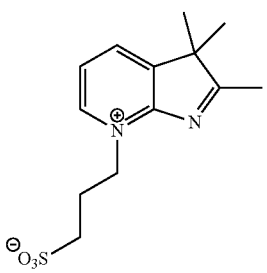

3-(2,3,3-Trimethyl-3H-pyrrolo[2,3-b]pyridin-7-ium-7-yl)propane-1-sulfonate (7)

A mixture of 9 g of 2,3,3-trimethyl-3H-pyrrolo[2,3-b]pyridine and 20.6 g of 1,3-propanesultone is heated at 60° C. for 3 h. The reaction mixture is then dissolved in 100 mL of acetonitrile, and 300 mL of ethyl acetate is added. The resulting sticky solid is again stirred in 300 mL of ethyl acetate to yield 22 g of the product.

Example 8

Preparation of (E)-N—((Z)-2-Bromo-3-(phenylamino)allylidene)benzenaminium Bromide (8)

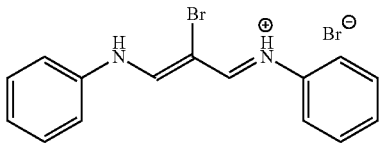

(E)-N—((Z)-2-Bromo-3-(phenylamino)allylidene) benzenaminium Bromide (8)

The procedure as disclosed in the literature (Simonis, H. Ber. Deut. Chem. Ges. 1901, 34, 509; U.S. Pat. No. 6,747, 159) is used. 3.54 g of aniline are dissolved in 15 mL of ethanol in a 100 mL beaker. Separately, 5 g of mucobromic acid are dissolved in 15 mL of ethanol in a 100 mL Erlenmeyer flask. This solution is added dropwise to the aniline/ethanol solution, with cooling. The reaction mixture turns immediately yellow, then orange, with development of $CO_2$. At the end of the addition, the mixture is heated in a water bath until its volume is reduced by one half. The resulting solution is cooled with an ice-salt mixture, forming a yellow crystalline precipitate. This solid is collected on a fritted glass filter to afford a first fraction of pure product 5 (3.84 g, 52% yield). Additional product 5 can be recovered from concentration and recrystallization of the mother liquor.

Example 9

Preparation of Sodium (E)-2-((2Z,4E)-3-Bromo-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (9)

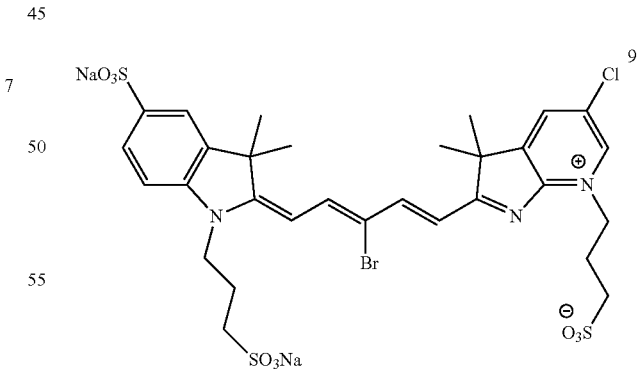

Sodium (E)-2-((2Z,4E)-3-Bromo-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (9)

A 100-mL round-bottom flask fitted with a reflux condenser was charged with 3-(5-chloro-2,3,3-trimethyl-3H- pyrrolo[2,3-b]pyridin-7-ium-7-yl)propane-1-sulfonate (55, 500 mg), sodium 2,3,3-trimethyl-1-(3-sulfonatopropyl)-3H-indolium-5-sulfonate (4, 500 mg), (E)-N—((Z)-2-bromo-3-(phenylamino)allylidene)benzenaminium bromide (8, 100 mg), pyridine (1 mL), and acetic anhydride (10 mL) were added to the flask. The mixture was heated at 115° C. for 2 h, allowed to cool to room temperature, and diluted with ethyl ether (25 mL). The resulting dark blue dye precipitate was collected by filtration, dissolved in water (20 mL), and purified by preparative reverse-phase HPLC to afford the 9 as a blue powder (285 mg, 50%, UV 668 nm).

Example 10

Preparation of Sodium (E)-2-(2Z,4E)-3-(3-(2-Carboxyethyl)phenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (10)

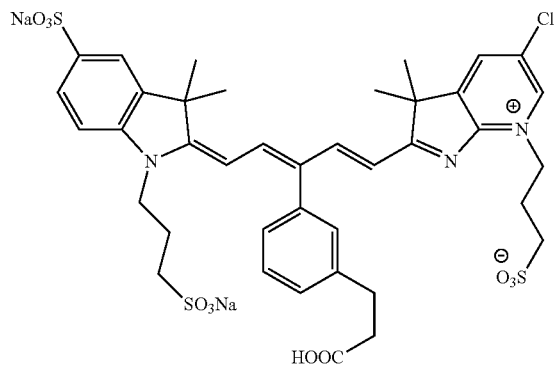

Sodium (E)-2-(2Z,4E)-3-(3-(2-Carboxyethyl)phenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl) indoline-5-sulfonate (10)

Compound 9 (80 mg), 3-(2-carboxyethyl)phenylboronic acid (40 mg), and cesium carbonate (20 mg) were stirred into water (20 mL) under nitrogen at room temperature. Tetrakis (triphenylphosphine)palladium (0) (10 mg) were added to the reaction mixture. The mixture was refluxed for 4 h, and the solvent and volatile compounds then were evaporated under vacuum. The crude product was purified by flash chromatography on silica 60, 200-400 mesh, eluting with a 20/80 acetonitrile/water mixture. The purified compound 56 had $\lambda_{MeOH}$=680 nm, $\lambda_{PBS}$=672 nm, $\epsilon$=160,000. The absorption and emission data is shown in Table 2 and FIG. 1.

TABLE 2

| Absorption and Emission of Compound 10 | | | |
|---|---|---|---|
| | Extinction Coefficient | Max. Abs. (nm) | Max. Emis. (nm) |
| PBS | 160,000 | 672 | 694 |
| MeOH | 170,000 | 680 | 694 |

Example 11

Preparation of Sodium (E)-2-((2Z,4E)-5-(5-Chloro-3,3-dimethyl-7-(3-sulfonatopropyl)-3H-pyrrolo[2,3-b]pyridin-7-ium-2-yl)-3-(3-(3-(2,5-dioxopyrrolidin-1-yloxy)-3-oxopropyl)phenyl)penta-2,4-dienylidene)-3,3-dimethyl-1-(3-sulfonatopropyl) indoline-5-sulfonate (11)

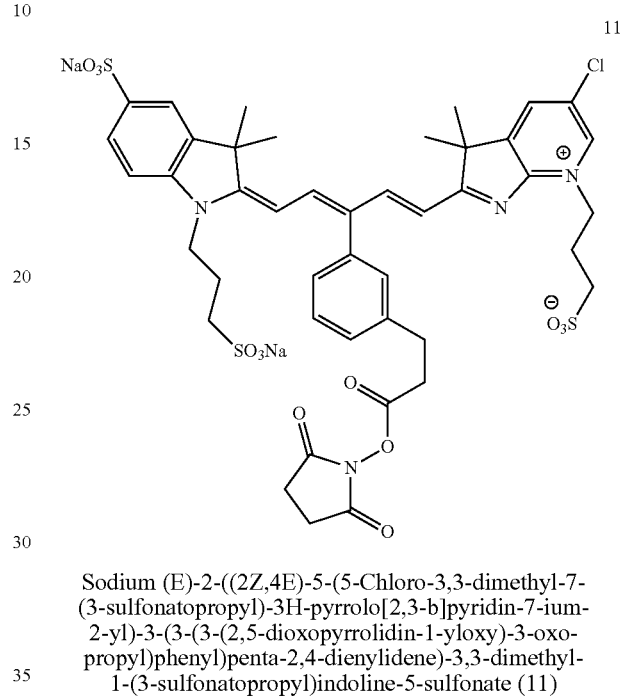

Sodium (E)-2-((2Z,4E)-5-(5-Chloro-3,3-dimethyl-7-(3-sulfonatopropyl)-3H-pyrrolo[2,3-b]pyridin-7-ium-2-yl)-3-(3-(3-(2,5-dioxopyrrolidin-1-yloxy)-3-oxopropyl)phenyl)penta-2,4-dienylidene)-3,3-dimethyl-1-(3-sulfonatopropyl)indoline-5-sulfonate (11)

To compound 10 (200 mg) and dry DMSO (15 mL) was added triethylamine (150 μL) and N,N'-disuccinimidyl carbonate (82 mg). The mixture was stirred at room temperature for 2 h and then precipitated into diethyl ether (100 mL). The resulting solid was dried under vacuum to yield the N-hydroxy succinimidyl ester.

Example 12

Preparation of Sodium (E)-2-((2Z,4E)-3-(4-(2-Carboxyethyl)phenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (12)

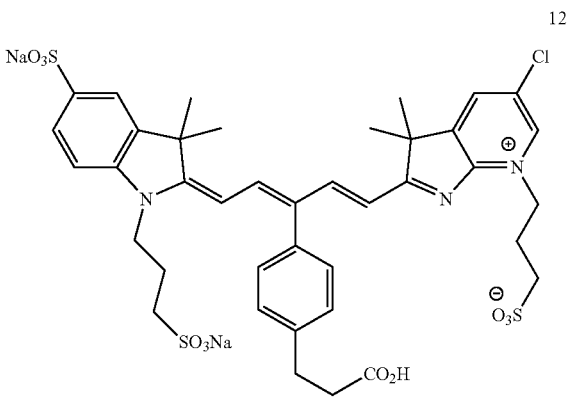

Sodium (E)-2-((2Z,4E)-3-(4-(2-Carboxyethyl)phenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (12)

Compound 12 is prepared analogously to compound 10 (Example 10), except that 4-(2-carboxyethyl)phenylboronic acid is used as a starting material.

Example 13

Preparation of Sodium (E)-2-((2Z,4E)-5-(5-chloro-3,3-dimethyl-7-(3-sulfonatopropyl)-3H-pyrrolo[2,3-b]pyridin-7-ium-2-yl)-3-(4-(3-(2,5-dioxopyrrolidin-1-yloxy)-3-oxopropyl)phenyl)penta-2,4-dienylidene)-3,3-dimethyl-1-(3-sulfonatopropyl)indoline-5-sulfonate (13)

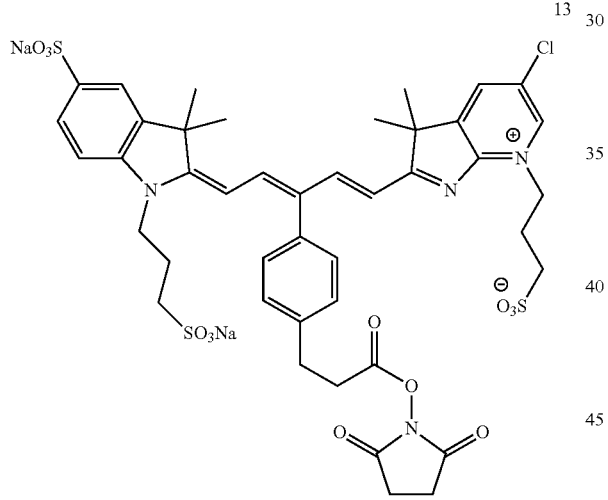

Sodium (E)-2-((2Z,4E)-5-(5-chloro-3,3-dimethyl-7-(3-sulfonatopropyl)-3H-pyrrolo[2,3-b]pyridin-7-ium-2-yl)-3-(4-(3-(2,5-dioxopyrrolidin-1-yloxy)-3-oxopropyl)phenyl)penta-2,4-dienylidene)-3,3-dimethyl-1-(3-sulfonatopropyl)indoline-5-sulfonate (13)

Compound 13 is prepared analogously to compound 11 (Example 11), except that compound 12 is used as a starting material.

Example 14

Preparation of Sodium (E)-2-((2Z,4E)-5-(5-Chloro-3,3-dimethyl-7-(3-sulfonatopropyl)-3H-pyrrolo[2,3-b]pyridin-7-ium-2-yl)-3-(3-(3-(2-(2,5-dioxo-2,5-dihydro-1H-pyrrol-1-yl)ethylamino)-3-oxopropyl)phenyl)penta-2,4-dienylidene)-3,3-dimethyl-1-(3-sulfonatopropyl)indoline-5-sulfonate (14)

Sodium (E)-2-((2Z,4E)-5-(5-Chloro-3,3-dimethyl-7-(3-sulfonatopropyl)-3H-pyrrolo[2,3-b]pyridin-7-ium-2-yl)-3-(3-(3-(2-(2,5-dioxo-2,5-dihydro-1H-pyrrol-1-yl)ethylamino)-3-oxopropyl)phenyl)penta-2,4-dienylidene)-3,3-dimethyl-1-(3-sulfonatopropyl)indoline-5-sulfonate (14)

The NHS ester dye 11 (0.18 mmol) is dissolved in 20 mL of dry DMSO and stirred at room temperature under dry nitrogen. Next, 2-maleimido ethyl amine (93.2 mg, 0.37 mmol) is added to the stirred solution, followed by diisopropyl ethyl amine (DIPEA) (95 mg, 0.55 mmol). The stirring is continued for 45 min. DMF (20 mL) is added to the reaction, and stirring continued until thorough mixing is achieved. The solution is then poured slowly into 400 mL of stirred diethyl ether to precipitate the product. The ether suspension is stirred for an additional 5 min and then allowed to stand for 1 hr. The ether is decanted, and an additional 20 mL of DMF is added to redissolve the solid. The DMF solution is then precipitated into a second 400 mL portion of stirred ether. The crude product is collected by filtration. Optionally, further purification can be performed, for example, by HPLC, column chromatography, or recrystallization.

Example 15

Preparation of Sodium (E)-2-((2Z,4E)-3-(4-carboxyphenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl) indoline-5-sulfonate (15)

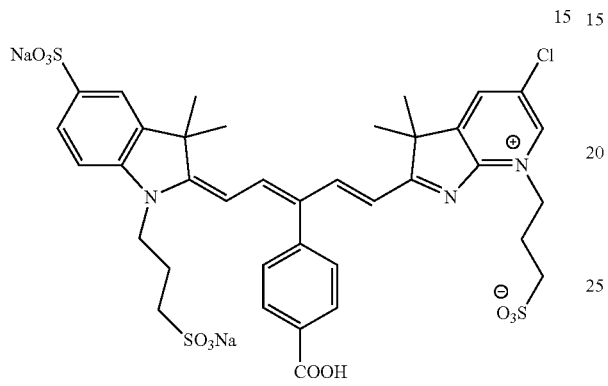

Sodium (E)-2-((2Z,4E)-3-(4-carboxyphenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl) indoline-5-sulfonate (15)

Compound 15 is prepared analogously to compound 10 (Example 10), except that 4-carboxyphenylboronic acid is used as a starting material. $\lambda_{MeOH}$=680 nm.

Example 16

Preparation of Sodium 2-((E)-2-((E)-2-Chloro-3-((E)-2-(3,3-dimethyl-7-(3-sulfonatopropyl)-3,7-dihydro-2H-pyrrolo[2,3-b]pyridin-2-ylidene)ethylidene)cyclohex-1-enyl)vinyl)-3,3-dimethyl-1-(3-sulfonatopropyl)-3H-indolium-5-sulfonate (16)

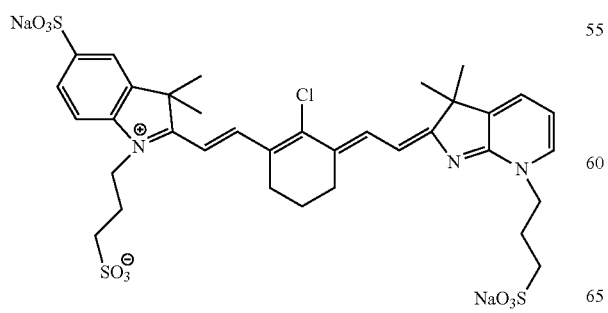

Sodium 2-((E)-2-((E)-2-Chloro-3-((E)-2-(3,3-dimethyl-7-(3-sulfonatopropyl)-3,7-dihydro-2H-pyrrolo[2,3-b]pyridin-2-ylidene)ethylidene)cyclohex-1-enyl)vinyl)-3,3-dimethyl-1-(3-sulfonatopropyl)-3H-indolium-5-sulfonate (16)

Compound 16 is prepared analogously to compound 9 (Example 9), except that compound 4, compound 7, and N-[(3-(anilinomethylene)-2-chloro-1-cyclohexen-1-yl)methylene]aniline monohydrochloride are used as starting materials.

Example 17

Preparation of Sodium (E)-2-((E)-2-(2-(4-Carboxyphenyl)-3-((E)-2-(3,3-dimethyl-7-(3-sulfonatopropyl)-3H-pyrrolo[2,3-b]pyridin-7-ium-2-yl)vinyl)cyclohex-2-enylidene)ethylidene)-3,3-dimethyl-1-(3-sulfonatopropyl)indoline-5-sulfonate (17)

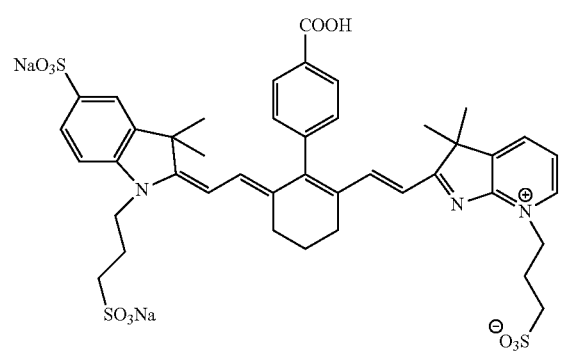

Sodium (E)-2-((E)-2-(2-(4-Carboxyphenyl)-3-((E)-2-(3,3-dimethyl-7-(3-sulfonatopropyl)-3H-pyrrolo[2,3-b]pyridin-7-ium-2-yl)vinyl)cyclohex-2-enylidene)ethylidene)-3,3-dimethyl-1-(3-sulfonatopropyl)indoline-5-sulfonate (17)

Compound 17 is prepared analogously to compound 10 (Example 10), except that 4-carboxyphenylboronic acid and compound 16 are used as starting materials.

Example 18

Preparation of (E)-N-((E)-4-Carboxy-2-((phenylamino)methylene)butylidene)benzenaminium chloride (18)

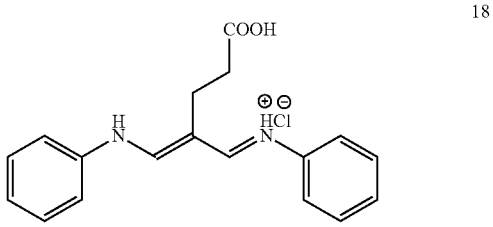

Compound 18 is made by using a modified procedure from W.I.P.O. Patent Publication WO 2010/054330s, which is incorporated by reference. (See also its priority document, U.S. Provisional Patent Application 61/112,535 (filed Nov. 7, 2008) and Jauer, E. A.; Foerster, E.; Hirsch, B. Journal Fuer Signalaufzeichnungsmaterialien 1975 3(2) 155-163, both of which are also incorporated by reference.) Anhydrous dimethylformamide (1.01 mL, 13 mmol) and phosphorus oxychloride (1.53 g, 10 mmol) are added sequentially into 30 mL anhydrous dichloromethane (DCM) in an acetone/dry ice bath. The mixture is allowed to warm to room temperature over 15 min. Methyl 5,5-dimethoxyvalerate (881 mg, 5 mmol) is then added dropwise to the reaction solution followed by heating at 70° C. for 2 h, allowing the DCM to evaporate. The resulting yellow oil is dissolved in 5 mL of 4 M aqueous NaOH, and the solution and is heated at 70° C. for 1 hour. Next, with constant cooling at 20° C., anline/EtOH [1:1, (v/v), 10 mL] is added dropwise. The reaction is continued for an additional 30 min after aniline addition, and then the yellow mixture is poured into ice-cold water/concentrated aqueous HCl (10:1, 11 mL). The final malonaldehyde dianil hydrochloride salts are precipitated as light yellow solids after the addition of 5 mL of 10% aqueous HCl and were collected by filtration. The products are above 95% pure and are used directly in the dye synthesis without further purification if not mentioned specifically.

Example 19

Preparation of Sodium (E)-2-((2E,4E)-3-(2-Carboxyethyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (19)

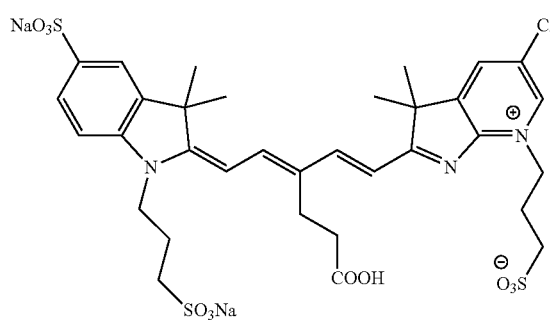

19

Sodium (E)-2-((2E,4E)-3-(2-Carboxyethyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (19)

Compound 19 is prepared analogously to compound 9 (Example 9), except that compound 18 is used as a starting material. $\lambda_{MeOH}$=680 nm.

Example 20

Preparation of Compound 11-Streptavidin Conjugates

Compound 11 is reconstituted in DMF to 1 mg/mL. Streptavidin is reconstituted typically at 10 mg/ml in PBS buffer (pH 8.5). The dyes are added (at various molar excesses) to the streptavidin samples and allowed to incubate for 2 h at room temperature in the dark. The conjugates are extensively dialyzed against PBS buffer to remove the unconjugated free dye. The ratio of moles of dye per mole of protein is calculated by using the equation below.

$$D/P = \left[\frac{A_{685}}{\varepsilon_{Dye}}\right] \div \left[\frac{A_{280} - (0.07 \times A_{685})}{\varepsilon_{Streptavidin}}\right]$$

In which:

$\varepsilon_{dye}$=160,000 $M^{-1}cm^{-1}$ $\varepsilon_{streptavidin}$=175,000 $M^{-1}cm^{-1}$ 0.07 is the correction factor for the dye absorption at 280 nm

Example 21

Western Blot Comparison of GAM/IRDye® 20 and GAM/10 Conjugates

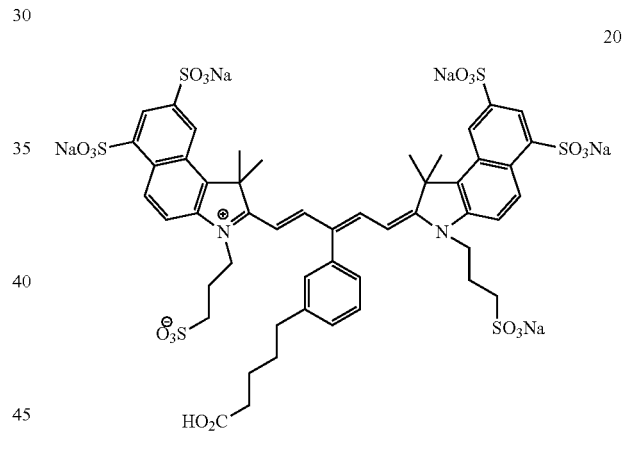

20

Western blots were performed to compare GAM/IRDye 20 (GAM/20) and GAM/10 (GAM/10) conjugates against a GAM/IRDye® 680 control (GAM/680). The blots were probed with two different primary antibodies to determine if the extra bands were specific or were caused by dye sticking to the lysate.

Jurkat lysate was run (5 μg to 78 ng) by SDS PAGE and transferred to nitrocellulose. Blots were blocked with Odyssey Blocking Buffer+0.2% Tween 20 (OBBT). Blots were probed with either monoclonal anti-actin (Neomarkers MS-1295-P1) or monoclonal anti-tubulin (Sigma T7816) diluted in OBBT. Blots were then detected with one of the following secondary antibodies diluted in OBBT to a final concentration of 0.1 μg/ml: GAM/20, D/P=1.6 (Lot JE524089); GAM/10, D/P=1.6 (Lot JE524089); or GAM/680.

Figure 2:
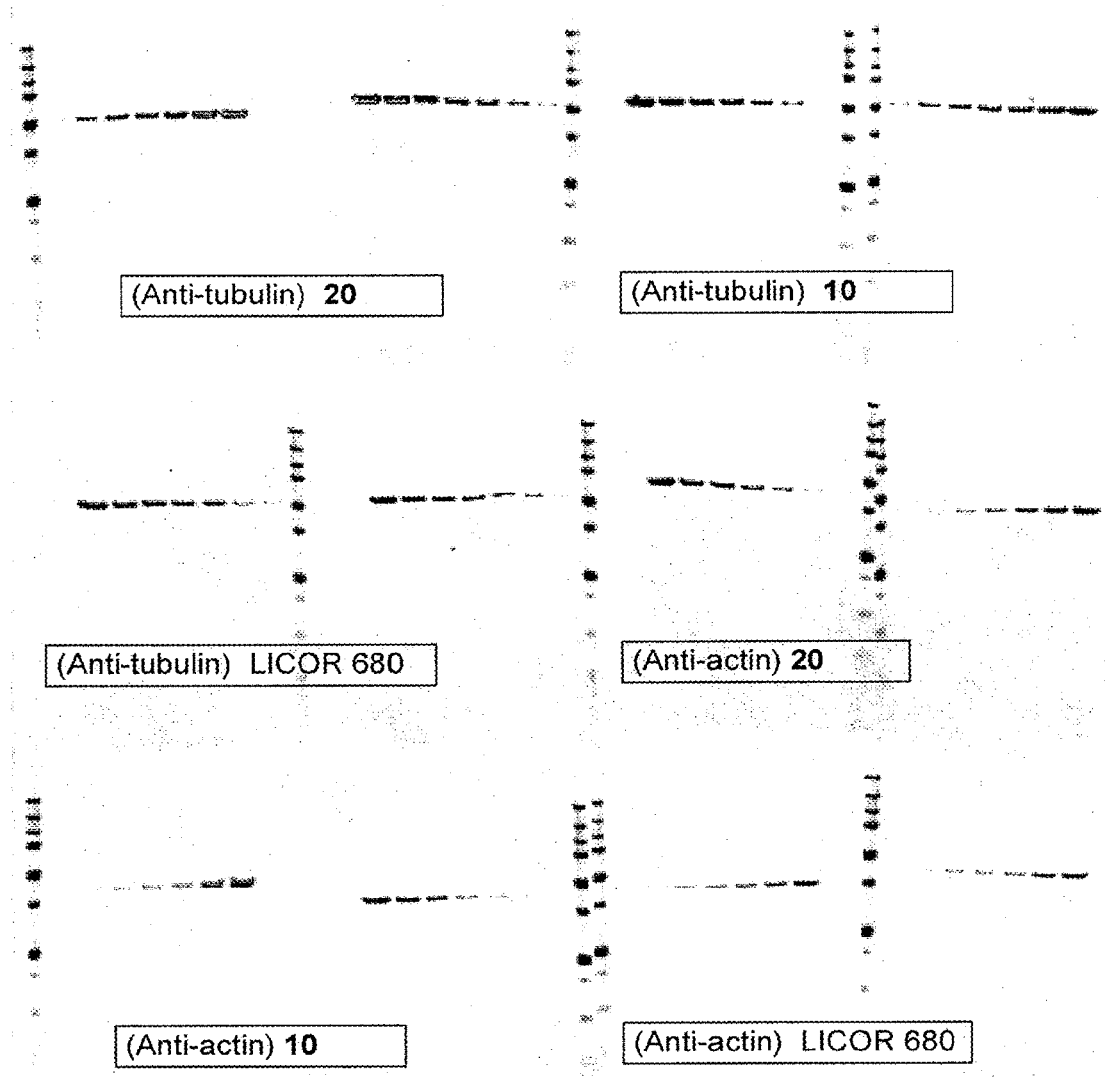
FIG. 2 illustrates a Western blot total fluorescence comparison of p38 GAR antibody conjugates with compound 10, compound 20, and IRDye® 680 ("LICOR 680").

The blots are shown in FIG. 2. A summary of intensities are listed in Table 3 below:

TABLE 3

Western Blot Comparison of Total Fluorescence of
GAM/20, GAM/10, and GAM/680 Antibody Bioconjugates

| Blots | Anti-tubulin | I.I. (K Counts) Sample | Bkgd Sample | Mean Intensity Sample | Std Dev. | % Intensity of Control | % Bkgd of Control |
|---|---|---|---|---|---|---|---|
| 1 | GAM/680 | 82.73 | 233 | 74.21 | 12.06 | control | control |
| 2 |  | 65.68 | 243 |  |  |  |  |
| 3 | GAM/20 | 171.16 | 262 | 191.85 | 29.26 | 259 | 108 |
| 4 |  | 212.54 | 250 |  |  |  |  |
| 5 | GAM/10 | 119.28 | 223 | 125.58 | 8.91 | 169 | 99 |
| 6 |  | 131.88 | 249 |  |  |  |  |
| 7 | GAM/680 | 18.21 | 246 | 17.24 | 1.37 | control | control |
| 8 |  | 16.27 | 255 |  |  |  |  |
| 9 | GAM/20 | 42.57 | 274 | 39.89 | 3.79 | 231 | 110 |
| 10 |  | 37.21 | 275 |  |  |  |  |
| 11 | GAM/10 | 18.51 | 255 | 21.73 | 4.55 | 126 | 100 |
| 12 |  | 24.95 | 248 |  |  |  |  |

The signal intensities are expressed in arbitrary fluorescence units ("Counts"), with the sample values divided by 1000 for convenience ("K Counts") after subtraction of background. In general, protein detection and quantitation are enhanced by increased fluorescence intensity and by low fluorescence background.

It appears that the GAM/20 is about 2× more intense than the GAM/680 control and the GAM/10 is about 1× more intense than the control. Both samples have comparable backgrounds to the control. The limit of detection was not determined.

Example 22

In-Cell Western Evaluation of GAM/20 and GAM/10

The low fluorescence background for biological materials in the NIR enables experiments in live or fixed cells in microplates. An important example is the In-Cell Western ("ICW") technique, a cell-based immunohistochemical assay of cellular proteins in fixed cells. In such systems it is important that the dye-labeled antibody used for detection maintains the very low fluorescence background of the original cellular environment. Thus, the dye molecules attached to the detection antibody must have very low non-specific binding to other cellular proteins, to membranes, etc., or the labeled antibody will stick to those features and ruin the experiment.

The GAM bioconjugate with compounds 20 and 10 were evaluated by ICW. LI-COR IRDye® 680/GAM bioconjugate (i.e., LI-COR Part No. 926-32220) and AlexaFluor® 680 (GAM/AF-680) were used as controls. A431 cells, ATCC Part No. CRL-1555, were seeded in a 96 well plate and incubated at 37° C. for 48 hours. Cells were then fixed with 37% formaldehyde and permeabilized with PBS+0.1% Triton® X-100. After permeabilization, cells were blocked with Odyssey® Blocking Buffer.

GAM/compound 10 and GAM/compound 20 conjugates were both diluted in Odyssey® Blocking Buffer+0.2% Tween® 20 and added to the plate at a final concentration of 2 μg/mL, 12 wells per sample. Samples were incubated with gentle shaking at room temperature for 1 hour. The plate was washed three times with PBS+0.2% Tween® 20 and scanned on a LI-COR Odyssey® Infrared Imager, using the Microplate 2 preset. The average integrated intensity was calculated for each sample and the compound 10- and 20-GAM antibody was compared to the controls. Average background values were calculated and compared to controls. The results are listed in Tables 4 and 5 below.

TABLE 4

Comparison of Average Background Values for Example 25

| Sample | GAM/680 | GAM/AF-680 | GAM/20 | GAM/10 | OBB Only |
|---|---|---|---|---|---|
| Average | 4.07 | 4.35 | 5.24 | 4.02 | 4.08 |
| Std. Dev. | 0.21 | 0.61 | 1.37 | 0.12 | 0.14 |
| % CV | 5.06 | 14.00 | 26.19 | 2.89 | 3.51 |

TABLE 5

Comparison of Average Intensities for Example 25

| Sample | Antibody | Ave. Intensity | % Control | <200% Control? |
|---|---|---|---|---|
| 1 | GAM/680 | 4.07 | control | control |
| 2 | GAM/20 | 5.24 | 129 | yes |
| 3 | GAM/10 | 4.02 | 99 | yes |
| 4 | GAM/AF-680 | 4.35 | control | control |
| 5 | GAM/20 | 5.24 | 120 | yes |
| 6 | GAM/10 | 4.02 | 92 | yes |

The inventive dyes (20/21, 10/11) performed well. The backgrounds and signal intensities were comparable to those for the commercial antibody conjugates.

Antibodies labeled with IRDye® 680 or with Alexa Fluor® 680 maintain very low non-specific binding to cells. The data of Table 4 demonstrate that the GAM antibody labeled with compound 20 also has very low non-specific background as good as or better than the other dyes tested. This dye can be used to produce labeled antibodies suitable for ICW and other cell-based (in vivo) applications.

Example 23

Preparation of sodium 2-((2S,5R,8S,11S)-5-benzyl-8-(4-(3-(3-((1E,3Z,5Z)-1-(5-chloro-3,3-dimethyl-7-(3-sulfonatopropyl)-3H-pyrrolo[2,3-b]pyridin-7-ium-2-yl)-5-(3,3-dimethyl-5-sulfonato-1-(3-sulfonatopropyl)indolin-2-ylidene)penta-1,3-dien-3-yl)phenyl)propanamido)butyl)-11-(3-guanidinopropyl)-3,6,9,12,15-pentaoxo-1,4,7,10,13-pentaazacyclopentadecan-2-yl)acetate (21)

Example 24

Evaluation of 10 for In Vivo Optical Imaging

The suitability of compound 10 for in vivo optical imaging was evaluated using an 10-labeled cyclo(Arg-Gly-Asp-D-Phe-Lys) (RGDfK) probe. This probe was specifically designed to target integrins. Integrins are cell surface heterodimeric glycoproteins important in cell adhesion and signal transduction. This receptor class is involved in tumor

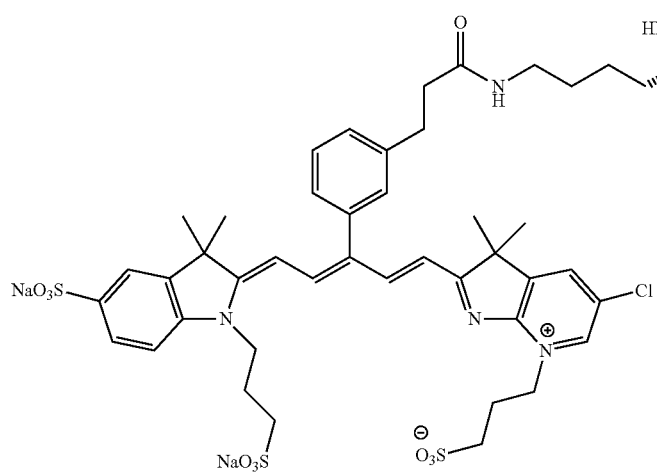
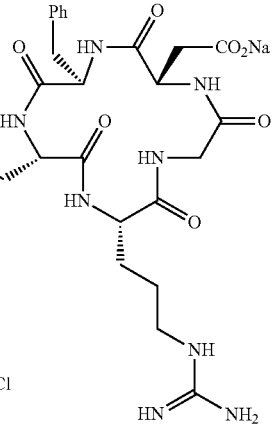

Sodium 2-((2S,5R,8S,11S)-5-benzyl-8-(4-(3-(3-((1E,3Z,5Z)-1-(5-chloro-3,3-dimethyl-7-(3-sulfonatopropyl)-3H-pyrrolo[2,3-b]pyridin-7-ium-2-yl)-5-(3,3-dimethyl-5-sulfonato-1-(3-sulfonatopropyl)indolin-2-ylidene)penta-1,3-dien-3-yl)phenyl)propanamido)butyl)-11-(3-guanidinopropyl)-3,6,9,12,15-pentaoxo-1,4,7,10,13-pentaazacyclopentadecan-2-yl)acetate
(21)

The NHS ester dye 13 (0.18 mmol) is dissolved in 20 mL of dry DMSO and stirred at room temperature under dry nitrogen. Next, the cyclic pentapeptide cyclo (Arg-Gly-Asp-D-Phe-Lys) (0.37 mmol) is added to the stirred solution, followed by diisopropyl ethyl amine (DIPEA) (95 mg, 0.55 mmol). The stirring is continued for 45 min. DMF (20 mL) is added to the reaction, and stirring continued until thorough mixing is achieved. The solution is then poured slowly into 400 mL of stirred diethyl ether to precipitate the product. The ether suspension is stirred for an additional 5 min and then allowed to stand for 1 hr. The ether is decanted, and an additional 20 mL of DMF is added to redissolve the solid. The DMF solution is then precipitated into a second 400 mL portion of stirred ether. The crude product is collected by filtration. Optionally, further purification can be performed, for example, by HPLC, column chromatography, or recrystallization.

growth, tumor invasiveness, metastasis, tumor-induced angiogenesis, inflammation, osteoporosis, and rheumatoid arthritis.

Figure 3:
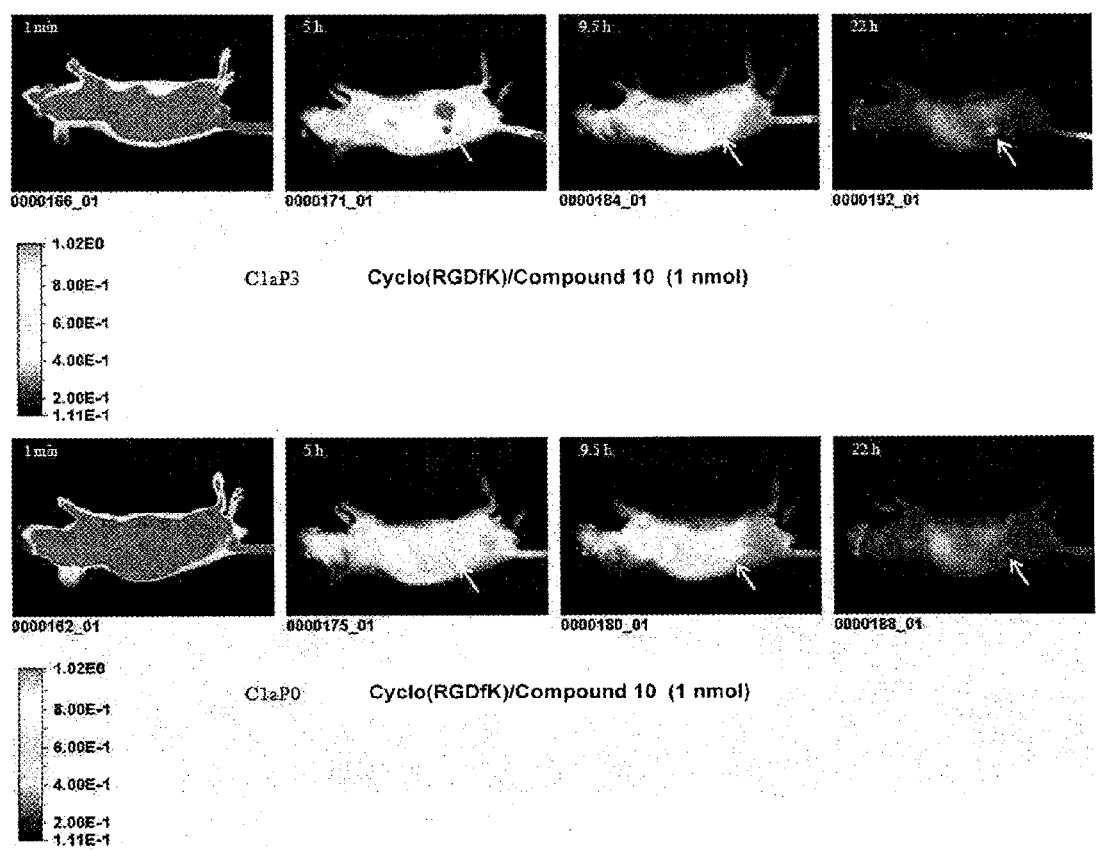
FIG. 3 shows a series of images from two tumor-bearing mice after intravenously receiving 1 nmol of an 10/cyclo (RGDfK) peptide conjugate. The tumors were visible by 5 h post-injection.
Figure 4:
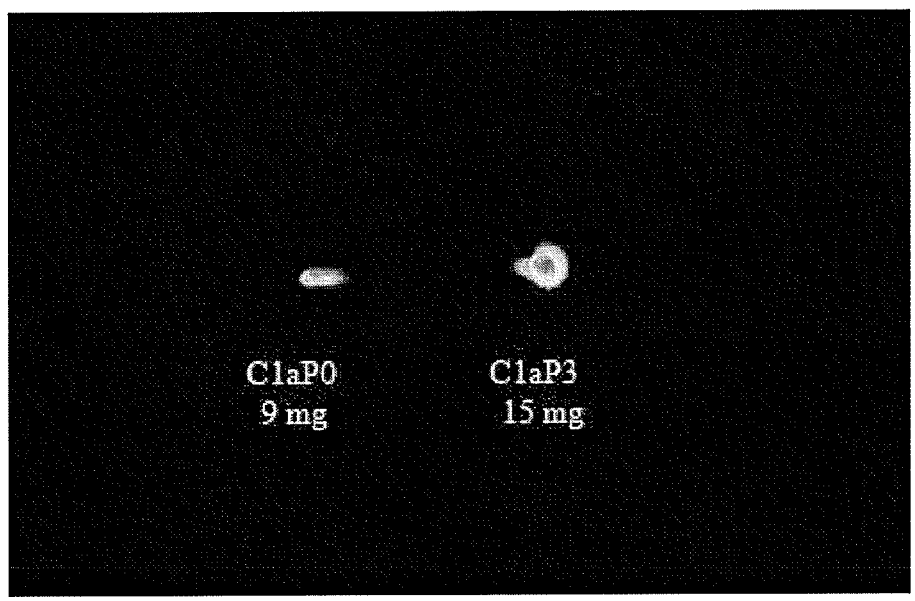
FIG. 4 shows the tumors from the two mice of FIG. 2. After the tumors' removal, they were imaged on the Pearl Impulse and weighed.

Mice were implanted with U87 tumor cells. The animals were injected and imaged while the tumors were still extremely small. This provided a good test of how visible the tumors are over any background signal that the probe detected. FIG. 3 shows the image series (lateral view) of two mice after receiving 1 nmol 10-labeled cyclo(Arg-Gly-Asp-D-Phe-Lys).

Tumors were excised, weighed, and imaged on a Pearl Imager (FIG. 3). These tumors were extremely small (9 and 15 mg), but were still easily detectable by the procedure.

The agent cleared the system without an undue level of background which would obscure the tumors. These results demonstrate the suitability of compound 10 conjugates (made, e.g., by reaction with NHS ester 13 as in Example 23) for in vivo optical imaging.

Example 25

Compound 10 NHS Labeling and Western Blots

This method is generally applicable for the conjugation of amino-containing molecules with NHS esters of inventive dye embodiments. As such, it provides a route to make the starting materials for many subsequent examples such as the Western blot experiments with antibody/dye conjugates.

Goat anti-mouse antibody (Southern Biotech) was labeled with research-grade 12 NHS ester dye (i.e., 13). Compound 13 was reconstituted in water to 1 mg/mL. Goat anti-mouse (GAM) IgG (H+L) were reconstituted typically at 1 mg/mL in phosphate buffer (pH 8.5). The dyes were added (at various molar ratios, e.g., 2, 4, 6, 8, or 10) to the GAM antibody samples and allowed to incubate for 2 hours at room temperature in the dark. If the reaction pH is too low, the amide coupling reaction will be inefficient, and the dye to protein (D/P) ratios will be much lower than expected. If necessary, additional equivalents of NHS ester can be used to drive the reaction to completion.

To purify the products, the free dye was removed by HPLC using Pierce Zeba columns. Alternatively, the conjugates are extensively dialyzed against phosphate buffered saline (1×PBS) to remove the unconjugated free dye.

Table 6 shows the absorbance results of all conjugates.

TABLE 6

Absorbance Readings and Calculation Results for Expanded Set of 10 NHS Dye Conjugations with GAM.

| GAM conjugate | Abs (280) | Abs (680) | D/P | Conc. (mg/mL) |
| --- | --- | --- | --- | --- |
| 2 equiv | 0.12088 | 0.08880 | 0.95 | 0.87 |
| 4 equiv | 0.14387 | 0.16139 | 1.47 | 1.03 |
| 6 equiv | 0.14730 | 0.22814 | 2.06 | 1.04 |
| 8 equiv | 0.15203 | 0.29371 | 2.60 | 1.06 |
| 10 equiv | 0.1284 | 0.34010 | 3.65 | 0.87 |
| 10 + 5 equiv (10B) | 0.11354 | 0.35807 | 4.42 | 0.76 |

Figure 5:
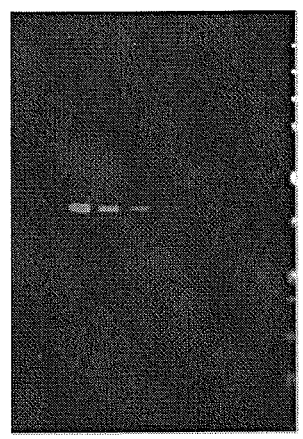
FIG. 5 illustrates a Western blot total fluorescence comparison of three GAM antibody conjugates with 10 at different D/P ratios. GAM antibody conjugates with 20, IRDye® 680, and AlexaFluor® 680 were used as controls. (A) 10; D/P 1.47. (B) 10; D/P 2.60. (C) 10; D/P 4.42. (D) 20; D/P 2. 16. (E) IRDye® 680; D/P 3.13. (F) AlexaFluor® 680; D/P 4.
Figure 5:
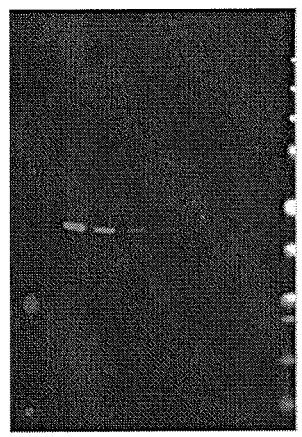
Figure 5:
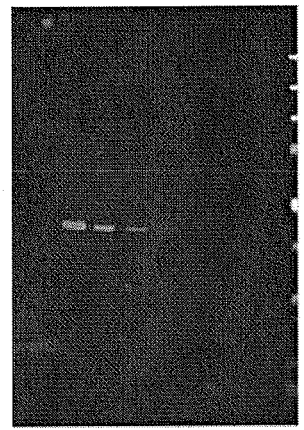
Figure 5:
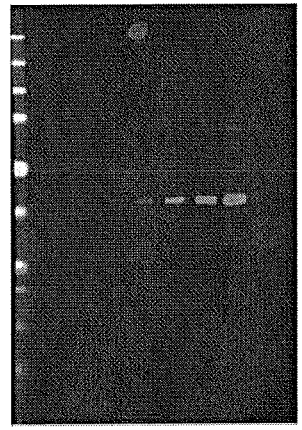
Figure 5:
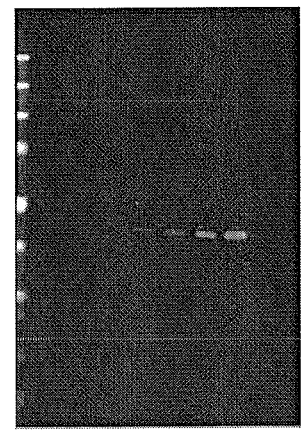
Figure 5:
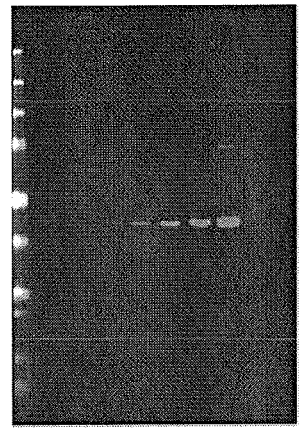
Figure 6A:
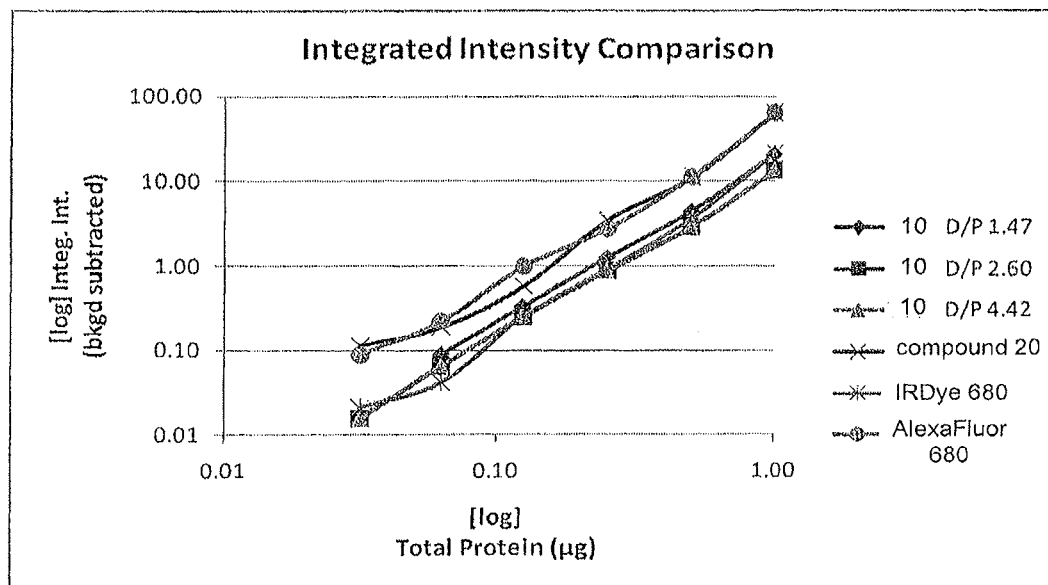
FIG. 6A shows the 10's integrated intensity values (local background subtracted) for each of the conjugates of FIG. 4.
Figure 6B:
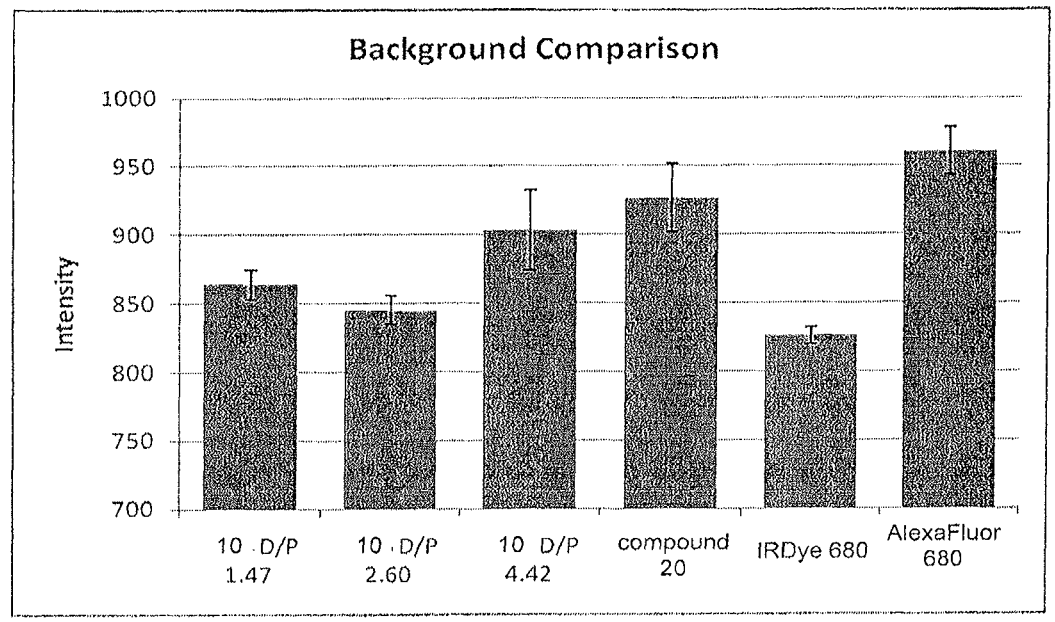
FIG. 6B provides the mean local background for each conjugate. The error bars represent standard deviation for six background sets.

Three conjugates with a low, medium, and high D/P ratio (1.47, 2.60, and 4.42 respectively) were tested in Western blots according to the procedure set forth in Example 21. Compound 20, IRDye® 680, and Alexa Fluor® 680 dye conjugates with GAM antibodies were included for comparison as controls. The results are shown in FIGS. 5, 6A, and 6B.

Example 26

Imaging with 10/BoneTag™ Dye Conjugate (4 nmol, IV or IP)

A conjugate of 10 and BoneTag™ was prepared by reaction of the NHS ester of 10 with BoneTag™. The NHS ester of the dye was conjugated to a tetracycline derivative containing a primary, aliphatic amine (pH 8, 25° C., 2 h). The product was purified by reverse-phase HPLC, aliquoted into tubes (20 nmol per tube), and lyophilized. As a skilled artisan will appreciate, binding of tetracycline and its derivatives to bone is well known in the art. For example, tetracycline, oxytetracycline, chlortetracycline and (1-pyrrolidinylmethyl)-tetracycline are taken up in newly-formed bone after injection into the living organism, to form a zone that is intensely fluorescent under ultra-violet light. This reaction, which occurs wherever there is active deposition of new bone, and can also be used for the detection of calcification. See, Perrin, Nature 208, 787-788 (20 Nov. 1965).

Figure 7:
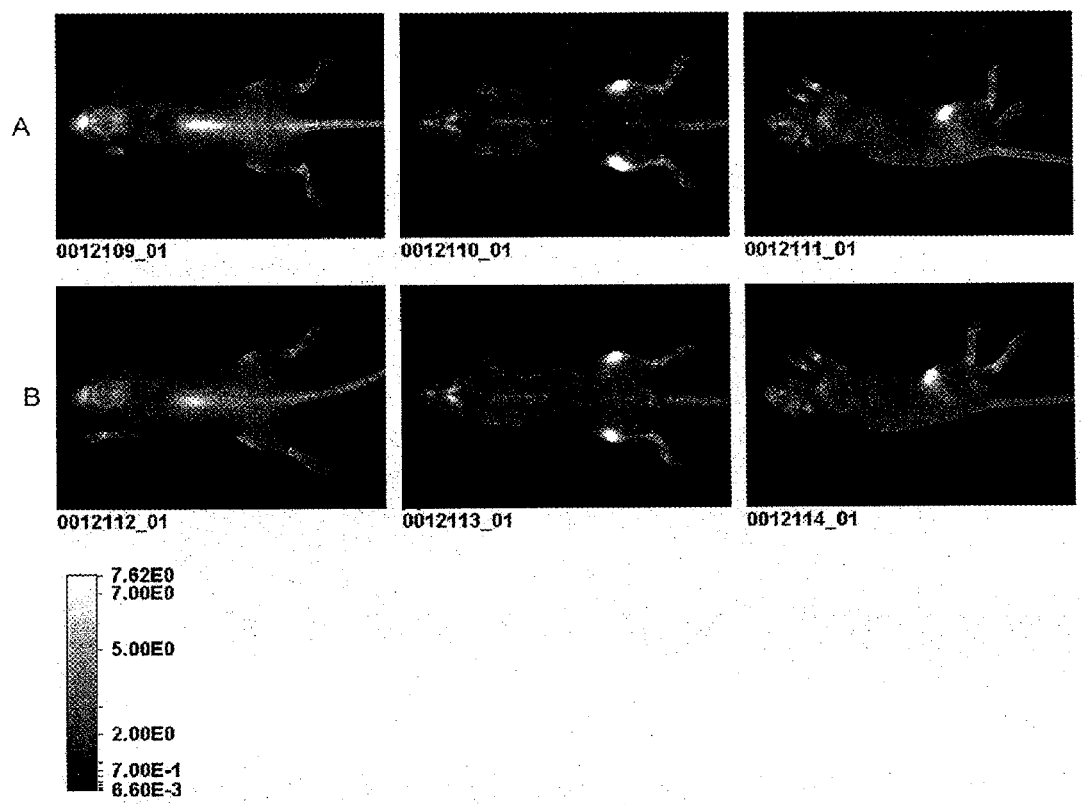
FIG. 7 shows Pearl® Impulse images of nude mice taken 24 h post-injection with a conjugate of 10 and a tetracycline antibiotic.

For the animal studies, a portion of the conjugate was redissolved in 1×PBS, and it was then filtered through a sterile, 0.1 micron filter. Nude mice were each injected with 4 nmol of conjugate and imaged 24 h later with a Pearl® Impulse infrared imaging system. FIG. 7 shows the results of intravenous (IV) and intraperitoneal (IP) administration. Bone structures are clearly visible in the resulting images because of the labeled tetracycline's binding to bone tissue.

Example 27

Lymph Imaging with 10/HA (2 nmol, ID)

A commercial sample of hyaluronan (approximately 30 kDal) was reacted with hexamethylene diamine as described in U.S. Pat. No. 7,196,180 to produce an amino-hyaluronan derivative. This aminohyaluronan was reacted with the NHS ester of 10 in aqueous solution (pH 8.5, 25° C., 3 h). The product was purified with a spin column followed by dialysis, aliquoted into tubes, and lyophilized.

For the animal studies, a portion of the conjugate was redissolved in 1×PBS, and it was then filtered through a sterile, 0.1 micron filter. Three different applications for the agent were evaluated: i) intradermal, to watch lymph flow; ii) intravenous, to systemically label lymph nodes; and iii) intravenous, to target a tumor. The mice were imaged in a Pearl Imager.

Figure 8:
FIG. 8 shows a Pearl Impulse image of a nude mouse taken approximately 10 min after intradermal (ID) injection of an 10/hyaluronin conjugate (10-HA). This animal was imaged over time and 96 h images are presented in FIG. 9.
Figure 9:
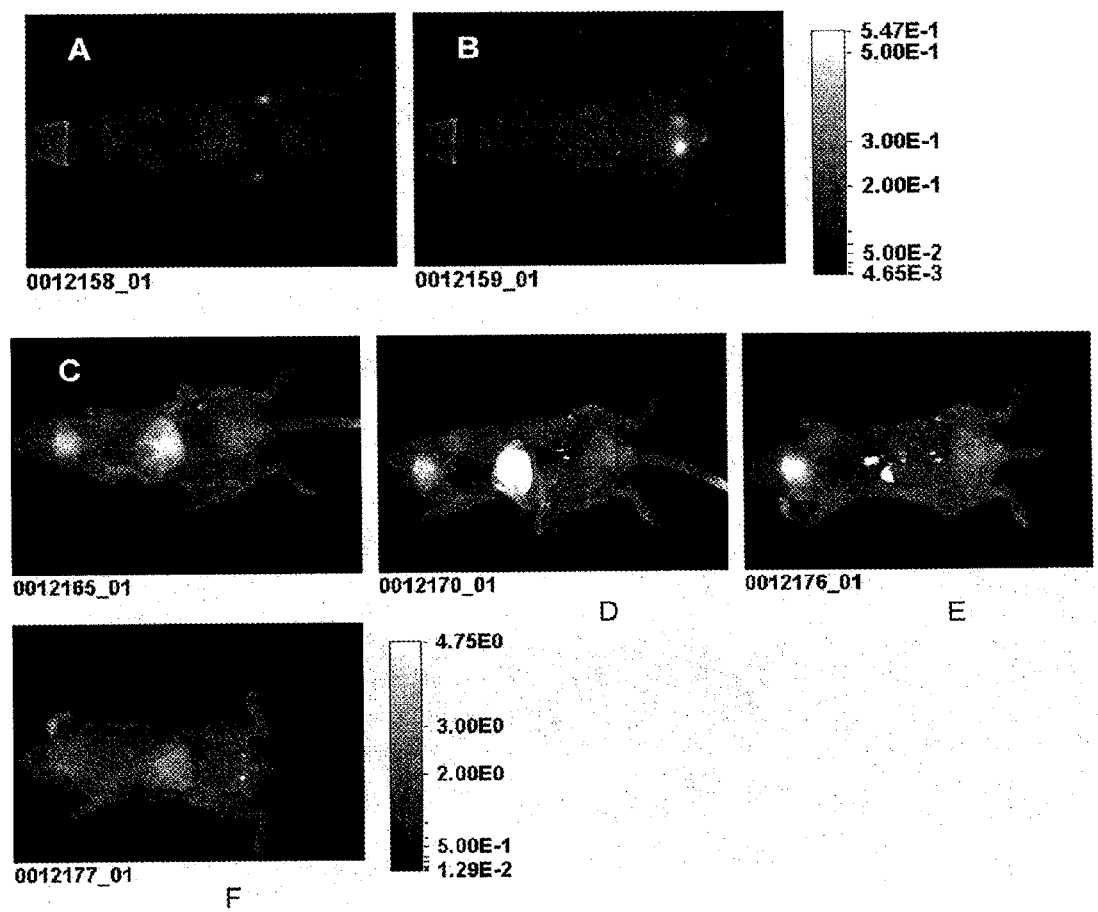
FIG. 9 shows Pearl Impulse images of nude mice taken approximately 96 h after ID injection of 10-HA. The images include (A) ventral and (B) dorsal views of the mouse prior to sacrifice and (C), (D), (E), and (F) are dissection panels.

The sentinel nodes of the mice were highlighted in a Pearl Imager after 10 min (FIG. 8) and after approximately 96 hours (FIG. 9). FIG. 8 illustrates how an dose of the agent (~0.5 nmol/3 µL) introduced intradermally at the base of the tail is picked up and pulsed to the nearest lymph nodes. FIG. 9 illustrates the systemic deposition of the agent in a number of lymph nodes. Panels A and B are non-invasive images of the subilliac and illiac/siatic lymph nodes. Panel C is four images of the same mouse after sacrifice and dissection to visualize deep nodes along the aorta.

Example 28

Tumor Imaging with 10/HA (1 nmol, ID)

Figure 10:
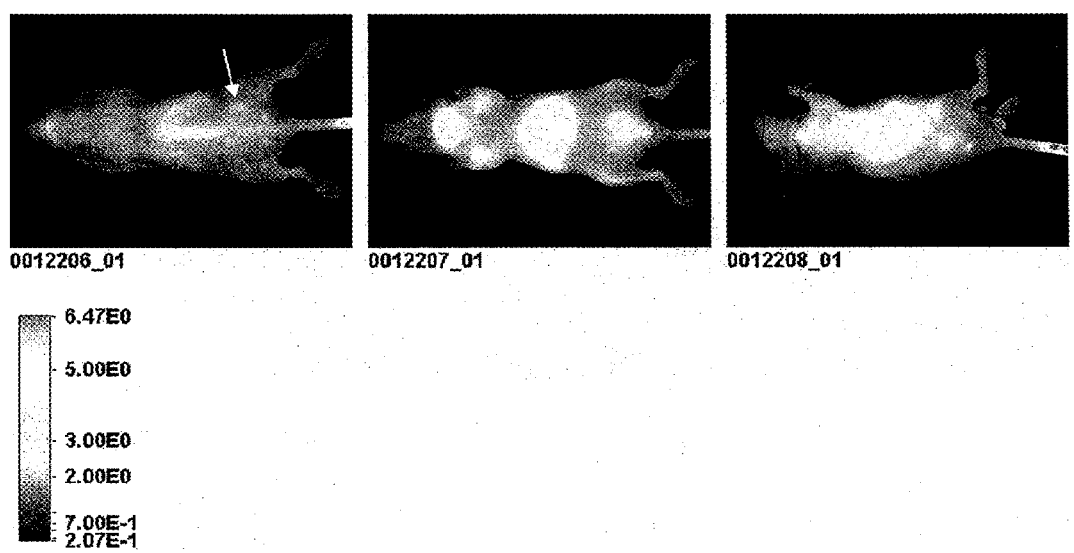
FIG. 10 shows Pearl Impulse images of nude mice taken approximately 24 h post IV injection of 10-HA. The white arrow points to tumor locations on the dorsal view.

A conjugate of 10 and hyaluronan was prepared according to the procedure of Example 27. The conjugate (1 nmol) was intravenously administered to a nude mouse bearing a CD44-expressing tumor cell xenograft. The mouse was imaged in a Pearl Imager after approximately 24 h (FIG. 10).

Example 29

Localization of 10-PEG in A431 Tumor Xenograft

A commercial sample of mono-amino polyethylene glycol (mPEG, 40 kDal) was reacted with the NHS ester of 10 in aqueous solution (pH 8.5, 25° C., 2 h). The product was purified with a spin column, aliquoted and lyophilized.

Figure 11:
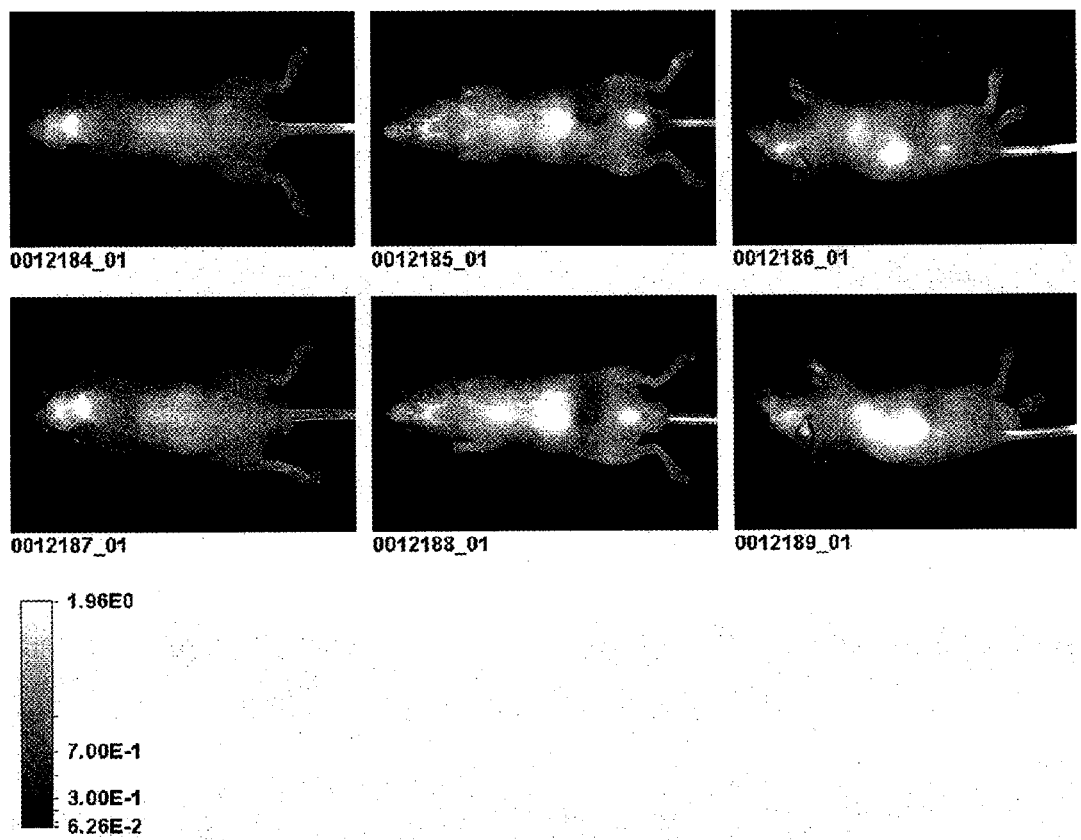
FIG. 11 shows Pearl Impulse images of two nude mice taken approximately 1 min post injection of 1 nmol 10/polyethylene glycol (PEG) conjugate. The mice had A431 tumors on their right hips.
Figure 12:
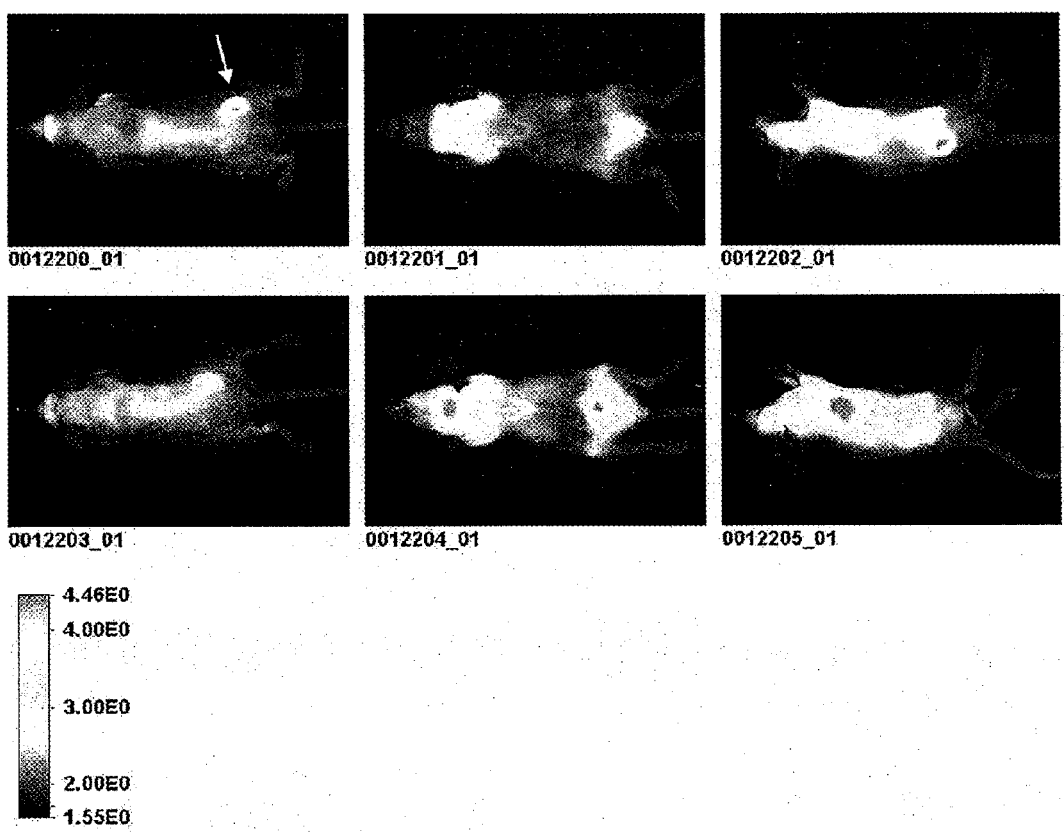
FIG. 12 shows Pearl Impulse images of two nude mice taken approximately 24 h post-injection of 1 nmol 10/PEG conjugate. The white arrow points to a tumor.

For the animal studies, a portion of the conjugate was redissolved in 1×PBS, and filtered through a sterile, 0.1 micron filter. Two nude mice bearing A431 xenograft tumors were injected with the conjugate (1 nmol, IV) and imaged over time with a Pearl® Impulse infrared imaging system. The mice were imaged after approximately 1 min (FIG. 11) and approximately 24 h (FIG. 12). The labeled mPEG accumulated in the tumor due to the malformed blood vessels there, allowing the tumor to be detected at 24 h post-injection (FIG. 12).

One characteristic for the labeled PEG agents is the ability to see vasculature early after administration for approximately 30 min post-injection. The vasculature around the tumor itself could be observed. 10-PEG was effective as a tumor-imaging agent, and even high background did not overwhelm the tumor signal.

Example 30

Preparation of 6-Hydrazino-1,3-naphthalene Disulfonated Salt

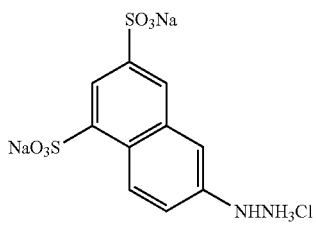

6-Hydrazino-1,3-naphthalene Disulfonated Salt (22)

6-Amino-1,3-naphthalene disulfonate disodium salt (25 g, 72 mmol) was dissolved in 150 mL of water and added to 50 mL of concentrated hydrochloric acid. The slurry was cooled to about 0° C. in an ice/salt bath, and sodium nitrite (5.46 g, 79.2 mmol) was added in 25 mL of cold water dropwise over 10 minutes. Stannous chloride (20.42 g, 108 mmol) was dissolved in 15 mL concentrated hydrochloric acid, cooled to 0° C. and added to the reaction mixture over 20 minutes. The resulting solution was allowed to warm to room temperature with stirring over 3 hours. The solution was reduced in volume by rotary evaporation, and the product was precipitated by the addition of isopropanol. Compound 22 was filtered, washed with isopropanol, and dried under vacuum.

Example 31

Preparation of 2,3,3-Trimethylbenzindole-6,8-disulfonate Salt

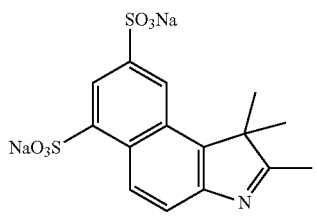

2,3,3-Trimethylbenzindole-6,8-disulfonate Salt (23)

6-Hydrazino-1,3-naphthalene disulfonated salt 1 (10 g, 25 mmol), isopropyl methyl ketone (12 g, 140 mmol) and potassium acetate (6 g, 61 mmol) were combined in 75 mL glacial acetic acid and heated to 145° C. for 22 hours. The solution was cooled, and the acetic acid was removed by rotary evaporation. The residue was dissolved in methanol and filtered. The compound 23 was then precipitated from the methanol filtrate with isopropanol, filtered, washed with isopropanol and ether, and dried under vacuum.

Example 32

Preparation of Sodium 1,1,2-Trimethyl-3-(3-sulfonatopropyl)-1H-benzo[e]indolium-6,8-disulfonate

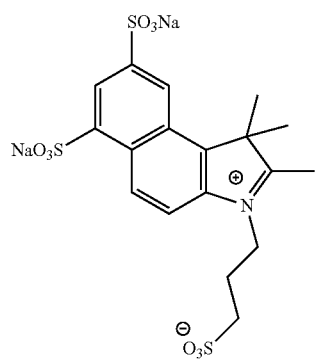

Sodium 1,1,2-Trimethyl-3-(3-sulfonatopropyl)-1H-benzo[e]indolium-6,8-disulfonate (23)

2,3,3-Trimethylbenzindole-6,8-disulfonate 2 (2.2 g, 5 mmol) was stirred in 50 mL of dry 1,2-dichlorobenzene. 1,3-propanesultone (2.8 g, 23 mmol) was added, and the solution was heated to 145° C. in a sealed tube for 15 hours. The solution was cooled, and the solvent was decanted off. The solid product 3 was washed on a filter with three 50 mL portions of isopropanol followed by 50 mL of ether and dried under vacuum, resulting in a dark purple solid (2.5 g, 90%).

Example 33

Preparation of Sodium 1,1,2-Trimethyl-3-(3-sulfonatobutyl)-1H-benzo[e]indolium-6,8-disulfonate

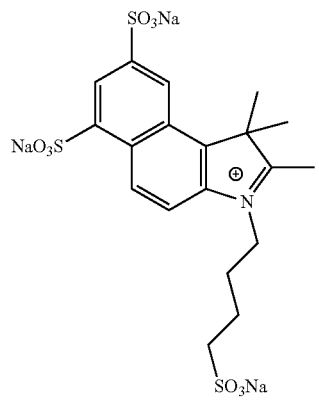

Sodium 1,1,2-Trimethyl-3-(3-sulfonatobutyl)-1H-benzo[e]indolium-6,8-disulfonate (24)

Compound 24 was prepared analogously to compound 23 (Example 23), except that 1,4-butanesultone is used as a starting material.

Example 34

Preparation of Sodium 2-((1E,3Z,5E)-3-Bromo-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate

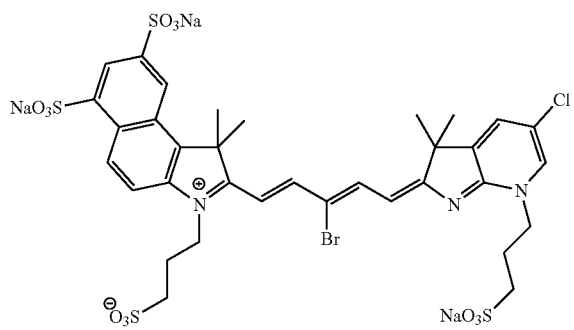

Sodium 2-((1E,3Z,5E)-3-Bromo-5-(1,1-dimethyl-6,8-disulfonato-3-(3-sulfonatopropyl)-1H-benzo[e]indol-2(3H)-ylidene)penta-1,3-dienyl)-1,1-dimethyl-3-(3-sulfonatopropyl)-1H-benzo[e]indolium-6,8-disulfonate (25)

Compound 25 is prepared analogously to compound 9 (Example 9), except that compound 23 is used as a starting material.

Example 35

Preparation of 4-(5-Chloro-2,3,3-trimethyl-3H-pyrrolo[2,3-b]pyridin-7-ium-7-yl)butane-1-sulfonate

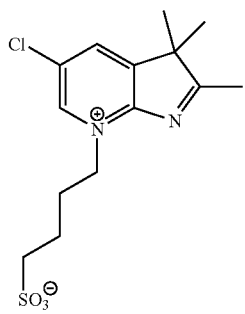

4-(5-Chloro-2,3,3-trimethyl-3H-pyrrolo[2,3-b]pyridin-7-ium-7-yl)butane-1-sulfonate (26)

Compound 26 is prepared analogously to compound 5 (Example 5), except that 1,4-butanesultone is used as a starting material.

Example 36

Preparation of Sodium 2-((1E,3Z,5E)-3-Bromo-5-(5-chloro-3,3-dimethyl-7-(4-sulfonatobutyl)-3,7-dihydro-2H-pyrrolo[2,3-b]pyridin-2-ylidene)penta-1,3-dienyl)-1,1-dimethyl-3-(4-sulfonatobutyl)-1H-benzo[e]indolium-6,8-disulfonate

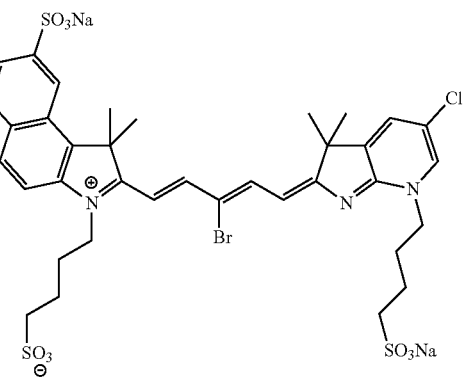

Sodium 2-((1E,3Z,5E)-3-Bromo-5-(1,1-dimethyl-6,8-disulfonato-3-(3-sulfonatobutyl)-1H-benzo[e]indol-2(3H)-ylidene)penta-1,3-dienyl)-1,1-dimethyl-3-(3-sulfonatobutyl)-1H-benzo[e]indolium-6,8-disulfonate (27)

Compound 27 is prepared analogously to compound 9 (Example 9), except that compounds 24 and 26 is used as a starting material.

Example 37

Preparation of Sodium 2-((1E,3Z,5E)-3-(3-(4-Carboxybutyl)phenyl)-5-(5-chloro-3,3-dimethyl-7-(4-sulfonatobutyl)-3,7-dihydro-2H-pyrrolo[2,3-b]pyridin-2-ylidene)penta-1,3-dienyl)-1,1-dimethyl-3-(4-sulfonatobutyl)-1H-benzo[e]indolium-6,8-disulfonate

Example 38

Preparation of Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(5-(2,5-dioxopyrrolidin-1-yloxy)-5-oxopentyl)phenyl)penta-1,3-dienyl)-1,1-dimethyl-3-(4-sulfonatobutyl)-1H-benzo[e]indolium-6,8-disulfonate

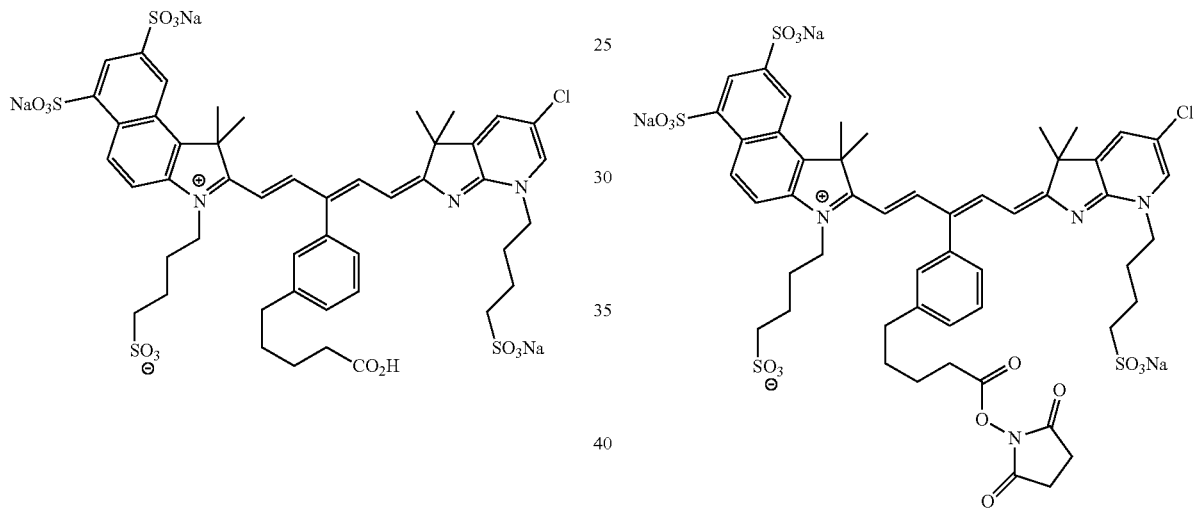

Sodium 2-((1E,3Z,5E)-3-(3-(4-Carboxybutyl)phenyl)-5-(5-chloro-3,3-dimethyl-7-(4-sulfonatobutyl)-3,7-dihydro-2H-pyrrolo[2,3-b]pyridin-2-ylidene)penta-1,3-dienyl)-1,1-dimethyl-3-(4-sulfonatobutyl)-1H-benzo[e]indolium-6,8-disulfonate (28)

Compound 27 (68 mg), 3-(4-carboxybutyl)phenylboronic acid (40 mg), and cesium carbonate (20 mg) are stirred into 1:1 water:ethanol (10 mL) under nitrogen at room temperature. Tetrakis(triphenylphosphine)palladium(0) (10 mg) is added to the reaction mixture. The mixture was refluxed for 4 hours, and the solvent and volatile compounds are evaporated under vacuum. The crude product is purified by flash chromatography on reverse-phase C18-functionalized silica by eluting with a 1:4 acetonitrile:water mixture.

Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(5-(2,5-dioxopyrrolidin-1-yloxy)-5-oxopentyl)phenyl)penta-1,3-dienyl)-1,1-dimethyl-3-(4-sulfonatobutyl)-1H-benzo[e]indolium-6,8-disulfonate (29)

To a solution of compound 28 (200 mg) in dry DMSO (15 mL) is added triethylamine (150 µL) and N,N'-disuccinimidyl carbonate (82 mg). The mixture is stirred at room temperature for 2 hours, and the solvent is removed to yield the succinimidyl ester.

Example 39

Preparation of Sodium 2-((1E,3Z,5E)-3-(3-(2-Carboxyethyl)phenyl)-5-(5-chloro-3,3-dimethyl-7-(4-sulfonatobutyl)-3,7-dihydro-2H-pyrrolo[2,3-b]pyridin-2-ylidene)penta-1,3-dienyl)-1,1-dimethyl-3-(4-sulfonatobutyl)-1H-benzo[e]indolium-6,8-disulfonate

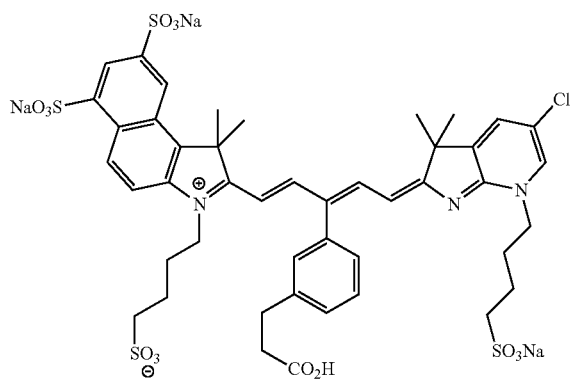

Sodium 2-((1E,3Z,5E)-3-(3-(2-Carboxyethyl)phenyl)-5-(5-chloro-3,3-dimethyl-7-(4-sulfonatobutyl)-3,7-dihydro-2H-pyrrolo[2,3-b]pyridin-2-ylidene)penta-1,3-dienyl)-1,1-dimethyl-3-(4-sulfonatobutyl)-1H-benzo[e]indolium-6,8-disulfonate (30)

Compound 30 is prepared analogously to compound 28 (Example 37), except that 3-(3-boronophenyl)propionic acid is used as a starting material.

Example 40

Preparation of Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(3-(2,5-dioxopyrrolidin-1-yloxy)-3-oxopropyl)phenyl)penta-1,3-dienyl)-1,1-dimethyl-3-(4-sulfonatobutyl)-1H-benzo[e]indolium-6,8-disulfonate

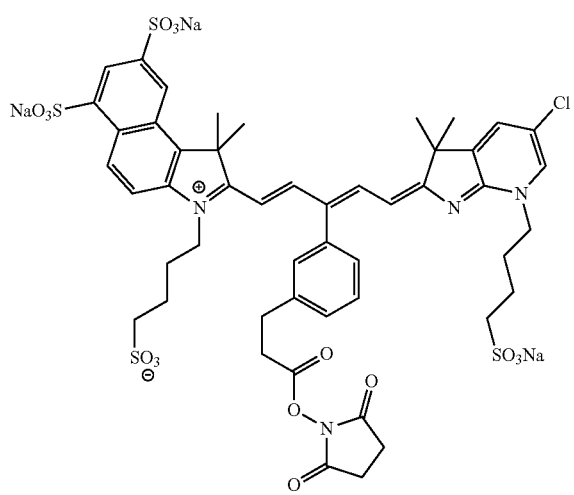

Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(3-(2,5-dioxopyrrolidin-1-yloxy)-3-oxopropyl)phenyl)penta-1,3-dienyl)-1,1-dimethyl-3-(4-sulfonatobutyl)-1H-benzo[e]indolium-6,8-disulfonate (31)

Compound 31 is prepared analogously to compound 29 (Example 38), except that compound 30 is used as a starting material.

Example 41

Preparation of Sodium (E)-2-((2Z,4E)-3-(3-(4-Carboxybutyl)phenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate

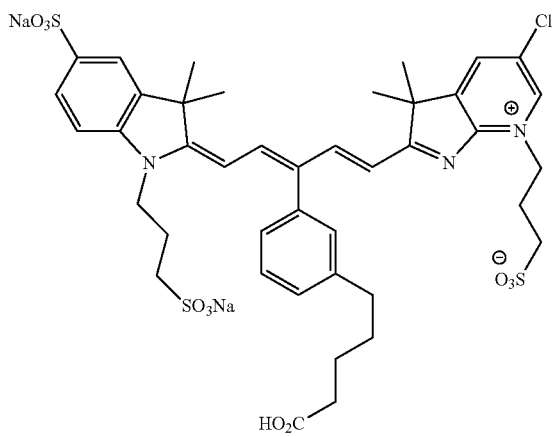

Sodium (E)-2-((2Z,4E)-3-(3-(4-Carboxybutyl)phenyl)-5-(5-chloro-3,3-dimethyl-7-(3-sulfonatopropyl)-3H-pyrrolo[2,3-b]pyridin-7-ium-2-yl)penta-2,4-dienylidene)-3,3-dimethyl-1-(3-sulfonatopropyl)indoline-5-sulfonate (32)

Compound 32 is prepared analogously to compound 10 (Example 10), except that 3-(3-boronophenyl)butanoic acid is used as a starting material.

Example 42

Preparation of Sodium (E)-2-((2Z,4E)-5-(5-Chloro-3,3-dimethyl-7-(3-sulfonatopropyl)-3H-pyrrolo[2,3-b]pyridin-7-ium-2-yl)-3-(3-(5-(2,5-dioxopyrrolidin-1-yloxy)-5-oxopentyl)phenyl)penta-2,4-dienylidene)-3,3-dimethyl-1-(3-sulfonatopropyl)indoline-5-sulfonate

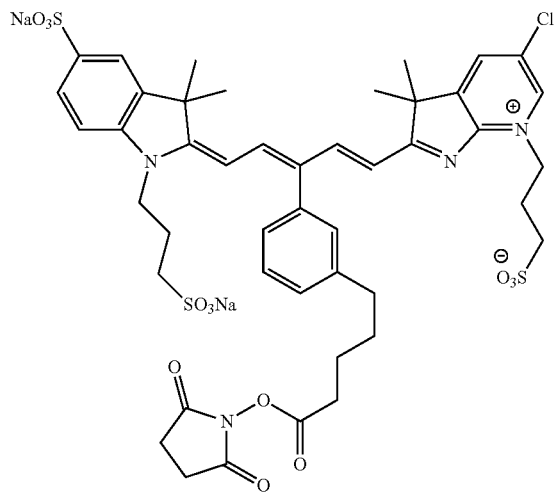

Sodium (E)-2-((2Z,4E)-5-(5-Chloro-3,3-dimethyl-7-(3-sulfonatopropyl)-3H-pyrrolo[2,3-b]pyridin-7-ium-2-yl)-3-(3-(5-(2,5-dioxopyrrolidin-1-yloxy)-5-oxopentyl)phenyl)penta-2,4-dienylidene)-3,3-dimethyl-1-(3-sulfonatopropyl)indoline-5-sulfonate (33)

Compound 33 is prepared analogously to compound 29 (Example 38), except that compound 32 is used as a starting material.

Example 43

Dot Blot Immunoassay Comparison of Total Fluorescence of Streptavidin Bioconjugate of Compound 10 with Commercially Available Streptavidin Bioconjugates of IRDye® 680 and Alexa 680 Dye Nitrocellulose membrane is spotted with different amounts of biotinylated anti-rabbit IgG. The membrane is blocked with LI-COR Odyssey® Blocking Buffer for 30 min, followed by incubation for 30 min with bioconjugates of compound 10 and streptavidin at different D/P ratios. The membrane is washed vigorously with 1×PBS and 1×PBS-T (1×PBS with 0.1% Tween-20).

The membranes are scanned on a LI-COR Odyssey® Infrared Imager to determine their fluorescence intensity (K Counts, with standard derivation), background intensity (including standard deviation), and limit of detection.

Example 44

Western Blot Comparison of Total Fluorescence of Streptavidin Conjugate to Compound 10 with Commercially Available Conjugates of TRDye® 680 Dye to Streptavidin Jurkat lysate is run on gels (5 μg to 78 ng). Blots are probed with ms anti-actin (Thermo No. MS-1295P) diluted 1:1000 in Odyssey® Blocking Buffer+0.2% Tween® 20 followed by Biotin-SP GAM (Jackson No. 115-065-166) diluted 1:20,000 in Odyssey® Blocker+0.2% Tween® 20. Blots are then detected with various 680 streptavidin bioconjugates in Odyssey® Blocking Buffer+0.2% Tween® 20.

Example 45

Preparation of Sodium (E)-2-((2Z,4E)-5-(5-Chloro-3,3-dimethyl-7-(3-sulfonatopropyl)-3H-pyrrolo[2,3-b]pyridin-7-ium-2-yl)-3-(3-(5-(2-(2,5-dioxo-2,5-dihydro-1H-pyrrol-1-yl)ethylamino)-5-oxopentyl)phenyl)penta-2,4-dienylidene)-3,3-dimethyl-1-(3-sulfonatopropyl)indoline-5-sulfonate

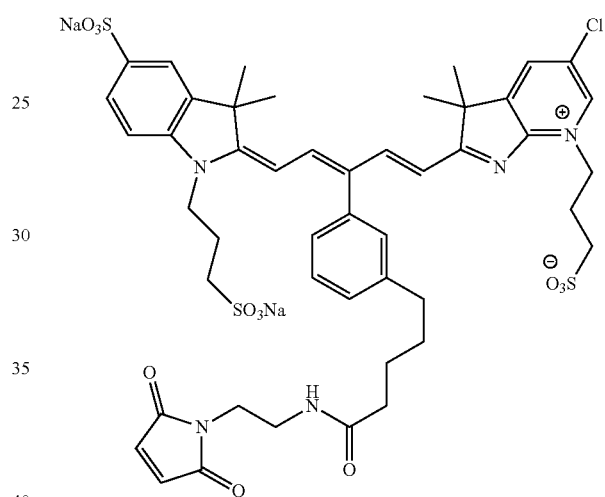

Sodium (E)-2-((2Z,4E)-5-(5-Chloro-3,3-dimethyl-7-(3-sulfonatopropyl)-3H-pyrrolo[2,3-b]pyridin-7-ium-2-yl)-3-(3-(5-(2-(2,5-dioxo-2,5-dihydro-1H-pyrrol-1-yl)ethylamino)-5-oxopentyl)phenyl)penta-2,4-dienylidene)-3,3-dimethyl-1-(3-sulfonatopropyl)indoline-5-sulfonate (34)

The NHS ester dye (33, 0.18 mmol) is dissolved in 20 mL of dry DMSO and stirred at room temperature under dry nitrogen. Next, 2-maleimido ethyl amine (93.2 mg, 0.37 mmol) is added to the stirred solution, followed by di-isopropyl ethyl amine (DIPEA) (95 mg, 0.55 mmol). The stirring is continued for 45 min. DMF (20 mL) is added to the reaction, and stirring continued until thorough mixing is achieved. The solution is then poured slowly into 400 mL of stirred diethyl ether to precipitate the product. The ether suspension is stirred for an additional 5 min, then allowed to stand for 1 hr. The ether is decanted and an additional 20 mL of DMF is added to redissolve the solid. The DMF solution is then precipitated into a second 400 mL portion of stirred ether. The crude product is collected by filtration. Optionally, further purification can be performed, for example, by HPLC, column chromatography, or recrystallization.

Example 46

Preparation of Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(5-(2-(2,5-dioxo-2,5-dihydro-1H-pyrrol-1-yl)ethylamino)-5-oxopentyl)phenyl)penta-1,3-dienyl)-1,1-dimethyl-3-(4-sulfonatobutyl)-1H-benzo[e]indolium-6,8-disulfonate

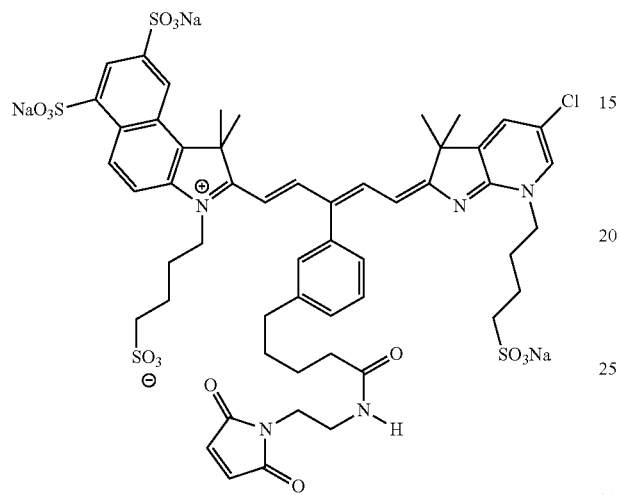

Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(5-(2-(2,5-dioxo-2,5-dihydro-1H-pyrrol-1-yl)ethylamino)-5-oxopentyl)phenyl)penta-1,3-dienyl)-1,1-dimethyl-3-(4-sulfonatobutyl)-1H-benzo[e]indolium-6,8-disulfonate (35)

Compound 35 is prepared analogously to compound 34 (Example 45), except that compound 29 is used as a starting material.

Example 47

Preparation of Sodium (E)-2-((E)-3-((E)-2-(5-Chloro-3,3-dimethyl-7-(3-sulfonatopropyl)-3H-pyrrolo[2,3-b]pyridin-7-ium-2-yl)vinyl)-6-(2,5-dioxopyrrolidin-1-yloxy)-6-oxohex-2-enylidene)-3,3-dimethyl-1-(3-sulfonatopropyl)indoline-5-sulfonate

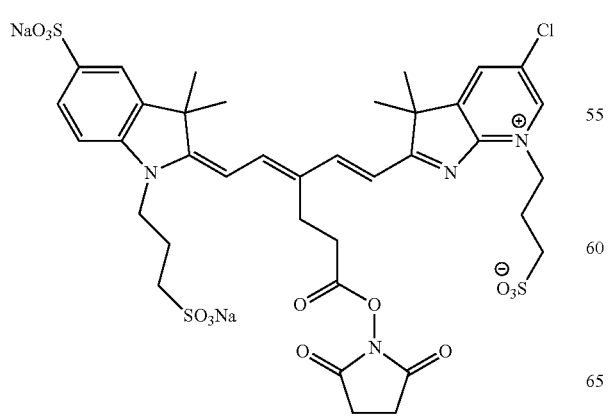

Sodium (E)-2-((E)-3-((E)-2-(5-Chloro-3,3-dimethyl-7-(3-sulfonatopropyl)-3H-pyrrolo[2,3-b]pyridin-7-ium-2-yl)vinyl)-6-(2,5-dioxopyrrolidin-1-yloxy)-6-oxohex-2-enylidene)-3,3-dimethyl-1-(3-sulfonatopropyl)indoline-5-sulfonate (36)

Compound 36 is prepared analogously to compound 29 (Example 38), except that compound 19 is used as a starting material.

Example 48

Preparation of Sodium (E)-2-((E)-3-((E)-2-(5-Chloro-3,3-dimethyl-7-(3-sulfonatopropyl)-3H-pyrrolo[2,3-b]pyridin-7-ium-2-yl)vinyl)-6-(2-(2,5-dioxo-2,5-dihydro-1H-pyrrol-1-yl)ethylamino)-6-oxohex-2-enylidene)-3,3-dimethyl-1-(3-sulfonatopropyl)indoline-5-sulfonate

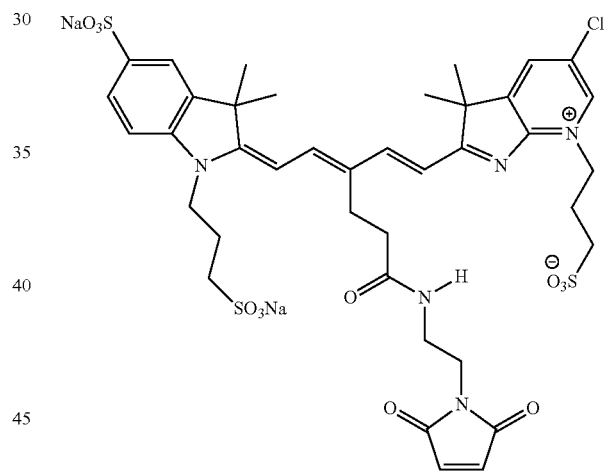

Sodium (E)-2-((E)-3-((E)-2-(5-Chloro-3,3-dimethyl-7-(3-sulfonatopropyl)-3H-pyrrolo[2,3-b]pyridin-7-ium-2-yl)vinyl)-6-(2-(2,5-dioxo-2,5-dihydro-1H-pyrrol-1-yl)ethylamino)-6-oxohex-2-enylidene)-3,3-dimethyl-1-(3-sulfonatopropyl)indoline-5-sulfonate (37)

Compound 37 is prepared analogously to compound 34 (Example 45), except that compound 36 is used as a starting material.

Example 49

Preparation of Sodium 2,3,3-Trimethyl-1-(3-sulfonatobutyl)-3H-indolium-5-sulfonate

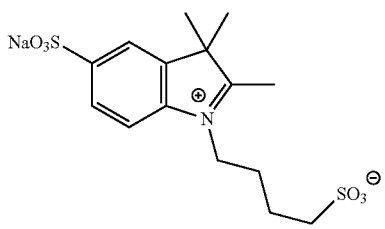

Sodium 2,3,3-Trimethyl-1-(3-sulfonatobutyl)-3H-indolium-5-sulfonate (38)

Compound 38 is prepared analogously to compound 4 (Example 4), except that 1,4-butanesultone is used as a starting material.

Example 50

Preparation of Sodium 2-((E)-2-((E)-2-chloro-3-((E)-2-(5-chloro-3,3-dimethyl-7-(4-sulfonatobutyl)-3,7-dihydro-2H-pyrrolo[2,3-b]pyridin-2-ylidene)ethylidene)cyclopent-1-enyl)vinyl)-3,3-dimethyl-1-(4-sulfonatobutyl)-3H-indolium-5-sulfonate

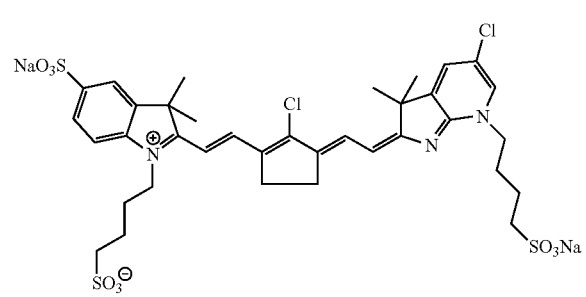

Sodium 2-((E)-2-((E)-2-chloro-3-((E)-2-(5-chloro-3,3-dimethyl-7-(4-sulfonatobutyl)-3,7-dihydro-2H-pyrrolo[2,3-b]pyridin-2-ylidene)ethylidene)cyclopent-1-enyl)vinyl)-3,3-dimethyl-1-(4-sulfonatobutyl)-3H-indolium-5-sulfonate (39)

Compound 39 is prepared analogously to compound 16, except with compound 38, compound 26, and the cyclopentyl chloro dye precursor as starting materials.

Example 51

Preparation of Sodium 2-((E)-2-((E)-2-(3-carboxyphenyl)-3-((E)-2-(5-chloro-3,3-dimethyl-7-(4-sulfonatobutyl)-3,7-dihydro-2H-pyrrolo[2,3-b]pyridin-2-ylidene)ethylidene)cyclopent-1-enyl)vinyl)-3,3-dimethyl-1-(4-sulfonatobutyl)-3H-indolium-5-sulfonate

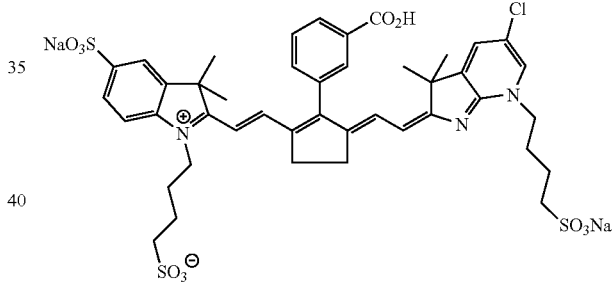

Sodium 2-((E)-2-((E)-2-(3-carboxyphenyl)-3-((E)-2-(5-chloro-3,3-dimethyl-7-(4-sulfonatobutyl)-3,7-dihydro-2H-pyrrolo[2,3-b]pyridin-2-ylidene)ethylidene)cyclopent-1-enyl)vinyl)-3,3-dim ethyl-1-(4-sulfonatobutyl)-3H-indolium-5-sulfonate (40)

Compound 40 is prepared analogously to compound 17 (Example 17), except with compound 39 and 3-boronobenzoic acid as starting materials.

The skilled person will appreciate that the boronic acid intermediates used here are versatile and can be modified by custom synthesis to meet various design changes. The phenyl ring can be substituted with various types of substituents and substituent lengths. One custom synthesis manufacture is Combi-Blocks, Inc. of San Diego, Calif.

Example 52

Preparation of Sodium 2-((E)-2-((E)-2-(3-(3-carboxypropyl)phenyl)-3-((E)-2-(5-chloro-3,3-dimethyl-7-(4-sulfonatobutyl)-3,7-dihydro-2H-pyrrolo[2,3-b]pyridin-2-ylidene)ethylidene)cyclopent-1-enyl)vinyl)-3,3-dimethyl-1-(4-sulfonatobutyl)-3H-indolium-5-sulfonate

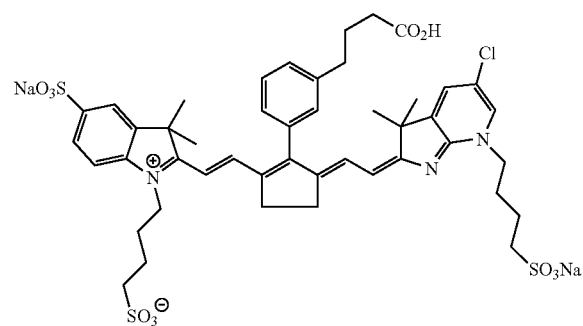

41 sodium 2-((E)-2-((E)-2-(3-(3-carboxypropyl)phenyl)-3-((E)-2-(5-chloro-3,3-dimethyl-7-(4-sulfonatobutyl)-3,7-dihydro-2H-pyrrolo[2,3-b]pyridin-2-ylidene)ethylidene)cyclopent-1-enyl)vinyl)-3,3-dimethyl-1-(4-sulfonatobutyl)-3H-indolium-5-sulfonate (41)

Compound 41 is prepared analogously to compound 40 (Example 51), except with 4-(3-boronophenyl)butanoic acid as a starting material.

Example 53

Preparation of Sodium 2-((1E,3Z,5E,7E)-4-chloro-7-(5-chloro-3,3-dimethyl-7-(4-sulfonatobutyl)-3,7-dihydro-2H-pyrrolo[2,3-b]pyridin-2-ylidene)hepta-1,3,5-trienyl)-3,3-dimethyl-1-(4-sulfonatobutyl)-3H-indolium-5-sulfonate

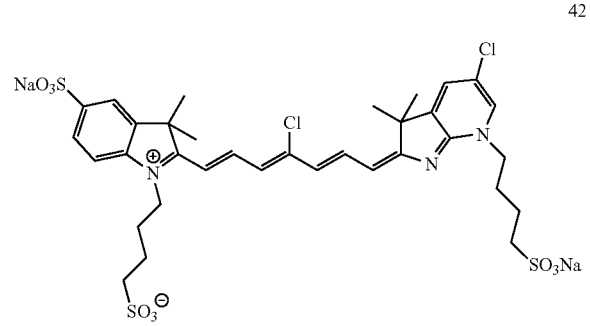

42 sodium 2-((1E,3Z,5E,7E)-4-chloro-7-(5-chloro-3,3-dimethyl-7-(4-sulfonatobutyl)-3,7-dihydro-2H-pyrrolo[2,3-b]pyridin-2-ylidene)hepta-1,3,5-trienyl)-3,3-dimethyl-1-(4-sulfonatobutyl)-3H-indolium-5-sulfonate (42)

Compound 42 is prepared analogously to compound 39 (Example 51), except with a non-cyclopentyl chloro precursor as a starting material.

Example 54

Preparation of Sodium 2-((1E,3Z,5E,7E)-4-(3-carboxyphenyl)-7-(5-chloro-3,3-dimethyl-7-(4-sulfonatobutyl)-3,7-dihydro-2H-pyrrolo[2,3-b]pyridin-2-ylidene)hepta-1,3,5-trienyl)-3,3-dimethyl-1-(4-sulfonatobutyl)-3H-indolium-5-sulfonate

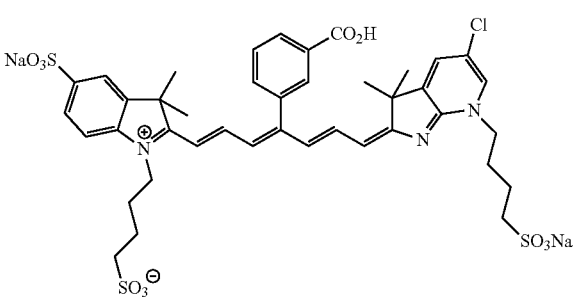

43

Sodium 2-((1E,3Z,5E,7E)-4-(3-carboxyphenyl)-7-(5-chloro-3,3-dimethyl-7-(4-sulfonatobutyl)-3,7-dihydro-2H-pyrrolo[2,3-b]pyridin-2-ylidene)hepta-1,3,5-trienyl)-3,3-dimethyl-1-(4-sulfonatobutyl)-3H-indolium-5-sulfonate (43)

Compound 43 is prepared analogously to compound 17 (Example 17), except with compound 42 and m-carboxyphenyl boronic acid as starting materials.

Example 55

Preparation of Sodium 2-((1E,3Z,5E,7E)-4-(3-(3-carboxypropyl)phenyl)-7-(5-chloro-3,3-dimethyl-7-(4-sulfonatobutyl)-3,7-dihydro-2H-pyrrolo[2,3-b]pyridin-2-ylidene)hepta-1,3,5-trienyl)-3,3-dimethyl-1-(4-sulfonatobutyl)-3H-indolium-5-sulfonate

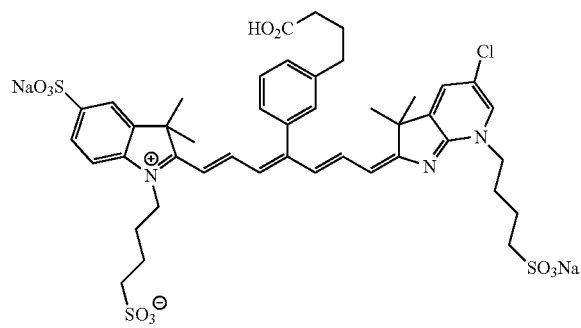

44

Sodium 2-((1E,3Z,5E,7E)-4-(3-(3-carboxypropyl)phenyl)-7-(5-chloro-3,3-dimethyl-7-(4-sulfonatobutyl)-3,7-dihydro-2H-pyrrolo[2,3-b]pyridin-2-ylidene)hepta-1,3,5-trienyl)-3,3-dimethyl-1-(4-sulfonatobutyl)-3H-indolium-5-sulfonate (44)

Compound 44 is prepared analogously to compound 43, except with 4-(3-boronophenyl)butanoic acid as a starting material.

Example 56

Preparation of Sodium (E)-2-((E)-2-(3-((E)-2-(5-chloro-3,3-dimethyl-7-(3-sulfonatopropyl)-3H-pyrrolo[2,3-b]pyridin-7-ium-2-yl)vinyl)-2-(3-(4-hydroxybutoxy)phenyl)cyclohex-2-enylidene)ethylidene)-3,3-dimethyl-1-(3-sulfonatopropyl)indoline-5-sulfonate

45

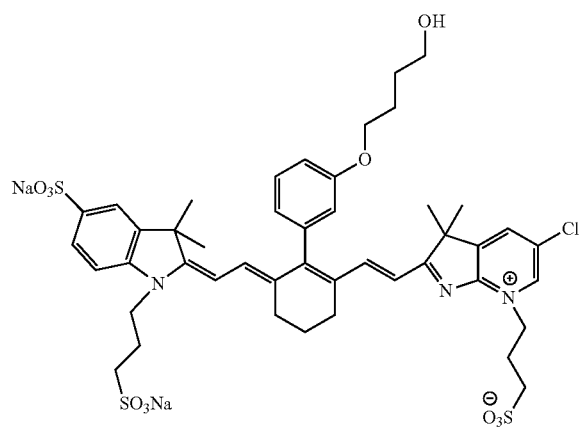

Sodium (E)-2-((E)-2-(3-((E)-2-(5-chloro-3,3-dimethyl-7-(3-sulfonatopropyl)-3H-pyrrolo[2,3-b]pyridin-7-ium-2-yl)vinyl)-2-(3-(4-hydroxybutoxy)phenyl)cyclohex-2-enylidene)ethylidene)-3,3-dimethyl-1-(3-sulfonatopropyl)indoline-5-sulfonate (45)

Compound 45 is prepared analogously to compound 17, except with 3-(4-hydroxybutoxy)phenylboronic acid as shown above.

Example 57

Preparation of Tetrabutylammonium 2-((E)-2-((E)-3-((E)-2-(3,3-Dimethyl-5-sulfonato-1-(3-sulfonatopropyl)indolin-2-ylidene)ethylidene)-2-(3-(4-hydroxybutoxy)phenyl)cyclohex-1-enyl)vinyl)-3,3-dimethyl-7-(3-sulfonatopropyl)-3H-pyrrolo[2,3-b]pyridin-7-ium-5-sulfonate

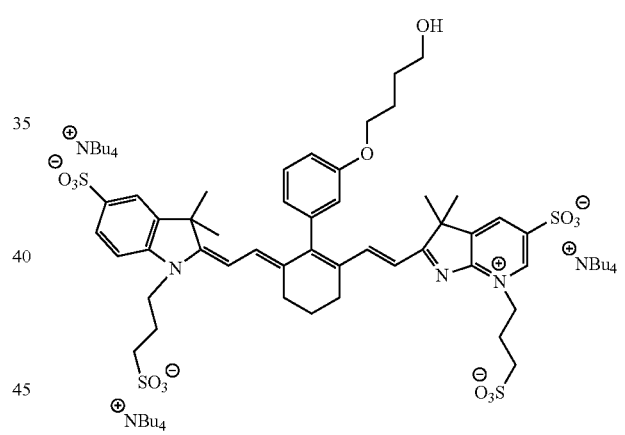

46

Tetrabutylammonium 2-((E)-2-((E)-3-((E)-2-(3,3-Dimethyl-5-sulfonato-1-(3-sulfonatopropyl)indolin-2-ylidene)ethylidene)-2-(3-(4-hydroxybutoxy)phenyl)cyclohex-1-enyl)vinyl)-3,3-dimethyl-7-(3-sulfonatopropyl)-3H-pyrrolo[2,3-b]pyridin-7-ium-5-sulfonate (46)

Compound 46 is prepared by ion exchange of the sodium ions of compound 45. Ion exchange to salts such as tetralkylammonium and the like will improve the solubility of the dye in organic solvents suitable for DNA synthesis (e.g., acetonitrile). This can be done with chromatography as part of the purification process for the hydroxy dye, or as a separate ion-exchange step. Commercial cationic ion exchange resins are widely available.

Example 58

Preparation of Tetrabutylammonium 2-((E)-2-((E)-2-(3-(4-((2-Cyanoethyl)(diisopropylamino)phosphinooxy)butoxy)phenyl)-3-((E)-2-(3,3-dimethyl-5-sulfonato-1-(3-sulfonatopropyl)indolin-2-ylidene)ethylidene)cyclohex-1-enyl)vinyl)-3,3-dimethyl-7-(3-sulfonatopropyl)-3H-pyrrolo[2,3-b]pyridin-7-ium-5-sulfonate

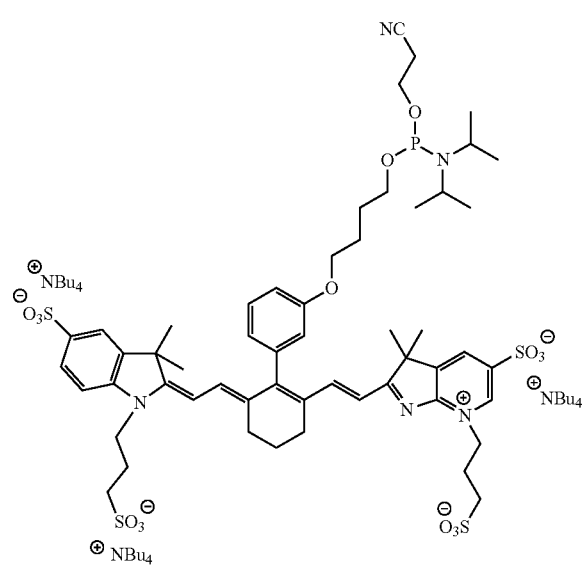

47

Tetrabutylammonium 2-((E)-2-((E)-2-(3-(4-((2-cyanoethoxy)(diisopropylamino)phosphinooxy)butoxy)phenyl)-3-((E)-2-(3,3-dimethyl-5-sulfonato-1-(3-sulfonatopropyl)indolin-2-ylidene)ethylidene)cyclohex-1-enyl)vinyl)-3,3-dimethyl-7-(3-sulfonatopropyl)-3H-pyrrolo[2,3-b]pyridin-7-ium-5-sulfonate The general procedure described in U.S. Pat. No. 6,027,709 is used. Compound 46 (0.140 mmol) is dissolved in 10 mL of dry methylene chloride and stirred under argon at about 0° C. in an ice/salt bath for 30 minutes. A solution of bis(N,N-diisopropylamino)-cyanoethyl phosphine (2.13 mL., 0.15 M in methylene chloride) is added to the dye solution. Tetrazole (0.128 mL., 0.5 M) in acetonitrile is then added to the cooled solution. The cooling is removed after 20 minutes and the reaction is continued for an additional 1.5 hours at room temperature. The reaction mixture is quenched with 5% aqueous sodium bicarbonate solution, washed twice with water, and dried with sodium sulfate. The solvent is removed under vacuum. The crude product is taken up in 1.5 mL of methylene chloride, and the product 47 is obtained by precipitation into hexane.

Example 59

Preparation of Oligonucleotide Bioconjugate with Phosphoramide Linking Group

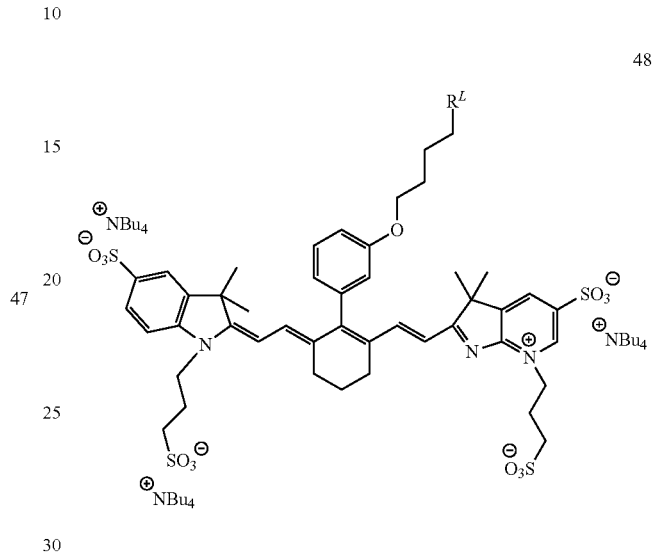

48

Oligonucleotide Bioconjugate with Phosphoramide Linking Group (48)

The general procedure described in U.S. Pat. No. 6,027,709 is used. The phosphoramidite of the fluorescent dye 47 can be used to label DNA molecules prepared in a DNA synthesis machine. The dye is attached to the 5' end of the protected, support-bonded oligonucleotide via standard phosphoramidite chemistry. Typical yields on a 200 nmol scale is expected to range from 50 to 100 nmol before purification.

Each of the DNA oligonucleotides M13 fwd (−29), M13 rev, T7, T3 and SP6, is synthesized in the PerSeptive Biosystems Expedite 8909 DNA synthesis machine in accordance with standard reagents and the methodology taught by the manufacturer. The same apparatus then is used to attach the fluorescent label to the 5' end of each oligonucleotide by treatment with a 0.1 M solution of the dye phosphoramidite produced above in acetonitrile. For the attachment of the dye phosphoramidite, a three-minute delay is inserted after the delivery of the dye in the tetrazole to the synthesis column to allow additional time for the coupling reaction. The 5'-fluorescent labeled DNA oligonucleotide is produced following oxidation, cleavage, deprotection and purification by HPLC.

For HPLC purification of the labeled oligonucleotide, a C18 reverse-phase column having 5μ particles, 300 A pore size (Waters DeltaPak), 1.7 mL/min may be used. Solvent A is 4% acetonitrile in aqueous 0.1 M triethylammonium acetate, and Solvent B is an 80% acetonitrile in aqueous 0.1 M triethylammonium acetate. The gradient profile is 10 to 45% B over 35 minutes, 45 to 100% B over 15 minutes, 100 to 10% B in 10 minutes. One of skill in the art may modify or replace these conditions as necessary for purification of various dyes.

The labeled oligonucleotide bioconjugate 48 can be used, for example, as a primer in the Sanger method of DNA sequencing, as a tailed primer for genotyping, or as a hybridization probe.

Example 60

Preparation of Sodium 2-((1E,3Z,5E)-3-(3-(4-Carboxybutyl)phenyl)-5-(5-chloro-3,3-dimethyl-7-(4-sulfonatobutyl)-3,7-dihydro-2H-pyrrolo[2,3-b]pyridin-2-ylidene)penta-1,3-dienyl)-3,3-dimethyl-1-(4-sulfonatobutyl)-3H-indolium-5-sulfonate

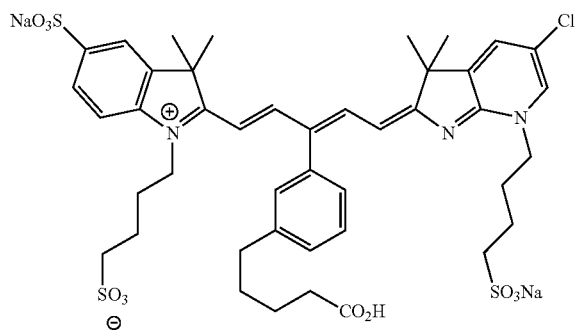

Sodium 2-((1E,3Z,5E)-3-(3-(4-Carboxybutyl)phenyl)-5-(5-chloro-3,3-dimethyl-7-(4-sulfonatobutyl)-3,7-dihydro-2H-pyrrolo[2,3-b]pyridin-2-ylidene)penta-1,3-dienyl)-3,3-dimethyl-1-(4-sulfonatobutyl)-3H-indolium-5-sulfonate (49)

Compound 49 is prepared analogously to compound 43 (Example 54), except with 5-(2-boronophenyl)pentanoic acid as a starting material.

Example 61

Preparation of Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(5-(2,5-dioxopyrrolidin-1-yloxy)-5-oxopentyl)phenyl)penta-1,3-dienyl)-3,3-dimethyl-1-(4-sulfonatobutyl)-3H-indolium-5-sulfonate

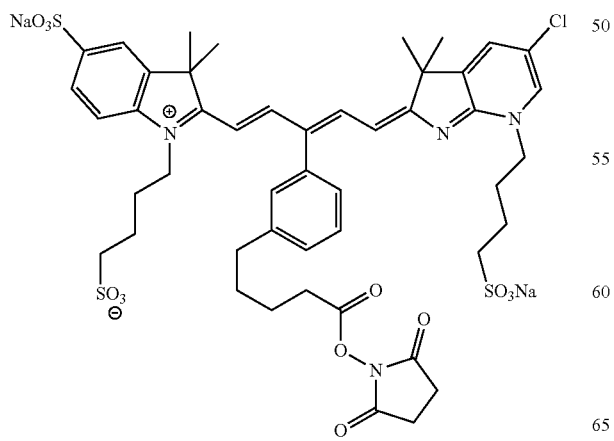

Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(5-(2,5-dioxopyrrolidin-1-yloxy)-5-oxopentyl)phenyl)penta-1,3-dienyl)-3,3-dimethyl-1-(4-sulfonatobutyl)-3H-indolium-5-sulfonate (50)

Compound 50 is prepared analogously to compound 29 (Example 38), except that compound 49 is used as a starting material.

Example 62

Preparation of Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(4-hydroxybutoxy)phenyl)penta-1,3-dienyl)-1,1-dimethyl-3-(4-sulfonatobutyl)-1H-benzo[e]indolium-6,8-disulfonate

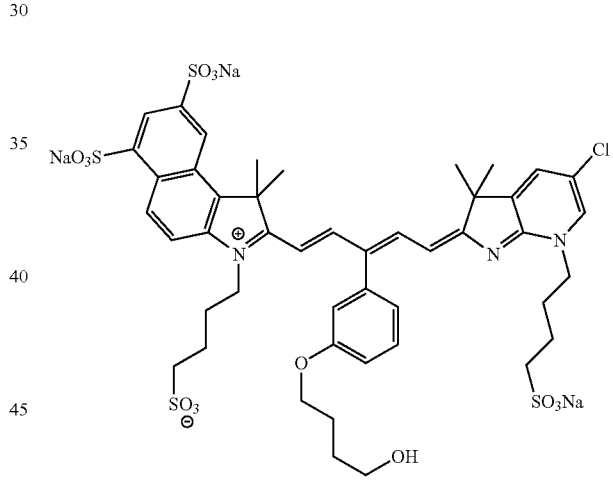

Sodium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(4-hydroxybutoxy)phenyl)penta-1,3-dienyl)-1,1-dimethyl-3-(4-sulfonatobutyl)-1H-benzo[e]indolium-6,8-disulfonate (51)

Compound 51 is prepared analogously to compound 28, except with 3-(4-hydroxybutoxy)phenylboronic acid as a starting material.

Example 63

Preparation of Tetrabutylammonium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(4-hydroxybutoxy)phenyl)penta-1,3-dienyl)-1,1-dimethyl-3-(4-sulfonatobutyl)-1H-benzo[e]indolium-6,8-disulfonate

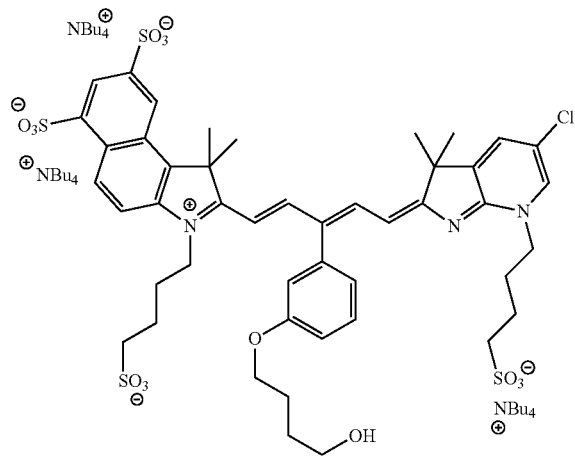

Tetrabutylammonium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(4-hydroxybutoxy)phenyl)penta-1,3-dienyl)-1,1-dimethyl-3-(4-sulfonatobutyl)-1H-benzo[e]indolium-6,8-disulfonate (52)

Compound 52 is prepared analogously to compound 46 (Example 57).

Example 64

Preparation of Tetrabutylammonium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(4-((2-cyanoethyl)(diisopropylamino)phosphinooxy)butoxy)phenyl)penta-1,3-dienyl)-1,1-dimethyl-3-(4-sulfonatobutyl)-1H-benzo[e]indolium-6,8-disulfonate

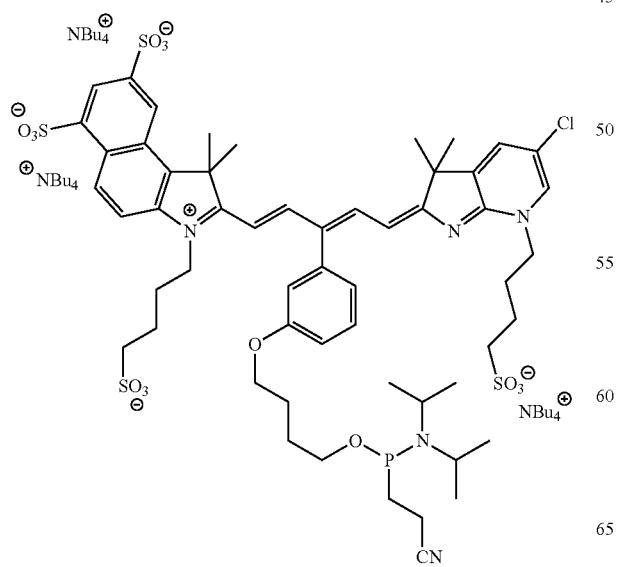

Tetrabutylammonium 2-((1E,3Z,5E)-5-(5-Chloro-3,3-dimethyl-7-(4-sulfonatobutyl)-3,7-dihydro-2H-pyrrolo[2,3-b]pyridin-2-ylidene)-3-(3-(4-((2-cyanoethyl)(diisopropylamino)phosphinooxy)butoxy)phenyl)penta-1,3-dienyl)-1,1-dimethyl-3-(4-sulfonatobutyl)-1H-benzo[e]indolium-6,8-disulfonate (53)

Compound 53 is prepared analogously to compound 47 (Example 58).

Example 65

Preparation of Oligonucleotide Bioconjugate II with Phosphoramide Linking Group

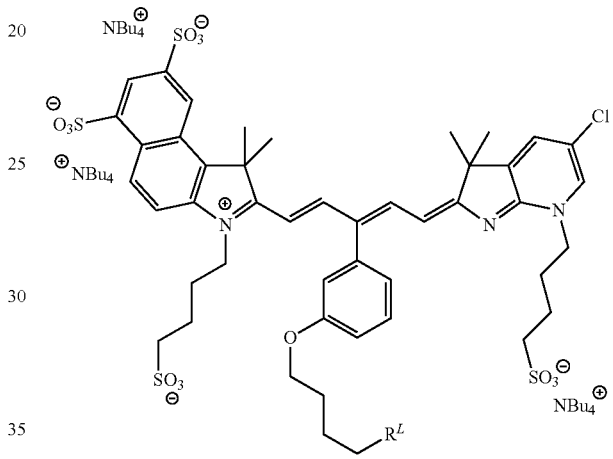

Oligonucleotide Bioconjugate II with Phosphoramide Linking Group (54)

Compound 54 is prepared and used analogously to compound 48 (Example 59).

Example 66

Preparation of Oligonucleotide Bioconjugate III with Phosphoramide Linking Group

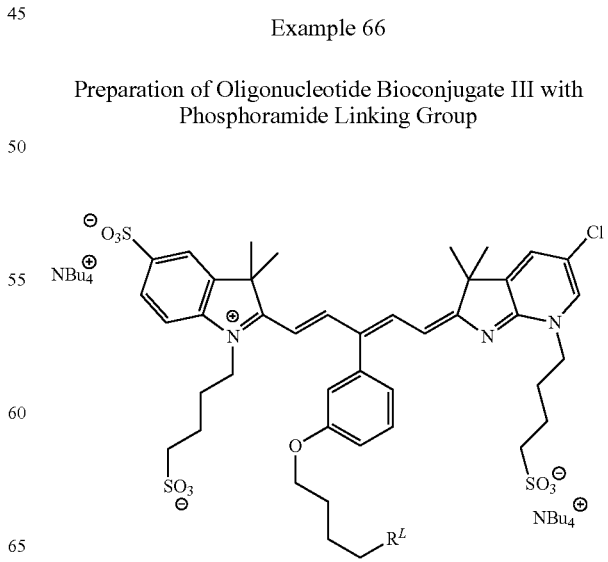

Oligonucleotide Bioconjugate III with
Phosphoramide Linking Group (55)

Compound 55 and its precursors are prepared analogously to compounds 9, 10, and 45-48.

Example 67

Dye Brightness

Compound 20

The baseline fluorescence of 20 was determined.

Figure 13A:
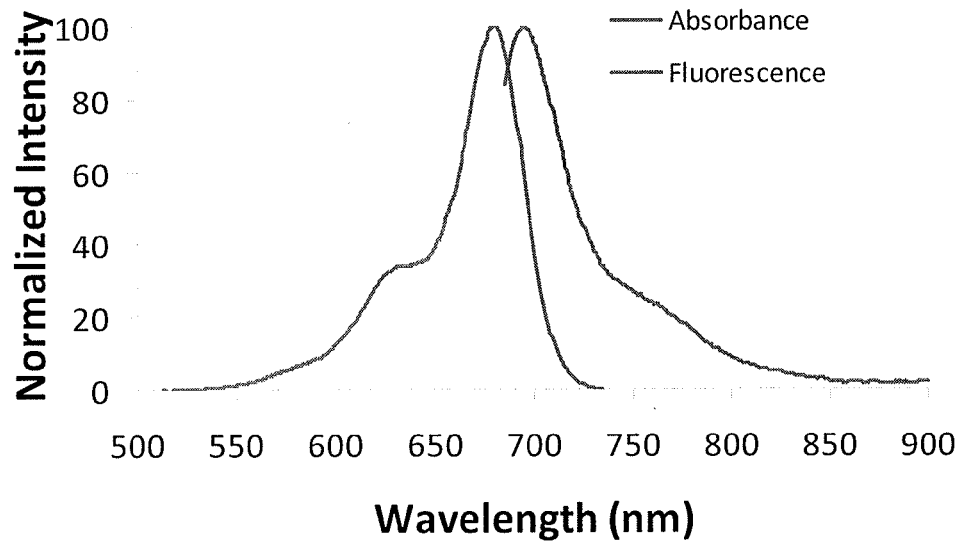
FIGS. 13A and B illustrate compound 20's absorbance and emission maxima in methanol (680 nm; Panel A); and in phosphate-buffered saline solution (676 nm; Panel B).
Figure 13B:
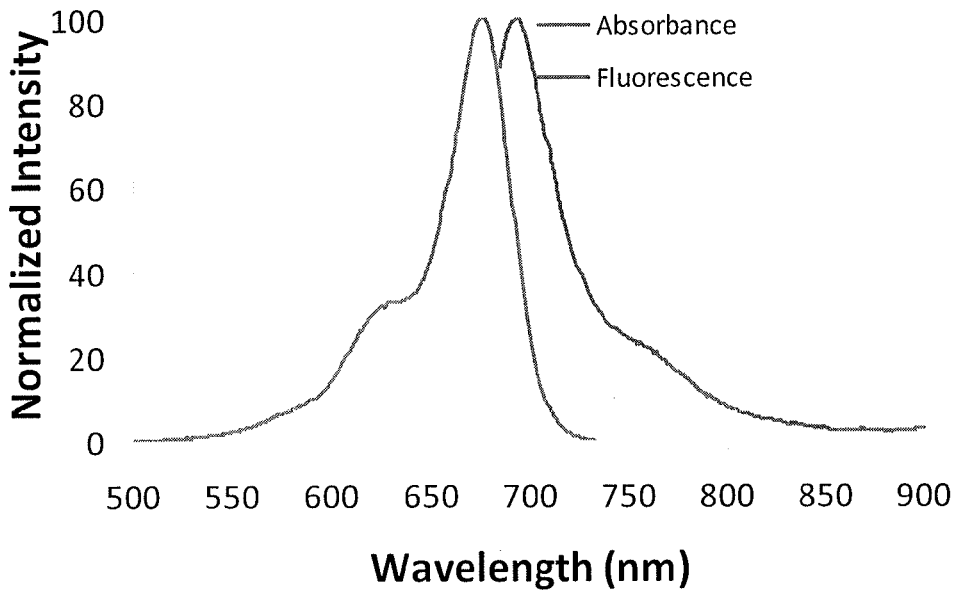
Figure 14:
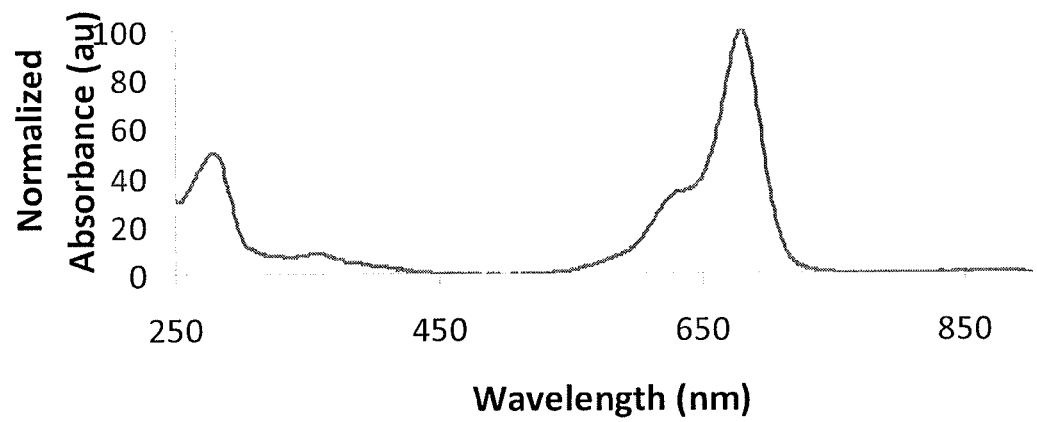
FIG. 14 illustrates the absorbance of compound 20-labeled GAM antibody in 1:1 PBS:methanol.
Figure 15:
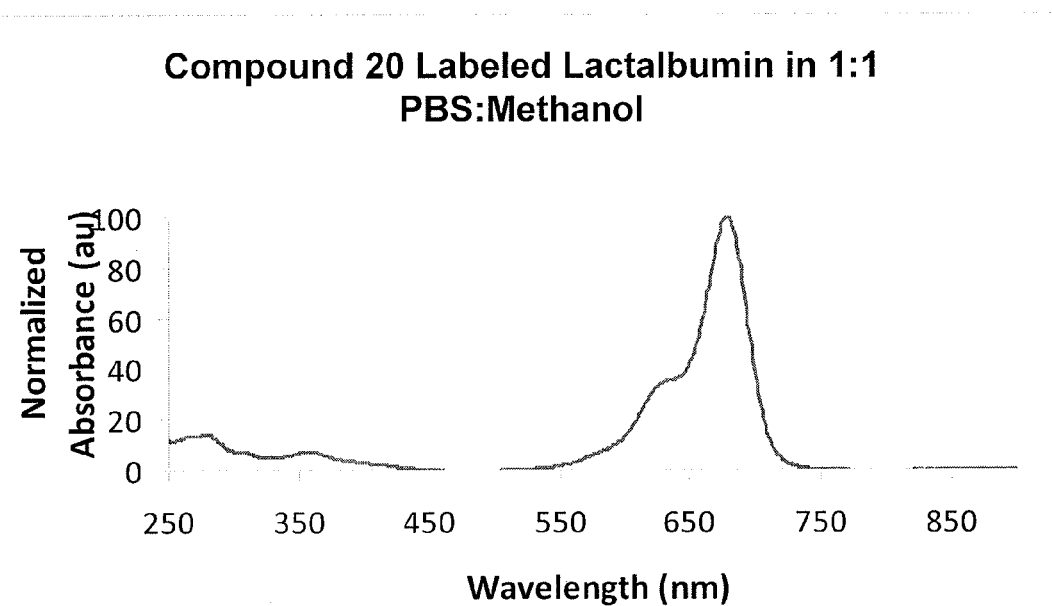
FIG. 15 illustrates the absorbance of compound 20-labeled lactalbumin in 1:1 phosphate-buffered saline (PBS):methanol.

Fluorescence determinations were made at a fixed antibody concentration of 10 μg/mL in physiological buffer using dye-labeled goat anti-rabbit (GAR) conjugates prepared at LI-COR (FIGS. 13A-B and 14). A dye-labeled lactalbumin conjugate was also tested (FIG. 15).

20's absorbance and emission maximum is at 676 nm in aqueous solution and at 693 nm in methanol. 20 is a highly water-soluble dye optimized for use on the Odyssey Infrared Imager and the Aerius Automated Imager in the 700 nm channel.

Example 68

Dye Brightness

Compound 10

The baseline fluorescence of 10 is determined analogously to 20 (Example 48).

Example 69

Comparison of Dye Brightness

Compound 20 and AlexaFluor® 680

A comparison of 20 with the commercially available dye AlexaFluor® 680 was conducted.

Fluorescence determinations were made at a fixed antibody concentration of 10 mg/mL in physiological buffer using dye labeled goat anti-rabbit (GAR) conjugates prepared at LI-COR. Fluorescence was measured using a PTI Fluorometer at the optimum excitation and emission wavelength of each dye.

Figure 16:
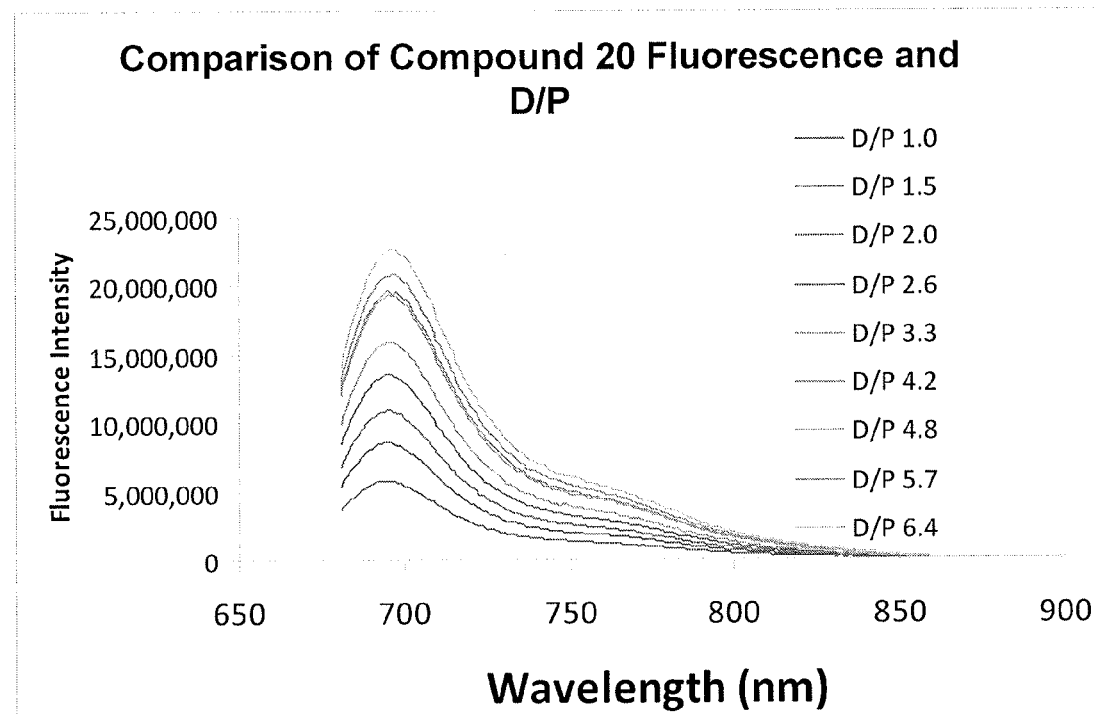
FIG. 16 illustrates a comparison of fluorescence and D/P for compound 20-labeled goat anti-rabbit (GAR) antibody.
Figure 17:
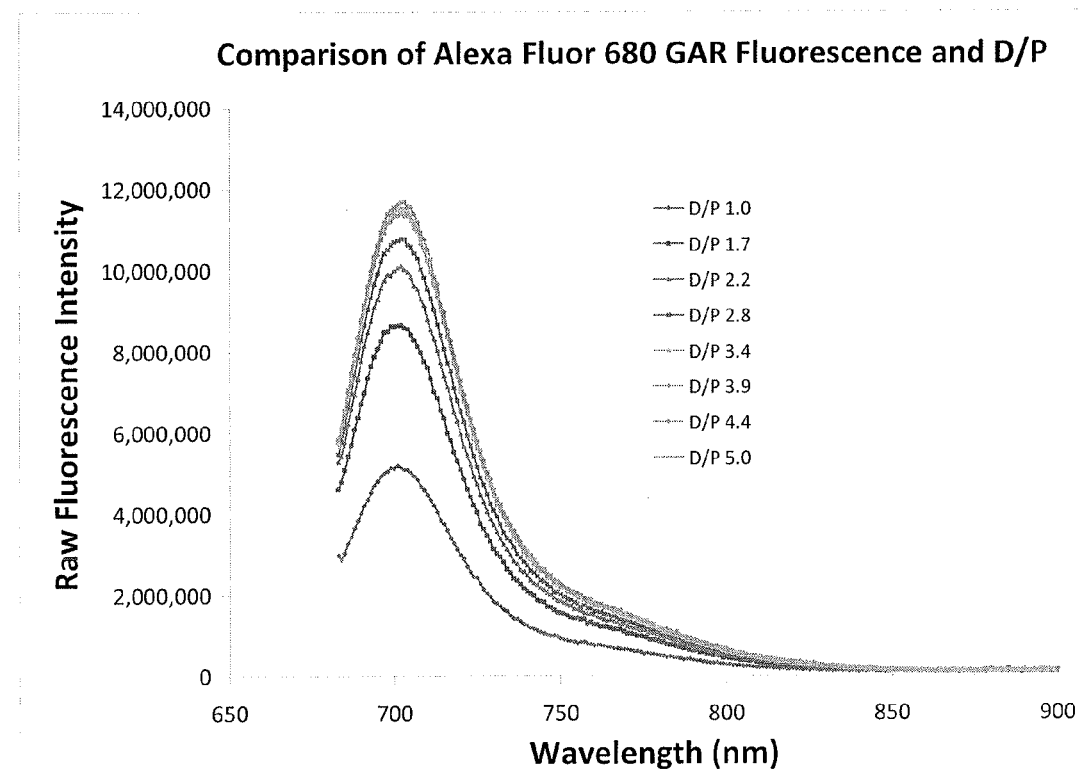
FIG. 17 illustrates a comparison of fluorescence and D/P for AlexaFluor® 680-labeled goat anti-rabbit (GAR) antibody.
Figure 18:
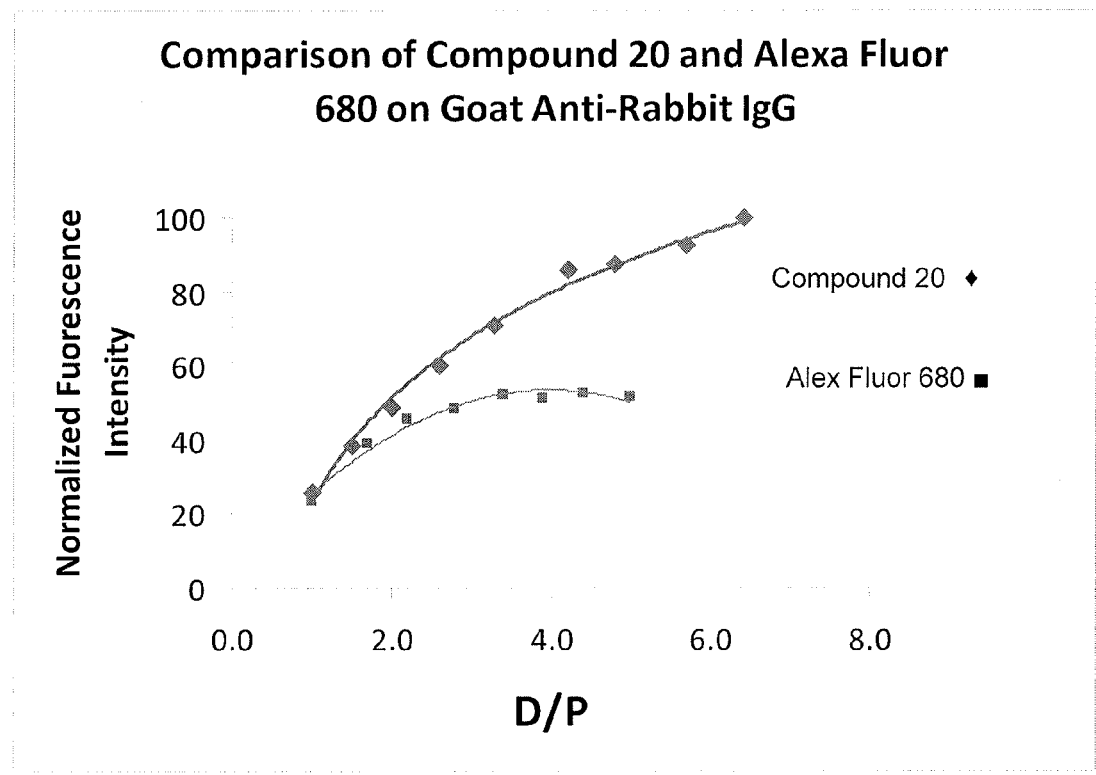
FIG. 18 illustrates a comparison of relative fluorescence between compound 20 and AlexaFluor® 680.

Fluorescence intensity was also tested with an Odyssey Infrared Imager (FIGS. 16 and 17). The fluorescence intensity of each conjugate increased with increased degree of labeling. A plot of degree of labeling versus fluorescence shows that the dynamic range for the 20/GAR was much broader than the AlexaFluor®, which quickly leveled off above D/P 3.4 (FIG. 18). The leveling off of the AlexaFluor® 680 conjugates may be due to self-quenching. Compound 20 conjugates continue to increase in fluorescence intensity to at least D/P 6.4. Overall, 20 is significantly brighter than AlexaFluor® 680.

Example 70

Comparison of Dye Brightness

Compound 10 and AlexaFluor® 680

A comparison of dye brightness for 10 is determined analogously to 20 (Example 69).

Example 71

Comparison of Photostability

Compound 20, IRDye 700Dx, and AlexaFluor® 680

Figure 19A:
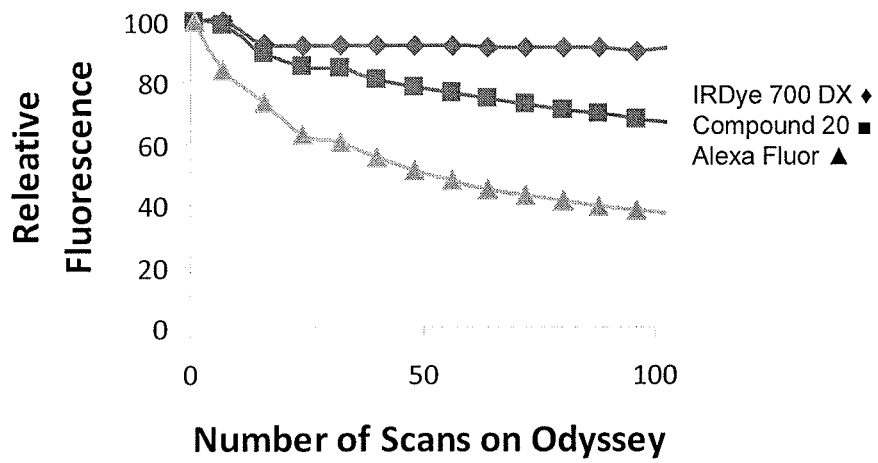
FIG. 19A-B illustrate a comparison of photostability among IRDye® 700DX, compound 20, and AlexaFluor® 680 at 50 fmoles (Panel A); and 25 fmoles (Panel B).
Figure 19B:
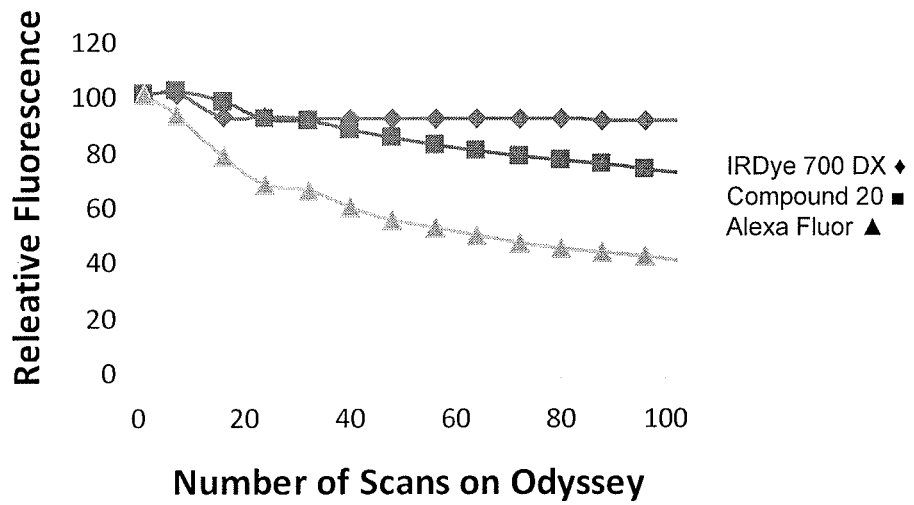

The photostability of 20 was compared to AlexaFluor®680 and IRDye 700Dx, which is considered to be one of the most stable 700 nm fluorescent dyes. Test samples were prepared by spotting equimolar amounts of dye (i.e., goat anti-rabbit (GAR) secondary antibodies labeled with the appropriate dye) onto nitrocellulose membrane. The membrane was then scanned repeatedly on an Odyssey Infrared Imager, and the signal intensity was normalized to the control signal at time zero (FIG. 19A-B).

The relative fluorescence of the 700DX samples was unchanged, the 680 LT fluorescence decreased slightly, and the AlexaFluor® 680 fluorescence decreased significantly. Therefore, the most stable dye was 700DX followed by 20 and AlexaFluor® 680.

Example 72

Comparison of Photostability

Compound 10 and AlexaFluor® 680

A comparison of photostability for 10 is determined analogously to 20 (Example 71).

Example 73

Comparison of GAR Cell Staining

Compound 20 and AlexaFluor® 680

Figure 20A:
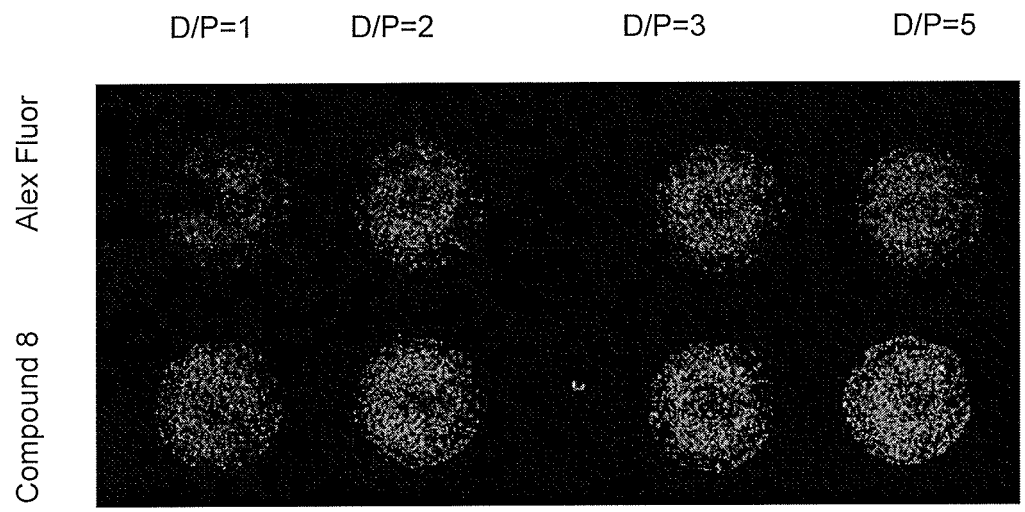
FIG. 20A-B illustrate a comparison of cell staining and relative fluorescence between compound 20 (Panel A); and AlexaFluor® 680 (Panel C).
Figure 20B:
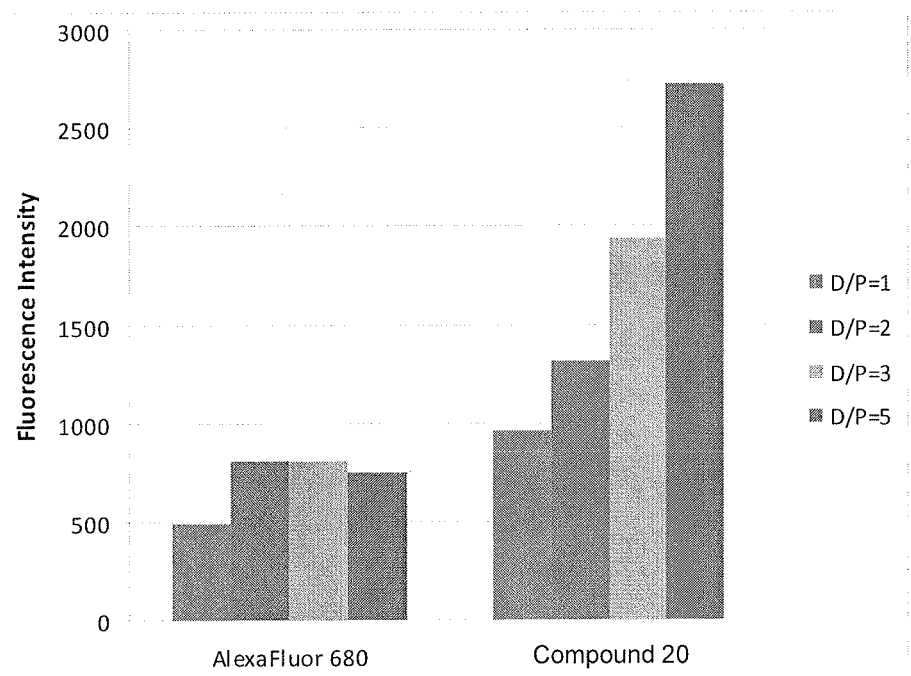

GAR secondary antibodies labeled with 20 or AlexaFluor® 680 for fluorescence measurements were used for cell staining (as previously described for the other GAR functional testing) (FIG. 20A-B).

Cultured SK-BR-3 (A) or SK-OV03 (B) were fixed with 3.7% formaldehyde and permeabilized with 0.1% Triton X-100. Cells were incubated with rabbit anti-HER2 mAb (CST), followed by goat and rabbit secondary antibodies labeled with IRDy3 680 LT or Alexa Fluor 680. The images were scanned on an Odysesy scanner. The original images are shown on the left, and the quantified signal intensities are shown on the right (FIG. 20A-D).

The brightness and photostability of 20 make it an excellent choice for microscopy and In-Cell Westerns™. The dynamic range for 20 was wider than for AlexaFluor® 680. As well, overall fluorescence intensity or "brightness" at comparable D/P ratios was greater for 20 than for AlexaFluor® 680. The signal intensity was two- to three-fold higher for cells stained with 20 labeled secondary antibody compared to the AlexaFluor® 680 conjugates. Later In-Cell Western data mimicked the fluorescence measurement data for the dye labeled conjugates.

Example 74

Comparison of GAR Cell Staining

Compound 10 and AlexaFluor® 680

A comparison of GAR cell staining for 10 is determined analogously to 20 (Example 73).

Example 75

Comparison of Immunofluorescence Staining

Compound 20 and AlexaFluor® 680

HER2 protein was stained with dye-labeled antibodies on SK-BR-3 cell membrane. GAR secondary antibodies labeled with 20 were used for fluorescence measurements.

Figures 21A, 21B, 21C:
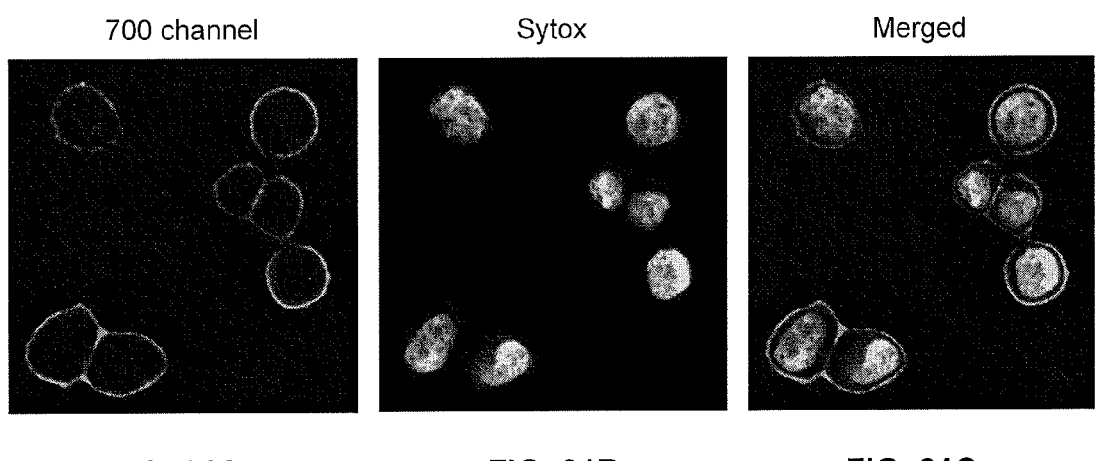
FIG. 21A-C illustrate the immunofluorescence staining of HER2 protein with compound 20-labeled GAR antibodies. Cells were incubated with rabbit anti-HER2 mAb, followed by 20-labeled GAR secondary antibody (Panel A). Sytox green was used to stain the nuclei (Panel B); a merged image is illustrated in Panel C.
Figure 23:
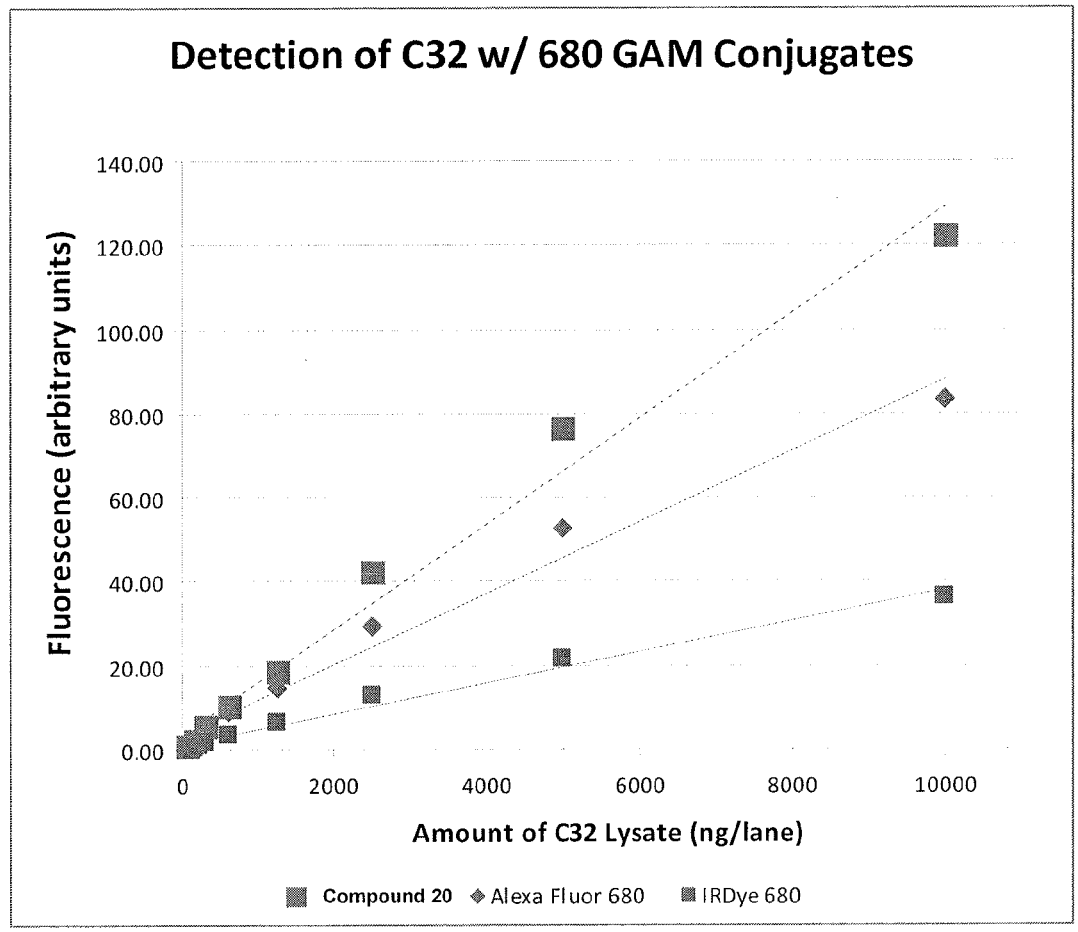
FIG. 23 illustrates the response of the β-actin GAM antibody conjugates' fluorescence intensity at increasing concentrations of cell lysate.

The cells were cultured on cover slips. After fixation and permeabilization as per Example 52, the cells were incubated with rabbit anti-HER2 mAb (CST), followed by 20-labeled GAR secondary antibody (D/P=3.3). Sytox green was used to stain the nuclei. Images were acquired on an Olympus microscope and deconvolved using the accompanying software (FIG. 21A-C).

Example 76

Comparison of Immunofluorescence Staining

Compound 10 and AlexaFluor® 680

A comparison of immunofluorescence staining for 10 is determined analogously to 20 (Example 75).

Example 77

Comparison of β-Actin Western Blots

Compound 20, IRDye® 680, and AlexaFluor® 680

Compound 20 conjugates were compared by Western blot to commercially available IRDye 680 and AlexaFluor® 680 goat anti-mouse (GAM) antibody conjugates. AlexaFluor® 680 antibody conjugates are supplied at 2 mg/mL and were diluted to 0.1 mg/mL (1:20,000). The IRDye 78 secondary antibodies are reconstituted to give a stock concentration of 1 mg/mL and were diluted to 0.1 mg/mL (1:10,000). A 1:20,000 dilution of AlexaFluor® 680 GAM has approximately equivalent amount of protein as a 1:10,000 dilution of the IRDye antibodies.

Western blots were performed to detect actin in C32 lysates. Two-fold dilutions starting at 10 μg of C32 whole cell lysate (Santa Cruz) were loaded on a 10% Bis-Tris reducing gel and transferred to a nitrocellulose membrane (Odyssey). The mouse primary antibody against β-actin (Thermo Fisher Scientific) was used at 1:1000 dilution in a buffer of 0.2% Tween 20 in Odyssey Blocking Buffer. The various goat anti-mouse secondary antibodies were diluted in the same way. All antibody incubation was for 1 hour at ambient temperature. The results of the Western blot are shown in FIG. 22A-C. All Western blots were performed in duplicate.

An assessment of signal intensity, background and working dilution of the 20 antibodies was made in comparison to both IRDye® 680 and AlexaFluor® secondary antibodies. (FIG. 13) Overall, the signal detected with 20/GAM is 3× greater than IRDye 680 and 1.5× higher than AlexaFluor® 680 GAM. The background on membranes treated with 20/GAM was comparable to that with the other 700 channel fluorophores. Visual inspection of the Western blots indicated a similar limit of detection between the three GAM-conjugated antibodies. Also, the 20/GAM, diluted 1:25,000, maintains superior performance in terms of signal when compared to IRDye® 680 GAM at the same dilution.

Example 78

Comparison of β-Actin Western Blots

Compound 10, IRDye® 680, and AlexaFluor® 680

A comparison of β-actin Western blots for 10 is determined analogously to 20 (Example 77).

Example 79

Comparison of p38 Western Blots

Compound 20, IRDye® 680, and AlexaFluor® 680

A Western blot was performed to detect the lower expressing protein p38 in Jurkat lysates. Conjugates of compound 20 were compared with commercially available IRDye® 680 and AlexaFluor® 680 goat anti-rabbit (GAR) antibody conjugates. The dye-labeled antibodies were diluted as described in Example 77.

Figures 24A, 24B, 24C:
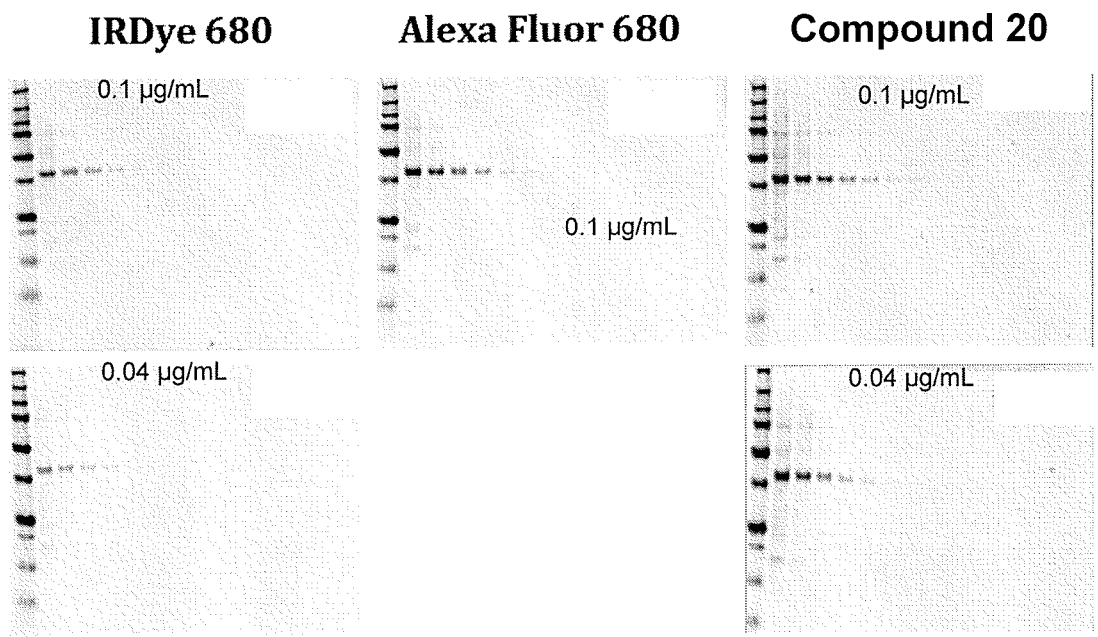
FIG. 24A-C illustrates a Western blot total fluorescence comparison of p38 GAR antibody conjugates with compound 20, IRDye® 680, and AlexaFluor® 680.

Two-fold dilutions starting at 10 μg of Jurkat cell lysate were loaded on a 10% Bis-Tris reducing gel and transferred to a nitrocellulose membrane (Odyssey). The rabbit primary antibody against p38 (Santa Cruz) was used at 1:1000 dilution in a buffer of 0.2% Tween 20 in Odyssey Blocking Buffer. The various goat anti-rabbit secondary antibodies were diluted in the same way. All antibody incubations were for 1 hour at ambient temperature. The results of the Western blot are shown in FIG. 24A-C. All Western blots were performed in duplicate.

The 20/GAR conjugates outperformed IRDye® 680 GAR with a 2× to 4× improvement in signal intensity. With this target, the visual limit of detection was also improved by the same factor (1:10,000-1:25,000 dilutions, respectively). The signal of IRDye 680 GAR is 1.7-0.9× as bright as the AlexaFluor® 680 GAR (AlexaFluor® 680 1:20,000 dilution), and the limit of detect was within a single two-fold dilution for the p38 target. Additional bands were seen on all Western blots, indicating that the primary antibody is detecting additional proteins.

Example 80

Comparison of p38 Western Blots

Compound 10, IRDye® 680, and AlexaFluor® 680

A comparison of p38 Western blots for 10 is determined analogously to 20 (Example 79).

Example 81

Akt Two-Color Western Blot

Compound 20, IRDye® 800CW, and AlexaFluor® 680

Balanced two-color Western blots to detect the low abundance protein Akt were performed with 20/GAM and IRDye® 800CW GAR antibodies. The dye-labeled antibodies were diluted as described in Example 58.

NIH 3T3 cell lysates (two-fold dilutions starting at 10 μg) were separated by SDS-PAGE and transferred to nitrocellulose. The membranes were blocked with LI-COR Blocking Buffer. The primary antibodies were against Akt (mouse mAb) and actin (rabit mAb), diluted 1:1000. The secondary antibody to detect actin was IRDye® 800CW GAR (1:10, 000). Akt was detected with (A) IRDye® 680 GAM (1:10, 000); (B) AlexaFluor® 680 GAM (1:20,000); (C) 20/GAM 1:10,000) on Odyssey (700 channel=5; 800 channel=5).

Figures 25A, 25B, 25C:
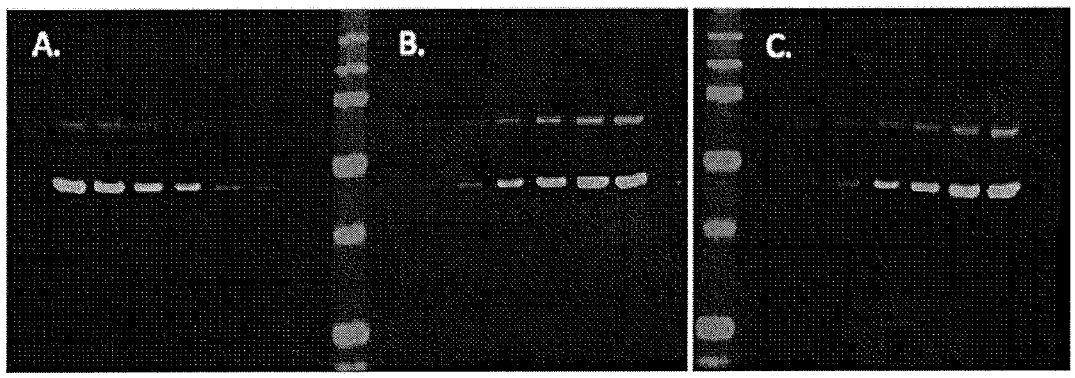
FIG. 25A-C illustrate a two-color Western blot total fluorescence comparison of Akt GAM antibody conjugates with IRDye® 680 (Panel A); compound 20 (Panel B); and AlexaFluor® 680 (Panel C). Rabbit mAb (actin) was detected with an IRDye® 800CW/GAR antibody conjugate.

Once again, 20 conjugates were brighter compared to IRDye® 680 (FIG. 25A and FIG. 25C). 20/GAM showed lower background than AlexaFluor® 680 GAM with an equivalent visual limit of detection (FIG. 25B-C).

Example 82

Comparison of Akt Two-Color Western Blots

Compound 10, IRDye® 680, and AlexaFluor® 680

A comparison of Akt two-color Western blots for 10 is determined analogously to 20 (Example 81).

Example 83

Akt Western Blot with Compound 20

Additional Western blot experiments (FIG. 26A-B) were performed using 20/GAM to detect Akt in A431 lysates. The dye-labeled antibodies were diluted as described in Example 77.

A431 lysates were separated on a 10% Bis-Tris gel, transferred to Odyssey nitrocellulose and blocked in Odyssey® Blocking Buffer. For experiment A, the membrane was incubated for 1 hour with Akt mAb (Cell Signaling Technologies) diluted in Odyssey® Blocking Buffer (1:1000), washed, and then incubated for 1 hour with 20/GAM (1:10,000). It was diluted in Odyssey® Blocking Buffer including 0.2% Tween 20. For experiment FIG. 26B, the membrane was incubated only in secondary antibody as described in A. All membranes were washed as directed and imaged on the Odyssey Infrared Imager.

Figure 26A:
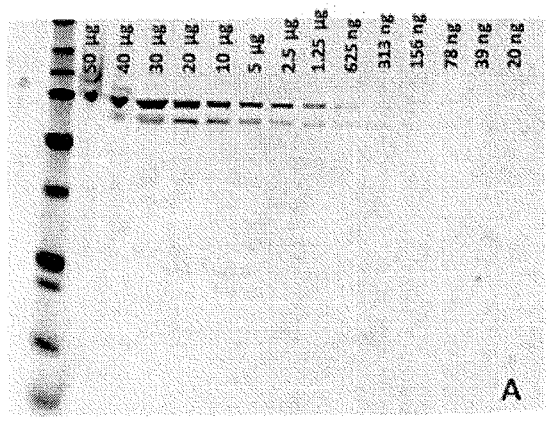
FIG. 26A-B illustrate a Western blot total fluorescence comparison of Akt GAR antibody conjugates with compound 20, IRDye® 680, and AlexaFluor® 680 in Panel A. A control experiment without primary antibody is illustrated in Panel B.

FIG. 26A illustrates the linearity of the conjugate over a large range of protein concentrations (50 µg-20 ng; $R^2$ is 0.9982 from 30 µg to 20 ng lysate).

Figure 26B:
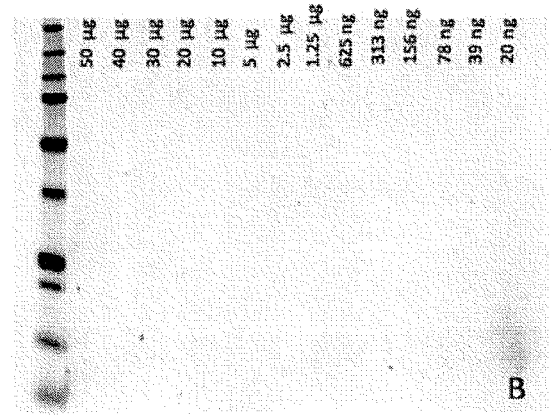

Compound 20 secondary antibodies have been shown to have low non-specific binding to proteins in a variety of lysates (Jurkat, HeLa, C32, A431 & NIH3T3). An example of this low binding is shown in FIG. 26B, as the Western blot was performed without primary antibody. Even in the presence of 50 µg of protein there is little signal detected from the 20/GAM antibody.

Example 84

Akt Two-Color Western Blot with Compound 10

An Akt Western blots for 10 is determined analogously to 20 (Example 83).

Example 85

Example 85 illustrates the synthesis of 2-((E)-2-((E)-3-((E)-2-(1-(1-azido-13-oxo-3,6,9-trioxa-12-azaoctadecan-18-yl)-3,3-dimethyl-5-sulfoindolin-2-ylidene)ethylidene)-2-(4-sulfophenoxy)cyclohex-1-enyl)vinyl)-3,3-dimethyl-1-(4-sulfobutyl)-3H-indolium-5-sulfonate (IRDye 800CW-PEG-Azide, 56).

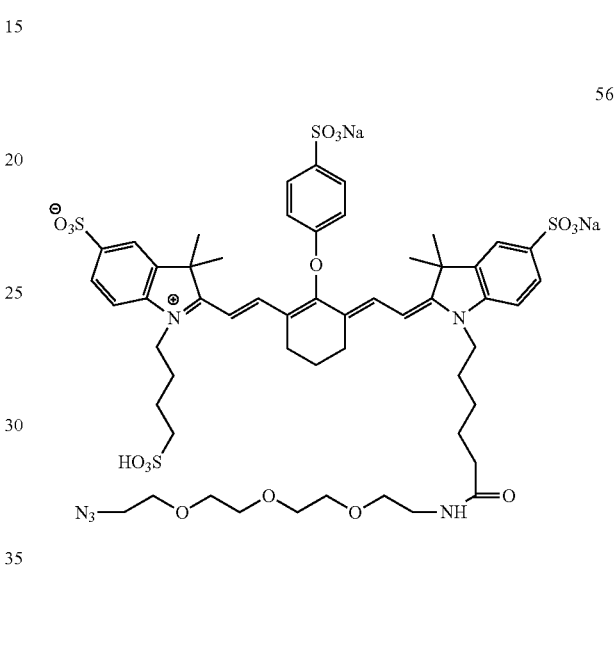

A solution of 11-azido-3,6,9-trioxaundecan-1-amine (Amino-PEG-Azide, 1.0 mg, $4.1 \times 10^{-3}$ mmol) and N,N-diisopropylethylamine (0.0020 mL, $1.1 \times 10^{-2}$ mmol) in anhydrous dimethyl sulfoxide (0.2 mL) was added to a reaction vessel containing IRDye 800CW NHS ester (5.0 mg, $4.3 \times 10^{-3}$ mmol). The reaction was allowed to proceed at ambient temperature for 2 hours, with periodic agitation every 15 minutes. After HPLC analysis indicated complete consumption of the IRDye 800CW NHS ester, the reaction mixture was precipitated into anhydrous diethyl ether. The ethereal layer was decanted and the crude product was purified by reverse-phase HPLC. Fractions containing the desired IRDye 800CW-PEG-Azide in ≥95% purity by HPLC analysis were combined and lyophilized to afford the product 56 as a green flocculent solid (3.4 mg, 66% based on Amino-PEG-Azide). UV/Vis (methanol) $\lambda_{max}$=778 nm; LRMS (ES/water), m/z calculated for 1203.37 $[M+H]^+$. found 1203.6 and 602.3 $[M+2H]^{2+}$.

Example 86

Example 86 illustrates a trityl-protected version of Compound 10 (Compound 10-NH-(PEG)$_2$-NH-Trt, 57).

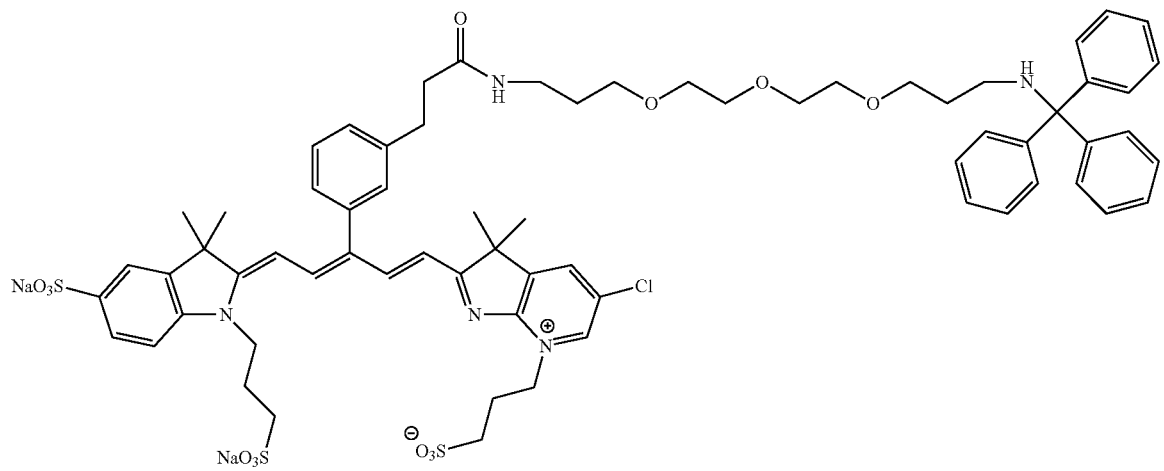

57

A solution of O—(N-trityl-3-aminopropyl)-O'-(3-aminopropyl)-diethyleneglycol (Trt-NH-PEG$_2$-NH$_2$, 1.0 mg, 2.2×10$^{-3}$ mmol) and N,N-diisopropylethylamine (0.001 mL, 5.7×10$^{-3}$ mmol) in anhydrous dimethyl sulfoxide (0.2 mL) was added to a reaction vessel containing Compound 11 (1.0 mg, 1.0×10$^{-3}$ mmol). The reaction was allowed to proceed at ambient temperature for 2 hours, with periodic vortexing at 15-minute intervals. After HPLC analysis showed complete consumption of Compound 11, the reaction was precipitated into anhydrous diethyl ether. The ethereal layer was decanted and the crude product was purified by HPLC. Fractions containing the presumed Compound 10-NH-PEG$_2$-NH-Trt in ≥95% purity were combined and concentrated in vacuo to afford a blue film; the yield was presumed to be quantitative.

To a flask containing Compound 10-NH-PEG$_2$-NH-Trt (1.3 mg, 8.6×10$^{-4}$) was added a solution of trifluoroacetic acid in dichloromethane (TFA/CH$_2$Cl$_2$=1:3, 5.0 mL). The purple reaction was briefly swirled and allowed to proceed at ambient temperature for 30 minutes. The volatiles were removed in vacuo and the residuals were treated again with TFA/CH$_2$Cl$_2$ (1:3, 5.0 mL) for 30 minutes. After removing the volatiles in vacuo, the residuals were washed with anhydrous diethyl ether. The ethereal layer was decanted, and the product 58 was used without further purification; the yield was presumed to be quantitative. UV/Vis (methanol) $\lambda_{max}$=676 nm; LRMS (water) m/z calculated for 1064.4 [M+H]$^+$. found 1064.6, 532.9 [M+2H]$^{2+}$.

Example 87

Example 87 illustrates another derivative of Compound 10 (Compound 10-NH-(PEG)$_2$-NH$_2$.2TFA, 58).

Example 88

Example 88 illustrates the synthesis of a phosphine Compound 10 derivative (Compound 10-PEG-Phosphine, 59).

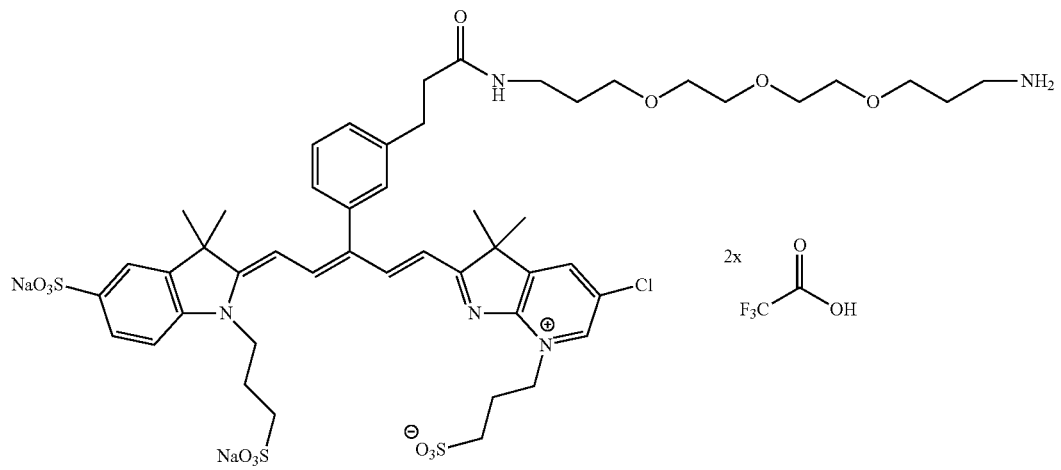

58

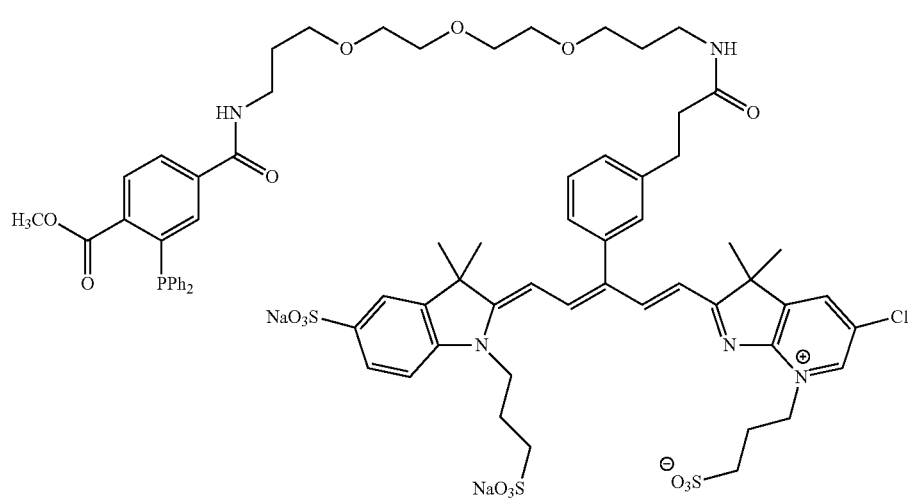

59

To a solution of Compound 10-NH-(PEG)$_2$-NH$_2$.2TFA (1.3 mg, 1.0×10$^{-3}$ mmol) in anhydrous dimethyl sulfoxide (0.2 mL) was added NHS-Phosphine (1.0 mg, 2.2×10$^{-3}$ mmol, ThermoScientific/Pierce) followed by N,N-diisopropylethylamine (0.001 mL, 5.7×10$^{-3}$ mmol). The reaction was allowed to proceed at ambient temperature for 2 hours, with periodic agitation at 15-minute intervals. After HPLC analysis showed near-complete consumption of the Compound 10-NH-(PEG)$_2$-NH$_2$.2TFA, the reaction was precipitated into anhydrous diethyl ether. The ethereal layer was decanted and the crude product was purified by HPLC. Fractions containing the presumed Compound 10-PEG-Phosphine in ≥95% purity were combined and concentrated in vacuo to afford a blue solid (0.7 mg, 51% based on Compound 10-NH-(PEG)$_2$-NH$_2$.2TFA); UV-Vis (methanol) $\lambda_{max}$=676 nm; LRMS (water) m/z calculated for 1410.4 [M+H]% found 705.8 [M+2H]$^{2+}$.

Example 89

Example 89 illustrates a phosphine oxide Compound 10 derivative (Compound 10-PEG-Phosphine Oxide, 60).

This compound was isolated as a substantial byproduct from the synthesis of Compound 10-PEG-Phosphine. This byproduct is nonfunctional and causes background problems. The compound is a blue solid (0.2 mg, 18% based Compound 10-NH-(PEG)$_2$-NH$_2$.2TFA); UV-Vis (methanol) $\lambda_{max}$=676 nm; LRMS (water) m/z calculated for 1426.4 [M+H]$^+$. found 1426.5, 713.9 [M+2H]$^{2+}$.

Example 90

Example 90 illustrates the synthesis of a two-dye Staudinger ligation product (IRDye 800CW-Compound 10 Click Product, 61).

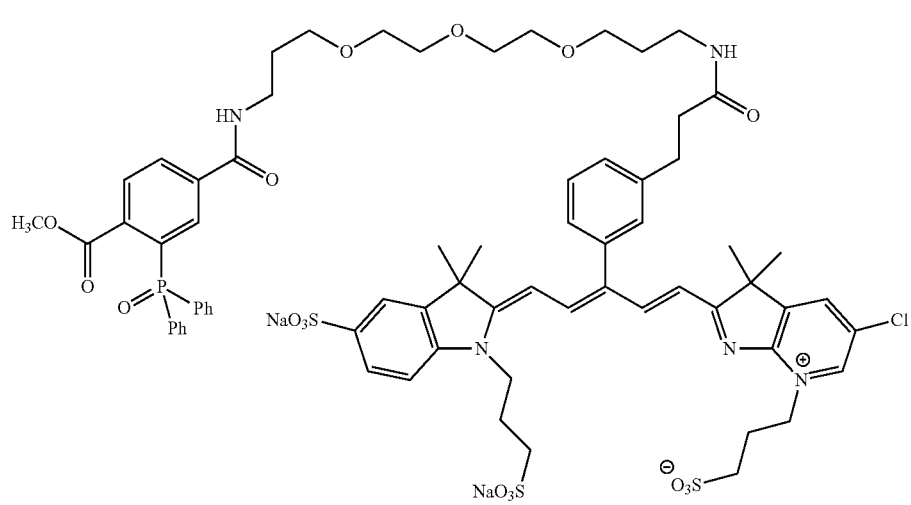

60

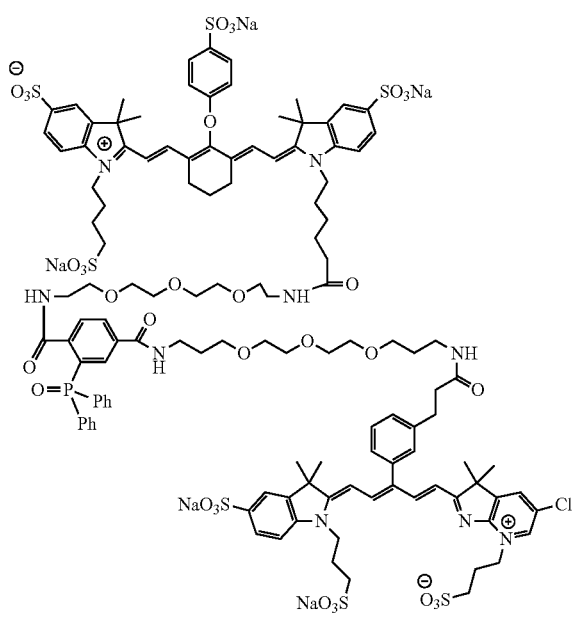

To a solution of IRDye 800CW-PEG-Azide (56) (55 µg, 4.3×10$^{-2}$ µmol) in water (20 µL) was added a solution of Compound 10-PEG-Phosphine (59) (73 µg, 5.0×10$^{-2}$ mmol) in water (150 µL). The reaction was allowed to proceed at ambient temperature for 1 hour, then maintained at 40° C. for 3 hours. After HPLC analysis showed near-complete consumption of both reagents, the reaction mixture was filtered and directly purified by HPLC. Fractions containing the presumed IRDye 800CW-Compound 10 Click Product were combined and concentrated in vacuo. The exact yield was not determined. UV/Vis (acetonitrile/water=1:1) $\lambda_{max}1$=778 nm, $\lambda_{max}2$=677 nm; LRMS (ES/water), m/z calculated for 2570.8 [M+H]$^+$. found 858.5 [M+3H]$^{3+}$.

Example 91

Example 91 illustrates a non-catalyzed click chemistry synthesis reaction.

Bertozzi et al. (Aldrichimica Acta, 2010, 43(i), 15-23 and references therein) have developed a bio-orthogonal labeling method that employs modified sugars. Cells incubated in a growth medium containing these modified azido sugars will absorb the sugars and perhaps incorporate the sugars on cell surface glycans (i.e., glyco-proteins and glycolipids). Upon exposing the azido-sugar labeled cells to appropriate phosphine or alkyne reagents, a click-type reactions will occur (either a Staudinger ligation or Huisgen cycloaddition, respectively). If the phosphine or alkyne bears a reporter group (e.g., a dye), then the cells are labeled as shown below in Scheme 1:

Scheme 1: Biocompatible Labeling with Click Chemistry

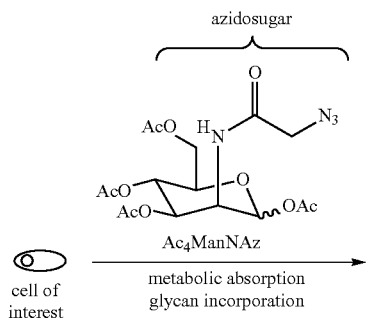

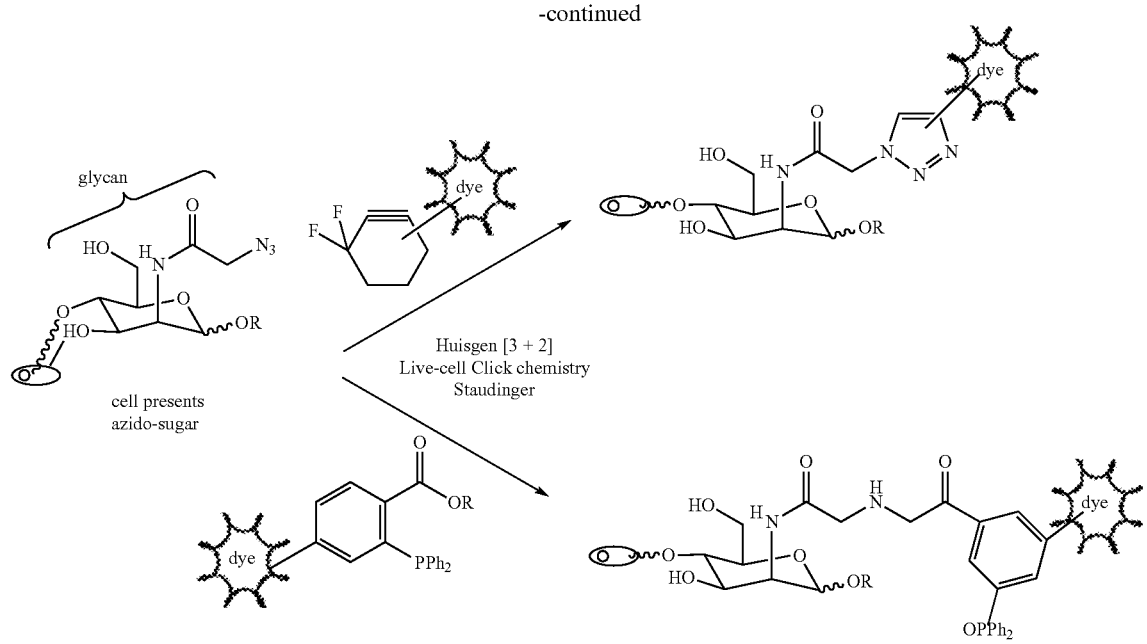

In this example, the reaction is performed with IRDye 800CW as the dye. The conjugate has the following advantages: (1) This type of bio-orthogonal labeling does not entail genetic engineering. Although many biological researchers study transgenic organisms, developmental biologists simply want to monitor "normal" changes in biochemical morphology. (2) The click reagents are highly chemoselective and typically do not react with biological nucleophiles (although strained alkynes may be susceptible to thiol attack). (3) The click chemistry can be performed on living cells and whole organisms.

In some embodiments, the compounds of the present invention are used to monitor azido-labeled molecules (e.g., azido sugar, protein bearing azido amino acids, lipids and site-specifically labeled proteins) in live cells. The metabolic precursor peracetylated N-azidoacetylmannosamine ($Ac_4ManNAz$) is metabolically adsorbed into cells of interest and incorporated into biomolecules that are expressed on the surface of the cells. In certain instances, the azido-sugar labeled cells are exposed to a cyclooctyne (strained alkyne) reagent conjugated to a reporter group (e.g., dye), which generates a Huisgen cycloaddition reaction. The cyclooctyne reagent can be added to cell culture medium and incubated with azido-sugar labeled cells under conditions that promote the click reaction. If the azido-sugar labeled cells are in a live organism, the cycloocyne reagent can be administered to the organism by methods such as, but not limited to oral, topical and transmembrane administration, and injection. As a result, the cyclooctyne-reporter conjugate covalently binds to the azido-sugar labeled cells, which then labels the cells with the reporter. In other instances, the azido-sugar labeled cells are exposed to a phosphine reagent conjugated to a reporter group (e.g., dye), which generates a Staudinger ligation between the phosphine and the azido sugar. This covalently binds the phosphine-reporter conjugate to the azido-sugar labeled cells, which are now detectable using commercially available imaging systems.

In other embodiments, $Ac_4ManNAz$ is administered to a whole organism. In certain instances, it is injected into an animal (e.g., zebrafish, rodents, rabbits, dogs, sheep, goats, pigs, monkey, and humans). This method delivers azides to cell surface sialoglycoconjugates on cells found in serum and various tissues, such as, but not limited to heart, spleen, liver, kidney, intestines and muscle. In some instances, a phosphine- or alkyne-reporter can be injected into the same animal to generate a Staudinger ligation or Huisgen cycloaddition reaction, respectively, in vivo. The labeled tissues and cells can be monitored and analyzed using whole animal imaging systems. In other instances, tissues or cells are extracted from an $Ac_4ManNAz$ injected animal, and then they are treated with a phosphine- or alkyne-reporter in vitro. Methods known to those skilled in the art, such as, but not limited to Western blotting, ELISA, immunocytochemistry, mass spectrometry, and high-performance liquid chromatography can then be used to detect labeled biomolecules.

Example 92

Example 92 illustrates methods of using compounds of the present invention to label biomolecules (e.g., proteins, lipids, carbohydrates, nucleic acids, amino acids, glycerol, fatty acids, and nucleotides) on cells as shown in Scheme 2. It also illustrates methods of in vitro and in vivo analysis of the labeled biomolecules that can serve as detection probes. The compounds can be applied to methodologies used to investigate disease and therapeutic development, such as but not limited to tumor imaging, glycan labeling, in vivo imaging, and cell surface modification.

Example 93 illustrates an ELISA using click chemistry.

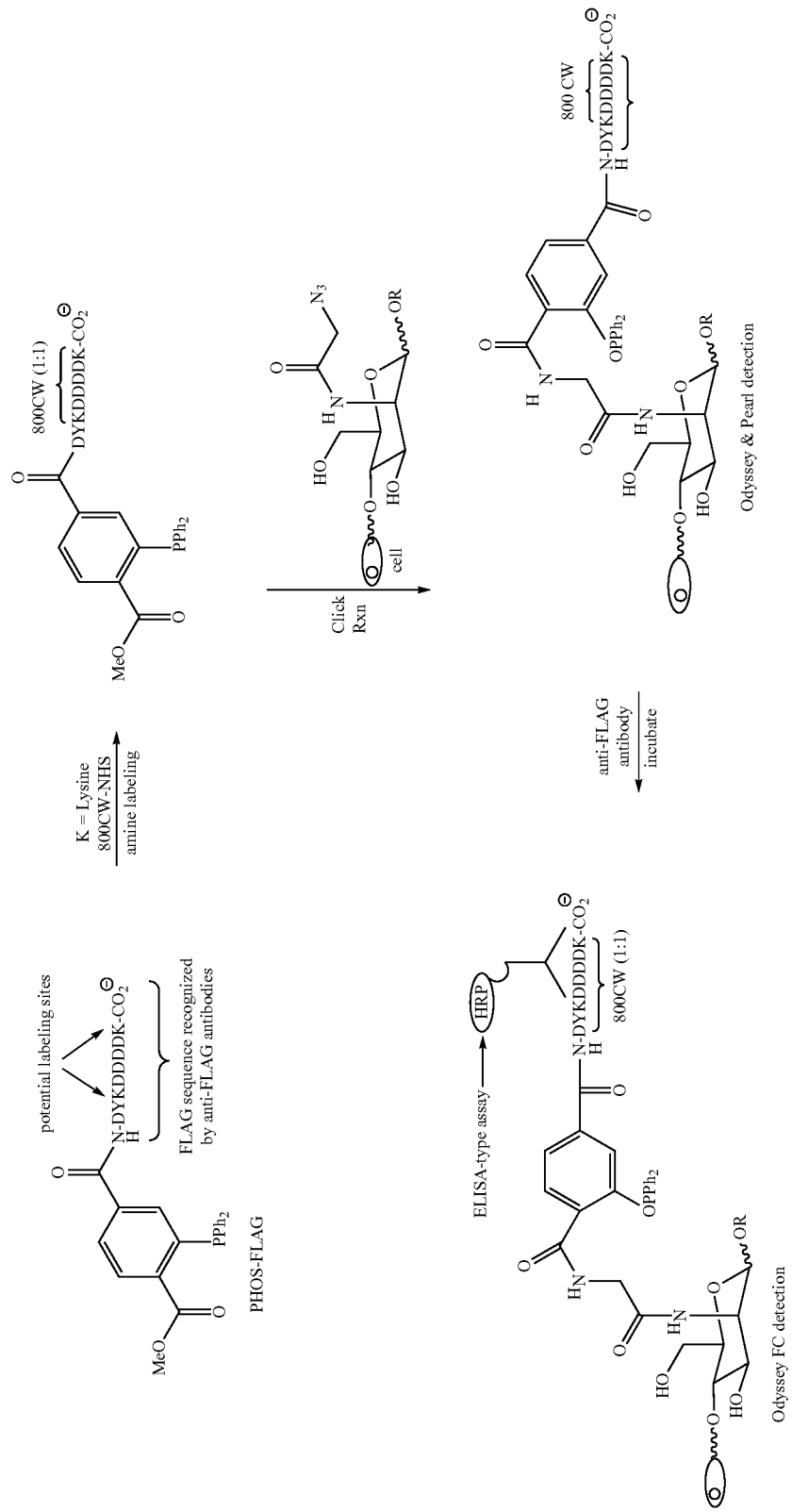
Scheme 2: ELISA with Click Chemistry

In this example, the reaction is carried-out with IRDye 800CW as the dye. A skilled artisan would appreciate that compounds of the present invention (e.g., compound 10) can be substituted for IRDye 800CW.

Metabolic Labeling of an Bioorthogonal Functional Group on Biomolecules

In some embodiments, an azido-labeled biomolecule is made using methods known to those skilled in the art. In certain instances, an unnatural azido sugar is commercially available from a supplier (e.g., Sigma-Aldrich). In other instances, the unnatural azido sugar, such as the metabolic precursor peracetylated N-azidoacetylmannosamine ($Ac_4ManNAz$)) is synthesized according to methods known to those skilled in the art (see, e.g., Laughlin et al., *Methods Enzymol*, 415:230-250 (2006)). To incorporate an azido sugar into biomolecules expressed on cells cultured in vitro, the modified sugar is added to the cell culture media and incubated with the cells (see, e.g., Bussink et al., J. Lipid Res., 48: 1417-1421 (2007); Prescher et al., Nature, 430: 873-877 (2004)). Typically, $Ac_4ManNAz$ is added to a cell culture at a final concentration of about 50 µM and incubated for about 3 days in cell culturing conditions. To label biomolecules expressed on cells in an organism, an azido sugar (e.g., $Ac_4ManNAz$) is administered in a solution to the organism by injection (e.g., intraperitoneal injection) at an appropriate injection schedule to ensure optimal incorporation and expression of the modified biomolecule. See Chang et al., Proc. Natl. Acad. Sci U.S.A., 107:1821-1826 (2010). Non-limiting examples of organisms include fish, rodents, rabbits, dogs, sheep, goats, pigs, monkey, and humans. Typically, $Ac_4ManNAz$ is injected intraperitoneally at a dose of 300 mg/kg in DMSO solution into mice once daily for 7 days.

Generation of PHOS-FLAG-Reporter Probe

Scheme 2 illustrates one embodiment of the invention, wherein a PHOS-FLAG-800CW probe is used to label specific azido-sugar labeled biomolecules in living cells and organisms. In some embodiments, a phosphine-FLAG peptide conjugate (PHOS-FLAG; described in Laughlin et al., *Methods Enzymol*, 415:230-250 (2006)) is coupled to a reporter group (e.g., dye) using methods known to those skilled in the art. In certain instances, the phosphine-FLAG peptide conjugate is labeled with IRDye 800CW NHS ester (LI-COR) according to the manufacturer's instructions. The resulting PHOS-FLAG-800CW probe can then be covalently linked via a Staudinger ligation to an azido-labeled biomolecule expressed by a cell.

Detection of Biomolecules Labeled by Copper-Free Click Chemistry

Scheme 2 also illustrates a method of labeling a modified biomolecule found on cell with a PHOS-FLAG-Reporter probe using "click" chemistry.

In some embodiments, a PHOS-FLAG-800CW probe is injected into an animal having cells that express azido-labeled biomolecules. In particular instances, mice are injected intraperitoneally once with PHOS-FLAG-800CW (0.16 mmol/kg). Labeling of the cells with the near-infrared dye is detected using a whole animal detection system (e.g., Pearl Imager (LI-COR)). Dye-labeled biomolecules, tissues and cells from the animal can be harvested from a euthanized animal and analyzed using imagers (e.g., Odyssey System (LI-COR)).

In other embodiments, a PHOS-FLAG-800CW probe is added to an in vitro cell culture and incubated in conditions that promote a Staudinger ligation reaction between the phosphine of the probe and the azide of the biomolecule. In certain instances, the "click" reaction is performed according to the following steps: 1) azido-labeled cells are collected; 2) they are centrifuged at 1,500 rpm for 10 minutes, 3) they are washed three times in cold PBS, 4) they are resuspended in 2% (v/v) fetal calf serum in PBS, 5) they are incubated with about 0.5 mM PHOS-FLAG-800CW probe at room temperature for 3 hours under mild shaking, 6) the cells are collected by centrifugation, and 7) they are washed three times with cold PBS. As a result of click chemistry, the labeled biomolecule is covalently linked to a FLAG tag and near-infrared dye via the click product. In some instances, the near-infrared dye-labeled cells or biomolecules are detected and analyzed using a detection system (e.g., Odyssey System (LI-COR)).

In certain embodiments, an ELISA-type assay is performed to detect the FLAG-tagged biomolecules expressed on cells. Protocols for ELISA-type assays and immunocytochemistry are known to those of skill and described in detail in reference books such as, *Antibodies: A Laboratory Manual* (ed. Harlow and Lane), Cold Spring Harbor Laboratory Press, New York, 1988; *Methods in Molecular Biology*, Volume 42: *ELISA, Theory and Practice* (ed. Coligan et al.), Humana Press, New Jersey, 1995; and *Immunoassay* (ed. Diamandis and Christopoulos), Academic Press, New York, 1996. In some aspects, the labeled cells are incubated with a horseradish peroxidase (HRP)-conjugated anti-FLAG antibody at conditions optimal for antibody binding. HRP conjugated anti-FLAG antibodies are commercially available from suppliers such as, but not limited to, Sigma-Aldrich (St. Louis, Mo.), Cell Signaling (Danvers, Mass.), Protein Mods (Madison, Wis.), Prospec Bio (East Brunswick, N.J.). The antibody-labeled cells are exposed to a luminol substrate that is oxidized by HRP in a chemiluminescent reaction. The light-emitting reaction is detectable using imaging systems such as, but not limited to Odyssey Fc System (LI-COR). In other aspects, the FLAG tagged biomolecules are extracted from the cells using methods known to those skilled in the art. Descriptions of methods for the isolation of biomolecules and the detection of FLAG-tagged biomolecules can be found in references such as, but not limited to, *Current Protocols in Molecular Biology* (ed. Ausubel et al.), Wiley, New Jersey, 2011; and *Current Protocols in Immunology* (ed. Coligan et al.), Wiley, New Jersey, 2011.

Example 94

Example 94 illustrates the compounds of the present invention with technology similar to Rutjes (cf. *Chem Bio Chem* 2007, 8, 1504-1508) using copper-free click chemistry reaction conditions as shown in Scheme 3. This example illustrates a method of covalently binding a near-infrared dye to selectively modified biomolecules that are expressed by cells. Non-limiting examples of applications of the methods described here in are tumor imaging, glycan labeling, in vivo labeling, cell surface modification, The method is based on a tandem [3+2] cycloaddition-retro-Diels-Alder ligation method that results in a stable 1,2,3-triazole linkage.

Scheme 3

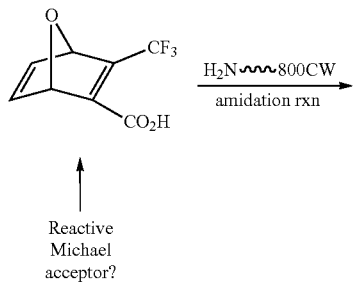

Reactive Michael acceptor?

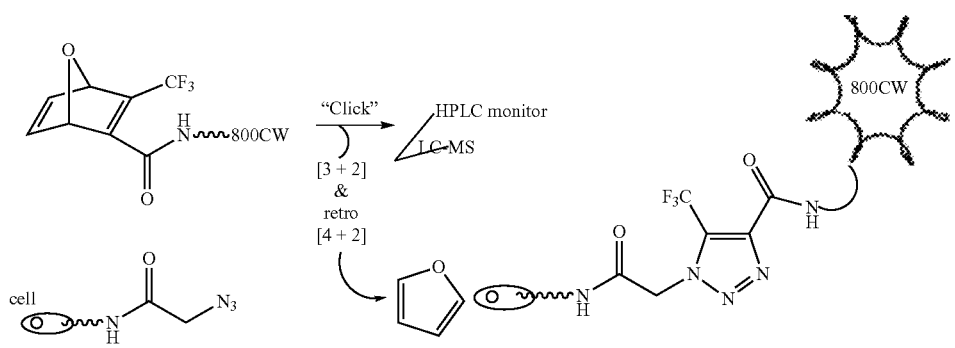

In this example, the reaction is carried-out with IRDye 800CW as the dye.

Scheme 3 illustrates a method of linking a near-infrared dye to an azido-labeled biomolecule. In some embodiments, firstly, an oxanorbornadiene is coupled to a near-infrared dye (e.g., IRDye 800CW) via an amidation reaction to generate an IRDye800CW-oxanorbornadiene. Next, the IRDye800CW-oxanorbornadiene reagent is incubated with cells expressing an azido labeled biomolecule, thereby creating a "click" reaction. Typically, azido labeled cells are generated following methods described in Example 112. The tandem [3+2] cycloaddition and retro-Diels-Alder reactions generate a furan molecule and a triazole linkage between the biomolecule and the dye, thereby labeling targeted cells with a dye.

In certain embodiments, a IRDye800CW-oxanorbornadiene reacts with a selectively modified azido-biomolecule on cells in an animal. The IRDye800CW-oxanorbornadiene can be administered (e.g., injection, oral, transdermal and topical) to an animal. In some instances, the IRDye800CW-labeled cells and biomolecules are monitored in the animal using an infrared detection system (e.g., Pearl Imager). In other instances, cells and tissues from the animal are harvested and analyzed using techniques known to those in skilled in the art, such as, but not limited to ELISA, FLISA, Western, histology, immunocytochemistry, and imaging. Methods including protocols are available in references such as, but not limited to *Current Protocols in Molecular Biology* (ed. Ausubel et al.), Wiley, New Jersey, 2011; *Current Protocols in Protein Science* (ed. Coligan et al.), Wiley, New Jersey, 2011; and *Current Protocols in Immunology* (ed. Coligan et al.), Wiley, New Jersey, 2011. In some instances, the labeled biomolecules and cells are monitored using techniques described herein.

In certain embodiments, the labeled biomolecule is detected and identified using methods such as, but not limited to high-performance liquid chromatography (HPLC) and liquid chromatography-mass spectrometry (LC-MS). Methods of detecting dye-labeled cells and biomolecules are described in references, for example, *Peptide Characterization and Application Protocols* (ed. Fields), Humana Press, New Jersey, 2007; *Sample Preparation in Biological Mass Spectrometry* (ed. Ivanov and Lazarev), Springer, New York, 2010; and *Proteomic Biology Using LC-MS: Large Scale Analysis of Cellular Dynamics and Function*, (ed. Takahashi and Isobe), Wiley, New Jersey, 2008. In some instances, the labeled biomolecule is a constituent of a molecular complex and methods of dissociating, separating or modifying the complex are used prior to performing methods for detecting and identifying the individual labeled peptides. Examples include, but are not limited to LC-MS with peptide mass fingerprinting and tandem MS (LC-MS/MS).

Example 95

Example 95 illustrates the synthesis of a fluorescence-quenching dye sodium 6-((E)-2-((E)-2-(3-((E)-2-(5-(bis(3-sulfonatopropyl)amino)-3,3-dimethyl-1-(3-sulfonatopropyl)-3H-indolium-2-yl)vinyl)-2-(2-fluorophenyecyclohex-2-enylidene)ethylidene)-1,1-dimethyl-7-sulfonato-1H-benzo[e]indol-3(2H)-yl)hexanoate (62).

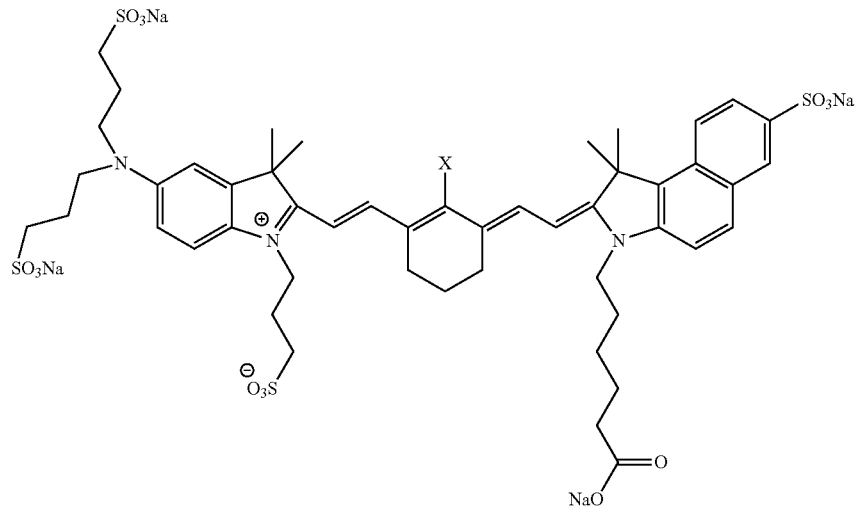

62 X = fluorophenyl
63 X = Cl

Compound 62 was prepared by combining 50 mg of IRDye® QC-1 Carboxylate (63, LI-COR Biosciences), 9.8 mg of 2-fluorophenylboronic acid, 4.0 mg of Pd(PPh$_3$)$_4$ 16.4 mg of sodium acetate, 200 μL of 2-methoxyethanol, and 2 mL of water. The mixture was heated at reflux for 1.5 hours under a nitrogen atmosphere. The compound was purified by reverse-phase C18 chromatography using acetonitrile/water yielding 50 mg of product. Absorbance: $\lambda_{Water}$=785 nm, $\lambda_{MeOH}$=777 nm.

Example 96

Example 96 illustrates the synthesis of sodium 3,3'-(2-((E)-2-((E)-3-((E)-2-(3-(6-(2,5-dioxopyrrolidin-1-yloxy)-6-oxohexyl)-1,1-dimethyl-7-sulfonato-1H-benzo[e]indol-2(3H)-ylidene)ethylidene)-2-(2-fluorophenyl)cyclohex-1-enyl)vinyl)-3,3-dimethyl-1-(3-sulfonatopropyl)-3H-indolium-5-ylazanediyl)dipropane-1-sulfonate (64).

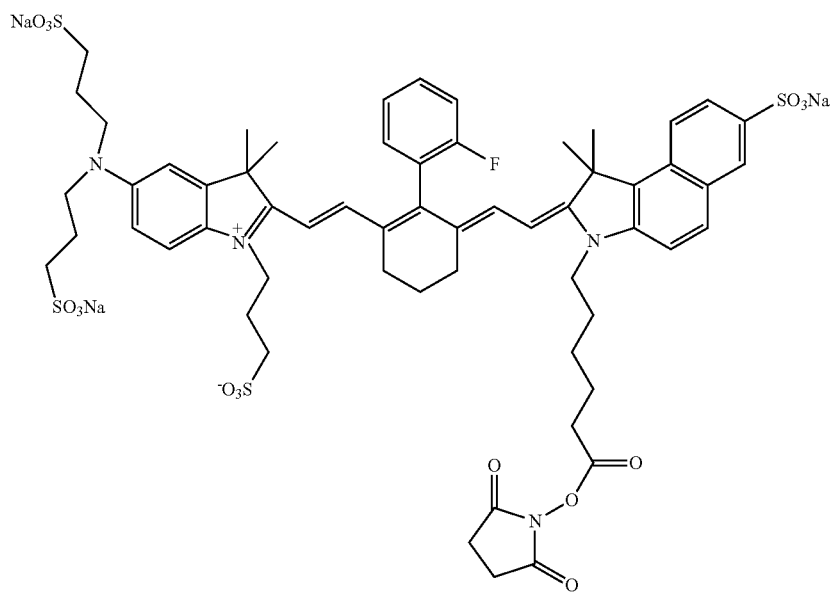

64

Compound 64 was prepared by combining 60 mg of compound 62, 32 mg of N,N'-disuccinimidyl carbonate, 10.8 μL of N,N-diisopropylethylamine, and 3 mL of DMSO. The mixture was stirred at room temperature for 30 minutes, precipitated into diethyl ether, and then purified by reverse-phase C18 chromatography using acetonitrile/water.

Example 97

Example 97 illustrates the synthesis of a fluorescence-quenching dye sodium 1-(6-(6-aminohexylamino)-6-oxo-hexyl)-2-((E)-2-((E)-3-((E)-2-(3,3-dimethyl-5-sulfonato-1-(4-sulfonatobutyl)indolin-2-ylidene)ethylidene)-2-(4-sulfonatophenoxy)cyclohex-1-enyl)vinyl)-3,3-dimethyl-3H-indolium-5-sulfonate (800CW-Hexamethylenediamine, 65).

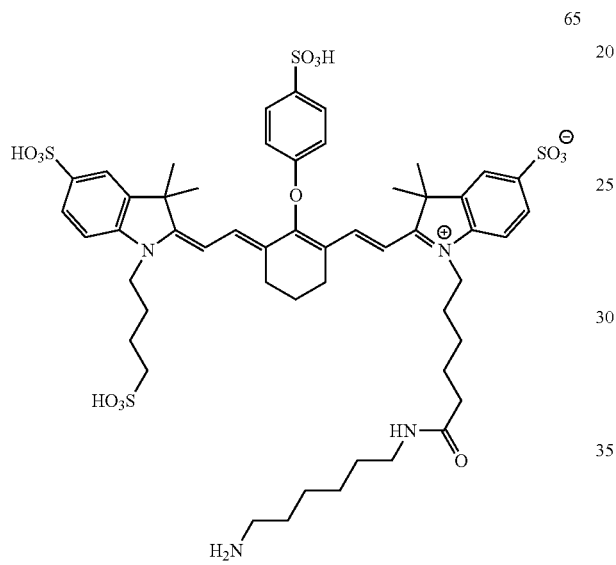

Example 98

Example 98 illustrates the synthesis of a strained cycloalkyne-containing Compound 79 derivative for click chemistry (Compound 79-DBCO, 66).

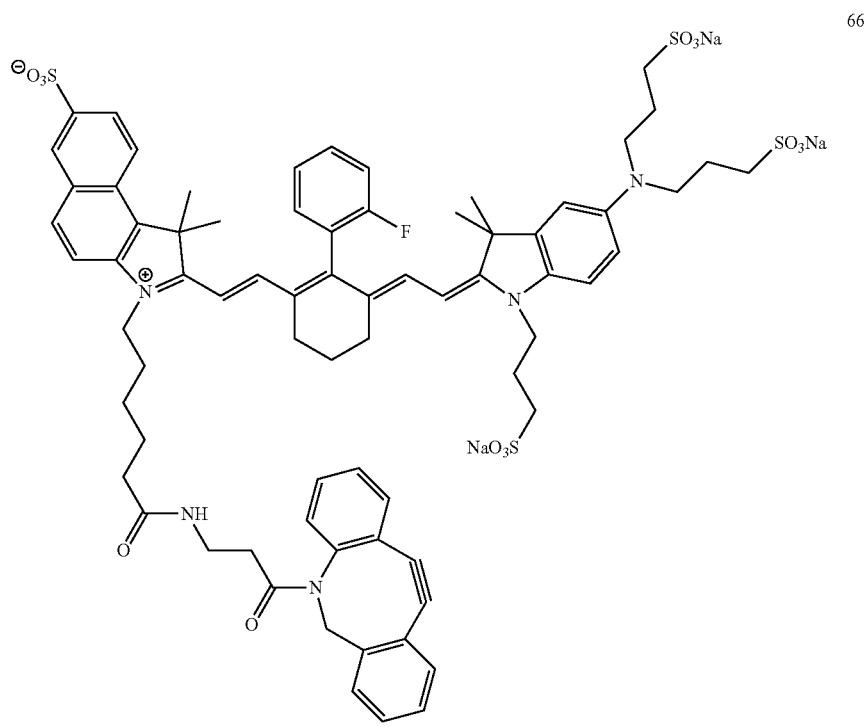

To a solution of Compound 64 (Example 96, 0.8 mg, 6.1× 10⁻⁴ mmol) and N,N-diisopropylethylamine (0.001 mL, 5.7× 10-3 mmol) in anhydrous dimethylsulfoxide (0.8 mL) was added DBCO-Amine (from Jena Bioscience, 0.5 mg, 1.8× 10-3 mmol) in one portion. The reaction was allowed to proceed at ambient temperature for 2 h, with periodic agitation at 15-min intervals. After HPLC analysis indicated complete consumption of Compound 64, the crude product was precipitated in anhydrous diethyl ether (10 mL). The ethereal supernatant was decanted and the precipitate was purified by prep-HPLC to afford the desired product Compound 87 as a teal solid (0.8 mg, 90%). UV/Vis (acetonitrile/water=1:1) λmax=790 nm; LRMS (ES/water), m/z calculated for C73H81FN5O14S4 [M+H]+ 1398.46. found 1398.5.

Example 99

Example 99 illustrates the synthesis of an azide-containing Compound 62 derivative for click chemistry (Compound 79-PEG-Azide, 67).

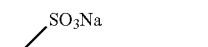

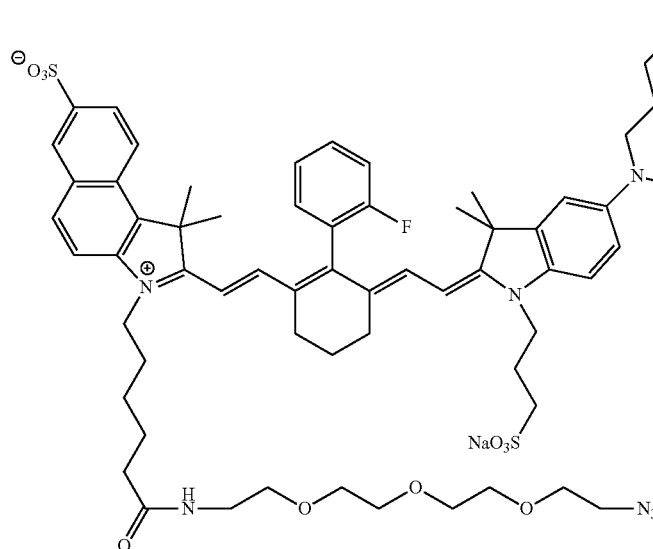

To a solution of Compound 64 (Example 96, 0.8 mg, 6.1× 10-4 mmol) and N,N-diisopropylethylamine (0.001 mL, 2.3× 10-3 mmol) in anhydrous dimethylsulfoxide (0.8 mL) was added 11-azido-3,6,9-trioxa-undecan-1-amine (0.5 mg, 1.8× 10-3 mmol) in one portion. The reaction was allowed to proceed at ambient temperature for 2 h, with periodic agitation at 15-min intervals. After HPLC analysis indicated complete consumption of Compound 81, the crude product was precipitated in anhydrous diethyl ether (10 mL). The ethereal supernatant was decanted and the precipitate was purified by prep-HPLC to afford the desired product Compound 67 as a teal solid (0.7 mg, 81%). UV/Vis (acetonitrile/water=1:1) λmax=790 nm; LRMS (ES/water), m/z calculated for C63H83FN7O16S4 [M+H]+ 1340.48. found 1340.5 and 671.0 [M+2H]2+.

Example 100

Example 100 illustrates the click chemistry synthesis of Compound 10/Compound 62 conjugate (Compound 10-Compound 62 Click Product, 68).

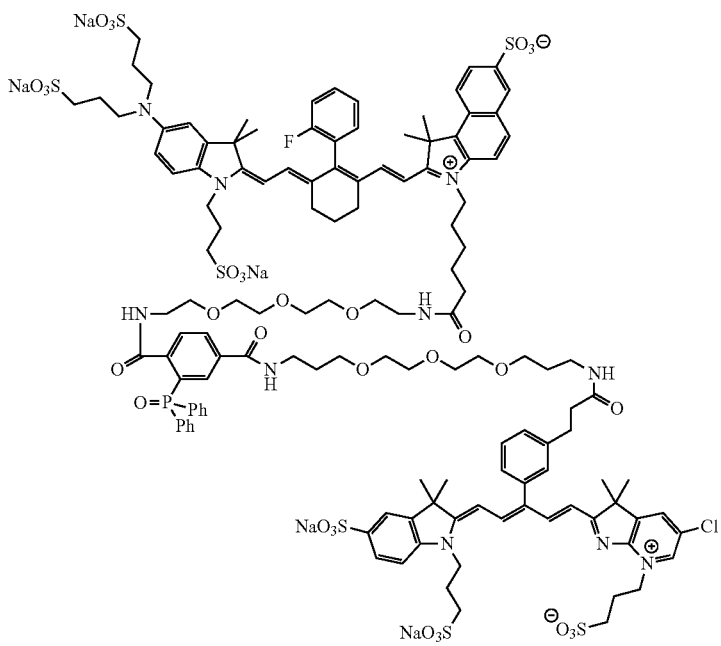

To a solution of azide 67 (150 µg, 1.1×10$^{-1}$ mmol) in water (150 µL) was added a solution of Compound 10-PEG-Phosphine (59) (92 µg, 6.3×10$^{-2}$ µmol) in water (50 µL). The reaction was allowed to proceed at ambient temperature for 1 hour, then maintained at 40° C. for 3 hours. After HPLC analysis showed complete consumption of Compound 10-PEG-Phosphine, the reaction mixture was filtered and directly purified by HPLC. Fractions containing the presumed Compound 10-Compound 79 Click Product 68 were combined and concentrated in vacuo. The exact yield was not determined. UV/Vis (acetonitrile/water=1:1) $\lambda_{max}1$=778 nm, $\lambda_{max}2$=677 nm; LRMS (ES/water), m/z calculated for $C_{123}H_{150}ClN_9O_{33}PS_7$ [M+H]$^+$ 2570.8. found 858.5 [M+3H]$^{3+}$.

Example 101

Example 101 illustrates the synthesis of the fluorescence-quenching dye sodium (E)-2-((E)-2-(3-((E)-2-(5-(bis(3-sulfonatopropyl)amino)-3,3-dimethyl-1-(3-sulfonatopropyl)-3H-indolium-2-yl)vinyl)-5-carboxy-2-(2-fluorophenyl)cyclohex-2-enylidene)ethylidene)-1,1-dimethyl-3-(3-sulfonatopropyl)-2,3-dihydro-1H-benzo[e]indole-6,8-disulfonate (69).

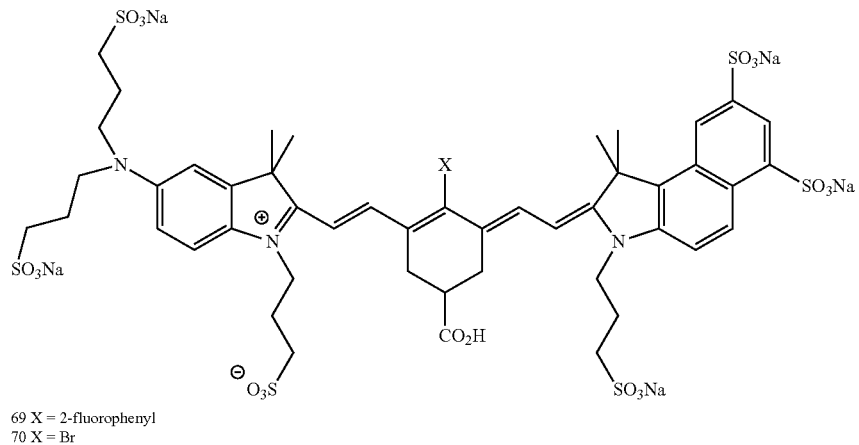

69 X = 2-fluorophenyl
70 X = Br

Compound 69 was prepared by combining 200 mg of Bromo Dye 70, 31 mg of 2-fluorophenylboronic acid, 12.7 mg of Pd(PPh$_3$)$_4$, 36.1 mg of sodium acetate, 800 µL of 2-methoxyethanol, and 8 mL of water. The mixture was heated at reflux for 45 minutes under a nitrogen atmosphere. To the reaction was then added 1 mL of 10% sulfuric acid solution and reflux was continued for 90 minutes. The compound was purified by reverse-phase C18 chromatography using acetonitrile/water yielding 130 mg of product. Absorbance: $\lambda_{Water}$=779 nm.

Example 102

Example 102 illustrates the synthesis of an NHS ester of Compound 93 (71).

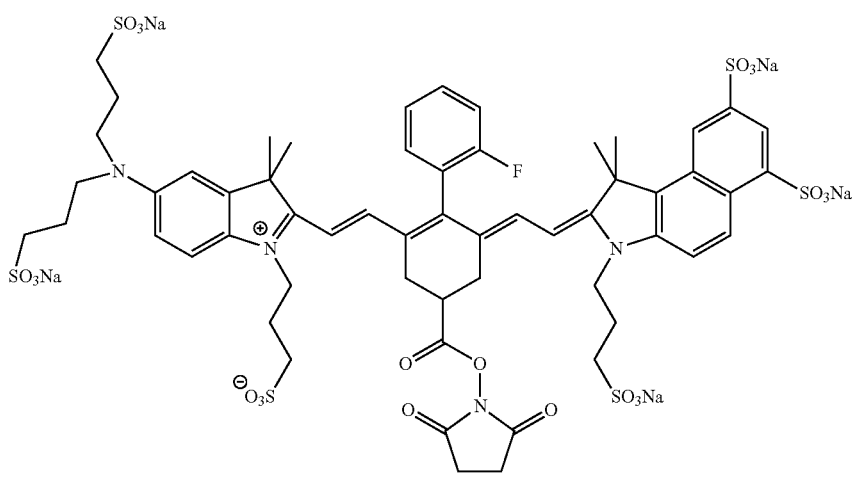

71

Compound 71 was prepared by combining 130 mg of compound 69, 72 mg of N,N'-disuccinimidyl carbonate, 25 µL of N,N-diisopropylethylamine, and 8 mL of DMSO. The mixture was sonicated at room temperature for 120 minutes, precipitated into diethyl ether, and then purified by reverse-phase C18 chromatography using acetonitrile/water yielding 80 mg of product.

Example 103

Example 103 illustrates the synthesis of a strained cycloalkyne-containing Compound 69 derivative for click chemistry (72).

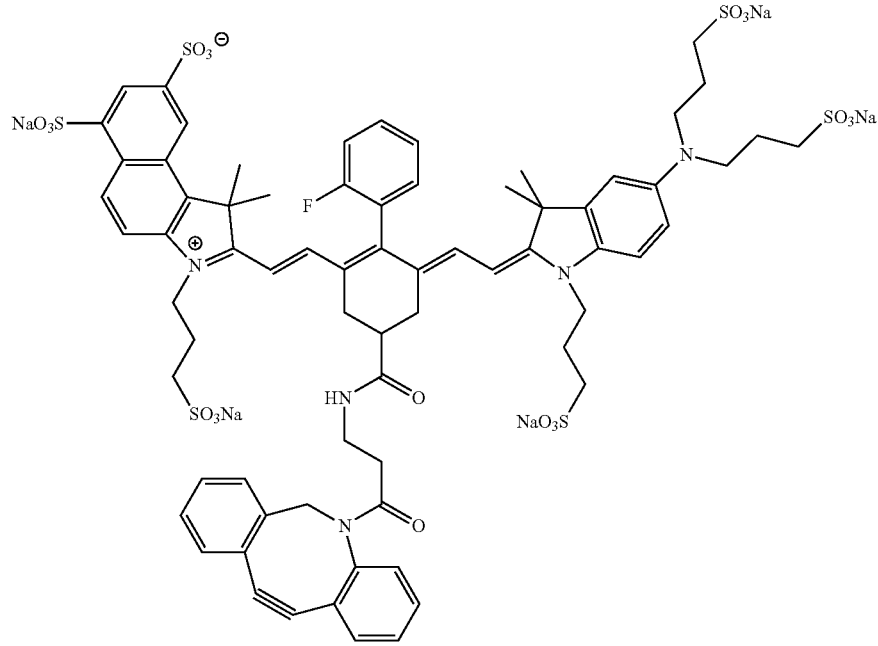

This compound was prepared in a manner similar to that used for 66 (Example 120) from the commercially available DBCO-Amine. The exact yield was not determined. UV/Vis (acetonitrile/water=1:1) $\lambda_{max}$=799 nm; LRMS (ES/water), m/z calculated for $C_{71}H_{77}FN_5O_{20}S_6$ $[M+H]^+$ 1530.34. found 765.9 $[M+2H]^{2+}$.

Example 104

Example 104 illustrates the synthesis of an azide-containing Compound 69 derivative for click chemistry (Compound 69-PEG-Azide, 73).

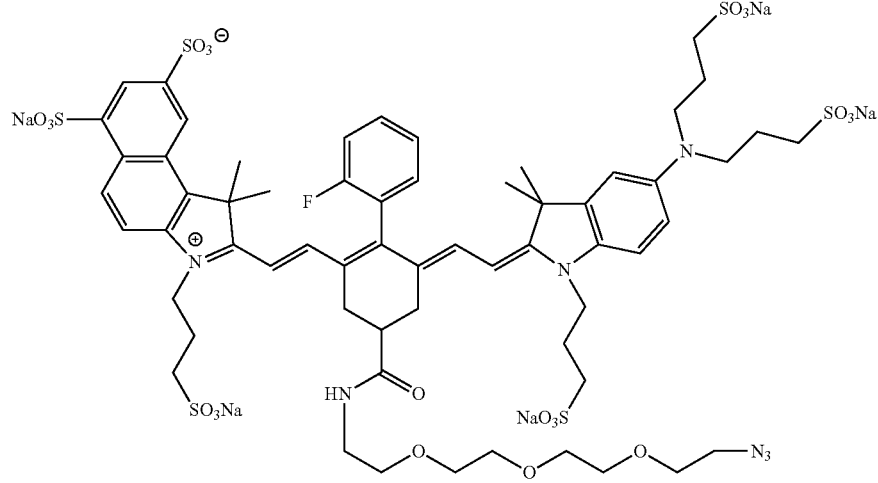

This compound was prepared in a manner similar to that used for 67 (Example 99) from commercially available 11-azido-3,6,9-trioxaundecan-1-amine. The exact yield was not determined. UV/Vis (acetonitrile/water=1:1) $\lambda_{max}$=799 nm; LRMS (ES/water), m/z calculated for $C_{61}H_{79}FN_7O_{22}S_6$ [M+H]$^+$ 1472.35. found 736.9 [M+2H]$^{2+}$.

Example 105

Example 105 illustrates the synthesis of an azide-containing Compound 10 derivative for click chemistry (Compound 10-PEG-Azide, 74).

Example 106

Example 106 illustrates the synthesis of an strained cycloalkyne-containing Compound 10 derivative for click chemistry (Compound 10-DBCO, 75).

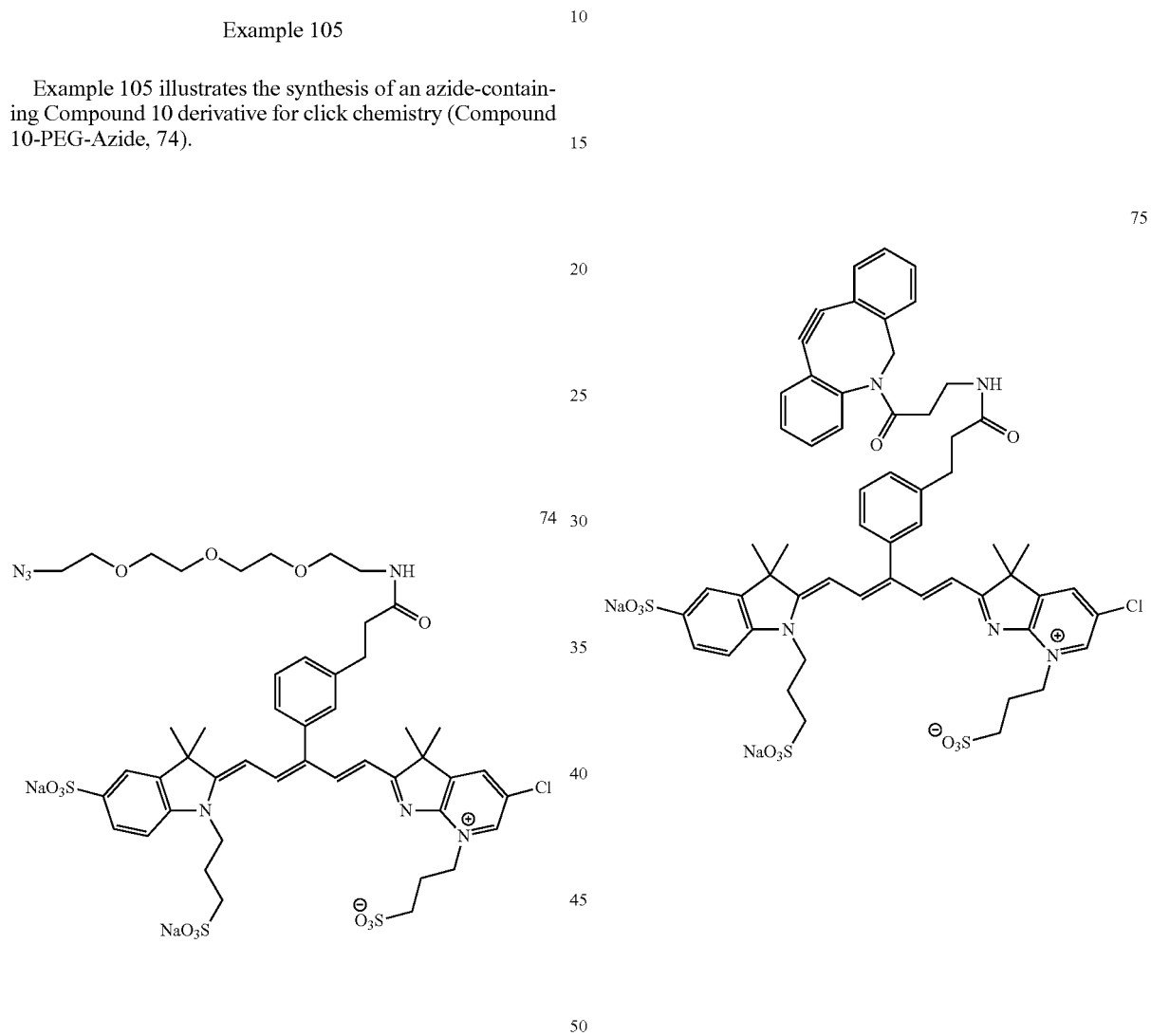

This compound was prepared in a manner similar to that used for compound 66 (Example 98) from the commercially available DBCO-Amine. The exact yield was not determined. UV/Vis (acetonitrile/water=1:1) $\lambda_{max}$=676 nm; UV/Vis (acetonitrile/water=1:1) $\lambda_{max}$=676 nm; LRMS (ES/water), m/z calculated for $C_{57}H_{59}ClN_5O_{11}S_3$ [M+H]$^+$ 1120.30. found 1120.6. 560.9 [M+2H]$^{2+}$.

Example 107

Example 107 illustrates the synthesis of Compound 10/Compound 69 conjugate (Compound 10/Compound 69 Click Product 1; 76).

This compound was prepared in a manner similar to that used for 67 (Example 99) from the commercially available 11-azido-3,6,9-trioxaundecan-1-amine. The exact yield was not determined. UV/Vis (acetonitrile/water=1:1) $\lambda_{max}$=676 nm; LRMS (ES/water), m/z calculated for $C_{47}H_{61}ClN_7O_{13}S_3$ [M+H]$^+$ 1062.31. found 1060.6 [M−H]$^-$, 1082.6 [M+Na−2H]$^{2-}$.

76

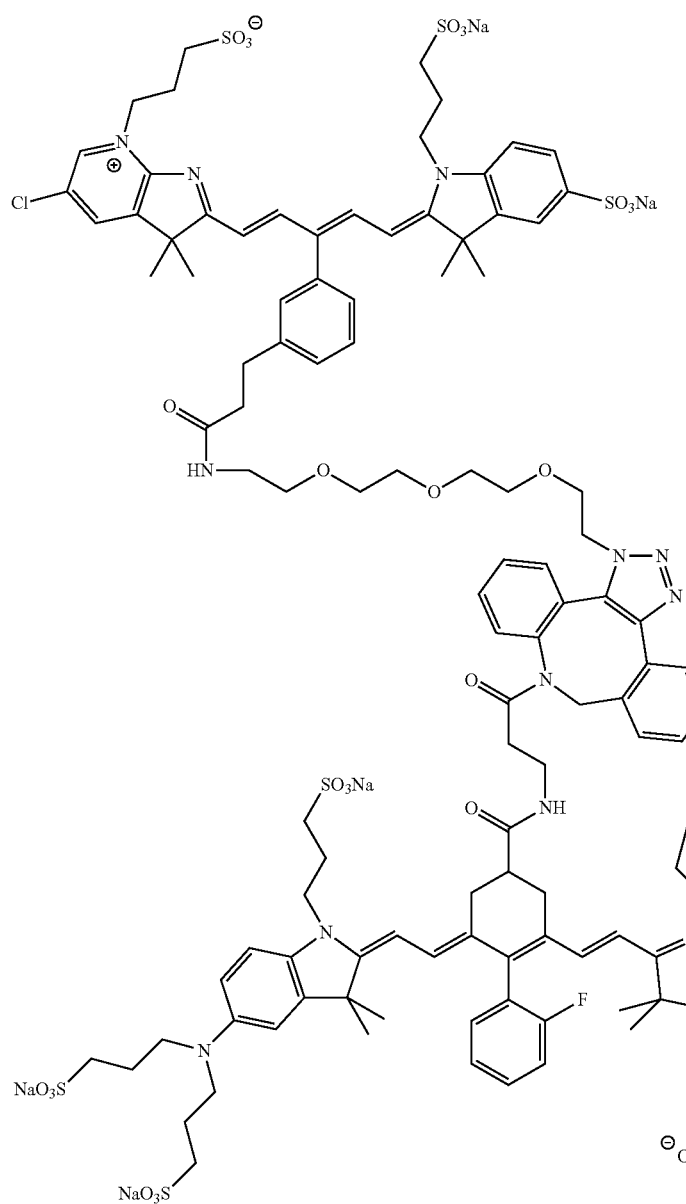

A solution of Compound 72 (0.165 mg, 1.0×10⁻⁴ mmol) in water (0.150 mL) was mixed with a solution of Compound 74 (0.055 mg, 5.0×10⁻⁵ mmol) in water (0.050 mL). The reaction mixture was agitated for 30 seconds and then allowed to proceed at ambient temperature for 2 hours. After HPLC analysis showed the complete consumption of Compound 74, the reaction mixture was directly purified by reverse-phase HPLC to afford the product Compound 76 as a blue solid that was a mixture of the two triazole cycloaddition regioisomers. The exact yield was not determined. UV/Vis (acetonitrile/water=1:1) $\lambda_{max}1$=679 nm, $\lambda_{max}2$=799 nm; LRMS (ES/water), m/z calculated for $C_{118}H_{137}ClF_{12}O_{33}S_9$ [M+H]⁺ 2591.65. found 1295.0 [M−2H]²⁻, 863.1 [M−3H]³⁻.

Example 108

Example 108 illustrates the synthesis of another Compound 10/Compound 69 conjugate (Compound 10/Compound 69 Click Product 2; 77).

127                                                                                         128

77

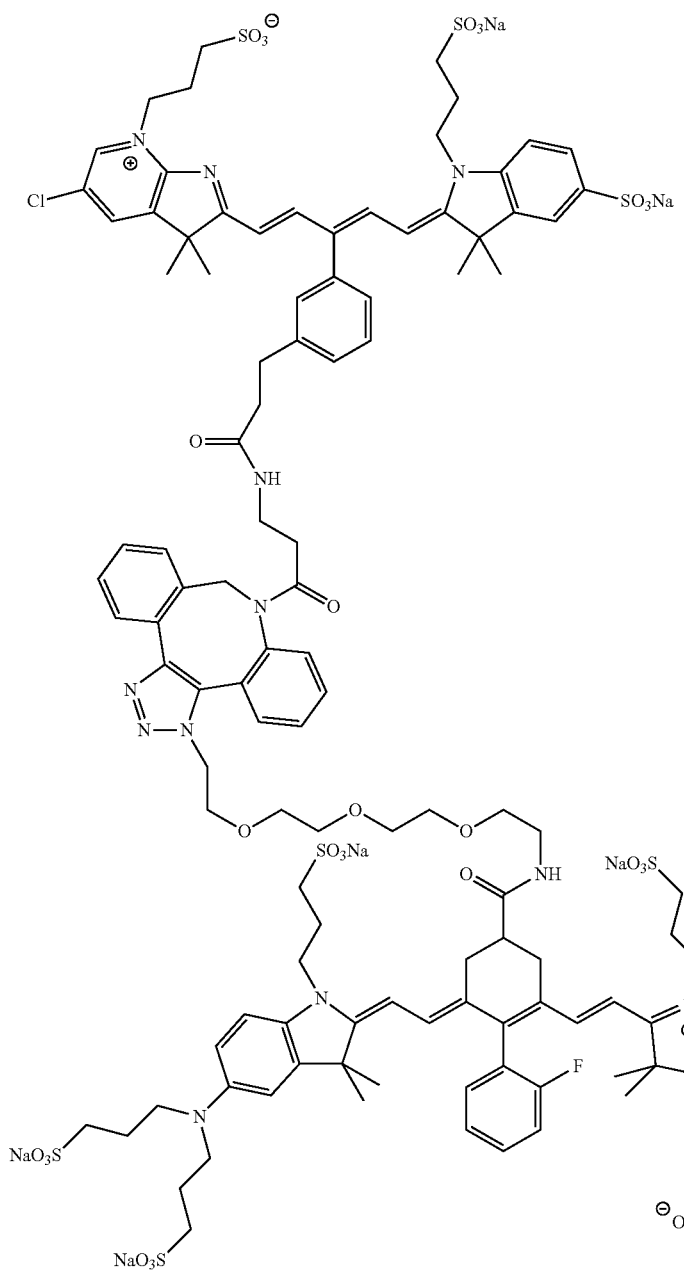

A solution of Compound 75 (0.060 mg, 5.0×10⁻⁵ mmol) in water (0.050 mL) was mixed with a solution of Compound 73 (0.160 mg, 1.0×10⁻⁴ mmol) in water (0.150 mL). The reaction mixture was agitated for 30 seconds and then allowed to proceed at ambient temperature for 2 hours. After HPLC analysis showed the complete consumption of Compound 73, the reaction mixture was directly purified by reverse-phase HPLC to afford the product Compound 77 as a blue solid that was a mixture of the two triazole cycloaddition regioisomers. The exact yield was not determined. UV/Vis (acetonitrile/water=1:1) $\lambda_{max}1$=679 nm, $\lambda_{max}2$=799 nm; LRMS (ES/water), m/z calculated for $C_{118}H_{137}ClFN_{12}O_{33}S_9$ [M+H]⁺ 2591.65. found 1295.6 [M−2H]²⁻

Example 109

Comparison of Dye Emission Maxima and Quenching

Solutions of dye-linker standards and dye-linker-quencher samples were diluted into PBS buffer (pH 7.4) to give a dye-specific absorbance less than 0.2 AU. The fluorescence spectra of each dilution were then taken at a consistent excitation wavelength (670 nm for Compound 10 and 770 nm for 800CW). The emission spectra were collected from 680-1000 nm for the Compound 10 samples and 780-1000 nm for the 800CW samples.

| Quencher Version | Sample Name | Example Number | Emission Maximum | Percent Quenching |
|---|---|---|---|---|
| Compound 62 | Compound 10-PHOS-OX (ref) (60) | Example 89 | $3.02 \times 10^6$ | |
| | Compound 10-Compound 62-Click 1 (68) | Example 100 | $1.05 \times 10^6$ | 65.1 |
| Compound 69 | Compound 10-PHOS-OX (ref) (60) | Example 89 | $3.02 \times 10^6$ | |
| | Compound 10-Compound 69-Click 1 (76) | Example 107 | $2.78 \times 10^5$ | 90.8 |
| | Compound 10-Compound 69.-Click 2 (77) | Example 108 | $4.99 \times 10^5$ | 83.5 |

Example 110

In Vivo Use of Evaluation of Compound 10

In vitro data was obtained to provide sufficient data on the relative non-specific binding of the dye which included tests with 10/RGD and 10/EGF conjugates, two targeted imaging agents. In vivo evaluation of the carboxylate 10 (non-reactive form) and a conjugated form targeted to EGFR, 10/EGF, were used to assess effective use in a working model on the Pearl Impulse Imaging System.

Procedure:

Compound 10/RGD and 10/EGF were prepared to be used in conjunction with 10 to estimate relative non-specific binding of the dye relative to a labeled targeted agent. The on-cell Western was the format used and imaged on the Odyssey Sa.

Nude mice were used for the clearance study with the carboxylate and for the targeted agent evaluation. A dose of 2 nmol 10 was administered intravenously (IV) via the tail vein of the mouse and serial imaged over the next 48 h with the Pearl Impulse imaging system. Excised organs were evaluated to assess organs with the highest retention.

Figure 27:
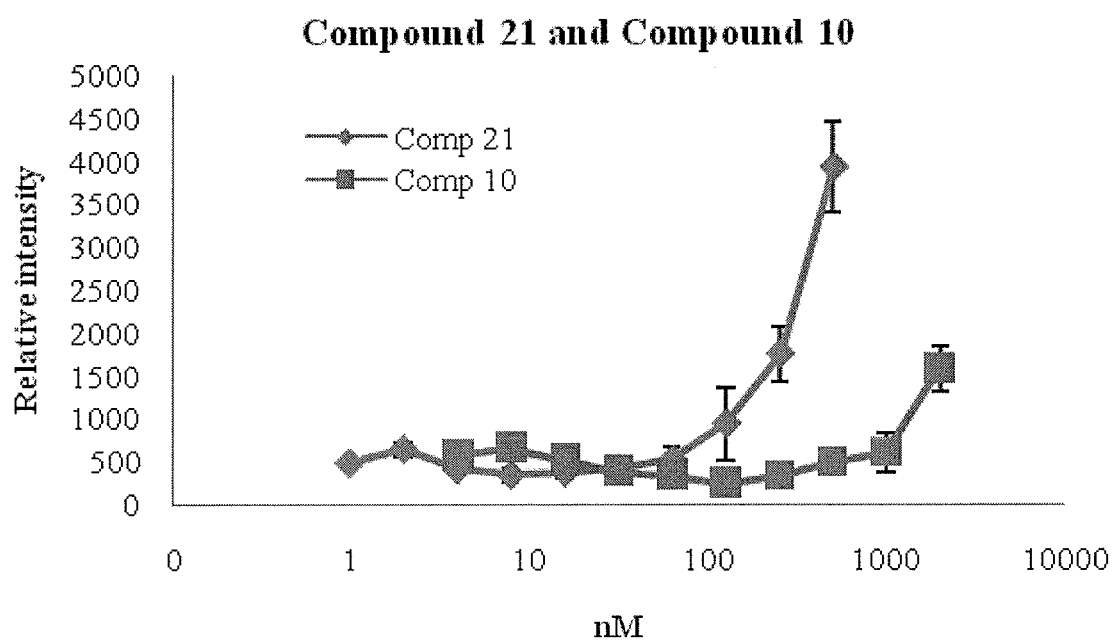
FIG. 27 illustrates the relative fluorescent intensity of compound 21 and compound 10 with increasing concentration.

Results:

In a plate-based evaluation of 10/RGD on U87GM cells, 10 was added to assess level of cell binding (FIG. 27). The results show low levels of cell binding <0.5 μM for the carboxylate in comparison to a specific targeted probe.

The initial batch was then tested in vivo to assess non-specific retention and clearance over a 44 hr period. The results showed that the probe clears via the liver/gall bladder/intestinal tract and very little retention in the kidneys, if at all.

Figure 28A:
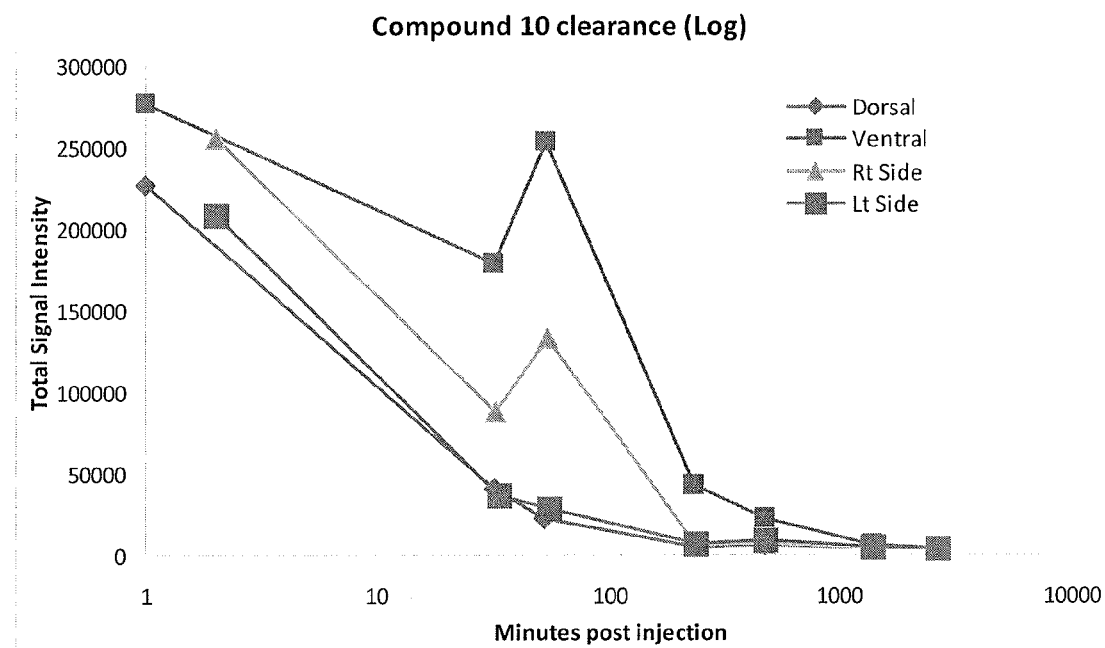
FIG. 28A-B illustrate in Panel A total intensity as a function of time post-injection of the Compound 10's clearance from various injection sites of an imaged mammal; Panel B shows total intensity as a function of time post-injection of Compound 10 clearance from various injection sites of an imaged mammal.
Figure 28B:
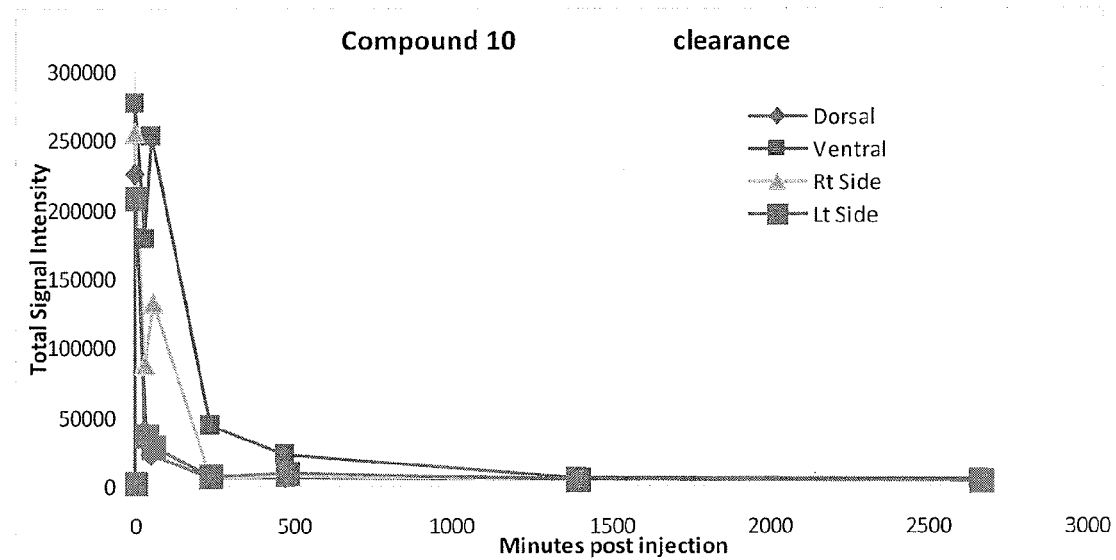

The Total Signal Intensity for each image was captured in a large ROI and plotted (FIG. 28). The carboxylate signal is dramatically reduced by 4 hours with the largest contribution of signal being located in the intestinal tract. The spike at about 1 hour reflects the movement of the probe to the periphery where it is closer to the surface of the skin and more easily detected. An examination of excised organs (i.e., liver, heart, kidney, spleen, intestine, muscle, tumor) show very little retention of probe after 44 hr post injection.

Figure 29:
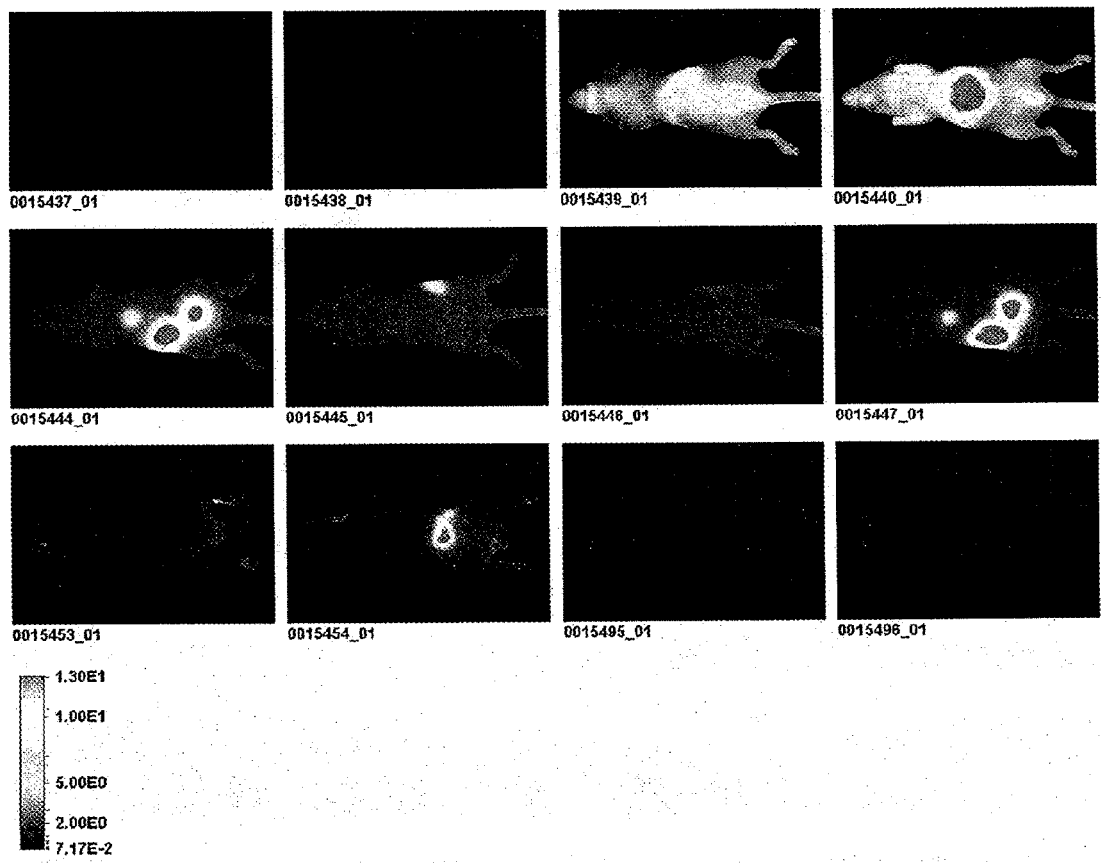
FIG. 29 illustrates an imaged mammal with compounds of the present invention.

A test dose of 2 nmol of 10 was administered to a nude mouse (FIG. 29). This test dose was selected for this evaluation because it is the optimal dose for two of the three probes (i.e., 10, 10/RGD, 10/EGF).

Figure 30A:
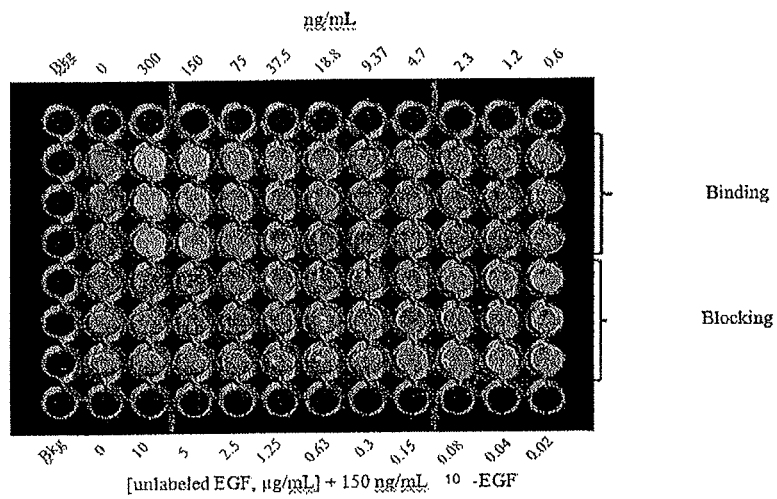
FIG. 30A-C illustrate in Panel A a plate based assay with compound 10; Panel B shows relative intensity of compound 10 binding in A431 cells; Panel C shows competitive binding of labeled and unlabeled Epidermal Growth Factor (EGF).
Figure 30B:
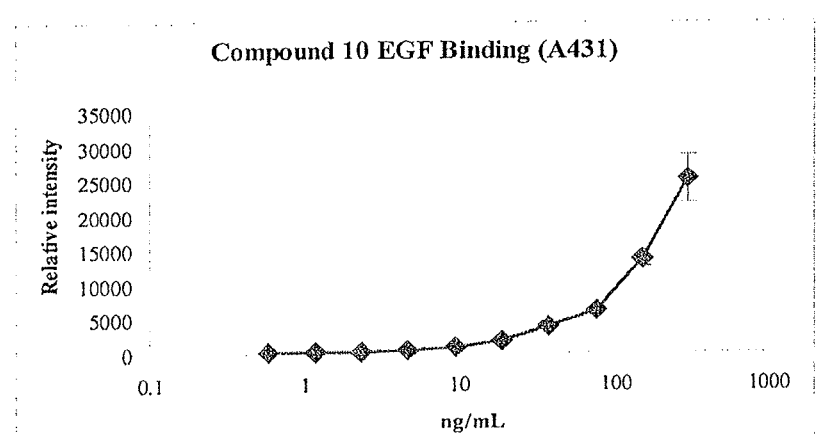
Figure 30C:
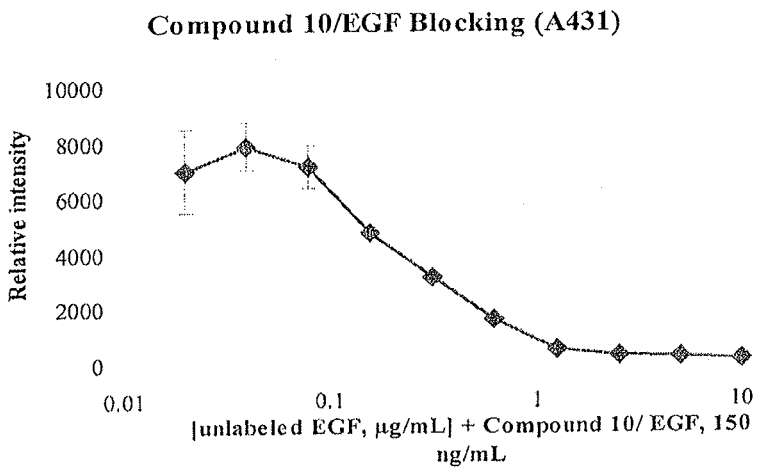

10/EGF Targeted Agent Testing:

Initial cell-based assays show the 10/EGF effectively binds to A431 cells (high EGFR). Results are shown in FIG. 30 where increasing concentrations of 10/EGF showed a dose dependent increase in binding. A competition assay confirms specificity to the EGFR. Results again show increasing concentrations of unlabeled EGF effectively blocked the binding of the labeled EGF.

Figure 31:
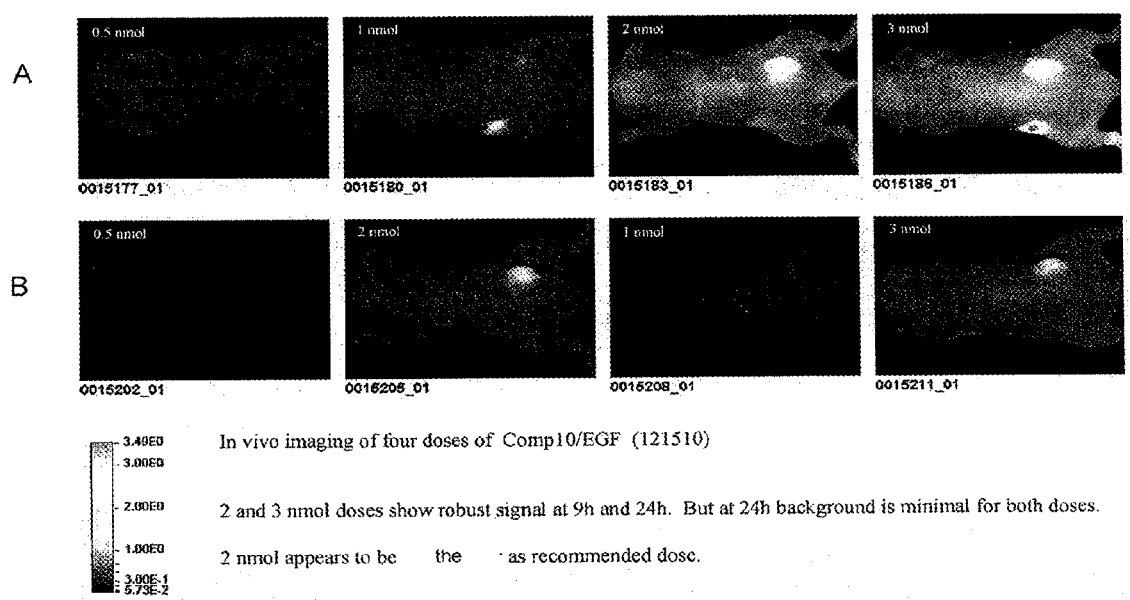
FIG. 31 illustrates in Panel A in vivo imaging of compound 10 conjugate binding in a mammal at various doses, 2 nmol is a preferred concentration; Panel B shows in vivo imaging of compound 10 conjugate binding in a mammal at various doses (e.g., 2 nmol).

In Vivo Analysis:

Testing for optimal dose in nude mice bearing A431 subcutaneous tumors was done. Four doses were tested: 0.5, 1, 2, and 3 nmoles. Two mice were used per treatment dosage. A431 tumor cells were implanted on the right hip and allowed to reach approximately 0.5 cm. FIG. 31 presents dorsal views of all animals under a common LUT.

Results of the dose testing suggest an effective dose for 10/EGF should be between 2-3 nmol per injection. A slightly higher level of background can be expected as the dose increases, but the tumor was visible for doses of 1-3 nmol.

Excised organs (48 h post injection) from mice in the dose study show that the level of signal retained in the tumor is highest for the doses 1-3 nmol. These doses produced much brighter signal from the tumor cells, especially when compared to 10 itself, which had very little signal from the tumor cells.

The disclosures of all articles and references cited in this application, including patent applications [e.g., U.S. Patent Application No. 61/170,579 (filed Apr. 17, 2009), 61/184,750 (filed Jun. 5, 2009), Ser. No. 12/820,077 (filed Jun. 17, 2010)], patents, PCT publications (e.g., W.I.P.O. Application No. PCT/US2010/031434, filed Apr. 16, 2010), and non-patent publications, are incorporated herein by reference for all purposes. This application also incorporates by reference the full text of the application "Fluorescent Imaging with Substituted Cyanine Dyes," PCT/US2011/057178, which also claims priority to U.S. Provisional Patent Application Nos. 61/405,158 and 61/405,161.

References regarding click chemistry are shown below and are hereby incorporated by reference.

1. Ghosh, A. K.; Duong, T. T.; McKee, S. P.; Thompson, W. J. "NN'-disuccinimidyl carbonate: a useful reagent for alkoxycarbonylation of amines." *Tetrahedron Lett.* 1992, 33, 2781-2784.
2. Ghosh, A. K.; McKee, S. P.; Duong, T. T.; Thompson, W. J. "An efficient synthesis of functionalized urethanes from azides." *Chem. Commun.* 1992, 1308-13010.
3. Højfeldt, J. W.; Blakskjær, P.; Gothelf, K. V. "A Cleavable Amino-Thiol Linker for Reversible Linking of Amines to DNA." *J. Org. Chem.* 2006, 71, 9556-9559.
4. Bertozzi, C. R.; Bednarski, M. D. "The synthesis of heterobifunctional linkers for the conjugation of ligands to molecular probes." *J. Org. Chem.* 1991, 56, 4326-4329.
5. Schwabacher, A. W.; Lane, J. W.; Scheisher, M. W.; Leigh, K. M.; Johnson, C. W. "Desymmetrization Reactions: Efficient Preparation of Unsymmetrically Substituted Linker Molecules." *J. Org. Chem.* 1998, 63, 1727-1729.
6. Website: http://www.baseclick.eu and references therein.
7. Chan, T. R.; Higraf, R.; Sharpless, K. B.; Fokin, V. V. "Polytriazoles as Copper(I)-Stabilizing Ligands in Catalysis." *Org. Lett.* 2004, 6, 2853-2855.
8. El-Sagheer, A. H.; Brown, T. "Click Chemistry with DNA." *Chem. Soc. Rev.* 2010, 39, 1388-1405.
9. C. W. Tornoe, C. Christensen, M. Meldal, *J. Org. Chem.* 2002, 67, 3057-3064; V. V. Rostovtsev, L. G. Green, V. V. Fokin, K. B. Sharpless, *Angew. Chem.* 2002, 114, 2708-2711; *Angew. Chem. Int. Ed.* 2002, 41, 2596-2599.
10. C. J. Burrows, J. G. Muller, *Chem. Rev.* 1998, 98, 1109-1151.
11. T. R. Chan, R. Hilgraf, K. B. Sharpless, V. V. Fokin, *Org. Lett.* 2004, 6, 2853-2855.

12. J. Gierlich, G. A. Burley, P. M. E. Gramlich, D. M. Hammond, T. Carell, *Org. Lett.* 2006, 8, 3639-3642. F. Seela, V. R. Sirivolu, Chem. *Biodiversity* 2006, 3, 509-514.
13. P. M. E. Gramlich, S. Warncke, J. Gierlich, T. Carell, *Angew. Chem.* 2008, 120, 3491-3493; *Angew. Chem. Int. Ed.* 2008, 47, 3442-3444.

All publications, patents and patent applications cited in this specification are herein incorporated by reference as if each individual publication, patent or patent application were specifically and individually indicated to be incorporated by reference. Although the foregoing invention has been described in some detail by way of illustration and example for purposes of clarity of understanding, it will be readily apparent to those of ordinary skill in the art that, in light of the teachings of this application, that certain changes and modifications may be made thereto without departing from the spirit or scope of the appended claims.

What is claimed is:
1. A bioconjugate compound of Formula II:

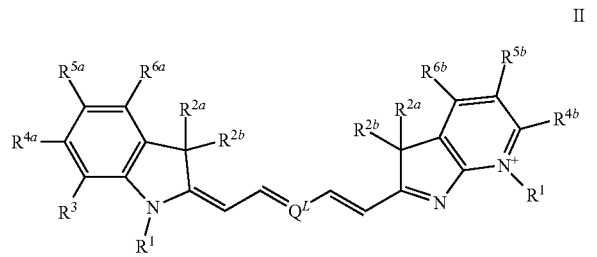

wherein
$Q^L$ is a portion of a polymethine bridge selected from the group consisting of:

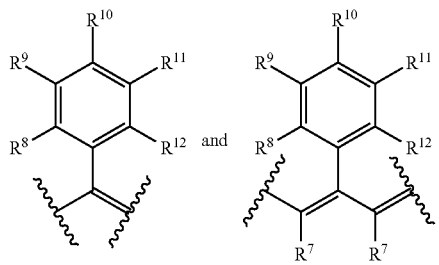

wherein $Q^L$ is the central portion of either a five- or a seven-polymethine-carbon polymethine bridge;
each $R^1$ is a member independently selected from the group consisting of -L-Y—Z and alkyl that is additionally substituted with from 0 to 1 $R^{13}$ and from 0 to 1 $R^L$; wherein the alkyl is optionally interrupted by at least one heteroatom;
each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, and sulfonatoalkyl; wherein a carbon of the member is additionally substituted with from 0 to 1 $R^L$; or, alternatively, a $R^{2a}$ and $R^{2b}$ pair, together with the ring carbon to which the $R^{2a}$ and $R^{2b}$ are bonded, join to form a spirocycloalkyl ring, wherein the spirocycloalkyl ring is additionally substituted with from 0 to 6 $R^{14}$ and from 0 to 1 $R^L$, or an exocyclic alkene, wherein the exocyclic alkene is additionally substituted with from 0 to 2 $R^{14}$ and from 0 to 1 $R^L$;
each $R^3$, $R^{4a}$, $R^{4b}$, $R^{5a}$, $R^{5b}$, $R^{6a}$, and $R^{6b}$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 $R^L$; or, alternatively, a pair of said members that is selected from the group consisting of $R^3$ and $R^{4a}$, an $R^{4a}$ and $R^{5a}$, and an $R^{5a}$ and $R^{6a}$, together with the pair of atoms to which the pair of said members is bonded, joins to form an aryl ring, wherein the aryl ring is additionally substituted with from 0 to 2 $R^{14}$ and from 0 to 1 $R^L$;
each $R^7$ is a member independently selected from the group consisting of hydrogen and alkyl; wherein the alkyl is additionally substituted with from 0 to 3 $R^{14}$ and from 0 to 1 $R^L$; or, alternatively, both $R^7$, together with the intervening segment of the polyene to which both $R^7$ are bonded, join to form a ring, wherein said ring is selected from the group consisting of a cycloalkyl and a heterocyclyl ring; wherein the ring is additionally substituted with from 0 to 3 $R^{14}$ and from 0 to 1 $R^L$;
$R^8$, $R^9$, $R^{10}$, $R^{11}$, and $R^{12}$ are each a member independently selected from the group consisting of hydrogen, alkyl, alkenyl, halo, alkoxy, sulfonato, hydroxyl, amino, carboxyl, alkoxycarbonyl, cyano, amido, thioacetyl, and -L-Y—Z; wherein, if present, at least one member selected from the group consisting of $R^8$, $R^9$, and $R^{10}$ is -L-Y—Z;
each $R^{13}$ is a member independently selected from the group consisting of hydroxyl, amino, carboxyl, alkoxycarbonyl, cyano, amido, sulfonato, and thioacetyl;
each $R^{14}$ is a member independently selected from the group consisting of alkyl, alkenyl, halo, hydroxyl, alkoxy, amino, cyano, carboxyl, alkoxycarbonyl, amido, sulfonato, alkoxycarbonylalkyl, and alkoxyalkyl; wherein the alkyl or alkenyl is additionally substituted with from 0 to 1 $R^{13}$ and from 0 to 1 $R^L$;
each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom;
each Y is an optional member independently selected from the group consisting of a bond, —O—, —S—, —NH—, —NHC(O)—, —C(O)NH—, —NR$^{15}$—, —NR$^{15}$C(O)—, —C(O)NR$^{15}$—, —N(Z)—, —N(Z)C(O)—, and —C(O)N(Z)—;
each Z is independently selected from the group consisting of -L-$R^{13}$ and -L-$R^L$;
alternatively, —Y—Z is a member selected from the group consisting of —N(Z)$_2$, —N(Z)C(O)Z, and —C(O)N(Z)$_2$, and the two Z groups may optionally be linked to form a cycloalkynyl group;
each $R^{15}$ is a member independently selected from the group consisting of alkyl and alkoxycarbonylalkyl, wherein the alkyl is optionally interrupted by at least one heteroatom;
each $R^L$ comprises a linking group and a biomolecule connected thereby, wherein the compound comprises at least one $R^L$; wherein the biomolecule is selected from the group consisting of hyaluronan, a tetracycline derivative, avidin, biotin, streptavidin, a peptide, and a protein; and
wherein said compound has a balanced charge.

2. The compound of claim 1, wherein Q is:

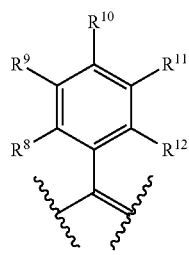

wherein each $R^1$ is an independently selected sulfonatoalkyl or an independently selected alkyl that is additionally substituted with from 0 to 1 $R^{13}$;

each $R^{2a}$ and $R^{2b}$ is a member independently selected from the group consisting of alkyl, carboxyalkyl, and sulfonatoalkyl;

$R^3$, $R^{4a}$, $R^{4b}$, $R^{5a}$, $R^{5b}$, $R^{6a}$, and $R^{6b}$ each is a member independently selected from the group consisting of hydrogen, alkyl, carboxy, carboxyalkyl, halo, sulfonato, and sulfonatoalkyl;

$R^8$, $R^9$, $R^{10}$, $R^{11}$, and $R^{12}$ are each a member independently selected from the group consisting of hydrogen, alkyl, halo, sulfonato, sulfonatoalkyl, and -L-Y—Z; wherein at least one member selected from the group consisting of $R^8$, $R^9$, and $R^{10}$ is -L-Y—Z;

each $R^{13}$ is a member independently selected from the group consisting of hydroxyl, amino, and carboxyl;

each $R^{14}$ is a member independently selected from the group consisting of alkyl, alkenyl, carboxyl, alkoxycarbonyl, amido, alkoxycarbonylalkyl, and halo;

each L is a member independently selected from the group consisting of a bond, a $C_1$-$C_{20}$ alkylene, and a $C_1$-$C_{20}$ alkenylene; and each Y is a member independently selected from the group consisting of a bond, —O—, —NHC(O)—, —C(O)NH—, —NR$^{15}$C(O)—, —C(O)NR$^{15}$—, —N(Z)—, —N(Z)C(O)—, and —C(O)N(Z)—;

alternatively, —Y—Z is a member selected from the group consisting of —N(Z)$_2$, —N(Z)C(O)Z, and —C(O)N(Z)$_2$, and the two Z groups may optionally be linked to form a cycloalkynyl group.

3. The compound of claim 2, having the formula:

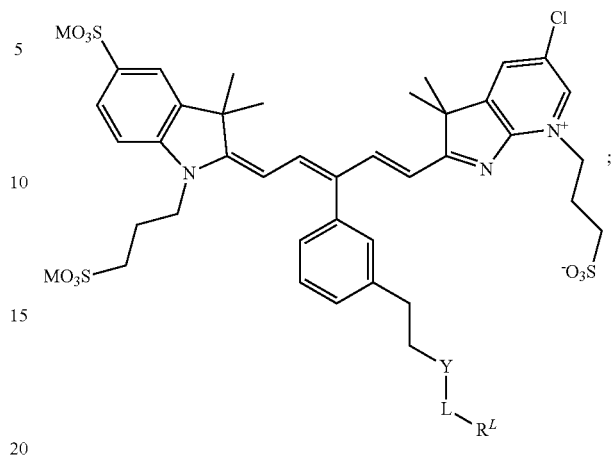

wherein M is an alkali metal ion.

4. The compound of claim 1, wherein the bioconjugate is hyaluronan.

5. The compound of claim 1, wherein the bioconjugate is selected from the group consisting of an avidin, streptavidin, and biotin.

6. The compound of claim 1, wherein the bioconjugate is a tetracycline derivative.

7. The compound of claim 1, wherein the bioconjugate is a peptide.

8. The compound of claim 7, wherein the peptide is a cyclic RGD peptide or an acyclic RGD peptide.

9. The compound of claim 1, wherein the bioconjugate is a protein.

10. The compound of claim 9, wherein the protein is EGF.

11. The compound of claim 9, wherein the protein is an antibody or an antibody fragment.

12. The compound of claim 11, wherein the antibody or antibody fragment is an antibody selected from the group consisting of a goat anti-mouse (GAM) antibody and a goat anti-rabbit (GAR) antibody.

13. The compound of claim 3, wherein the bioconjugate is hyaluronan.

14. The compound of claim 3, wherein the bioconjugate is selected from the group consisting of an avidin, streptavidin, and biotin.

15. The compound of claim 3, wherein the bioconjugate is a tetracycline derivative.

16. The compound of claim 3, wherein the bioconjugate is a peptide.

17. The compound of claim 16, wherein the peptide is a cyclic RGD peptide or an acyclic RGD peptide.

18. The compound of claim 3, wherein the bioconjugate is a protein.

19. The compound of claim 18, wherein the protein is EGF.

20. The compound of claim 18, wherein the protein is an antibody or an antibody fragment.

21. The compound of claim 20, wherein the antibody or antibody fragment is an antibody selected from the group consisting of a goat anti-mouse (GAM) antibody and a goat anti-rabbit (GAR) antibody.

* * * * *